US012473563B2

(12) United States Patent
Meng

(10) Patent No.: US 12,473,563 B2
(45) Date of Patent: Nov. 18, 2025

(54) IMMATURE INFLORESCENCE MERISTEM EDITING

(71) Applicant: KWS SAAT SE & Co. KGaA, Einbeck (DE)

(72) Inventor: Ling Meng, Saint Louis, MO (US)

(73) Assignee: KWS SAAT SE & Co. KGaA, Einbeck (DE)

( * ) Notice: Subject to any disclaimer, the term of this patent is extended or adjusted under 35 U.S.C. 154(b) by 218 days.

(21) Appl. No.: 17/799,348

(22) PCT Filed: Feb. 26, 2021

(86) PCT No.: PCT/EP2021/054799
§ 371 (c)(1),
(2) Date: Aug. 12, 2022

(87) PCT Pub. No.: WO2021/170785
PCT Pub. Date: Sep. 2, 2021

(65) Prior Publication Data

US 2023/0081632 A1 Mar. 16, 2023

Related U.S. Application Data

(60) Provisional application No. 62/982,900, filed on Feb. 28, 2020.

(51) Int. Cl.
*C12N 15/82* (2006.01)
*C12N 5/00* (2006.01)

(52) U.S. Cl.
CPC ....... *C12N 15/8213* (2013.01); *C12N 5/0025* (2013.01); *C12N 15/821* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 6,528,701 | B1 | 3/2003 | Wang et al. |
| 6,825,397 | B1 | 11/2004 | Lowe et al. |
| 7,763,774 | B2 | 7/2010 | Hehl et al. |
| 7,767,801 | B2 | 8/2010 | Hehl et al. |
| 7,960,612 | B2 | 6/2011 | Zhang et al. |
| 2008/0229439 | A1 | 9/2008 | La Rosa et al. |
| 2010/0162427 | A1 | 6/2010 | Riechmann et al. |
| 2011/0165679 | A1 | 7/2011 | Gordon-Kamm et al. |
| 2014/0219925 | A1 | 8/2014 | Bertrand et al. |
| 2014/0237681 | A1 | 8/2014 | Gordon-Kamm et al. |
| 2017/0121722 | A1 | 5/2017 | Anand et al. |
| 2017/0233756 | A1 | 8/2017 | Begemann et al. |
| 2018/0028686 | A1 | 2/2018 | Brinker et al. |
| 2019/0225974 | A1 | 7/2019 | D'Halluin et al. |
| 2021/0277407 | A1 | 9/2021 | Kong et al. |
| 2022/0025388 | A1 | 1/2022 | Meng |
| 2024/0191248 | A1 | 6/2024 | Meng |
| 2024/0417743 | A1 | 12/2024 | Meng |

FOREIGN PATENT DOCUMENTS

| | | | |
|---|---|---|---|
| CN | 101750487 | A | 6/2010 |
| CN | 101849009 | A | 9/2010 |
| CN | 109879944 | A | 6/2019 |
| CN | 109983122 | A | 7/2019 |
| EP | 2771468 | B1 | 2/2015 |
| EP | 3 159 413 | A1 | 4/2017 |
| EP | 3009511 | B1 | 5/2017 |
| EP | 3252162 | A1 | 12/2017 |
| EP | 3456825 | A1 | 3/2019 |
| WO | 94/18313 | | 8/1994 |
| WO | 95/09233 | | 4/1995 |
| WO | 03/004659 | | 1/2003 |
| WO | 03/080809 | | 10/2003 |
| WO | 2010/079430 | A1 | 7/2010 |
| WO | 2011/072246 | | 6/2011 |
| WO | 2011/082310 | A2 | 7/2011 |

(Continued)

OTHER PUBLICATIONS

Du, Yujuan, and Ben Scheres. "PLETHORA transcription factors orchestrate de novo organ patterning during *Arabidopsis* lateral root outgrowth." Proceedings of the National Academy of Sciences 114.44 (2017): 11709-11714. (Year: 2017).*
Gordon-Kamm, Bill, et al. "Using morphogenic genes to improve recovery and regeneration of transgenic plants." Plants 8.2 (2019): 38. (Year: 2019).*
Potsenkovskaia, Elina, et al. "Novel NF-Y genes expressed during somatic embryogenesis in Medicago truncatula." Plant Gene 31 (2022): 100364. (Year: 2022).*
Zhang, James Z. "Overexpression analysis of plant transcription factors." Current opinion in plant biology 6.5 (2003): 430-440. (Year: 2003).*
Eid, Ayman, Sahar Alshareef, and Magdy M. Mahfouz. "CRISPR base editors: genome editing without double-stranded breaks." Biochemical Journal 475.11 (2018): 1955-1964. (Year: 2018).*
GenBank Accession AGL53583.1 "Wuschel homeobox protein WOX5 [Picea abies]" dated Jun. 20, 2013 https://www.ncbi.nlm.nih.gov/protein/AGL53583.1/ (Year: 2013).*

(Continued)

*Primary Examiner* — Amjad Abraham
*Assistant Examiner* — Kelsey L Mcwilliams
(74) *Attorney, Agent, or Firm* — Troutman Pepper Locke LLP

(57) ABSTRACT

The present invention relates to a method for plant genome modification of at least one plant cell being in the developmental stage of a plant immature inflorescence meristem (IIM) cell, wherein the modification of the specific cell type is achieved by providing a genome modification or editing system, optionally together with at least one regeneration booster, preferably wherein the effector molecules are introduced by particle bombardment. To this end, new artificial and precisely controllable booster genes and proteins are provided. Further, the modified plant cells are regenerated in a direct or an indirect way. Finally, methods, tools, constructs and strategies are provided to effectively modify at least one genomic target site in a plant cell, to obtain the modified plant cell and to regenerate a plant tissue, organ, plant or seed from the modified plant cell.

20 Claims, 26 Drawing Sheets

Specification includes a Sequence Listing.

(56) References Cited

FOREIGN PATENT DOCUMENTS

| | | | | |
|---|---|---|---|---|
| WO | 2011/082318 A2 | 7/2011 | | |
| WO | 2011/146121 A1 | 11/2011 | | |
| WO | 2011/154393 | 12/2011 | | |
| WO | 2012/001527 | 1/2012 | | |
| WO | 2012/093833 | 7/2012 | | |
| WO | 2012/104729 | 8/2012 | | |
| WO | 2012/138927 | 10/2012 | | |
| WO | 2012/138939 A1 | 10/2012 | | |
| WO | 2013/103369 A1 | 7/2013 | | |
| WO | 2013/103370 A1 | 7/2013 | | |
| WO | 2016/021973 A1 | 2/2016 | | |
| WO | 2016146552 A1 | 9/2016 | | |
| WO | 2016184955 A2 | 11/2016 | | |
| WO | WO-2016184989 A1 * | 11/2016 | | A01H 5/04 |
| WO | 2017/074547 A1 | 5/2017 | | |
| WO | 2018042346 A2 | 3/2018 | | |
| WO | 2018236548 A1 | 12/2018 | | |
| WO | WO-2019060383 A1 * | 3/2019 | | C12N 15/8241 |
| WO | 2019122360 A1 | 6/2019 | | |
| WO | 2019238908 A1 | 12/2019 | | |
| WO | 2019238909 A1 | 12/2019 | | |
| WO | 2019238911 A1 | 12/2019 | | |

OTHER PUBLICATIONS

Komor, A., Kim, Y., Packer, M. et al. Programmable editing of a target base in genomic DNA without double-stranded DNA cleavage. Nature 2016, vol. 533, pp. 420-424. https://doi.org/10.1038/nature17946.

Kim et al., "The AtGRF family of putative transcription factors is involved in leaf and cotyledon growth in *Arabidopsis*", The Plant Journal, 2003, vol. 36, pp. 94-104. doi: 10.1046/j.1365-313X.2003.01862.x.

Mahonen, A.P., et al., "PLETHORA gradient formation mechanism separates auxin responses", Nature, 2014, vol. 515: pp. 125-129.

Ravi and Chan, "Haploid plants produced by centromere-mediated genome elimination", Nature, 2010, vol. 464, pp. 615-619. https://doi.org/10.1038/nature08842.

International Search Report issued in International Application No. PCT/EP2021/054799 dated May 31, 2021.

Du and Scheres, "PLETHORA transcription factors orchestrate de novo organ patterning during *Arabidopsis* lateral root outgrowth", PNAS 2017, vol. 114, No. 44, pp. 11709-11714. https://doi.org/10.1073/pnas.1714410114.

Lowe et al., "Morphogenic Regulators Baby boom and Wuschel Improve Monocot Transforamation", The Plant Cell, Sep. 2016, vol. 28(9), pp. 1998-2015.

Gaudelli, N., Komor, A., Rees, H. et al., "Programmable base editing of A•T to G•C in genomic DNA without DNA cleavage", Nature, Nov. 1, 2017, vol. 551, pp. 464-471. https://doi.org/10.1038/nature24644.

Zong, Y., Wang, Y., Li, C. et al., "Precise base editing in rice, wheat and maize with a Cas9-cytidine deaminase fusion", Nat. Biotechnol., 2017, vol. 35, pp. 438-440. https://doi.org/10.1038/nbt.3811.

Yan et al., "Highly Efficient A-T to G-C Base Editing by Cas9n-Guided tRNA Adenosine Deaminase in Rice", Molecular Plant, Apr. 2, 2018, vol. 11, issue 4, pp. 631-634.

Hua et al., "Precise A T to G C Base Editing in the Rice Genome", Molecular Plant, Apr. 2018, vol. 11(4): pp. 627-630.

Anzalone et al., "Search and replace genome editing without double-strand breaks or donor DNA", Nature, Oct. 21, 2019, vol. 576, pp. 149-157.

Smith, T.F. & Waterman, M.S. "Identification of common molecular subsequences" Journal of Molecular Biology, 1981, vol. 147(1): pp. 195-197.

Mayer, K. F. et al., "Role of WUSCHEL in regulating stem cell fate in the *Arabidopsis* shoot meristem", Cell, Dec. 11, 1998, vol. 95, pp. 805-815.

Yadav, R. K. et al., "WUSCHEL protein movement mediates stem cell homeostasis in the *Arabidopsis* shoot apex", Genes Dev., 2011, vol. 25, pp. 2025-2030.

Laux, T., Mayer, K. F., Berger, J. & Jurgens, G., "The WUSCHEL gene is required for shoot and floral meristem integrity in *Arabidopsis*", Development, 1996, vol. 122, pp. 87-96.

Leibfried, A. et al., "WUSCHEL controls meristem function by direct regulation of cytokinin-inducible response regulators", Nature, Dec. 22, 2005, vol. 438(7071), pp. 1172-1175. doi: 10.1038/nature04270.

Hofmann, "A Breakthrough in Monocot Transformation Methods", The Plant Cell, Sep. 2016, vol. 28: p. 1989.

Nic-Can et al., "New Insights into Somatic Embryogenesis: Leafy COTYLEDON1, BABY BOOM1 and WUSCHEL-Related HOMEOBOX4 Are Epigenetically Regulated in Coffea canephora", PLoS One, Aug. 2013, vol. 8(8), 31 pages, e72160. PMID: 23977240.

Ling Min et al., "Leafy COTYLEDON1-CASEIN Kinase I-TCP15-PHYTOCHROME Interacting FACTOR4 Network Regulates Somatic Embryogenesis by Regulating Auxin Homeostasis", Plant Physiology, Dec. 2015, vol. 169, pp. 2805-2821.

A. Cagliari et al., "New insights on the evolution of Leafy cotyledon1 (LEC1) type genes in vascular plants", Genomics, 2014, vol. 103, pp. 380-387.

Choi et al., "Whole Genome Analysis of the OsGRF Gene Family Encoding Plant Specific Putative Transcription Activators in Rice (*Oryza sativa* L.)", Plant Cell Physiol, 2004, vol. 45(7): pp. 897-904.

Ellerström et al., "Etopic Expression of Effector of Transcription perturbs gibberellin-mediated plant developmental proceses", Plant Molecular Biology, 2005, vol. 59: pp. 663-681.

Aida, M., et al., "The PLETHORA genes mediate patterning of the *Arabidopsis* root stem cell niche", Cell, 2004, vol. 119: pp. 109-120.

Santuari et al., "The PLETHORA Gene Regulatory Network Guides Growth and Cell Differentiation in *Arabidopsis* Roots", The Plant Cell, Dec. 2016, vol. 28: pp. 2937-2951 DOI: https://doi.org/10.1105/tpc.16.00656.

El Ouakfaoui, S. et al., "Control of somatic embryogenesis and embryo development by AP2 transcription factors", Plant Molecular Biology, 2010, vol. 74(4-5): pp. 313-326.

Helenius et al., "Gene delivery into intact plants using the Helios™ Gene Gun", Plant Molecular Biology Reporter, 2000, 18 (3):287a-287l.

Written Opinion issued in International Application No. PCT/EP2021/054799 dated May 31, 2021.

Zhang et al., "Chemical probes in plant epigenetics studies", Plant Signaling & Behavior, 2013, vol. 8, No. 9, e25364.

Nasti et al., 2022, Defining the Parameters to Improve Plant Regeneration with Developmental Regulators, BioRxiv, 24 pages.

Guo et al., 2004, "Protein tolerance to random amino acid change", Proceedings of the National Academy of Sciences, vol. 101, No. 25, pp. 9205-9210.

Horlbeck et al., 2016, "Nucleosomes impede Cas9 access to DNA in vivo and in vitro", elife, vol. 5, e12677.

Definition of derivative—NCI Dictionary of Cancer Terms—NCI (https://www.cancer.gov/publications/dictionaries/cancer-terms/def/derivative) viewed on Jan. 24, 2023 (Year: 2023).

Variant Definition & Meaning—Merriam-Webster (https://www.meriamp-webster.com/dictionary/variant) viewed on Jan. 24, 2023 (Year: 2023).

Yang et al., "Trichostatin A and 5-azacytidine both cause an increase in global histone H4 acetylation and a decrease in global DNA and H3K9 methylation during mitosis in maize", BMC Plant Biology, 2010, vol. 10, No. 178, 11 pages.

Prasad et al., "*Arabidopsis* PLETHORA transcription factors control phyllotaxis", Current Biology, 2011, vol. 21, No. 13, pp. 1123-1128.

Purwestri et al., "RWP-PK Domain 3 (OsRKD3) Induces somatic embryogenesis in black rice", BMC Plant Biology, 2023, vol. 23, No. 202, 15 pages.

Sprunck et al., "Elucidating small RNA pathways in *Arabidopsis thaliana* egg cells", BioRxiv, 2019, doi: https://doi.org/10.1101/525956, 39 pages.

(56) References Cited

OTHER PUBLICATIONS

Zhang et al., "CRISPR ribonucleoprotein-mediated genetic engineering in plants", Plant Communications, 2021, vol. 2, pp. 1-13.
Tanaka et al., "The *Arabidopsis* histone deacetylases HDA6 and HDA19 contribute to the repression of embryonic properties after germination", Plant Physiology, 2008, vol. 146, No. 1, pp. 149-161.
"RWP-RK domain containing protein [Triticum aestivum]", AEB26836.1, GenBank; Aug. 5, 2011.
Li et al., "Analysis of pepper RWP-RK transcription factors", Journal of Anhui Agricultural University, 2018, vol. 45, No. 1, pp. 187-194. (with English abstract).
Tsuwamoto et al., "*Arabidopsis* EMBRYOMAKER encoding an AP2 domain transcription factor plays a key role in developmental change from vegetative to embryonic phase", Plant Molecular Biology, 2010, vol. 73, pp. 481-492.
Horstman et al., "A transcriptional view on somatic embryogenesis", Regeneration, 2017, vol. 4, No. 4, pp. 201-216.
Isalan et al., "A rapid, generally applicable method to engineer zinc fingers illustrated by targeting the HIV-1 promoter", Nature Biotechnology, 2001, vol. 19, No. 7, pp. 656-660.
Liu et al. "Design of polydactyl zinc-finger proteins for unique addressing within complex genomes", Proceedings of the National Academy of Sciences, 1997, vol. 94, No. 11, pp. 5525-5530.
Boch et al., "Breaking the code of DNA binding specificity of TAL-type III effectors", Science, 2009, vol. 326, No. 5959, pp. 1509-1512.
Moscou et al., "A simple cipher governs DNA recognition by TAL effectors", Science, 2009, vol. 326, No. 5959, p. 1501.
Zetsche et al., "Cpf1 Is a Single RNA-Guided Endonuclease of a Class 2 CRISPR-Cas System", Cell, 2015, vol. 163, pp. 759-771.
Makarova et al., "An updated evolutionary classification of CRISPR-Cas systems", Nature Rev. Microbiol., 2015, vol. 13, No. 11, pp. 722-736.
Jinek et al., "A programmable dual-RNA-guided DNA endonuclease in adaptive bacterial immunity", Science, 2012, vol. 337, No. 6096, pp. 816-821.
Burstein et al., "New CRISPR-Cas systems from uncultivated microbes", Nature, 2017, vol. 542, pp. 237-241.
Jore et al., "Structural basis for CRISPR RNA-guided DNA recognition by Cascade", Nature Structural & Molecular Biology, 2011, vol. 18, No. 5, pp. 529-536.
Sterner et al., "Acetylation of histones and transcription-related factors", Microbiology and Molecular Biology Reviews, 2000, vol. 64, No. 2, pp. 435-459.
Zhang et al., "Transcription regulation by histone methylation: interplay between different covalent modifications of the core histone tails", Genes & Development, 2001, vol. 15, No. 18, pp. 2343-2360.
Shilatifard, "Chromatin modifications by methylation and ubiquitination: implications in the regulation of gene expression", Annu. Rev. Biochem., 2006, vol. 75, pp. 243-269.
Nowak et al., "Phosphorylation of histone H3: a balancing act between chromosome condensation and transcriptional activation", Trends in Genetics, 2004, vol. 20 , No. 4, pp. 214-220.
Nathan et al., "Histone sumoylation is a negative regulator in *Saccharomyces cerevisiae* and shows dynamic interplay with positive-acting histone modifications", Genes & Development, 2006, vol. 20, No. 8, pp. 966-976.
Hassa et al., "Nuclear ADP-ribosylation reactions in mammalian cells: where are we today and where are we going?", Microbiology and Molecular Biology Reviews, 2006, vol. 70, No. 3, pp. 789-829.
Andrews et al., "Nucleosome structure(s) and stability: Variations on a theme", Annu. Rev. Biophys., 2011, vol. 40, pp. 99-117.
Bannister et al., "Regulation of chromatin by histone modifications", Cell Research, 2011, vol. 21, pp. 381-395.
Zhang et al., "An epigenetic perspective on developmental regulation of seed genes", Molecular Plant, 2009, vol. 2, No. 4, pp. 610-627.
Miguel et al., "An epigenetic view of plant cells cultured in vitro: somaclonal variation and beyond", Journal of Experimental Botany, 2011, vol. 62, No. 11, pp. 3713-3725.
Li et al., "The Histone Deacetylase Inhibitor Trichostatin A Promotes Totipotency in the Male Gametophyte", The Plant Cell, 2014, vol. 26, pp. 195-209.
Waki et al., "The *Arabidopsis* RWP-RK protein RKD4 triggers gene expression and pattern formation in early embryogenesis", Current Biology, 2011, vol. 21, No. 15, pp. 1277-1281.
Rice et al., "EMBOSS: The European Molecular Biology Open Software Suite", Trends in Genetics, 2000, vol. 16, No. 6, pp. 276-277.
U.S. Appl. No. 62/609,508, filed Dec. 22, 2017.
International Search Report and Written Opinion issued in International Application No. PCT/EP2019/065643 dated Oct. 2, 2019.
Svitashev et al., "Genome editing in maize directed by CRISPR-Cas9 ribonucleoprotein complexes", Nature Communications, vol. 7, 2016, p. 13274, 7 pages.
Bouchabke-Coussa et al., "Wuschel overexpression promotes somatic embryogenesis and induces organogenesis in cotton (*Gossypium hirsutum* L.) tissues cultured in vitro", Plant Cell Reports, 2013, vol. 32, No. 5, pp. 675-686.
International Search Report and Written Opinion issued in International Application No. PCT/EP2019/065645 dated Oct. 7, 2019.
Database EMBL [Online] May 1, 2009 (May 1, 2009), "*Ginkgo biloba* (maidenhair tree) putative wuschel homeobox protein WUS ID—CAT02906; sv 1.; linear; mRNA; STD; PLN; 786 BP", XP002794173, retrieved from EBI accession No. EMBL:CAT02906 sequence.
Database EMBL [Online] May 1, 2009 (May 1, 2009), "Ginkgo biloba mRNA for putative wuschel homeobox protein WUS (wus gene)", XP002794174, retrieved from EBI accession No. EMBL: FM882128 Database accession No. FM882128 sequence.
International Search Report and Written Opinion issued in International Application No. PCT/EP2019/065647 dated Nov. 29, 2019.
International Search Report and Written Opinion issued in International Application No. PCT/IB2020/000063 dated Jun. 16, 2020.
Koszegi et al., "Members of the RKD transcription factor family induce an egg cell-like gene expression program", The Plant Journal, 2011, vol. 67, No. 2, pp. 280-291.
Koi et al., "An Evolutionarily Conserved Plant RKD Factor Controls Germ Cell Differentiation", Current Biology, 2016, vol. 26, No. 13, pp. 1775-1781.
Zuo et al., "An estrogen receptor-based transactivator XVE mediates highly inducible gene expression in transgenic plants", The Plant Journal, 2000, vol. 24, No. 2, pp. 265-273.
Samalova et al., "pOp6/LhGR: a stringently regulated and highly responsive dexamethasone-inducible gene expression system for tobacco", The Plant Journal, 2005, vol. 41, No. 6, pp. 919-935.
Durr et al., "Highly efficient heritable targeted deletions of gene clusters and non-coding regulatory regions in *Arabidopsis* using CRISPR/Cas9", Scientific Reports, 2018, vol. 8, 4443, 11 pages.
Zuo et al., "Chemical-inducible systems for regulated expression of plant genes", Current Opinion in Biotechnology, 2000, vol. 11, No. 2, pp. 146-151.
Craft et al., "New pOp/LhG4 vectors for stringent glucocorticoid—dependent transgene expression in *Arabidopsis*", The Plant Journal, 2005, vol. 41, No. 6, pp. 899-918.
https://www.uniprot.org/uniprot/Q9S292; May 2009.
Nardmann et al., "The Shoot Stem Cell Niche in Angiosperms: Expression Patterns of WUS Orthologues in Rice and Maize Imply Major Modifications in the Course of Mono- and Dicot Evolution", Molecular Biology and Evolution, 2006, vol. 23, No. 12, pp. 2492-2504.
Soderlund et al., "Sequencing, Mapping, and Analysis of 27,455 Maize Full-Length cDNAs", PLoS Genetics, 2009, vol. 5, Issue 11, e1000740, pp. 1-13.
Milne et al., "An Approach to gene-specific transcription inhibition using oligonucleotides complementary to the template strand of the open complex", PNAS, 2000, vol. 97, No. 7, pp. 3136-3141.
Zhang et al., "Predicting DNA Hybridization Kinetics from Sequence", Nature Chemistry, 2018, vol. 10, pp. 91-98.

(56) References Cited

OTHER PUBLICATIONS

Zhang et al., "A Two-Step Model for de Novo Activation of WUSCHEL during Plant Shoot Regeneration", The Plant Cell, 2017, vol. 29, pp. 1073-1087.
Nardmann et al., Accession CAT02906, published 2009.
Kareem et al., "PLETHORA Genes Control Regeneration by a Two-step Mechanism", Curr Biol., 2015, vol. 25, No. 8, pp. 1017-1030.
Lowe et al., "Rapid genotype "independent" *Zea mays* L. (maize) transformation via direct somatic embryogenesis", In Vitro Cellular & Developmental Biology—Plant, 2018, vol. 54(8), pp. 240-252.
International Search Report and Written Opinion issued in PCT/EP2021/054805 dated May 21, 2021.
Collins et al., Accession No. GO662999, 2010.
Hortsman et al., 2014, "Aintegumenta-Like proteins: hubs in a plethora of networks", Trends in Plant Science, vol. 19, No. 3, pp. 146-157.
Laforest et al., "Advances in Delivery Mechanisms of CRISPR Gene-Editing Reagents in Plants", Frontiers in Genome Editing, 2022, vol. 4, Article 830178; 10 pages.
Lv et al., "Nanoparticle-mediated gene transformation strategies for plant genetic engineering", The Plant Journal, 2020, vol. 104, pp. 880-891.
Sun et al., "Delivery of Abscisic Acid to Plants Using Glutathione Responsive Mesoporous Silica Nanoparticles", Journal of Nanoscience and Nanotechnology, 2018, vol. 18, No. 3, pp. 1615-1625.

* cited by examiner

Figure 9

A 0.0% wild type: TTTGATTTACTCGTCACGATTCCCCTC|TCCTGG|TCGAACTTTTCAGGTGGGGAAAGCTGCTGGCGA
41.817% 34bp deletion: TTTGATTTACTCGTCA-----------|------|-----------------GGAAAGCTGCTGGCGACAGGTGGAAATC
39.323% 7bp deletion: TTTGATTTACTCGTCACGATTCC----|--TGG|TCGAACTTTTCAGGTGGGGAAAGCTGCTGGCG
3.045% 34bp deletion: TTTGATTTAC-----------------|------|-----------AGGTGGGGAAAGCTGCTGGCGACAGGTGGAAATC
R square: 0.9202019923032575

B 44.949% wild type: TTTGATTTACTCGTCACGATTCCCCTC|TCCTGG|TCGAACTTTTCAGGTGGGGAAAGCTGCTGG
31.05% 10bp deletion: TTTGATTTACTCGTCACGATTCCCC--|------|--GAACTTTTCAGGTGGGGAAAGCTGCTGGCGA
12.165% 10bp deletion: TTTGATTTACTCGTCACGATTCCCCT-|------|---AACTTTTCAGGTGGGGAAAGCTGCTGGCGA
R square: 0.9643538559259094

Sanger sequencing trace decomposition for GE events'|': cut sites ;'-': deletion; lower case: Insertion Figure 10
A
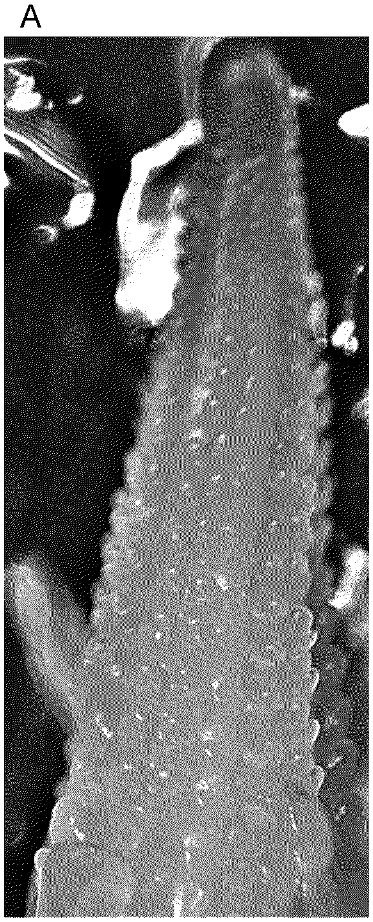
B
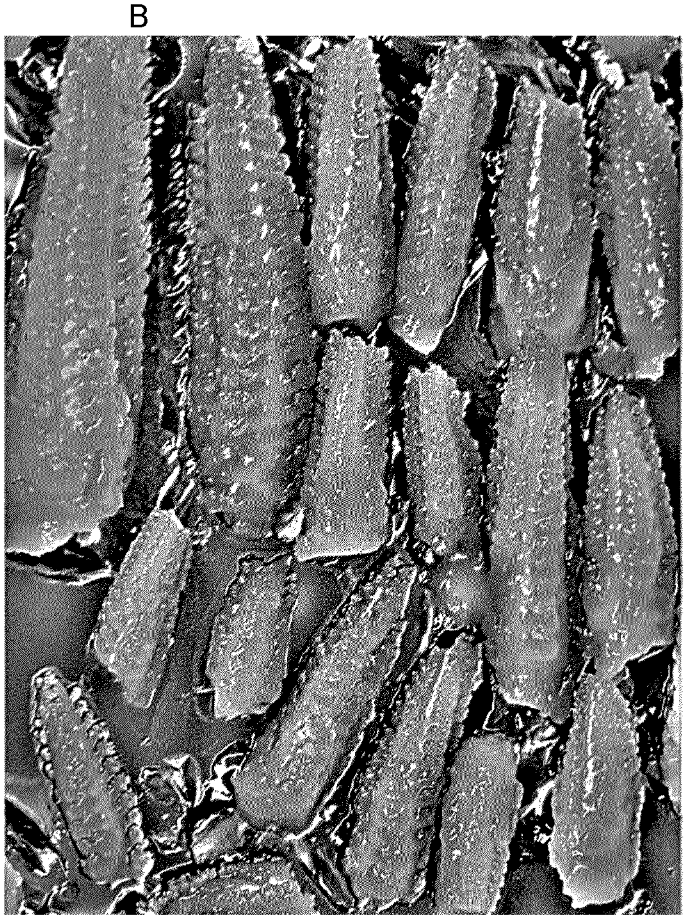

Figure 29
A
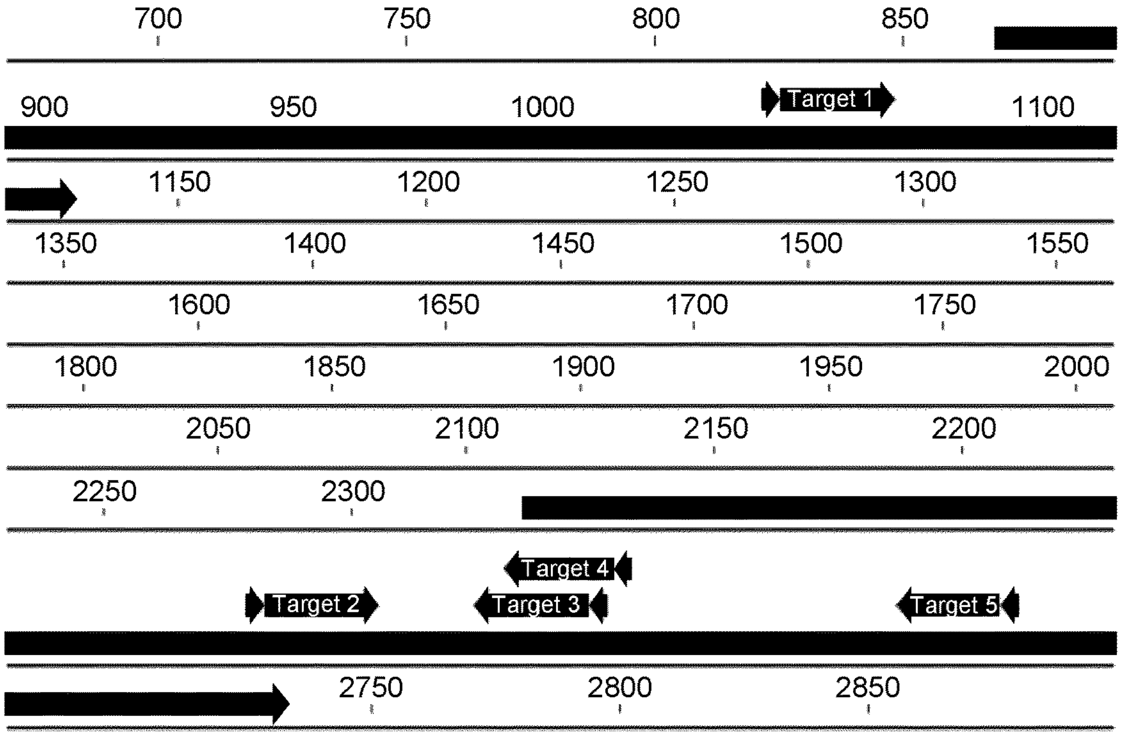
B
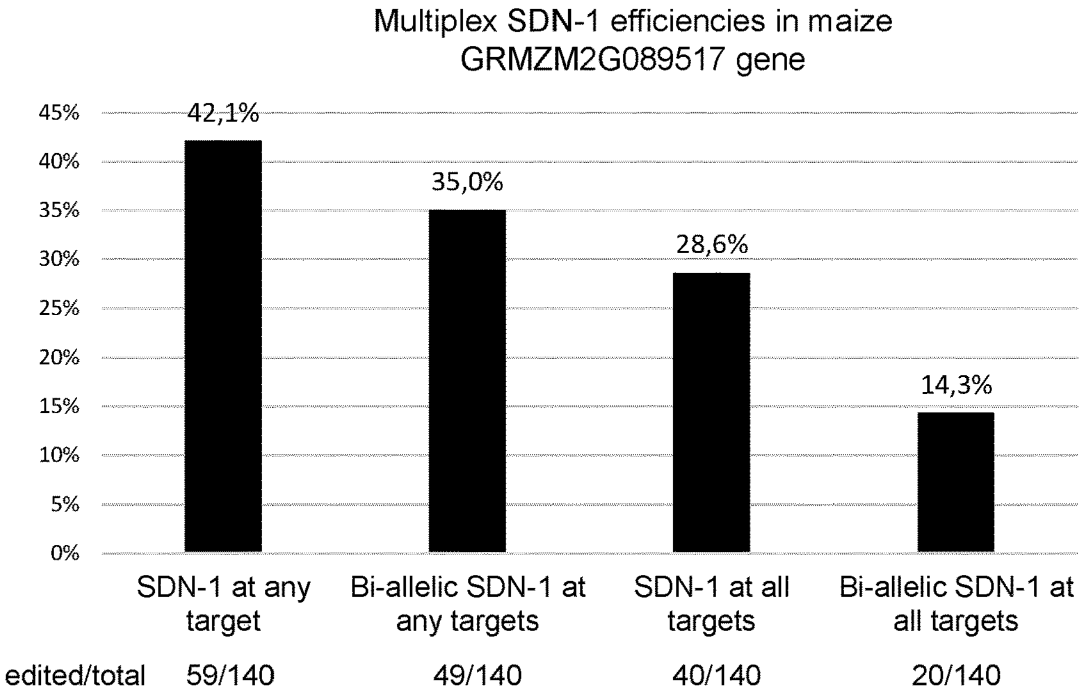

IMMATURE INFLORESCENCE MERISTEM EDITING

CROSS-REFERENCE TO RELATED APPLICATIONS

This application is a U.S. National Phase of International Patent Application No. PCT/EP2021/054799, filed on Feb. 26, 2021, which claims priority to U.S. Provisional Application No. 62/982,900, filed Feb. 28, 2020. The entire contents of these applications are incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 23, 2025, is named 245761_000181_SL.txt and is 253,659 bytes in size.

TECHNICAL FIELD

The present invention relates to the field of genome engineering or gene editing of specific plant cells. In particular, the present invention relates to the modification of at least one plant cell being in the developmental stage of a plant immature inflorescence meristem (IIM) cell, wherein the modification of the specific cell type is achieved by providing a genome modification or editing system, optionally together with at least one regeneration booster, preferably wherein the effector molecules are introduced by means of particle bombardment. To this end, new artificial and precisely controllable booster genes (RBGs) and proteins (RBPs) are provided. Further, the modified plant cells are regenerated in a direct or an indirect way. Finally, methods, tools, constructs and strategies are provided to effectively modify at least one genomic target site in a plant cell, to obtain said modified cell and to regenerate a, plant tissue, organ, plant or seed from the such modified cell.

BACKGROUND OF INVENTION

To cope with the increasing challenges of climate change, food safety and a growing world population, traditional plant breeding, usually being rather time consuming, has to be supported by new techniques of molecular biology to provide new crop plants having desired traits in safe manner, but needing less development time.

Having more and more potentially suitable site-specific nuclease tools at hand, transformation or transfection and subsequent regeneration are still the major bottleneck technologies for plant genome engineering, such as genome editing (GE). To obtain a modified plant, the two events have to fall on the same cell. Up to date, particle bombardment and *Agrobacterium*-mediated biomolecule delivery are the most efficient methods for plant transformation. In agrobacterial transformation, the Agrobacteria first find the suitable cells and attach to the plant cell walls, which is generally referred as "inoculation". Following the inoculation, the Agrobacteria are growing with plant cells under suitable conditions for a period of time—from several hours to several days—to allow T-DNA transfer. *Agrobacterium*-plant interaction, plant tissue structure, plant cell type, etc. constrain agrobacterial transformation. Limited by plant cell susceptibility and accessibility it is generally believed that *Agrobacterium*-mediated transformation is plant species, plant tissue-type and plant cell-type dependent. Conversely, based on physical forces particle bombardment is—at least in theory—plant species and plant cell-type independent, and is able to transform any cells when appropriate pressure applied. Still, many plant cells, in particular plant cells freshly isolated from a plant depending on the developmental stage and the tissue they are derived from, suffer severe stress or even cell death when physically bombarded with micro- or nanoparticles of various kinds. Further, bombardment may be associated with a low transformation and/or integration frequencies also caused by the severe cell damage or rupture. Physical bombardment per se offers great advantages as it is easy, rapid and versatile and allows for transient and stable expression of the inserted molecules, if desired. Potentially toxic chemicals needed for transfection, or bacterial transformations can be avoided.

For genome modification, there is thus a great need in identifying new plant cells and protocols in a suitable developmental stage, which have the capacity to be isolated directly from a living plant, which can be effectively bombarded, e.g., for gene editing, or for any kind of expressing a tool to be inserted stably or transiently, and which can later on be regenerated to a whole plant.

Plant cells are developmentally plastic and likely regenerative. The regenerative capacity of plant cell depends on cell identity, age, and environmental signals. There are at least two types of plant cells: somatic cells and stem cells. Somatic cells are the descendants of a stem cell. They are differentiated cells with specific features morphologically, metabolically, and functionally. The regeneration of somatic cells requires cell fate reprogramming via dedifferentiation into a regenerative cell. On the other hand, plant stem cells are undifferentiated and able to generate new cells, tissues and finally develop into a new plant. Plant stem cells are mainly located on a specialized tissue named plant meristem, including shoot, root meristem, and inflorescence meristem.

For important cereal crops (e.g., maize, wheat, rye, oat, barley, sorghum, rice), the most widely used explant for genome engineering is immature zygotic embryo. The epidermal and sub-epidermal cells from the scutellum surface of immature embryo are ideal recipient cells for *Agrobacterium*-mediated transformation, and also for particle bombardment. However, the regeneration from the epidermal and sub-epidermal cells on the scutellum surface of immature embryo are highly genotype dependent, and genetic engineering in cereal crops generally rely on several regenerative genotypes, e.g., maize Hi II and A188. Moreover, production of immature zygotic embryos is a time and resource demanding process. It takes at least 12 weeks from seed planting to immature embryo harvesting in maize, and requires well-equipped and highly remained greenhouse conditions and facilities. The quality of immature embryos are also greenhouse and season dependent. Therefore, developing alternative explants that are regenerative and do not rely on long greenhouse periods is highly desirable for genome engineering in cereal crops.

Plants produce abundant inflorescence meristems. An inflorescence meristem is the modified shoot meristem that contains multipotent stem cells and is able to produce floral primordia, and eventually develops into an inflorescence, i.e., a cluster of flowers arranged on a main stem. Today, reliable protocols for efficient plant genome editing are not available for specifically and efficiently transfecting inflorescence meristem, in particular by physical means, to rapidly introduce traits of interest into the genome of a given plant in an inheritable manner.

Another problem in the targeted modification of plants is that it is believed that transformed cells are less regenerable than wild type cells. These circumstances may result in poor rates of genome editing in view of the fact that the transformed/transfected material may not be viable enough after the introduction of the GE tools. For example, transformed cells are susceptible to programmed cell death due to presence of foreign DNA inside of the cells. Stresses arising from delivery (e.g. bombardment damage) may trigger a cell death as well.

Plant development is characterized by repeated initiation of meristems, regions of dividing cells that give rise to new organs. During lateral root (LR) formation, new LR meristems are specified to support the outgrowth of LRs along a new axis. The determination of the sequential events required to form this new growth axis has been hampered by redundant activities of key transcription factors. The effects of three PLETHORA (PLT) transcription factors, PLT3, PLT5, and PLT7, during LR outgrowth were already characterized. It was found that in plt3/plt5/plt7 triple mutants, the morphology of lateral root primordia (LRP), the auxin response gradient, and the expression of meristem/tissue identity markers are impaired from the "symmetry-breaking" periclinal cell divisions during the transition between stage I and stage II, wherein cells first acquire different identities in the proximodistal and radial axes. Particularly, PLT1, PLT2, and PLT4 genes that are typically expressed later than PLT3, PLT5, and PLT7 during LR outgrowth are not induced in the mutant primordia, rendering "PLT-null" LRP. Reintroduction of any PLT clade member in the mutant primordia completely restores layer identities at stage II and rescues mutant defects in meristem and tissue establishment. Therefore, all PLT genes can activate the formative cell divisions that lead to de novo meristem establishment and tissue patterning associated with a new growth axis (Du and Scheres, PNAS 2017, doi.org/10.1073/pnas.1714410114). Still, the role of PLT proteins and variants thereof in gene editing in specific meristematic cells to promote gene editing in a concerted manner was not described yet. Again, reliable and efficient protocols are lacking combining the knowledge on plant regeneration boosters with the further powerful gene editing mechanisms, in particular in view of the fact that both techniques require the introduction of huge molecular complexes into a given cell, which has to be in a state susceptible for transformation.

As disclosed in Lowe et al. (Plant Cell, 2016, 28(9)) there is another problem associated with the use of naturally occurring regeneration boosters in artificial settings of plant genome modifications: the usually growth-stimulating effect of regeneration boosters—if not as precisely controlled as in the natural environment, where the transcription factors are only expressed in a tightly controlled spatio-temporal manner, the ectopic expression of regeneration boosters used in plant genome modification easily leads to pleiotropic effects on plant growth and fertility. These uncertainties and negative effects are, however, not desired for targeted genome editing. To address this problem, Lowe et al. suggests a rather cumbersome technique of integrating and later on inactivation booster activity by removal of the relevant expression cassettes.

Given the current obstacles in highly efficient plant transformation strategies and/or effective site-specific plant genome editing in relevant monocot and dicot plants, it was thus an object of the present invention to provide new plant cell amenable to be transfected/transformed and efficient protocols for transforming specific plant tissue in a defined manner to increase transfection/transformation efficiencies by targeting plant cells in an optimum developmental stage. Finally, it was an object to achieve genome modification, e.g. gene editing, with single-cell origin allowing a homogenous and regenerable genome editing without a conventional selection to speed-up and facilitate current protocols relying on cumbersome and expensive screening and regeneration steps, or suffering from poor and rather singular gene editing events.

SUMMARY OF THE INVENTION

The above object was achieved by elucidating that plant immature inflorescence meristem (IIM) cells provides an ideal alternative explant for genome engineering and modifications in general and especially for targeted genome editing. The present invention involves direct delivery of biological molecules, e.g. DNA, RNA, protein, RNP, or chemicals into the inflorescence meristem cells as specific target cells, preferably mediated by micro-particle carriers. Following the biolistic delivery of biomolecules, the transformed cells from the immature inflorescence meristem are regenerated in a flexible manner into entire plants via either direct meristem regeneration, or via indirect callus regeneration.

In one aspect, there is provided a method for plant genome modification, preferably for the targeted modification of at least one genomic target sequence, by obtaining a modification of at least one plant immature inflorescence meristem cell, wherein the method comprises the following steps: (a) providing at least one immature inflorescence meristem (IIM) cell; (b) introducing into the at least one immature inflorescence meristem cell: (i) at least one genome modification system, preferably a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same; (ii) optionally: at least one regeneration booster, or a sequence encoding the same, or a regeneration booster chemical, wherein steps (i) and (ii) take place simultaneously, or subsequently, for promoting plant cell proliferation and/or to assist in a targeted modification of at least one genomic target sequence; (iii) and, optionally at least one repair template, or a sequence encoding the same; and (c) cultivating the at least one immature inflorescence meristem cell under conditions allowing the expression and/or assembly of the at least one genome modification system, preferably the at least one genome editing system and optionally the at least one regeneration booster, and optionally of the at least one guide molecule and/or optionally of the at least one repair template; and (d) obtaining at least one modified immature inflorescence meristem cell; or (e) obtaining at least one plant tissue, organ, plant or seed regenerated from the at least one modified cell; and (f) optionally: screening for at least one plant tissue, organ, plant or seed regenerated from the at least one modified cell in the T0 and/or T1 generation carrying a desired targeted modification.

In a further aspect, there are provided isolated nucleic acid sequences, and the polypeptide sequences encoding the same, and recombinant genes, expression cassettes and expression constructs comprising isolated nucleic acid sequences, wherein the polypeptide sequences have the function of a regeneration booster artificially optimized to be perfectly suitable to promote genome modification or gene editing and suitable to be used in combination with at least one further regeneration booster.

In a further aspect, there are provided methods for regenerating recalcitrant plants/plant genotypes using the methods for plant genome modification as provided in the first aspect.

In yet a further aspect, there are provided methods providing at least one regeneration booster, or a specific combination of regeneration boosters, or the sequence(s) encoding the same, for efficiently producing haploid or doubled haploid plant cells, tissues, organs, plants, or seeds.

In one aspect, an IIM cell is preferably transformed by physical bombardment, optionally together with at least one regeneration booster.

In one aspect, the method comprises a regeneration step, wherein the regeneration is direct meristem organogenesis, in another aspect, the regeneration step comprises a step of indirect callus embryogenesis or organogenesis.

In one aspect, the methods specifically rely on the use of at least one regeneration booster, or a sequence encoding the same, or of at least one regeneration booster chemical, wherein the booster fulfils the dual function of enhancing plant regeneration after transfection/transformation and/or of increasing genome modification efficiencies, in particular gene editing efficiencies after inducing a targeted DNA break (single- or double-stranded) by at least one site-directed nuclease.

In a further aspect, specific combinations of regeneration boosters are provided having synergistic activities in promoting plant regeneration and/or genome modification efficiencies, preferably gene editing efficiencies.

In one aspect, particle bombardment is used for transforming or transfecting at least one plant immature inflorescence cell of interest.

In a further aspect, there is provided a plant cell, tissue, organ, plant or seed obtainable by or obtained by a method according to any of the preceding claims.

In yet a further aspect, there is provided the use of a genome modification system, or of a genome editing system for efficiently transforming or transfecting at least one immature inflorescence cell.

In another aspect, expression constructs and expression cassettes are provided encoding the genome modification system, or encoding the genome editing system to be introduced into at least one plant immature inflorescence meristem cell.

Further provided is an expression construct assembly comprising the relevant constructs and cassettes for conducting the methods as disclosed herein.

In a further aspect, methods for staging plants are provided for various relevant crop plants to identify the correct developmental stage when plant immature inflorescence meristem cells are present and thus available for the methods for plant genome modification provided.

In yet another aspect, there is provided a plant cell, preferably an IIM cell, comprising an expression construct assembly, or comprising the recombinant gene, or comprising an expression cassette or an expression construct as disclosed herein, or there is provided a plant tissue, organ, whole plant, or a part thereof or a seed comprising this plant cell.

Further uses of and methods for constructing multiple purpose expression constructs and expression cassettes for use according to the present invention are provided.

BRIEF DESCRIPTION OF DRAWINGS

Whenever the Figures show black/white pictures of originally fluorescence images, brighter spots represent the accumulation of the respective fluorescent protein.

FIG. 9 shows a Sanger sequencing trace decomposition analysis of genome editing events in the regenerated TO plantlets from a 28-day-old A188 immature tassel by direct meristem regeneration. (A) The sequencing results from one of the 12 regenerated plantlets with ~100% SDN-1 editing (biallelic); (B) the sequencing result from the plantlet with ~50% SDN-1 editing (monoallelic). FIGS. 9A and 9B disclose SEQ ID NOS 55-61, respectively, in order of appearance.

FIG. 10 shows genome editing SDN-1 by transient biolistic transformation and direct meristem regeneration of immature ears from maize elite 4V-40171 plants harvested at 39 days after planting. (A): A freshly isolated immature ear from elite 4V-40171; (B): the immature ears on osmotic medium (IM_OSM) and ready for biolistic bombardment.

FIG. 29 shows multiplex genome editing SDN-1 at 5 target locations of the maize target gene annotated as UV-B-insensitive 4-like gene in A188. (A): maize gene structure and target sequence locations; (B) summary of the multiplex genome editing SDN-1 efficiencies in above maize target gene.

DESCRIPTION OF SEQUENCES

In the following, the term "RBG" means a regeneration booster gene, and "RBP" means a regeneration booster protein. As used herein, the term "RBP" may be used interchangeably to refer to a regeneration booster protein, but also to the cognate gene encoding this regeneration booster protein. Vice versa, a "RBG" may refer to a gene and the protein encoded by this gene accordingly.

Figure 4:
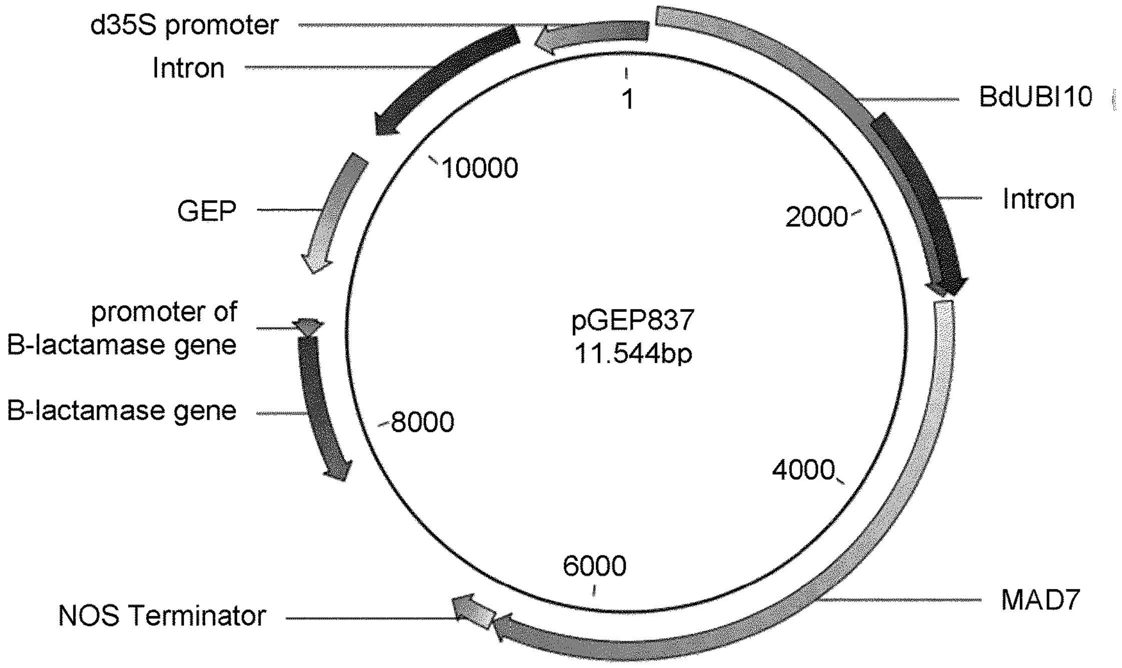
FIG. 4 shows a genome editing nuclease MAD7 expression construct pGEP837 map. A green fluorescent marker was used in this example (indicated as GEP). Any kind of fluorescent protein-encoding marker gene may be used instead depending on the plant target cell/tissue to be transformed and visualized. MAD7 defines the maize codon-optimized CDS of the *Eubacterium rectale* CRISPR/MAD7 gene (Inscripta). BdUBI10 defines the *Brachypodium* Ubiquitin 10 promoter. Tnos defines the nos terminator.
Figure 11:
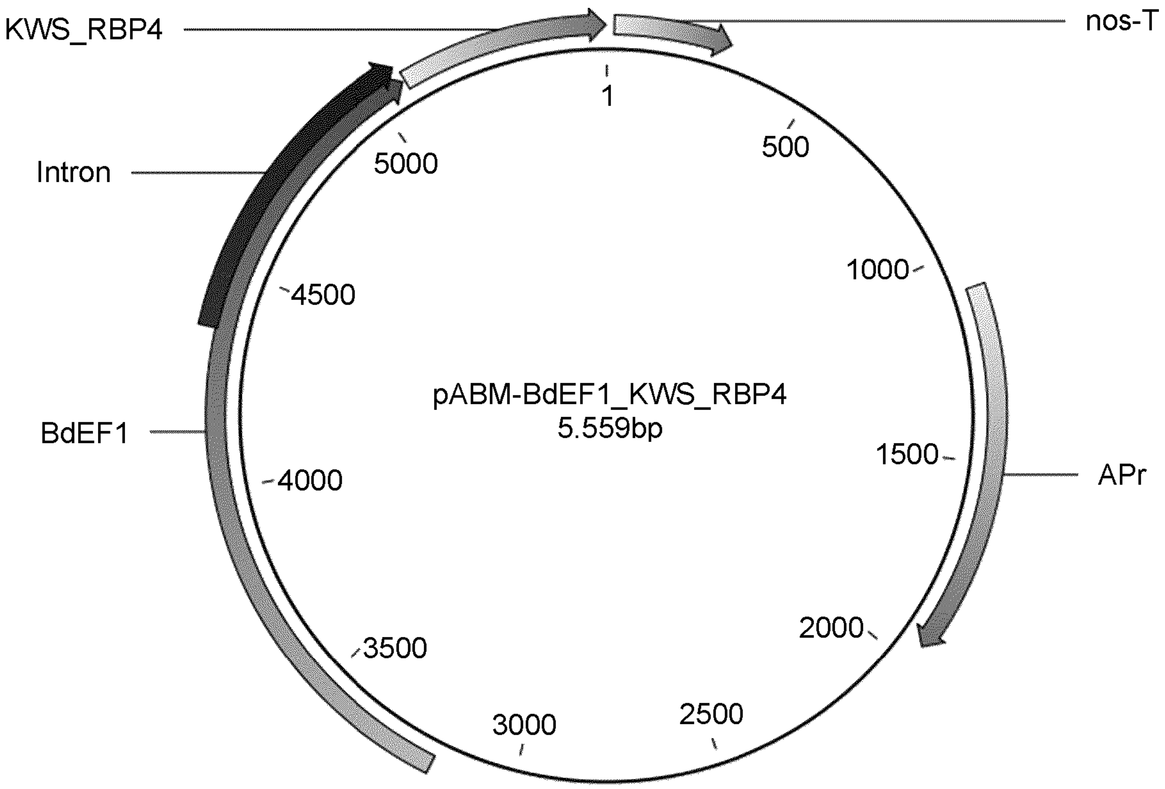
FIG. 11 shows the KWS_RBP4 expression construct pABM-BdEF1_RBP4 map. KWS_RBP4 is driven by the strong constitutive EF1 promoter from *Brachypodium* (pBdEF1).
Figure 12:
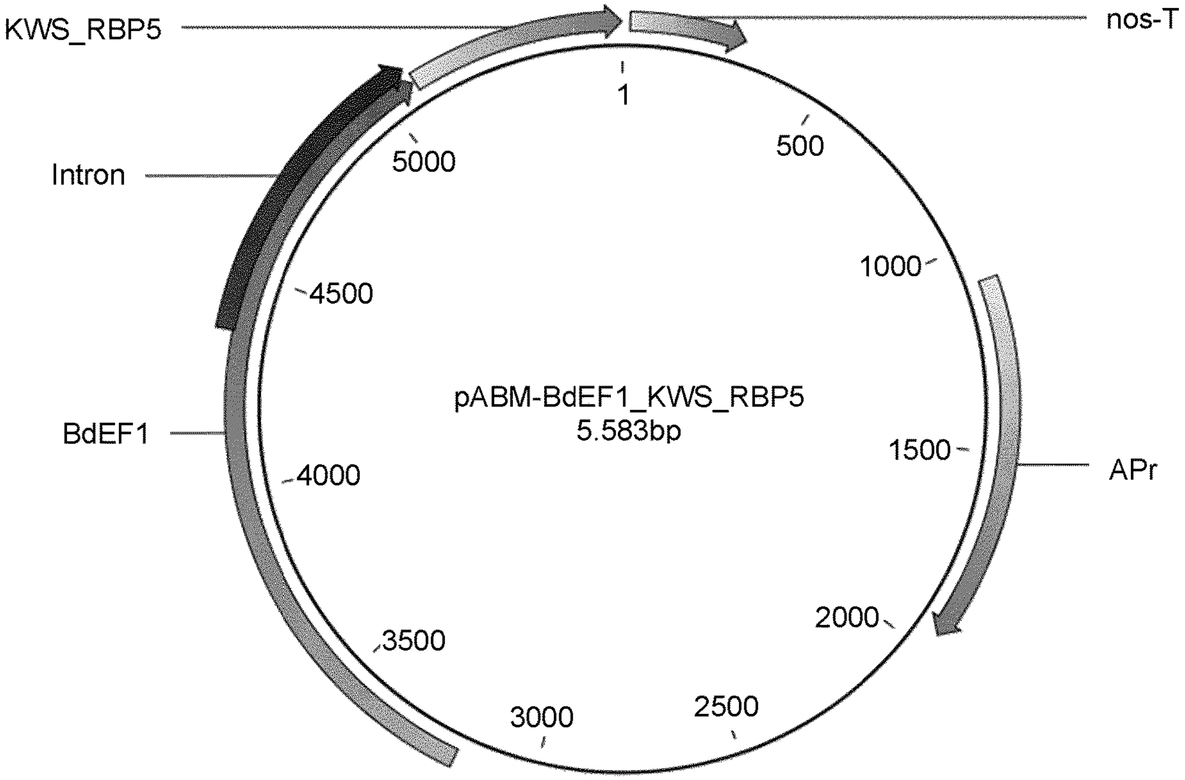
FIG. 12 shows the KWS_RBP5 expression construct pABM-BdEF1_RBP5 map. KWS_RBP5 is driven by the strong constitutive EF1 promoter from *Brachypodium* (pBdEF1).
Figure 18:
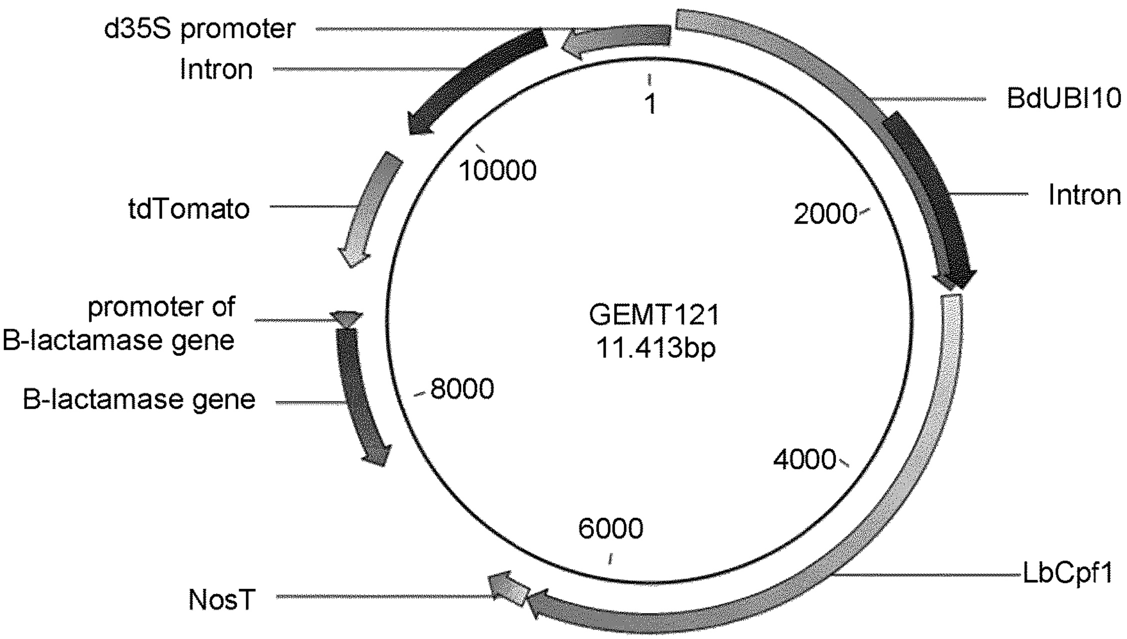
FIG. 18 shows a genome editing nuclease Cpf1 expression construct GEMT121 map. tdTomato defines the fluorescent report gene tDTomato driven by double 35S promoter and intron. LbCpf1 defines the maize codon-optimized CDS of *Lachnospiraceae bacterium* CRISPR/Cpf1 (LbCpf1) gene. BdUBI0 defines the *Brachypodium* Ubiquitin 10 promoter. Tnos defines the nos terminator.
Figure 19:
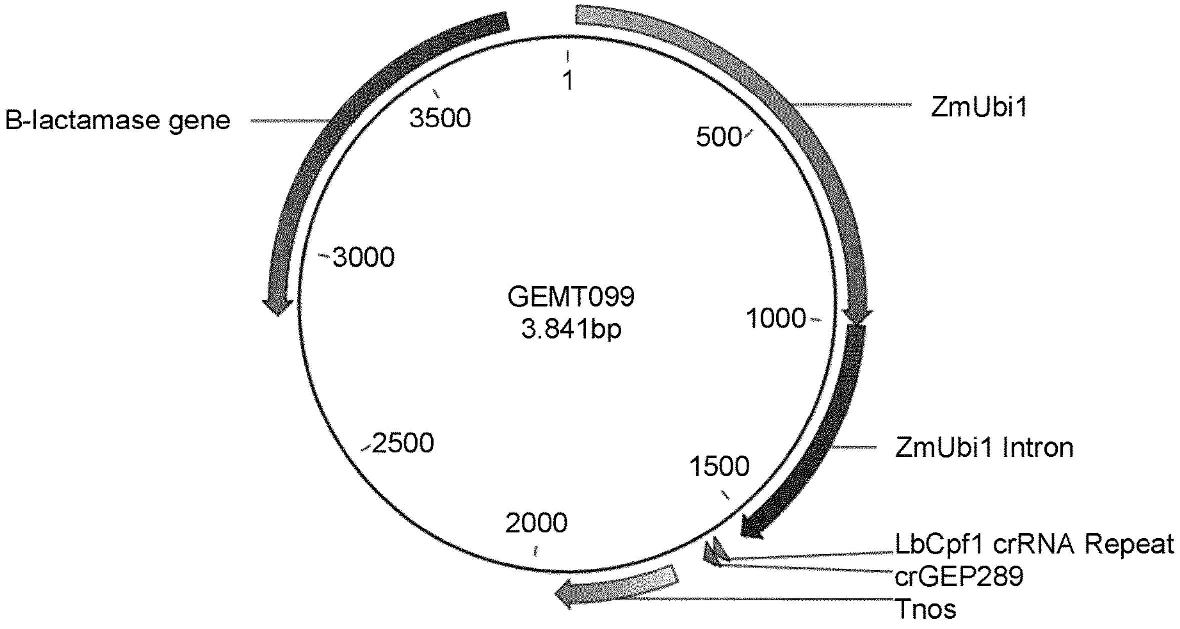
FIG. 19 shows a genome editing crRNA expression construct GEMT099 map. crGEP289 defines the crRNA, which target to wheat CPL3 (C-terminal domain phosphatase-like 3) gene. ZmUbi1 defines the promoter and intron from maize Ubiquitin 1 gene. Tnos defines the nos terminator.

| SEQ ID NO | Brief description |
|---|---|
| 1 | RBG1 CDS sequence |
| 2 | RBG2 CDS sequence |
| 3 | RBG3 CDS sequence |
| 4 | RBG4 CDS sequence |
| 5 | RBG5 CDS sequence |
| 6 | RBG6 CDS sequence |
| 7 | RBG7 CDS sequence |
| 8 | RBG8 CDS sequence |
| 9 | *Zea mays*, ZmPLT3-17207_CDS |
| 10 | *Zea mays*, ZmPLT5_CDS |
| 11 | *Zea mays*, ZmPLT7_CDS |
| 12 | Protein RBP1 |
| 13 | Protein RBP2 |
| 14 | Protein RBP3 |
| 15 | Protein RBP4 |
| 16 | Protein RBP5 |
| 17 | Protein RBP6 |
| 18 | Protein RBP7 |
| 19 | Protein RBP8 |
| 20 | Protein PLT3-17207-A188 |
| 21 | Protein ZmPLT5 |
| 22 | Protein ZmPLT7 |
| 23 | BdEF1_RBG1_expression_cassette |
| 24 | BdEF1_RBG2_expression_cassette |
| 25 | BdEF1_RBG3_expression_cassette |
| 26 | BdEF1_RBG4_expression_cassette |
| 27 | BdEF1_RBG5_expression_cassette |
| 28 | BdEF1_RBG6_expression_cassette |
| 29 | BdEF1_RBG7_expression_cassette |
| 30 | BdEF1_RBG8_expression_cassette |
| 31 | BdEF1_ZmPLT3_expression_cassette |
| 32 | BdEF1_ZmPLT5_expression_cassette |
| 33 | BdEF1_ZmPLT7_expression_cassette |
| 34 | pABM-BdEF1. This sequence represents the booster gene expression vector pABM-BdEF1. BdEF1 defines the strong constitutive EF1 promoter from *Brachypodium*. |
| 35 | pABM-BdEF1_RBG1 |
| 36 | pABM-BdEF1_RBG2 |
| 37 | pABM-BdEF1_RBG3 |
| 38 | pABM-BdEF1_RBG4 (FIG. 11) |
| 39 | pABM-BdEF1_RBG5 (FIG. 12) |
| 40 | pABM-BdEF1_RBG6 |
| 41 | pABM-BdEF1_RBG7 |
| 42 | pABM-BdEF1_RBG8 (FIG. 14) |
| 43 | pABM-BdEF1_ZmPLT3 |
| 44 | pABM-BdEF1_ZmPLT5 (FIG. 7) |
| 45 | pABM-BdEF1_ZmPLT7 |
| 46 | Plasmid pGEP837 MAD7 (FIG. 4) |
| 47 | Plasmid pGEP842 sgRNA m7GEP1 (FIG. 6) |
| 48 | Plasmid pGEP1054 Map and Plasmid tdTomato (FIG. 16) |
| 49 | Plasmid pGEP1067 sgRNA m7GEP22 (FIG. 15) |
| 50 | Construct GEMT121 encoding tdT as marker and LbCpf1 (FIG. 18) |
| 51 | Construct GEMT099 encoding sgRNA crGEP289 targeting wheat CPL3 (FIG. 19) |
| 52 | CDS of *Triticum aestivum* RKD4 |
| 53 | Protein TaRKD4 |

Definitions

Unless defined otherwise, technical and scientific terms used herein have the same meaning as commonly understood by one of ordinary skill in the art to which this invention belongs.

As used in the context of the present application, the term "about" means+/−10% of the recited value, preferably +/−5% of the recited value. For example, about 100 nucleotides (nt) shall be understood as a value between 90 and 110 nt, preferably between 95 and 105 nt.

A "base editor" as used herein refers to a protein or a fragment thereof having the same catalytic activity as the protein it is derived from, which protein or fragment thereof, alone or when provided as molecular complex, referred to as base editing complex herein, has the capacity to mediate a targeted base modification, i.e., the conversion of a base of interest resulting in a point mutation of interest which in turn can result in a targeted mutation, if the base conversion does not cause a silent mutation, but rather a conversion of an amino acid encoded by the codon comprising the position to be converted with the base editor. Usually, base editors are thus used as molecular complex. Base editors, including, for example, CBEs (base editors mediating C to T conversion) and ABEs (adenine base editors mediating A to G conversion), are powerful tools to introduce direct and programmable mutations without the need for double-stranded cleavage (Komor et al., Nature, 2016, 533(7603), 420-424; Gaudelli et al., Nature, 2017, 551, 464-471). In general, base editors are composed of at least one DNA targeting module and a catalytic domain that deaminates cytidine or adenine. All four transitions of DNA (A→T to G→C and C→G to T→A) are possible as long as the base editors can be guided to the target site. Originally developed for working in mammalian cell systems, both BEs and ABEs have been optimized and applied in plant cell systems. Efficient base editing has been shown in multiple plant species (Zong et al., *Nature Biotechnology*, vol. 25, no. 5, 2017, 438-440; Yan et al., *Molecular Plant*, vol. 11, 4, 2018, 631-634; Hua et al., *Molecular Plant*, vol. 11, 4, 2018, 627-630). Base editors have been used to introduce specific, directed substitutions in genomic sequences with known or predicted phenotypic effects in plants and animals. But they have not been used for directed mutagenesis targeting multiple sites within a genetic locus or several loci to identify novel or optimized traits.

A "CRISPR nuclease", as used herein, is a specific form of a site-directed nuclease and refers to any nucleic acid guided nuclease which has been identified in a naturally occurring CRISPR system, which has subsequently been isolated from its natural context, and which preferably has been modified or combined into a recombinant construct of interest to be suitable as tool for targeted genome engineering. Any CRISPR nuclease can be used and optionally reprogrammed or additionally mutated to be suitable for the various embodiments according to the present invention as long as the original wild-type CRISPR nuclease provides for DNA recognition, i.e., binding properties. CRISPR nucleases also comprise mutants or catalytically active fragments or fusions of a naturally occurring CRISPR effector sequences, or the respective sequences encoding the same. A CRISPR nuclease may in particular also refer to a CRISPR nickase or even a nuclease-dead variant of a CRISPR polypeptide having endonucleolytic function in its natural environment. A variety of different CRISPR nucleases/systems and variants thereof are meanwhile known to the skilled person and include, inter alia, CRISPR/Cas systems, including CRISPR/Cas9 systems (EP2771468), CRISPR/Cpf1 systems (EP3009511B1), CRISPR/C2C2 systems, CRISPR/CasX systems, CRISPR/CasY systems, CRISPR/Cmr systems, CRISPR/MAD systems, including, for example, CRISPR/MAD7 systems (WO2018236548A1) and CRISPR/MAD2 systems, CRISPR/CasZ systems and/or any combination, variant, or catalytically active fragment thereof. A nuclease may be a DNAse and/or an RNAse, in particular taking into consideration that certain CRISPR effector nucleases have RNA cleavage activity alone, or in addition to the DNA cleavage activity.

A "CRISPR system" is thus to be understood as a combination of a CRISPR nuclease or CRISPR effector, or a nickase or a nuclease-dead variant of said nuclease, or a functional active fragment or variant thereof together with the cognate guide RNA (or pegRNA or crRNA) guiding the relevant CRISPR nuclease.

As used herein, the terms "(regeneration) booster", "booster gene", "booster polypeptide", "boost polypeptide", "boost gene" and "boost factor", refer to a protein/peptide(s), or a (poly)nucleic acid fragment encoding the protein/polypeptide, causing improved plant regeneration of transformed or gene edited plant cells, which may be particularly suitable for improving genome engineering, i.e., the regeneration of a modified plant cell after genome engineering. Such protein/polypeptide may increase the capability or ability of a plant cell, preferably derived from somatic tissue, embryonic tissue, callus tissue or protoplast, to regenerate in an entire plant, preferably a fertile plant. Thereby, they may regulate somatic embryo formation (somatic embryogenesis) and/or they may increase the proliferation rate of plant cells. The regeneration of transformed or gene edited plant cells may include the process of somatic embryogenesis, which is an artificial process in which a plant or embryo is derived from a single somatic cell or group of somatic cells. Somatic embryos are formed from plant cells that are not normally involved in the development of embryos, i.e. plant tissue like buds, leaves, shoots etc. Applications of this process may include: clonal propagation of genetically uniform plant material; elimination of viruses; provision of source tissue for genetic transformation; generation of whole plants from single cells, such as protoplasts; development of synthetic seed technology. Cells derived from competent source tissue may be cultured to form a callus. Further, the term "regeneration booster" may refer to any kind of chemical having a proliferative and/or regenerative effect when applied to a plant cell, tissue, organ, or whole plant in comparison to a no-treated control. The particular artificially created regeneration booster polypeptides according to the present invention may have the dual function of increasing plant regeneration as well as increasing desired genome modification and gene editing outcomes.

As used herein, a "flanking region", is a region of the repair nucleic acid molecule having a nucleotide sequence which is homologous to the nucleotide sequence of the DNA region flanking (i.e. upstream or downstream) of the preselected site.

A "genome" as used herein is to be understood broadly and comprises any kind of genetic information (RNA/DNA) inside any compartment of a living cell. In the context of a "genome modification", the term thus also includes artificially introduced genetic material, which may be transcribed and/or translated, inside a living cell, for example, an episomal plasmid or vector, or an artificial DNA integrated into a naturally occurring genome.

The term of "genome engineering" as used herein refers to all strategies and techniques for the genetic modification of any genetic information (DNA and RNA) or genome of a plant cell, comprising genome transformation, genome editing, but also including less site-specific techniques, including TILLING and the like. As such, "genome editing" (GE) more specifically refers to a special technique of genome engineering, wherein a targeted, specific modification of any genetic information or genome of a plant cell. As such, the terms comprise gene editing of regions encoding a gene or protein, but also the editing of regions other than gene encoding regions of a genome. It further comprises the editing or engineering of the nuclear (if present) as well as other genetic information of a plant cell, i.e., of intronic sequences, non-coding RNAs, miRNAs, sequences of regulatory elements like promoter, terminator, transcription activator binding sites, cis or trans acting elements. Furthermore, "genome engineering" also comprises an epigenetic editing or engineering, i.e., the targeted modification of, e.g., DNA methylation or histone modification, such as histone acetylation, histone methylation, histone ubiquitination, histone phosphorylation, histone sumoylation, histone ribosylation or histone citrullination, possibly causing heritable changes in gene expression.

A "genome modification system" as used herein refers to any DNA, RNA and/or amino acid sequence introduced into the cell, on a suitable vector and/or coated on particles and/or directly introduced, wherein the "genome modification system" causes the modification of the genome of the cell in which it has been introduced. A "genome editing system" more specifically refers to any DNA, RNA and/or amino acid sequence introduced into the cell, on a suitable vector and/or coated on particles and/or directly introduced, wherein the "genome editing system" comprises at least one component being, encoding, or assisting a site-directed nuclease, nickase or inactivated variant thereof in modifying and/or repairing a genomic target site.

A "genomic target sequence" as used herein refers to any part of the nuclear and/or organellar genome of a plant cell, whether encoding a gene/protein or not, which is the target of a site-directed genome editing or gene editing experiment.

A "plant material" as used herein refers to any material which can be obtained from a plant during any developmental stage. The plant material can be obtained either in planta or from an in vitro culture of the plant or a plant tissue or organ thereof. The term thus comprises plant cells, tissues and organs as well as developed plant structures as well as sub-cellular components like nucleic acids, polypeptides and all chemical plant substances or metabolites which can be found within a plant cell or compartment and/or which can be produced by the plant, or which can be obtained from an extract of any plant cell, tissue or a plant in any developmental stage. The term also comprises a derivative of the plant material, e.g., a protoplast, derived from at least one plant cell comprised by the plant material. The term therefore also comprises meristematic cells or a meristematic tissue of a plant.

The term "operatively linked", "operably linked" or "functionally linked" specifically in the context of molecular constructs, for example plasmids or expression vectors, means that one element, for example, a regulatory element, or a first protein-encoding sequence, is linked in such a way with a further part so that the protein-encoding nucleotide sequence, i.e., is positioned in such a way relative to the protein-encoding nucleotide sequence on, for example, a nucleic acid molecule that an expression of the protein-encoding nucleotide sequence under the control of the regulatory element can take place in a living cell.

As used herein "a preselected site", "predetermined site" or "predefined site" indicates a particular nucleotide sequence in the genome (e.g. the nuclear genome, or the organellar genome, including the mitochondrial or chloroplast genome) at which location it is desired to insert, replace and/or delete one or more nucleotides. The predetermined site is thus located in a "genomic target sequence/site" of interest and can be modified in a site-directed manner using a site- or sequence-specific genome editing system.

The terms "plant", "plant organ", or "plant cell" as used herein refer to a plant organism, a plant organ, differentiated and undifferentiated plant tissues, plant cells, seeds, and derivatives and progeny thereof. Plant cells include without limitation, for example, cells from seeds, from mature and immature embryos, meristematic tissues, seedlings, callus tissues in different differentiation states, leaves, flowers, roots, shoots, male or female gametophytes, sporophytes, pollen, pollen tubes and microspores, protoplasts, macroalgae and microalgae. The different eukaryotic cells, for example, animal cells, fungal cells or plant cells, can have any degree of ploidity, i.e. they may either be haploid, diploid, tetraploid, hexaploid or polyploid.

The term "plant parts" as used herein includes, but is not limited to, isolated and/or pre-treated plant parts, including organs and cells, including protoplasts, callus, leaves, stems, roots, root tips, anthers, pistils, seeds, grains, pericarps, embryos, pollen, sporocytes, ovules, male or female gametes or gametophytes, cotyledon, hypocotyl, spike, floret, awn, lemma, shoot, tissue, petiole, cells, and meristematic cells.

A "Prime Editing system" as used herein refers to a system as disclosed in *Anzalone* et al. (2019). Search-and-replace genome editing without double-strand breaks (DSBs) or donor DNA. Nature, 1-1). Base editing as detailed above, does not cut the double-stranded DNA, but instead uses the CRISPR targeting machinery to shuttle an additional enzyme to a desired sequence, where it converts a single nucleotide into another. Many genetic traits in plants and certain susceptibility to diseases caused by plant pathogens are caused by a single nucleotide change, so base editing offers a powerful alternative for GE. But the method has intrinsic limitations, and is said to introduce off-target mutations which are generally not desired for high precision GE. In contrast, Prime Editing (PE) systems steer around the shortcomings of earlier CRISPR based GE techniques by heavily modifying the Cas9 protein and the guide RNA. The altered Cas9 only "nicks" a single strand of the double helix, instead of cutting both. The new guide RNA, called a pegRNA (prime editing extended guide RNA), contains an RNA template for a new DNA sequence, to be added to the genome at the target location. That requires a second protein, attached to Cas9 or a different CRISPR effector nuclease: a reverse transcriptase enzyme, which can make a new DNA strand from the RNA template and insert it at the nicked site. To this end, an additional level of specificity is introduced into the GE system in view of the fact that a further step of target specific nucleic acid::nucleic acid hybridization is required. This may significantly reduce off-target effects. Further, the PE system may significantly increase the targeting range of a respective GE system in view of the fact that BEs cannot cover all intended nucleotide transitions/mutations (C→A, C→G, G→C, G→T, A→C, A→T, T→A, and T→G) due to the very nature of the respective systems, and the transitions as supported by BEs may require DSBs in many cell types and organisms.

As used herein, a "regulatory sequence", or "regulatory element" refers to nucleotide sequences which are not part of the protein-encoding nucleotide sequence, but mediate the expression of the protein-encoding nucleotide sequence. Regulatory elements include, for example, promoters, cis-regulatory elements, enhancers, introns or terminators. Depending on the type of regulatory element it is located on the nucleic acid molecule before (i.e., 5' of) or after (i.e., 3' of) the protein-encoding nucleotide sequence. Regulatory elements are functional in a living plant cell.

An "RNA-guided nuclease" is a site-specific nuclease, which requires an RNA molecule, i.e. a guide RNA, to recognize and cleave a specific target site, e.g. in genomic DNA or in RNA as target. The RNA-guided nuclease forms a nuclease complex together with the guide RNA and then recognizes and cleaves the target site in a sequence-dependent matter. RNA-guided nucleases can therefore be programmed to target a specific site by the design of the guide RNA sequence. The RNA-guided nucleases may be selected from a CRISPR/Cas system nuclease, including CRISPR/Cpf1 systems, CRISPR/C2C2 systems, CRISPR/CasX systems, CRISPR/CasY systems, CRISPR/Cmr systems, CRISPR/Cms systems, CRISPR/MAD7 systems, CRISPR/MAD2 systems and/or any combination, variant, or catalytically active fragment thereof. Such nucleases may leave blunt or staggered ends. Further included are nickase or nuclease-dead variants of an RNA-guided nuclease, which may be used in combination with a fusion protein, or protein complex, to alter and modify the functionality of such a fusion protein, for example, in a base editor or Prime Editor.

The terms "SDN-1", "SDN-2", and "SDN-3" as used herein are abbreviations for the platform technique "site-directed nuclease" 1, 2, or 3, respectively, as caused by any site directed nuclease of interest, including, for example, Meganucleases, Zinc-Finger Nucleases (ZFNs), Transcription Activator Like Effector Nucleases (TALENs), and CRISPR nucleases. SDN-1 produces a double-stranded or single-stranded break in the genome of a plant without the addition of foreign DNA. A "site-directed nuclease" is thus able to recognize and cut, optionally assisted by further molecules, a specific sequence in a genome or an isolate genomic sequence of interest. For SDN-2 and SDN-3, an exogenous nucleotide template is provided to the cell during the gene editing. For SDN-2, however, no recombinant foreign DNA is inserted into the genome of a target cell, but the endogenous repair process copies, for example, a mutation as present in the template to induce a (point) mutation. In contrast, SDN-3 mechanism use the introduced template during repair of the DNA break so that genetic material is introduced into the genomic material.

A "site-specific nuclease" herein refers to a nuclease or an active fragment thereof, which is capable to specifically recognize and cleave DNA at a certain location. This location is herein also referred to as a "target sequence". Such nucleases typically produce a double-strand break (DSB), which is then repaired by non-homologous end-joining (NHEJ) or homologous recombination (HR). Site-specific nucleases include meganucleases, homing endonucleases, zinc finger nucleases, transcription activator-like nucleases and CRISPR nucleases, or variants including nickases or nuclease-dead variants thereof.

The terms "transformation", "transfection", "transformed", and "transfected" are used interchangeably herein for any kind of introduction of a material, including a nucleic acid (DNA/RNA), amino acid, chemical, metabolite, nanoparticle, microparticle and the like into at least one cell of interest by any kind of physical (e.g., bombardment), chemical or biological (e.g., *Agrobacterium*) way of introducing the relevant at least one material.

The term "transgenic" as used according to the present disclosure refers to a plant, plant cell, tissue, organ or material which comprises a gene or a genetic construct, comprising a "transgene" that has been transferred into the plant, the plant cell, tissue organ or material by natural means or by means of transformation techniques from another organism. The term "transgene" comprises a nucleic acid sequence, including DNA or RNA, or an amino acid sequence, or a combination or mixture thereof. Therefore, the term "transgene" is not restricted to a sequence commonly identified as "gene", i.e. a sequence encoding a protein. It can also refer, for example, to a non-protein encoding DNA or RNA sequence, or part of a sequence. Therefore, the term "transgenic" generally implies that the respective nucleic acid or amino acid sequence is not naturally present in the respective target cell, including a plant, plant cell, tissue, organ or material. The terms "transgene" or "transgenic" as used herein thus refer to a nucleic acid sequence or an amino acid sequence that is taken from the genome of one organism, or produced synthetically, and which is then introduced into another organism, in a transient or a stable way, by artificial techniques of molecular biology, genetics and the like.

As used herein, the term "transient" implies that the tools, including all kinds of nucleic acid (RNA and/or DNA) and polypeptide-based molecules optionally including chemical carrier molecules, are only temporarily introduced and/or expressed and afterwards degraded by the cell, whereas "stable" implies that at least one of the tools is integrated into the nuclear and/or organellar genome of the cell to be modified. "Transient expression" refers to the phenomenon where the transferred protein/polypeptide and/or nucleic acid fragment encoding the protein/polypeptide is expressed and/or active transiently in the cells, and turned off and/or degraded shortly with the cell growth. Transient expression thus also implies a stably integrated construct, for example, under the control of an inducible promoter as regulatory element, to regulate expression in a fine-tuned manner by switching expression on or off.

As used herein, "upstream" indicates a location on a nucleic acid molecule which is nearer to the 5' end of said nucleic acid molecule. Likewise, the term "downstream" refers to a location on a nucleic acid molecule which is nearer to the 3' end of said nucleic acid molecule. For avoidance of doubt, nucleic acid molecules and their sequences are typically represented in their 5' to 3' direction (left to right).

The terms "vector", or "plasmid (vector)" refer to a construct comprising, inter alia, plasmids or (plasmid) vectors, cosmids, artificial yeast- or bacterial artificial chromosomes (YACs and BACs), phagemides, bacterial phage based vectors, *Agrobacterium* compatible vectors, an expression cassette, isolated single-stranded or double-stranded nucleic acid sequences, comprising sequences in linear or circular form, or amino acid sequences, viral vectors, viral replicons, including modified viruses, and a combination or a mixture thereof, for introduction or transformation, transfection or transduction into any eukaryotic cell, including a plant, plant cell, tissue, organ or material according to the present disclosure. A "nucleic acid vector, for instance, is a DNA or RNA molecule, which is used to deliver foreign genetic material to a cell, where it can be transcribed and optionally translated. Preferably, the vector is a plasmid comprising multiple cloning sites. The vector may further comprise a "unique cloning site" a cloning site that occurs only once in the vector and allows insertion of DNA sequences, e.g. a nucleic acid cassette or components thereof, by use of specific restriction enzymes. A "flexible insertion site" may be a multiple cloning site, which allows insertion of the components of the nucleic acid cassette according to the invention in an arrangement, which facilitates simultaneous transcription of the components and allows activation of the RNA activation unit.

Whenever the present disclosure relates to the percentage of the homology or identity of nucleic acid or amino acid sequences to each other over the entire length of the sequences to be compared to each other, wherein these identity or homology values define those as obtained by using the EMBOSS Water Pairwise Sequence Alignments (nucleotide) programme nucleic acids or the EMBOSS Water Pairwise Sequence Alignments (protein) programme for amino acid sequences. Those tools provided by the European Molecular Biology Laboratory (EMBL) European Bioinformatics Institute (EBI) for local sequence alignments use a modified Smith-Waterman algorithm (see ebi.ac.uk/Tools/psa/ and Smith, T. F. & Waterman, M. S. "Identification of common molecular subsequences" *Journal of Molecular Biology,* 1981 147 (1):195-197). When conducting an alignment, the default parameters defined by the EMBL-EBI are used. Those parameters are (i) for amino acid sequences: Matrix=BLOSUM62, gap open penalty=10 and gap extend penalty=0.5 or (ii) for nucleic acid sequences: Matrix=DNAfull, gap open penalty=10 and gap extend penalty=0.5.

DETAILED DESCRIPTION

The present invention provides generally applicable genome and gene editing techniques relying on immature inflorescence meristem (IIM) cells as target material to be transformed/transfected providing better transformation and/or editing efficiencies in variety of relevant crop plants.

For all kinds of efficient plant transformations or transfections, the determination of the correct age and thus physiological status of the cells or material to be transformed is critical. Further, the decision on the target material to be transformed of interest may not only influence the susceptibility of the material for uptake of tools to be inserted, it may also significantly influence the outcome of a transformation. Efficiency of transformation or transfection, capability of regeneration after transformation and expression of molecular tools introduced, but, when it comes to gene editing, also factors like the epigenetic state of a material transformed may play an important role due to accessibility of a genome to be modified. Any off-target activity of the gene editing tools has to be avoided. Additionally, it is a very important factor that the desired modifications intended to be introduced during gene editing in a site-specific manner, but not necessarily the molecular tools transiently inserted, can be inherited to the offspring of a modified cell. For plant gene editing, this additionally implies that the modification is stable inherited in the relevant reproductive cells so that the resulting cells or organs, e.g., gametes, pollen, embryos etc., can be easily used for breeding new valuable plants. In view of these specific characteristics gene editing in usually rather complex plant genomes is still very often associated with severe problems and there is no convenient and straightforward way to transfer protocols gained in one system with a given gene editing machinery to another target plant and another genomic target region of interest to be modified.

Figure 1A:
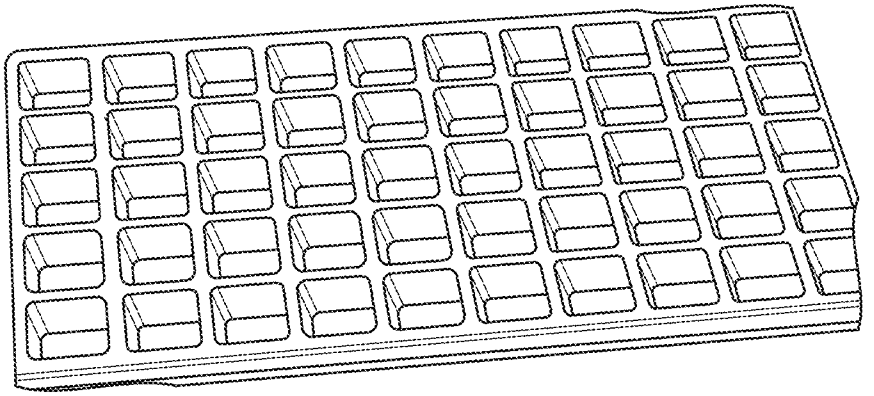
FIG. 1 shows a deep 50-well plus tray (A) and a 1020 Greenhouse (no holes) tray (B) used for maize seedling cultivation.
Figure 1B:
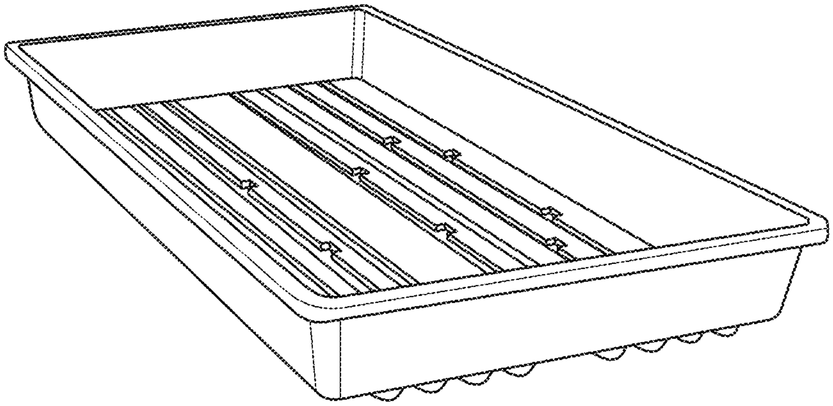
Figure 2:
FIG. 2 shows 28-day-old maize seedlings at late V6 stage growing at 50-well tray in greenhouse are ready for immature tassel harvesting.

An inflorescence meristem is the modified shoot meristem that contains multipotent stem cells and is able to produce floral primordia, and eventually develops into an inflorescence, i.e., a cluster of flowers arranged on a main stem. The initiation of inflorescence meristem transition from shoot meristem is quite early in some cereal crops. For example, it takes about four weeks from seed planting to the IIM harvesting in maize (FIG. 2). The maize seeds can be planted and growing in a multiple-well tray (e.g. 50-well tray, FIG. 1) in any growth areas with simple lighting and temperature controls. Without the need for pollination and fertilization—processes which are very sensitive to environments and heavily depend on pollen and plant qualities—the IIM preparation can be performed greenhouse and growth season independent. Compared to using immature zygotic embryo, using IIM as the alternative donor explant further eliminates the problem of pollen contamination issues, and saves space, time, labour, and other resources for donor material preparation.

In one aspect, there is provided a method for plant genome modification, preferably for the targeted modification of at least one genomic target sequence, by obtaining a modification of at least one plant immature inflorescence meristem (JIM) cell, wherein the method comprises the following steps: (a) providing at least one immature inflorescence meristem cell; (b) introducing into the at least one immature inflorescence meristem cell: (i) at least one genome modification system, preferably a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same; (ii) optionally: at least one regeneration booster, or a sequence encoding the same, or a regeneration booster chemical, wherein steps (i) and (ii) take place simultaneously, or subsequently, for promoting plant cell proliferation and/or to assist in a targeted modification of at least one genomic target sequence; (iii)

and, optionally at least one repair template, or a sequence encoding the same; and (c) cultivating the at least one immature inflorescence meristem cell under conditions allowing the expression and/or assembly of the at least one genome modification system, preferably the at least one genome editing system and optionally the at least one regeneration booster, and optionally of the at least one guide molecule and/or optionally of the at least one repair template; and (d) obtaining at least one modified immature inflorescence meristem cell, optionally by specifically screening for at least modified cell; or (e) obtaining at least one plant tissue, organ, plant or seed regenerated from the at least one modified cell; and (f) optionally: screening for at least one plant tissue, organ, plant or seed regenerated from the at least one modified cell in the T0 and/or T1 generation carrying a desired targeted modification.

To provide immature inflorescence meristem cells particularly suitable and accessible for effective particle bombardment and thus allowing for highly efficient genome editing, the present inventors tested immature inflorescence meristem cells from various cultivars of major crop plants. It was found that an explant comprising at least one immature inflorescence meristem cell could be favourably provided as cross-sectioned probe to better serve as an explant for biolistic transformation and to enhance subsequent regeneration to increase utilization efficiency. This finding is particularly important for some elite lines, including maize elite lines, where the initiation and development of axillary branches are significantly behind that of the center spike, so that the immature tassels therefore consist almost solely of center spike when harvested. The use of cross-section discs of immature center spike comprising at least one immature inflorescence meristem cell according to the present disclosure is thus an efficient solution for such genotypes in general to optimize regeneration and/or to achieve highly efficient genome editing in multiple locations simultaneously.

In certain embodiments, the at least one immature inflorescence meristem cell provided in step (a) in a method of the above first aspect thus may originate from a cross-section of a spike, or a structure being comparable to a spike with respect to developmental and overall morphological characteristics, wherein a spike comprises at least one immature inflorescence meristem cell, particularly wherein the at least one immature inflorescence meristem cell originates from a cross-section of a center spike of a crop plant of interest, for example, from a maize, wheat or barley plant. As it is known in the field of plant breeding and development, the spike is a structure that is usually formed from the inflorescence meristem through cell divisions to produce a main stem (rachis) and a spikelet meristem at each rachis node. Even though there are some morphological differences between spike and spikelet structure and development in different crop plants, the skilled person can determine the relevant developmental stages for a given crop plant of interest to obtain a cross-section of a spike, particularly of a center spike, as defined herein below.

In one embodiment, the introduction may preferably be at least one plant immature inflorescence meristem (IIM) cell may be mediated by biolistic bombardment.

In one aspect, there is provided a method of staging, i.e., defining a given developmental stage of a plant and the developing plant cells, including IIM cells, in a variety of crop plants.

Preferably, all exogenously provided elements or tools of a genome or gene editing system as well as optionally provided regeneration booster, or sequences encoding the same, and optionally provided repair template sequences are provided either simultaneously or subsequently, wherein the terms simultaneously and subsequently refers to the temporal order of introducing the relevant at least one tool, which may be introduced to be expressed transiently or in a stable manner, with the proviso that both simultaneous and subsequent introduction guarantee that one and the same IIM cell will comprise the relevant tools in an active and/or expressible manner. Ultimately, all genome modification or gene editing system elements are thus physically present in one IIM cell.

Figure 3:
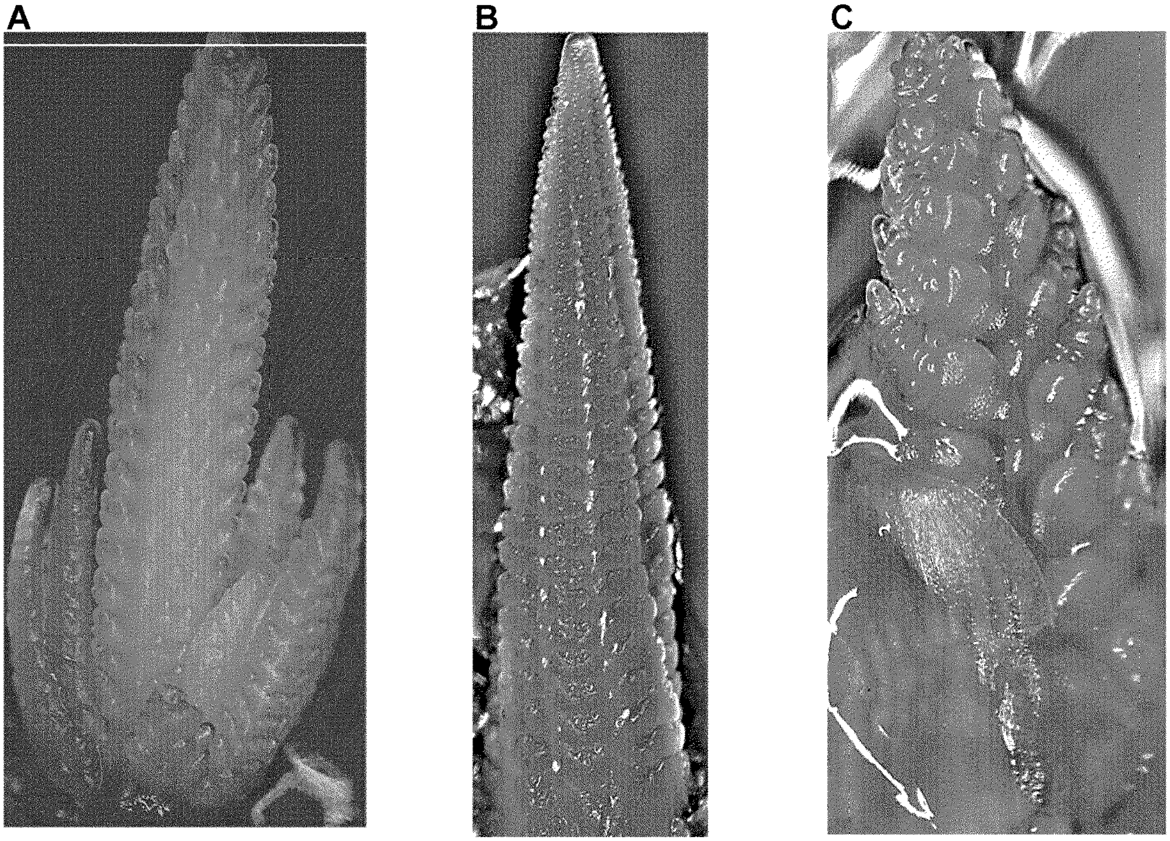
FIG. 3 shows freshly isolated immature inflorescences from maize. (A) An immature tassel from a 28-day-old maize A188 seedling; (B) an immature ear from a 36-day-old maize 4V-40171 seedling; (C) an immature inflorescence at AM (anther primordia) stage isolated from a (KWS Bono mature rye plant. GP indicates a glume primordium, and LP for a lemma primordium. An asterisk points to a stamen primordium.

The immature inflorescence meristem (IIM) from Poaceae plants, including relevant crop plants, e.g., maize, wheat, rye, oat, barley, sorghum, rice, etc., is open at the stages when the floral bract primordia are underdeveloped (see FIG. 3). Therefore, the IIM cells are apt for genetic modification. The IIM cells are mitotically active and ready for regeneration without a need for cell identity reprogramming, and thus the IIM cells are highly regenerative and their regenerations are likely genotype-independent. The IIM cells are ideal recipients for transformation and regeneration. Moreover, the IIM cells are in reproduction phase, and developmentally close to meiosis, and thus the IIM cells may be in a HDR (Homology-Directed Repair)-friendly cell environment and suitable for HDR based genome editing. HDR may be preferable for different GE settings in view of the fact that targeted repair in the desired way can be achieved, in contrast to error-prone cellular repair processes.

Figure 21:
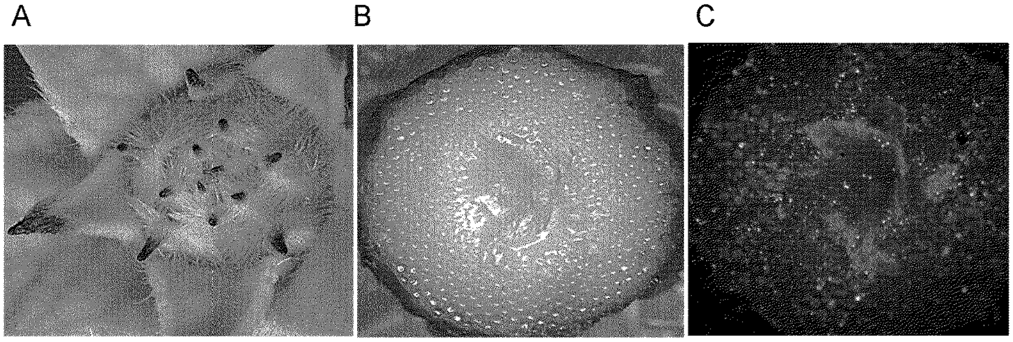
FIG. 21 shows images of an immature inflorescence from a 34 day-old sunflower (*Helianthus annuus*) cultivar velvet Queen plant. (A): the immature inflorescence head with many-pointed star-like appearance at development R1 stage; (B) the fresh isolated immature inflorescence meristem head ready for bombardment; (C): tDTomato fluorescent image of the immature inflorescence head 14 hours after bombarded with plasmid GEMT121 (FIG. 18).

Also for dicot plants, it could be demonstrated that staging of IIM cells and an efficient transformation of this specific cell type is possible according to the methods disclosed herein as, for example, shown in FIG. 21.

Based on the central findings of specifically choosing IIM cells for transformation, and the examples provided herein below giving guidance for the correct developmental staging to identify IIM tissues and cells in the developing inflorescence, the method of the present invention is applicable in any plant species, including monocot or dicot, of interest, preferably the methods may be performed in a plant being able to produce complex inflorescences (e.g., spike, spadix, capitulum or head) with sessile flowers (e.g., maize, rice, wheat, barley, sorghum, rye, sunflower, various kinds of berries).

In a further embodiment according to the various aspects of the present invention, at least one regeneration booster, or a sequence encoding the same, or a regeneration booster chemical is provided during genome or gene editing for promoting plant cell proliferation and/or to assist in a targeted modification of at least one genomic target sequence.

Certain regeneration booster sequences, usually representing transcription factors active during various stages of plant development and also known as morphogenic regulators in plants, are known for long, including the Wuschel (WUS) and babyboom (BBM) class of boosters (Mayer, K. F. et al. Role of WUSCHEL in regulating stem cell fate in the *Arabidopsis* shoot meristem. *Cell* 95, 805-815 (1998); Yadav, R. K. et al. WUSCHEL protein movement mediates stem cell homeostasis in the *Arabidopsis* shoot apex. *Genes Dev* 25, 2025-2030 (2011); Laux, T., Mayer, K. F., Berger, J. & Jürgens, G. The WUSCHEL gene is required for shoot and floral meristem integrity in *Arabidopsis. Development* 122, 87-96 (1996); Leibfried, A. et al. WUSCHEL controls meristem function by direct regulation of cytokinin-inducible response regulators. *Nature* 438, 1172-1175 (2005); for BBM: Hofmann, A Breakthrough in Monocot Transformation Methods, The Plant Cell, Vol. 28: 1989, September 2016). Others, including the RKD (including TaRKD4 disclosed herein as SEQ ID NOs: 52 and 53, or a variant, or a codon-optimized version thereof) and LEC family of transcription factors have been steadily emerging and are meanwhile known to the skilled person (Hofmann, A Breakthrough in Monocot Transformation Methods The Plant Cell, Vol. 28: 1989, September 2016; New Insights into Somatic Embryogenesis: LEAFY COTYLEDON1, BABY BOOM1 and WUSCHEL-RELATED HOMEOBOX4 Are Epigenetically Regulated in *Coffea canephora*, PLos one August 2013, vol. 8(8), e72160; LEAFY COTYLEDON1-CASEIN KINASE I-TCP15-PHYTOCHROME INTERACTING FACTOR4 Network Regulates Somatic Embryogenesis by Regulating Auxin Homeostasis Plant Physiology_, December 2015, Vol. 169, pp. 2805-2821; A. Cagliari et al. New insights on the evolution of Leafy cotyledon1 (LEC1) type genes in vascular plants Genomics 103 (2014) 380-387, U.S. Pat. No. 6,825,397B1; U.S. Pat. No. 7,960,612B2, WO2016146552A1).

The Growth-Regulating Factor (GRF) family of transcription factors, which is specific to plants, is also known to the skilled person. At least nine GRF polypeptides have been identified in *Arabidopsis thaliana* (Kim et al. (2003) Plant J 36: 94-104), and at least twelve in *Oryza sativa* (Choi et al. (2004) Plant Cell Physiol 45(7): 897-904). The GRF polypeptides are characterized by the presence in their N-terminal half of at least two highly conserved domains, named after the most conserved amino acids within each domain: (i) a QLQ domain (InterPro accession IPR014978, PFAM accession PF08880), where the most conserved amino acids of the domain are Gln-Leu-Gln; and (ii) a WRC domain (InterPro accession IPR014977, PFAM accession PF08879), where the most conserved amino acids of the domain are Trp-Arg-Cys. The WRC domain further contains two distinctive structural features, namely, the WRC domain is enriched in basic amino acids Lys and Arg, and further comprises three Cys and one His residues in a conserved spacing (CX9CX10CX2H) (SEQ ID NO: 54), designated as the Effector of transcription (ET) domain (Ellerstrom et al. (2005) Plant Molec Biol 59: 663-681). The conserved spacing of cysteine and histidine residues in the ET domain is reminiscent of zinc finger (zinc-binding) proteins. In addition, a nuclear localisation signal (NLS) is usually comprised in the GRF polypeptide sequences.

Another class of potential regeneration boosters, yet not studied in detail for their function in artificial genome/gene editing, is the class of PLETHORS (PLT) transcription factors (Aida, M., et al. (2004). The PLETHORA genes mediate patterning of the *Arabidopsis* root stem cell niche. Cell 119: 109-120; Mähönen, A. P., et al. (2014). PLETHORA gradient formation mechanism separates auxin responses. Nature 515: 125-129). Organ formation in animals and plants relies on precise control of cell state transitions to turn stem cell daughters into fully differentiated cells. In plants, cells cannot rearrange due to shared cell walls. Thus, differentiation progression and the accompanying cell expansion must be tightly coordinated across tissues. PLETHORA (PLT) transcription factor gradients are unique in their ability to guide the progression of cell differentiation at different positions in the growing *Arabidopsis thaliana* root, which contrasts with well-described transcription factor gradients in animals specifying distinct cell fates within an essentially static context. To understand the output of the PLT gradient, we studied the gene set transcriptionally controlled by PLTs. Our work reveals how the PLT gradient can regulate cell state by region-specific induction of cell proliferation genes and repression of differentiation. Moreover, PLT targets include major patterning genes and autoregulatory feedback components, enforcing their role as master regulators of organ development (Santuari et al., 2016, DOI: doi.org/10.1105/tpc.16.00656). PLT, also called AIL (AINTEGUMENT-LIKE) genes, are members of the AP2 family of transcriptional regulators. Members of the AP2 family of transcription factors play important roles in cell proliferation and embryogenesis in plants (El Ouakfaoui, S. et al., (2010) Control of somatic embryogenesis and embryo development by AP2 transcription factors. PLANT MOLECULAR BIOLOGY 74(4-5):313-326.). PLT genes are expressed mainly in developing tissues of shoots and roots, and are required for stem cell homeostasis, cell division and regeneration, and for patterning of organ primordia. PLT family comprises an AP2 subclade of six members. Four PLT members, PLT1/AIL3 PLT2/, AIL4, PLT3/A/L6, and BBM/PLT4/AIL2, are expressed partly overlap in root apical meristem (RAM) and required for the expression of QC (quiescent center) markers at the correct position within the stem cell niche. These genes function redundantly to maintain cell division and prevent cell differentiation in root apical meristem. Three PLT genes, PLT3/AIL6, PLT5/AIL5, and PLT7/AIL7, are expressed in shoot apical meristem (SAM), where they function redundantly in the positioning and outgrowth of lateral organs. PLT3, PLT5, and PLT7, regulate de novo shoot regeneration in *Arabidopsis* by controlling two distinct developmental events. PLT3, PLT5, and PLT7 required to maintain high levels of PIN1 expression at the periphery of the meristem and modulate local auxin production in the central region of the SAM which underlies phyllotactic transitions. Cumulative loss of function of these three genes causes the intermediate cell mass, callus, to be incompetent to form shoot progenitors, whereas induction of PLT5 or PLT7 can render shoot regeneration in a hormone-independent manner. PLT3, PLT5, PLT7 regulate and require the shoot-promoting factor CUP-SHAPED COTYLEDON2 (CUC2) to complete the shoot-formation program. PLT3, PLT5, and PLT7, are also expressed in lateral root founder cells, where they redundantly activate the expression of PLT1 and PLT2, and consequently regulate lateral root formation.

Regeneration boosters derived from naturally occurring transcription factors, as, for example, BBM or WUS, and variants thereof, may have the significant disadvantage that uncontrolled activity in a plant cell over a certain period of time will have deleterious effects on a plant cell. Therefore, the present inventors conducted a series of in silico work to create fully artificial regeneration booster proteins after a series of multiple sequence alignment, domain shuffling, truncations and codon optimization for various target plants. By focusing on core consensus motifs, it was an object to identify new variants of regeneration boosters not occurring in nature that are particularly suitable for us in methods for genome modifications and gene editing. Various gymnosperm sequences occurring in different species presently not considered as having a regeneration booster activity of described booster genes and proteins were particularly considered in the design process of the new booster sequences.

Based on this work, it was now found that specific regeneration boosters (cf. SEQ ID NOs: 1 to 8, 12 to 19), as well as certain modified regeneration boosters naturally acting as transcription factors (e.g., SEQ ID NOs: 9 to 11, 20 to 22) artificially created perform particularly well in combination with the methods disclosed herein, as they promote regeneration and additionally have the capacity to improve genome modification or gene editing efficiencies. Further, the artificially created and then stepwise selected and tested regeneration boosters do not show pleiotropic effects and are particularly suitable to be used during any kind of genome modification such as gene editing.

In one aspect, there is provided an isolated nucleic acid sequence encoding a regeneration booster polypeptide, wherein the nucleic acid sequence comprises a sequence selected from any one of SEQ ID NOs: 1 to 8, or a nucleic acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to the respective sequence of SEQ ID NOs: 1 to 8 with the proviso that the sequence encodes a regeneration booster with the same function as the respective reference sequence, or a nucleic acid sequence encoding a polypeptide comprises a sequence selected from any one of SEQ ID NOs: 12 to 19, or a sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence.

In a further aspect, there is provided a recombinant gene comprising an isolated nucleic acid sequence encoding a regeneration booster polypeptide, wherein the nucleic acid sequence comprises a sequence selected from any one of SEQ ID NOs: 1 to 8, or a nucleic acid sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to the respective sequence of SEQ ID NOs: 1 to 8 with the proviso that the sequence encodes a regeneration booster with the same function as the respective reference sequence, or a nucleic acid sequence encoding a polypeptide comprises a sequence selected from any one of SEQ ID NOs: 12 to 19, or a sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence.

In one embodiment, the recombinant gene may comprise at least one regulatory element as detailed below. In view of the fact that the regeneration booster genes disclosed herein are fully artificial, there is no classical "natural" regulatory element, e.g., a promoter, to be used. Therefore, the choice of at least one suitable regulatory element will be guided by the question of the host cell of interest and/or spatio-temporal expression patterns of interest, so that the optimum regulatory elements can be chosen to achieve a specific expression of the at least one regeneration booster gene of interest.

In one embodiment, wherein more than one regeneration booster gene are used, different promoters may be chosen, for example, the promoters having different activities so that the at least two genes can be expressed in a defined and controllable manner to have a stronger expression of a first regeneration booster protein/polypeptide (RBP) and a weaker expression of a second RBP, where a differential expression pattern may be desired.

In one aspect, there is provided isolated regeneration booster polypeptide wherein the polypeptide comprises a sequence selected from any one of SEQ ID NOs: 12 to 19, or a sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence.

In yet another aspect, there is provided an expression cassette or an expression construct comprising a sequence encoding a regeneration booster polypeptide comprising a nucleic acid sequence selected from any one of SEQ ID NOs: 12 to 19, or a nucleic acid sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence, or a nucleic acid sequence encoding a polypeptide comprises a sequence selected from any one of SEQ ID NOs: 12 to 19, or a sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence. In certain embodiments, the expression cassette or the expression construct may be selected from any one of SEQ ID NOs: 23 to 30, or 35 to 42, or a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to the respective sequence'.

In still another aspect, there is provided a plant cell comprising a recombinant gene comprising an nucleic acid sequence encoding a regeneration booster polypeptide, wherein the nucleic acid sequence comprises a sequence selected from any one of SEQ ID NOs: 1 to 8, or a sequence having at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identity to the respective sequence of SEQ ID NOs: 1 to 8 with the proviso that the sequence encodes a regeneration booster with the same function as the respective reference sequence, or comprising an expression cassette or an expression construct comprising a sequence encoding a regeneration booster polypeptide comprising a sequence selected from any one of SEQ ID NOs: 12 to 19, or a sequence having at least 90%, 91%, 92%, 93%, 94%, 95%, 96%, 97%, 98%, 99% identity to the respective sequence of SEQ ID NOs: 12 to 19 with the proviso that the sequence has regeneration booster function as the respective reference sequence.

In one aspect, there is provided a plant tissue, organ, whole plant, or a part thereof or a seed of a monocot or dicot plant of interest comprising the plant cell comprising the recombinant gene or comprising the expression cassette or the expression construct as defined above.

Based on the effects of the new regeneration boosters, or the new combination of regeneration boosters, as disclosed herein, it is possible to transform or transfect even recalcitrant plants/plant genotypes, or cells, tissues or organs comprised by, or obtained from a recalcitrant plant/plant genotype. i.e., those plants/plant genotypes usually known to be very hard to transform or transfect with exogenous material and/or which are known to have a weak regeneration and/or developmental activity. As detailed in Example 8 below, the various methods as disclosed herein are particularly suitable for modifying, i.e., transforming or transfecting, recalcitrant plants/plant genotypes or plant cells.

In one embodiment, the regeneration booster comprises at least one RBP, or an regeneration booster gene (RBG) sequence encoding the RBP, wherein the at least one of an RBP sequence is individually selected from any one of SEQ ID NOs: 13, or 15 to 19, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the RBP is encoded by at least one RBG sequence, wherein the at least one of an RBP sequence is individually selected from any one of SEQ ID NOs: 2, or 4 to 8, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a cognate codon-optimized sequence.

Additionally, the regeneration booster sequences, or the sequences encoding the same, according to SEQ ID NOs: 1 to 8 and 12 to 19 were studied in detail to identify suitable combinations of regeneration boosters to be provided during genome or gene editing to achieve even synergistic activities in promoting regeneration, e.g., during any kind of plant transformation, and/or to optimize gene editing frequencies.

In one embodiment, the regeneration booster comprises at least one RBP and at least one PLT encoding sequence, wherein the RBP and the PLT regeneration booster sequence is individually selected from any one of SEQ ID NOs: 12 to 22, or a sequence having at least 80%, 81%, 82%, 83%, 84%, 85%, 86%, 87%, 88%, 89%, 90%, 91%, 92%, 93%, 94%, 95%, 96%, 97%, 98% or 99% sequence identity thereto, or a catalytically active fragment thereof, or wherein the at least one regeneration booster sequence is encoded by a sequence individually selected from any one of SEQ ID NOs: 1 to 11, or a sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity thereto, provided that the sequence encodes the respective regeneration booster according to SEQ ID NOs: 12 to 22 or a catalytically active fragment thereof.

In another embodiment of the various methods disclosed herein, the at least one further regeneration booster is introduced, wherein the further regeneration booster, or the sequence encoding the same is selected from BBM, WUS, WOX, (Ta)RKD4, growth-regulating factors (GRFs), LEC, or a variant thereof.

In yet another embodiment of the various methods disclosed herein, the regeneration booster comprises at least one first RBG or PLT sequence, or the sequence encoding the same, preferably at least one RBG sequence, or the sequence encoding the same, and wherein the regeneration booster further comprises: (i) at least one further RBG and/or PLT sequence, or the sequence encoding the same, or a variant thereof, and/or (ii) at least one BBM sequence, or the sequence encoding the same, or a variant thereof, and/or (iii) at least one WOX sequence, including WUS1, WUS2, or WOX5, or the sequence encoding the same, or a variant thereof, and/or (iv) at least one RKD4 sequence, including wheat RKD4, or the sequence encoding the same, or a variant thereof, and/or (v) at least one GFR sequence, including GRF1 or GRF5, or the sequence encoding the same, or a variant thereof, and/or (vi) at least one LEC sequence, including LEC1 and LEC2, or the sequence encoding the same, or a variant thereof as at least one second regeneration booster, or sequence encoding the same, different to the first regeneration booster.

In preferred embodiments according to the methods disclosed herein, at least the first, or the exclusive, regeneration booster used, or the sequence encoding the same, is a RBP, or the respective RBG sequence, according to SEQ ID NOs: 1 to 8 and 12 to 19, respectively, or a sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity thereto.

In embodiments, where a single regeneration booster is used, the regeneration booster may be selected from SEQ ID NOs: 13, and 15 to 19, or the sequences encoding the same, or from SEQ ID NOs: 20 to 22, or the sequences encoding the same, or a sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity thereto.

In embodiments, where a combination of two regeneration boosters is used, these combinations may be selected from (i) a specific combination of RBP8, RBP7, RBP5, RBP2, RBP6, RBP4, or RBP3 as first booster with either one of PLT3, PLT5, or PLT7 (for reference regarding abbreviations and corresponding SEQ ID NOs, see Description of Sequences above); (ii) RBP8, RBP7, RBP5, RBP2, RBP6, RBP4, or RBP3 as first booster and a suitable BBM, e.g., ZmBBM; (iii) PLT3, PLT5, or PLT7 as first regeneration booster and WUS1, or WUS2, e.g. ZmWUS1 and WUS2; (iv) RBP8, RBP7, RBP5, RBP2, RBP6, RBP4, or RBP3 as first booster and RKD4, preferably TaRKD4 (from *Triticum aestivum* L., cf. SEQ ID NOs: 52 and 53); (v) PLT3, PLT5, or PLT7 as first regeneration booster and RKD4, preferably TaRKD4; (vi) RBP8, RBP7, RBP5, RBP2, RBP6, RBP4, or RBP3 as first booster and LEC1 or LEC2, for example, ZmLEC1 or ZmLEC2, as second booster; (vii) PLT3, PLT5, or PLT7 as first regeneration booster and a LEC1 or LEC2 as second booster; (viii) RBP8, RBP7, RBP5, RBP2, RBP6, RBP4, or RBP3 as first booster and a GRF, for example GRF5, as second booster; (ix) PLT3, PLT5, or PLT7 as first regeneration booster and a GRF as second booster; (x) RKD4, for example, TaRKD4 as first regeneration booster and a GRF family member as second booster; or (xi) a GRF family member as first regeneration booster and LEC1 or LEC2, or the corresponding sequences encoding the same, or a sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity thereto.

According to the various embodiments and aspects disclosed herein, it may be preferable to use a naturally occurring regeneration booster in addition to an artificial RBP according to the present invention, wherein the naturally occurring regeneration booster, e.g., BBM, WUS1/2, LEC1/2, GRF, or a PLT may be derived from a target plant to be transformed, or from a closely related species. For monocot plant modifications, for example, a booster protein with monocot origin (e.g., from *Zea mays* (Zm)) may be preferred, whereas for dicot plant modifications, a booster protein with dicot origin (e.g., originating from *Arabidopsis thaliana* (At), or *Brassica napus* (Bn)) may be preferred. The relevant booster sequences can be easily identified by sequence searches within the published genome data. Notably, regeneration boosters from one plant species may show a certain cross-species applicability so that, for example, a wheat-derived booster gene may be used in *Zea mays*, and vice versa, or a *Arabidopsis*- or *Brachypodium*-derived booster gene may be used in *Helianthus*, and vice versa. A PLT, WUS, WOX, BBM, LEC, RKD4, or GRF sequence as used herein, or a protein with a comparable regeneration booster function, may thus be derived from any plant species harbouring a corresponding gene encoding the respective booster in its genome.

In embodiments, where a combination of three regeneration boosters is used, these combinations may be selected from (i) RBP8, RBP7, RBP5, RBP2, RBP6, RBP4, or RBP3 as first booster, PLT3, PLT5, or PLT7, or a BBM as second regeneration booster, and RKD4 as third regeneration booster; (ii) PLT3, PLT5, or PLT7, or a BBM as first regeneration booster, RKD4 as second regeneration booster, and WUS1 or WUS2 as third regeneration booster; (iii) RBP8, RBP7, RBP5, RBP2, RBP6, RBP4, or RBP3 as first booster, a PLT3, PLT5, or PLT7, or a BBM as second regeneration booster, and a LEC1 or LEC2 as third regeneration booster; (iv) ZmPLT3, ZmPLT5, or ZmPLT7 as first regeneration booster, ZmLEC1 or ZmLEC2 as second regeneration booster, and a WUS1 or WUS2 as third regeneration booster; (v) RBP8, RBP7, RBP5, RBP2, RBP6, RBP4, or RBP3 as first regeneration booster, an RKD4 as second regeneration booster and a LEC1 or a LEC2 as third regeneration booster; (vi) a PLT3, PLT5, or PLT7 as first regeneration booster, a RKD4 as second regeneration booster, and a LEC1 or LEC2 as third regeneration booster; (vii) RBP8, RBP7, RBP5, RBP2, RBP6, RBP4, or RBP3 as first regeneration booster, a GRF as second regeneration booster, and a PLT3, PLT5, PLT7 or a BBM as third regeneration booster; (viii) a PLT3, PLT5, or PLT7 as first regeneration booster, a GRF as second regeneration booster, and a WUS1 or WUS2 as third regeneration booster; (ix) RBP8, RBP7, RBP5, RBP2, RBP6, RBP4, or RBP3 as first regeneration booster, a GRF as second regeneration booster, and a RKD4 as third regeneration booster; or (x) a PLT3, PLT5, or PLT7 as first regeneration booster, a GRF as second regeneration booster, and a RKD4 as third regeneration booster, or the corresponding sequences encoding the same, or a sequence having at least 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity thereto.

It was found that the use of at least one regeneration booster, preferably a booster, or a specific combination of boosters as detailed above, in connection with the methods of the present invention can have a dual effect: either the improvement of any kind of transient or stable transformation in which a transgene is ectopically expressed, or in the specific setting of gene editing relying on the use of at least one site-specific nuclease, wherein the editing efficiency is improved by the presence of at least one booster as disclosed herein.

A "regeneration booster" as used herein may not only refer to a protein, or a sequence encoding the same, having plant proliferative activity, as defined above. A "regeneration booster" may also be a chemical added during genome modification of an IIM cell, or tissue or plant comprising the same.

In one embodiment, the regeneration booster may thus be a chemical selected from $MgCl_2$ or $MgSO^4$, for example in a range from about 1 to 100 mM, preferably in a range from about 10 to 20 mM, spermidine in a range from about 0.1-1 mM, preferably in a range from about 0.1-0.5 mM, TSA (trichostatin A), and TSA-like chemicals.

The use of at least one regeneration booster in an artificial and controlled context according to the methods disclosed herein thus has the effect of promoting plant cell proliferation. This effect is highly favourable for any kind of plant genome modification, as it promotes cell regeneration after introducing any plasmid or chemical into the at least one plant cell via transformation and/or transfection, as these interventions necessarily always cause stress to a plant cell.

Additionally, or alternatively, the at least one regeneration booster according to the methods disclosed herein may have a specific effect in enhancing plant genome editing efficiency. In particular, this kind of intervention caused by at least one site-specific nuclease, nickase or a variant thereof, causes a certain repair and stress response in a plant. The presence of at least one regeneration booster can thus also improve the efficiency of genome modification or gene editing by increasing the regeneration rate of a plant cell after a modification of the plant genome.

In one embodiment, at least one regeneration booster, or a sequence encoding the same, or a regeneration booster chemical, can be provided simultaneously with other tools to be inserted, namely the at least one genome modification system, preferably the genome editing system to reduce the number of transformation/transfection acts potentially stressful for a cell. For certain cells sensitive to transformation/transfection, regeneration booster chemicals may thus represent a suitable option, which may be provided before, simultaneously with, or soon after transforming/transfecting further genome or gene editing tools to reduce the cellular stress and to increase transformation and/or editing efficiency by stabilizing a cell and thus by reducing potentially harmful cellular stress responses.

In another embodiment, the at least one genome modification system, preferably the genome editing system and the at least one regeneration booster, or the sequence encoding the same, may be provided subsequently or sequentially. By separating the introduction steps, the editing construct DNA integration of the site-directed nuclease, nickase or an inactivated nuclease encoding sequence can be avoided, where transient outcomes are of interest.

In certain embodiments, it is favourable that the at least one regeneration booster is active in a cell before further tools are introduced to put the cell into a state of low cellular stress before performing genome or gene editing.

For any simultaneous or subsequent introduction of at least one regeneration booster, the regeneration booster and the optional further genome modification or genome editing system should be active, i.e., present in the active protein and/or RNA stage, in one and the same cell to be modified, preferably in the nucleus of the cell, or in an organelle comprising genomic DNA to be modified.

Without a reasonable strategy to regenerate (effectively) transformed plant cells, there is little impact of a GE protocol. IIM cells, if transformed in the correct developmental stage following the protocols provided herein, have the intrinsic capacity to be regenerated in various ways to plant tissues, organs, whole plants and seeds in a flexible manner in addition to the fact that these cells can be modified in a targeted manner according to the methods disclosed herein.

In one aspect, there is provided a method of producing a haploid or doubled haploid plant cell, tissue, organ, plant, or seed.

The generation and use of haploids is one of the most powerful biotechnological means to improve cultivated plants. The advantage of haploids for breeders is that homozygosity can be achieved already in the first generation after dihaploidization, creating doubled haploid plants, without the need of laborious backcrossing steps to obtain a high degree of homozygosity. Furthermore, the value of haploids in plant research and breeding lies in the fact that the founder cells of doubled haploids are products of meiosis, so that resultant populations constitute pools of diverse recombinant and at the same time genetically fixed individuals. The generation of doubled haploids thus provides not only perfectly useful genetic variability to select from with regard to crop improvement, but is also a valuable means to produce mapping populations, recombinant inbreds as well as instantly homozygous mutants and transgenic lines.

Haploid plants can be obtained by interspecific crosses, in which one parental genome is eliminated after fertilization. It was shown that genome elimination after fertilization could be induced by modifying a centromere protein, the centromere-specific histone CENH3 in *Arabidopsis thaliana* (Ravi and Chan, Haploid plants produced by centromere-mediated genome elimination, *Nature*, Vol. 464, 2010, 615-619). With the modified haploid inducer lines, haploidization occurred in the progeny when a haploid inducer plant was crossed with a wild type plant. Interestingly, the haploid inducer line was stable upon selfing, suggesting that a competition between modified and wild type centromere in the developing hybrid embryo results in centromere inactivation of the inducer parent and consequently in uniparental chromosome elimination.

In one embodiment, the methods of the present invention thus comprise the generation of at least one haploid cell, tissue or organ having activity of a haploid inducer, preferably wherein the haploid cell, tissue or organ comprises a callus tissue, male gametophyte or microspore. In this embodiment, the methods as disclosed herein may comprise the introduction of a nucleotide or amino acid sequence encoding or being a sequence allowing the generation of a haploid inducer cell, for example a sequence encoding a KINETOCHORE NULL2 (KNL2) protein comprising a SANTA domain, wherein the nucleotide sequence comprises at least one mutation causing in the SANTA domain an alteration of the amino acid sequence of the KNL2 protein and said alteration confers the activity of a haploid inducer (as disclosed in EP 3 159 413 A1) in a method for plant genome modification, preferably for the targeted modification of at least one genomic target sequence, for obtaining a modification of at least one plant immature inflorescence meristem cell. In this embodiment, the at least one genome modification system does not comprise a genome editing system, but the sequence allowing the generation of a haploid inducer line, which is introduced into a plant cell to be modified stably or transiently, in a constitutive or inducible manner.

In another embodiment, the modified cell according to the methods of the present invention is a haploid cell, wherein the haploid cell is generated by introducing a genome editing system into at least one cell, preferably an IIM cell, to be modified, wherein the genome editing system is capable of introducing at least one mutation into the genomic target sequence of interest resulting in a cell having haploid inducer activity.

In yet a further aspect, there is provided a method for producing a haploid or doubled haploid plant cell, tissue, organ, plant, or seed, wherein the method comprises providing at least one regeneration booster, or a specific combination of regeneration boosters, or the sequence(s) encoding the same, to at least one cell to be modified, wherein the at least one cell is preferably a haploid cell, for example, a gametophyte or microspore. These inherently haploid cells of plants produced during the reproduction cycle have the intrinsic characteristic of being very inert to any kind of chromosome doubling and transformation. The methods as disclosed herein can thus be favourably used to introduce or apply at least one regeneration booster, or a sequence encoding the same, or a regeneration booster chemical for promoting the regenerative capacity of a haploid plant cell to increase the capacity of the haploid cell for a conversion during chromosome doubling, as the doubled haploid material is of particular interest for breeding and ultimately cultivating plants. The methods as disclosed herein thus overcome the difficulties in handling haploid plants cells and tissues, including callus tissue, as the frequency of induced and/or spontaneous chromosome doubling can be increased by providing at least one booster sequence, or preferably a specific combination of booster sequences, as disclosed herein.

Various methods for doubling chromosomes in plant biotechnology are available to the skilled person for various cultivars. In one embodiment, chromosome doubling can be achieved by using colchicine treatment. Other chemicals for chromosome doubling, are available for use according to the methods disclosed herein, wherein these chemicals may be selected from antimicrotubule herbicides, including amiprophosmethyl (APM), pronamide, oryzalin, and trifluralin, which are all known for their chromosome doubling activity.

In certain embodiments, there is provided a method comprising a regeneration step, wherein the regeneration may be performed either by direct meristem organogenesis, i.e., by directly obtaining a viable plant cell, tissue, organ, plant or seed modified as detailed above, or wherein the regeneration may be performed indirectly, i.e., via an additional cell culture step proceeding through callus organogenesis. Further provided are suitable methods for regenerating at least one immature inflorescence meristem cell, into which at least one genome or gene editing tool has been inserted according to the methods for plant genome modification disclosed herein either by direct meristem organogenesis, or by indirect callus embryogenesis or organogenesis.

The fact that the regeneration can be performed either directly or indirectly, as detailed below in various Examples, is a huge advantage as it offers several options and flexible strategies, depending on a target plant of interest, to obtain viable plant material from at least one treated IIM cell for various relevant crop plants and allows rapid progress in breeding programs, when combining them with the methods disclosed herein.

In one embodiment, the at least one genome modification system, preferably the at least one genome editing system and optionally the at least one regeneration booster, or the sequences encoding the same, are introduced into the cell by transformation or transfection mediated by biolistic bombardment, *Agrobacterium*-mediated transformation, micro- or nanoparticle delivery, or by chemical transfection, or a combination thereof, preferably wherein the at least one genome modification system, preferably the at least one genome editing system, and optionally the at least one regeneration booster are introduced by biolistic bombardment.

Particle or biolistic bombardment may be a preferred strategy according to the methods disclosed herein, as it allows the direct and targeted introduction of exogenous nucleic acid and/or amino acid material in a precise manner not relying on the biological spread and expression of biological transformation tools, including *Agrobacterium.*

In certain embodiments, the biolistic bombardment comprises a step of osmotic treatment before and/or after bombardment. Osmotic treatment can be highly suitable to enhance the transformation/transfection capacity of a cell before bombardment. Further, it can increase the transformation/transfection efficiency after bombardment. Various osmotic treatment protocols are disclosed below, and further cell-type specific protocols are available to the skilled person in the field of plant biotechnology.

As introduced above, IIM cells, due to their state of development and the physical accessibility to transformation/transfection techniques, thus represent a valuable target cell type for efficient methods for plant genome modification. To increase the genome or gene editing efficiency, the methods can not only rely on the introduction of a genome modification system, i.e., any vector or pre-assembled complex comprising nucleic acid and/or amino acid material, the methods as disclosed herein may be particularly effective in case at least one specific regeneration booster as disclosed herein is provided (introduced or, for chemicals, applied) in parallel to alleviate stress responses in a cell and to allow rapid recovery and regeneration after a manipulation.

Additionally, in certain embodiments, the methods as disclosed herein for the targeted modification of the plant genome of at least one IIM cell can comprise the introduction of a genome modification system or a genome editing system comprising at least one site-directed nuclease, nickase or an inactivated nuclease, preferably a nucleic acid guided nuclease, nickase or an inactivated nuclease, or a sequence encoding the same, and optionally at least one guide molecule, or a sequence encoding the same, optionally together with the introduction of at least one repair template, or a sequence encoding the same.

The at least one genome editing system may be provided with or without the provision of at least one regeneration booster in view of the fact that IIM cells as disclosed herein as new targets for efficient plant genome modification of various relevant crop plants as such represent valuable and easily accessible target structures with the capacity to regenerate into viable plant cells, tissues, organs, whole plants or seeds thereof.

Genome modification and site-directed genome editing efficiency is largely controlled by host cell statuses. Cells undergoing rapid cell-division, like those in plant meristems, in particular IIM cells studied herein, were shown to be the most suitable recipients for genome engineering according to the methods established herein. It was further shown that promoting cell division by providing suitable regeneration boosters and combinations thereof increases DNA integration or modification during DNA replication and division process, and thus significantly increases genome editing efficiency.

In certain embodiments, at least one genome modification system, preferably a genome editing system may be provided together with, i.e., simultaneously, or subsequently, but to one and the same target cell, the at least one regeneration booster, or regeneration booster chemical. This strategy does not only profit from the general effects of regeneration boosters on the regenerative capacity of a plant cell, the combined use may also increase genome editing efficiency in a synergistic way. Any kind of site-directed genome editing leaves a single- or double-strand break and/or modified a certain base in a genomic target sequence of interest. This manipulation initiates stress and cellular repair responses hampering a generally high genome editing efficiency. The combined introduction of at least one genome editing system and at least one regeneration booster, or a regeneration booster chemical, can thus dramatically increase the frequency of site-directed positive (i.e., desired) genome editing events detectable throughout a high proportion of relevant target cells transformed/transfected.

In certain embodiments, where at least one genome editing system is introduced according to the methods disclosed herein, the methods include the introduction of at least one site-directed nuclease, nickase or an inactivated nuclease, or a sequence encoding the same, wherein the site-directed nuclease, nickase or an inactivated nuclease may be selected from the group consisting of a CRISPR nuclease or a CRISPR system, including a CRISPR/Cas system, preferably from a CRISPR/MAD7 system, a CRISPR/Cfp1 system, a CRISPR/MAD2 system, a CRISPR/Cas9 system, a CRISPR/CasX system, a CRISPR/CasY system, a CRISPR/Cas13 system, or a CRISPR/Csm system, a zinc finger nuclease system, a transcription activator-like nuclease system, or a meganuclease system, or any combination, variant, or catalytically active fragment thereof.

In certain embodiments, wherein at least one genome editing system is introduced, the at least one genome editing system may further comprise at least one reverse transcriptase and/or at least one cytidine or adenine deaminase, preferably wherein the at least one cytidine or adenine deaminase is independently selected from an apolipoprotein B mRNA-editing complex (APOBEC) family deaminase, preferably a rat-derived APOBEC, an activation-induced cytidine deaminase (AID), an ACF1/ASE deaminase, an ADAT family deaminase, an ADAR2 deaminase, or a PmCDA1 deaminase, a TadA derived deaminase, and/or a transposon, or a sequence encoding the aforementioned at least one enzyme, or any combination, variant, or catalytically active fragment thereof.

A variety of suitable genome editing systems that can be employed according to the methods of the present invention, is available to the skilled person and can be easily adapted for use in the methods used herein.

In embodiments, wherein the site-directed nuclease or variant thereof is a nucleic acid-guided site-directed nuclease, the at least one genome editing system additionally includes at least one guide molecule, or a sequence encoding the same. The "guide molecule" or "guide nucleic acid sequence" (usually called and abbreviated as guide RNA, crRNA, crRNA+tracrRNA, gRNA, sgRNA, depending on the corresponding CRISPR system representing a prototypic nucleic acid-guided site-directed nuclease system), which recognizes a target sequence to be cut by the nuclease. The at least one "guide nucleic acid sequence" or "guide molecule" comprises a "scaffold region" and a "target region". The "scaffold region" is a sequence, to which the nucleic acid guided nuclease binds to form a targetable nuclease complex. The scaffold region may comprise direct repeats, which are recognized and processed by the nucleic acid guided nuclease to provide mature crRNA. A pegRNAs may comprise a further region within the guide molecule, the so-called "primer-binding site". The "target region" defines the complementarity to the target site, which is intended to be cleaved. A crRNA as used herein may thus be used interchangeably herein with the term guide RNA in case it unifies the effects of meanwhile well-established CRISPR nuclease guide RNA functionalities. Certain CRISPR nucleases, e.g., Cas9, may be used by providing two individual guide nucleic acid sequences in the form of a tracrRNA and a crRNA, which may be provided separately, or linked via covalent or non-covalent bonds/interactions. The guide RNA may also be a pegRNA of a Prime Editing system as further disclosed below. The at least one guide molecule may be provided in the form of one coherent molecule, or the sequence encoding the same, or in the form of two individual molecules, e.g., crRNA and tracr RNA, or the sequences encoding the same.

In certain embodiments, the genome editing system may be a base editor (BE) system.

In yet another embodiment, the genome editing system may be a Prime Editing system.

Any nucleic acid sequence comprised by, or encoding a genome modification or genome editing system disclosed herein, or a regeneration booster sequence, may be "codon optimized" for the codon usage of a plant target cell of interest. This means that the sequence is adapted to the preferred codon usage in the organism that it is to be expressed in, i.e. a "target cell of interest", i.e., an IIM cell, which may have its origin in different target plants (wheat, maize, sunflower, sugar beet, for example) so that a different codon optimization may be preferable, even though the encoded effector on protein level may be the same. If a nucleic acid sequence is expressed in a heterologous system, codon optimization increases the translation efficiency significantly.

In certain embodiments according to the methods as disclosed herein, it may be preferable to achieve homology-directed repair (HDR)-mediated genome editing instead of In certain embodiments according to the various aspects and methods disclosed herein, wherein at least one genome editing system is introduced, the at least one genome editing system comprises at least one repair template (or donor), and wherein the at least one repair template comprises or encodes a double- and/or single-stranded nucleic acid sequence.

In a further embodiment of the genome editing system according to any of the embodiments described above, the system may thus additionally comprise at least one repair template, or a sequence encoding the same. A "repair template", "repair nucleic acid molecule", or "donor (template)" refers to a template exogenously provided to guide the cellular repair process so that the results of the repair are error-free and predictable. In the absence of a template sequence for assisting a targeted homologous recombination mechanism (HDR), the cell typically attempts to repair a genomic DNA break via the error-prone process of non-homologous end-joining (NHEJ).

In one embodiment, the at least one repair template may comprise or encode a double- and/or single-stranded sequence.

In another embodiment, the at least one repair template may comprise symmetric or asymmetric homology arms.

In a further embodiment, the at least one repair template may comprise at least one chemically modified base and/or backbone.

In one embodiment, a genome modification or editing system according to any of the embodiments described above, the at least one site-directed nuclease, nickase or an inactivated nuclease, or a sequence encoding the same, and/or optionally the at least one guide nucleic acid, or the sequence encoding the same, and/or optionally the at least one repair template, or the sequence encoding the same, are provided simultaneously, or one after another.

At least one repair template can be delivered with the at least one genome modification or editing system and/or the at least one regeneration booster simultaneously or subsequently with the proviso that it will be active, i.e., present and readily available at the site of a genomic target sequence in an IIM cell to be modified together with the at least one further tools of interest.

The repair template can be additionally introduced by bombardment at least one more time 1-8 hours after first bombardment, especially when genome editing components are delivered as sequences encoding the same to increase repair template availability for a targeted repair process.

In one embodiment, the at least one repair template may comprise symmetric or asymmetric homology arms.

In another embodiment, the at least one repair template may comprise at least one chemically modified base and/or backbone, including a phosphothioate modified backbone, or a fluorescent marker attached to a nucleic acid of the repair template and the like.

In certain embodiments, the at least one genome editing system, optionally the at least one regeneration booster, and optionally the at least one repair template, or the respective sequences encoding the same, are introduced transiently or stably, or as a combination thereof. Whereas the stable integration of at least one genome editing system, in particular the site-directed nuclease or variant thereof, but not necessarily including at least one guide RNA, may allow a stable expression of this effector, the methods as disclosed herein can be performed in a full transient way. This implies that the tools as such are not integrated into the genome of a cell to be modified, unless at least one repair template is used. This transient approach may be preferably for a highly controllable gene editing event.

In a preferred embodiment, the plants which may be subject to the methods and uses of the present invention are preferably monocot plants, including plants from the order of Poales, and most preferably the plants from the family of Poaceae, comprising the genus *Agrostis, Aira, Aegilops, Alopecurus, Ammophila, Anthoxanthum, Arrhenatherum, Avena, Beckmannia, Brachypodium, Bromus, Calamagrostis, Coix, Cortaderia, Cymbopogon, Cynodon, Dactylis, Deyeuxia, Deschampsia, Elymus, Elytrigia, Eremopyrum, Eremochloa, Festuca, Glyceria, Helictotrichon, Hordeum, Holcus, Koeleria, Leymus, Lolium, Melica, Muhlenbergia, Poa, Paspalum, Polypogon, Oryza, Panicum, Phragmites, Pryza, Puccinellia, Saccharum, Secale, Sesleria, Setaria, Sorghum, Stipa, Stenotaphrum, Trisetum, Triticum, Zea, Zizania*, or *Zoysia.*

In certain embodiments, plants with enlarged inflorescence meristem resulting from mutations (e.g., cauliflower, broccoli) may be used in the methods disclosed herein, i.e., plants of the genus *Brassica*, in particular *Brassica oleracea* var. *botrytis* L., and *Brassica oleracea* var. *italica.*

In another embodiment, the plants which may be subject to the methods and uses of the present invention are preferably dicot plants, including plants from the order of Heliantheae or Betoideae, comprising the genus *Helianthus* or *Beta.*

In a further embodiment, the plant cell, tissue, organ, plant or seed disclosed in context of the present invention, originates from a genus selected from the group consisting of *Hordeum, Sorghum, Saccharum, Zea, Setaria, Oryza, Triticum, Secale, Triticale, Malus, Brachypodium, Aegilops, Daucus, Beta, Eucalyptus, Nicotiana, Solanum, Coffea, Vitis, Erythrante, Genlisea, Cucumis, Marus, Arabidopsis, Crucihimalaya, Cardamine, Lepidium, Capsella, Olmarabidopsis, Arabis, Brassica, Eruca, Raphanus, Citrus, Jatropha, Populus, Medicago, Cicer, Cajanus, Phaseolus, Glycine, Gossypium, Astragalus, Lotus, Torenia, Allium, Spinacia* or *Helianthus*, preferably, the plant cell, tissue, organ, plant or seed originates from a species selected from the group consisting of *Hordeum vulgare, Hordeum bulbusom, Sorghum bicolor, Saccharum officinarium, Zea* spp., including *Zea mays, Setaria italica, Oryza minuta, Oryza sativa, Oryza australiensis, Oryza alta, Triticum aestivum, Triticum durum, Secale cereale, Triticale, Malus domestica, Brachypodium distachyon, Hordeum marinum, Aegilops tauschii, Daucus glochidiatus, Beta* spp., including *Beta vulgaris, Daucus pusillus, Daucus muricatus, Daucus carota, Eucalyptus grandis, Nicotiana sylvestris, Nicotiana tomentosiformis, Nicotiana tabacum, Nicotiana benthamiana, Solanum lycopersicum, Solanum tuberosum, Coffea canephora, Vitis vinifera, Erythrante guttata, Genlisea aurea, Cucumis sativus, Marus notabilis, Arabidopsis arenosa, Arabidopsis lyrata, Arabidopsis thaliana, Crucihimalaya himalaica, Crucihimalaya wallichii, Cardamine nexuosa, Lepidium virginicum, Capsella bursa pastoris, Olmarabidopsis pumila, Arabis hirsute, Brassica napus, Brassica oleracea, Brassica rapa, Raphanus sativus, Brassica juncacea, Brassica nigra, Eruca vesicaria* subsp. *sativa, Citrus sinensis, Jatropha curcas, Populus trichocarpa, Medicago truncatula, Cicer yamashitae, Cicer bijugum, Cicer arietinum, Cicer reticulatum, Cicer judaicum, Cajanus cajanifolius, Cajanus scarabaeoides, Phaseolus vulgaris, Glycine max, Gossypium* sp., *Astragalus sinicus, Lotus japonicas, Torenia fournieri, Allium cepa, Allium fistulosum, Allium sativum, Allium tuberosum, Helianthus annuus, Helianthus tuberosus* and/or *Spinacia oleracea.*

In one aspect, there is provided plant cell, tissue, organ, plant or seed obtainable by or obtained by a method for plant genome modification as disclosed herein, wherein the plant cell, tissue, organ, plant or seed obtained may be a monocotyledonous (monocot) or a dicotyledonous (dicot) a plant cell, tissue, organ, plant or seed.

In certain embodiments, the inflorescence from a plant, for example, a Poaceae plant the at least one IIM cell to be modified according to the methods as disclosed herein originates from, may be a panicle, spike, or a raceme based on the morphological characteristics of the inflorescence. Each type has a spikelet, which may, however, have all kinds of shape. A spikelet is a pair of variously shaped bracts (also known as glumes, modified leaves) with enclosed floret(s). A floret is a small flower comprised of two bracts, which enclose the reproductive organs: stamens, comprised of anthers with supporting filaments, represent the male sex; the pistil, comprised of the stigma, style, and ovary represent the female sex.

The plant development is generally divided into vegetative, transition, and reproductive phases. Specifically, for embodiments referring to plants from the Poaceae family, the vegetative phase is characterized by the shoot meristem producing leaves and branches (tillers) and remaining at or near the soil surface. Vegetative phase includes 7 development stages: seed germination, first leaf emergency. first leaf, two leaves, three leaves, initial tillering, and tillering, sequentially. Transition phase is described by an elevation of the apical meristem and its transition to inflorescence meristem development. During the transition phase, leaf sheaths begin to elongate, raising the meristematic collar zone to a grazable height. Transition phase includes: shoot elongation, first node, second node, and third node. The reproductive phase defines the development stages of inflorescence meristem producing flowers and seeds, comprising of: flag leaf (flag leaf collar visible, pollen development starts), early boot, boot (which is defined as the time when the seed-head is enclosed within the sheath of the flag leaf), seed-head emergence, early anthesis, and anthesis.

In the case of Triticeae tribe species (e.g., including the important crops like wheat, barley, rye), the plants bear an inflorescence in the form of a spike, with a main axis of two ranks of lateral sessile distichous spikelets directly attaching to the rachis. The inflorescence development involves a series of morphological changes to the shoot apex—begins with spike initiation or spikelet formation, which occurs before the beginning of stem elongation. The transition of shoot apical meristem to inflorescence meristem triggers stem elongation. After the transition the inflorescence meristem develops ridges composed of bract primordia, followed by the development of spikelet meristems as axillary buds. The inflorescence meristem development is divided into four stages: 1) the double ridge/spikelet meristem (DR) stage when the spikelet meristem development is initiated and the first node is visible; 2) the floret meristem (FM) stage when the floret meristem development starts (it is marked by the emergency of the second node); 3) the anther meristem (AM) stage when anther meristems are formed, the flag leaf is emerging, and the third node begin to extend; and 4) the young floret stage when the styles have just emerged from the pistils (TS), and the flag leaf is elongating. At the young floret stage tetrads are formed in the elongating styles.

The development stages of maize (*Zea mays*) are also divided into vegetative, transition, and reproductive phases, morphologically.

In one aspect, there is thus provided a method of staging plants, i.e., a method of determining the developmental stage at which IIM cells according to the methods of the present disclosure, can be identified and obtained to be modified as disclosed herein.

The vegetative phase includes VE (the first leaf emergence) to V14 (the $14^{th}$ leaf collar is visible) stages, transition phase occurs when tassel is emerging, while reproductive phase starts at R1 stage (silk is emerging) to R6 (kernel full maturity). Maize plant development includes the following stages in a sequential order:

VE: emergence of the first leaf

V1: the collar of the first leaf is visible

V2 to V14: the collar of the second leaf to the collar of $14^{th}$ leaf is visible VT: tassel emergence R1: any silk is visible.

R2 to R6: kernels development starts to physiological maturity of the kernels.

From development point of view, the maize reproductive phase however starts quite early. The inflorescence meristem development initiates at V5 to V6 stages (plants with 5-6 visible leaf collars; see FIG. 1). At about the same time when the tassel is started, axillary meristem at leaf base node (behind the leaf sheath) transits to the ear primordium, where husk leave development is initiated, and followed by ear meristem at the tip of the ear shank. The transition of axillary meristem to ear primordium begins at the low leaf nodes of the stalk and continuing toward the top except for the upper six to eight nodes of the plant. By the development stage of V10, all inflorescent primordia initiation is initiated, and the potential number of rows (ear girth) is determined. The ear shoots located at the lower stalk nodes are first bigger than the ones at the upper stalk nodes because the lower ones were produced earlier. As development moves on, the upper one or two ear shoots take on priority over all the lower ones and ultimately become the harvestable ears.

The skilled person is well aware of the fact that protocols, usually based on morphological characteristics are available for all relevant crop plants so that the teaching as provided herein can be transferred to other target plants for defining, isolating and/or providing immature inflorescence cells for transformation.

In certain embodiments, any immature inflorescences with underdeveloped floral bracts (e.g. glume, lemma, palea) may be preferred as immature inflorescence meristem cells to be transformed.

In one embodiment, for example in the case of Triticeae tribe species as target plants, e.g., wheat, barley, rye, the immature inflorescences at the development stages of early double ridge/spikelet meristem (DR) to early young floret may be preferably subjected to the methods disclosed herein, preferably the immature inflorescences at late DR stage to late anther primordium (AM). In the case of maize, the immature tassels and ears are both applicable to the methods in the present invention. The immature tassels derived from the plants at the development stages of V5 to V10, and preferably from the plants at development stages of V6 to V8 may be particularly suitable for the methods disclosed herein. The immature ears from the plants at the development stages of V5 to V12, and preferably from the plants at development stages of V6 to V10, may also be applicable for the methods as uses disclosed herein.

The developmental stages of an inflorescence of a plant of interest may be determined by macroscopic, microscopic and/or molecular techniques, including visual inspection of plant morphology and growth, microscopy, e.g., using a stereo microscope, or by defining the expression of marker genes or metabolites characteristic of a special developmental stage. Such techniques are known to the skilled person for all relevant monocot and dicot crop plants and can be adapted based on the methods of staging plants to identify IIM cells as disclosed herein.

Plant cells for use according to the methods disclosed herein can be part of, or can be derived or isolated from any type of plant inflorescent meristems in intro, or in vivo. It is possible to use isolated plant cells as well as plant material, i.e. whole plants or parts of plants containing the plant cells. A part or parts of plants may be attached to or separated from a whole intact plant.

In certain embodiments, plant growth regulators like auxins or cytokinins in the tissue culture medium can be added to manipulated to induce callus formation and subsequently changed to induce embryos to form from the callus.

Somatic embryogenesis has been described to occur in two ways: directly or indirectly. Direct embryogenesis occurs when embryos are started directly from explant tissue creating an identical clone. Indirect embryogenesis occurs when explants produced undifferentiated, or partially differentiated, cells (i.e. callus) which then is maintained or differentiated into plant tissues such as leaf, stem, or roots.

A variety of delivery techniques may be suitable according to the methods of the present invention for introducing the components of a genome modification or editing system and/or at least one booster gene and/or at least one transgene, or the respective sequences encoding the same, into a cell, in particular an IIM cell, the delivery methods being known to the skilled person, e.g. by choosing direct delivery techniques ranging from polyethylene glycol (PEG) treatment of protoplasts, procedures like electroporation, microinjection, silicon carbide fiber whisker technology, viral vector mediated approaches and particle bombardment. A common biological means, and a preferred cargo according to the present invention, is transformation with *Agrobacterium* spp. which has been used for decades for a variety of different plant materials. Viral vector mediated plant transformation represents a further strategy for introducing genetic material into a cell of interest.

A particularly preferred delivery technique may be the introduction by physical delivery methods, like (micro-) particle bombardment or microinjection. Particle bombardment includes biolistic transfection or microparticle-mediated gene transfer, which refers to a physical delivery method for transferring a coated microparticle or nanoparticle comprising a nucleic acid or a genetic construct of interest into a target cell or tissue. Physical introduction means are suitable to introduce nucleic acids, i.e., RNA and/or DNA, and proteins. Particle bombardment and microinjection have evolved as prominent techniques for introducing genetic material into a plant cell or tissue of interest. Helenius et al., "Gene delivery into intact plants using the Helios™ Gene Gun [gene gun]", Plant Molecular Biology Reporter, 2000, 18 (3):287-288 discloses a particle bombardment as physical method for introducing material into a plant cell.

The term "(micro-)particle bombardment" as used herein, also named "biolistic transfection" or "microparticle-mediated gene transfer" refers to a physical delivery method for transferring a coated microparticle or nanoparticle comprising boost genes, booster polypeptides, genome engineering components, and/or transgenes into a target cell or tissue. The micro- or nanoparticle functions as projectile and is fired on the target structure of interest under high pressure using a suitable device, often called gene-gun. The transformation via particle bombardment uses a microprojectile of metal covered with the construct of interest, which is then shot onto the target cells using an equipment known as "gene gun" (Sandford et al. 1987) at high velocity fast enough (−1500 km/h) to penetrate the cell wall of a target tissue, but not harsh enough to cause cell death. For protoplasts, which have their cell wall entirely removed, the conditions are different logically. The precipitated construct on the at least one microprojectile is released into the cell after bombardment. The acceleration of microprojectiles is accomplished by a high voltage electrical discharge or compressed gas (helium). Concerning the metal particles used it is mandatory that they are non-toxic, non-reactive, and that they have a lower diameter than the target cell. The most commonly used are gold or tungsten. There is plenty of information publicly available from the manufacturers and providers of gene-guns and associated system concerning their general use.

In one embodiment using particle bombardment, the various components of a genome modification or editing system and/or at least one booster gene and/or at least one transgene, or the respective sequences encoding the same, are co-delivered via microcarriers comprising gold particles having a size in a range of 0.4-1.6 micron (pm), preferably 0.4-1.0 pm. In an exemplary process, 10-1,000 pg of gold particles, preferably 50-300 pg, are used per one bombardment.

The various components of a genome modification or editing system and/or at least one booster gene and/or at least one transgene, or the respective sequences encoding the same, can be delivered into target cells for example using a Bio-Rad PDS-1000/He particle gun or handheld Helios gene gun system. When a PDS-1000/He particle gun system used, the bombardment rupture pressures are from about 450 psi to 2200 psi, preferred from about 450 to 1800 psi, while the rupture pressures are from about 100-600 psi for a Helios gene gun system. More than one chemical or construct can be co-delivered with genome engineering components into target cells simultaneously. The above-described delivery methods for transformation and transfection can be applied to introduce the tools of the present invention simultaneously. Likewise, specific transformation or transfection methods exist for specifically introducing a nucleic acid or an amino acid construct of interest into a plant cell, including electroporation, microinjection, nanoparticles, and cell-penetrating peptides (CPPs). Furthermore, chemical-based transfection methods exist to introduce genetic constructs and/or nucleic acids and/or proteins, comprising inter alia transfection with calcium phosphate, transfection using liposomes, e.g., cationic liposomes, or transfection with cationic polymers, including DEAD-dextran or polyethylenimine, or combinations thereof. The above delivery techniques, alone or in combination, can be used for in vivo (including in planta) or in vitro approaches. Particle bombardment may have the advantage that this form of physical introduction can be precisely timed so that the material inserted can reach a target compartment together with other effectors in a concerted manner for maximum activity. IIM cells were shown to be particularly susceptible to particle bombardment and tolerate this kind of introduction well.

In one embodiment, more than one different transformation/transfection technique as disclosed above is combined, preferably, wherein at least one of the components of a genome modification or editing system and/or at least one booster gene and/or at least one transgene, or the respective sequences encoding the same, is introduced via particle bombardment.

In certain embodiments, the methods for plant genome modification as disclosed herein may comprise a preceding step of preparing plant cells as part of preferably immature inflorescence meristem (IIM) for providing at least one immature inflorescence meristem cell.

In certain embodiments of the methods disclosed herein, the regeneration of the at least one modified cell may be a direct meristem regeneration comprising the steps of: shoot meristem induction for about 1 to 4 weeks, preferably 10-25 days, shoot meristem propagation for about 1 to 4 weeks, preferably 10-25 days, shoot outgrowth for about 1 to 4 weeks, preferably 10-20 days, and root outgrowth for about 1 to 4 weeks, preferably 3-20 days.

In other embodiments of the methods disclosed herein, the regeneration of the at least one modified cell may be an indirect meristem regeneration comprising the steps of: inducing embryogenic callus formation for about 1 to 6 weeks, preferably 2-4 weeks, most preferably 3 weeks, shoot meristem development and outgrowth for about 1 to 6 weeks, preferably 2-4 weeks, most preferably 10-25 days, and root outgrowth for about 1 to 4 weeks, preferably 3-14 days; and optionally: screening for genetic modification events in the regenerated TO plants; and further optionally: growing the modified TO plants for T1 seed production and optionally screening T1 progeny for desirable genetic modification events.

In a further aspect, there is provided a generally applicable expression construct assembly, which may be used according to the methods disclosed herein, wherein the expression construct assembly comprises (i) at least one vector encoding at least one site-directed nuclease, nickase or an inactivated nuclease of a genome editing system, preferably wherein the genome editing system is as defined above, and (ii) optionally: at least one vector encoding at least one regeneration booster, preferably wherein the regeneration booster is as defined above, and (iii) optionally, when the at least one site-directed nuclease, nickase or an inactivated nuclease of a genome editing system is a nucleic acid guided nuclease: at least one vector encoding at least one guide molecule guiding the at least one nucleic acid guided nuclease, nickase or an inactivated nuclease to the at least one genomic target site of interest; and (iv) optionally: at least one vector encoding at least one repair template; wherein (i), (ii), (iii), and/or (iv) are encoded on the same, or on different vectors.

In one embodiment, the expression construct assembly may further comprise a vector encoding at least one marker, preferably wherein the marker is introduced in a transient manner, see, for example, SEQ ID NO: 48.

In one embodiment, the expression construct assembly comprises or encodes at least one regulatory sequence, wherein the regulatory sequence is selected from the group consisting of a core promoter sequence, a proximal promoter sequence, a cis regulatory sequence, a trans regulatory sequence, a locus control sequence, an insulator sequence, a silencer sequence, an enhancer sequence, a terminator sequence, an intron sequence, and/or any combination thereof.

Notably different components of a genome modification or editing system and/or a regeneration booster sequence and/or a guide molecule and/or a repair template present on the same vector of an expression vector assembly may be comprise or encode more than one regulatory sequence individually controlling transcription and/or translation.

In one embodiment of the expression construct assembly described above, the construct comprises or encodes at least one regulatory sequence, wherein the regulatory sequence is selected from the group consisting of a core promoter sequence, a proximal promoter sequence, a cis regulatory sequence, a trans regulatory sequence, a locus control sequence, an insulator sequence, a silencer sequence, an enhancer sequence, a terminator sequence, an intron sequence, and/or any combination thereof.

In another embodiment of the expression construct assembly described above, the regulatory sequence comprises or encodes at least one promoter selected from the group consisting of ZmUbi1, BdUbi10, ZmEf1, a double 35S promoter, a rice U6 (OsU6) promoter, a rice actin promoter, a maize U6 promoter, PcUbi4, Nos promoter, AtUbi10, BdEF1, MeEF1, HSP70, EsEF1, MdHMGR1, or a combination thereof.

In a further embodiment of the expression construct assembly described above, the at least one intron is selected from the group consisting of a ZmUbi1 intron, an FL intron, a BdUbi10 intron, a ZmEf1 intron, a AdH1 intron, a BdEF1 intron, a MeEF1 intron, an EsEF1 intron, and a HSP70 intron.

In one embodiment of the expression construct assembly according to any of the embodiments described above, the construct comprises or encodes a combination of a ZmUbi1 promoter and a ZmUbi1 intron, a ZmUbi1 promoter and FL intron, a BdUbi10 promoter and a BdUbi10 intron, a ZmEf1 promoter and a ZmEf1 intron, a double 35S promoter and a AdH1 intron, or a double 35S promoter and a ZmUbi1 intron, a BdEF1 promoter and BdEF1 intron, a MeEF1 promoter and a MeEF1 intron, a HSP70 promoter and a HSP70 intron, or of an EsEF1 promoter and an EsEF1 intron.

In addition, the expression construct assembly may comprise at least one terminator, which mediates transcriptional termination at the end of the expression construct or the components thereof and release of the transcript from the transcriptional complex.

In one embodiment of the expression construct assembly according to any of the embodiments described above, the regulatory sequence may comprise or encode at least one terminator selected from the group consisting of nosT, a double 35S terminator, a ZmEf1 terminator, an AtSac66 terminator, an octopine synthase (ocs) terminator, or a pAG7 terminator, or a combination thereof. A variety of further suitable promoter and/or terminator sequences for use in expression constructs for different plant cells are well known to the skilled person in the relevant field.

The methods as disclosed herein, in particular for transient particle bombardment and direct meristem regeneration of IIM cells, are highly effective and efficient and able to achieve single-cell origin regeneration and homogenous genome editing without a conventional selection (e.g., using an antibiotic or herbicide resistant gene).

Exemplary elements of an expression vector assembly of the present invention, which may be individually combined, may comprise (i) a suitable vector backbone, for example, according to SEQ ID NO: 34, wherein a variety of suitable vectors are available in plant biotechnology; (ii) an expression cassette, i.e., a cassette encoding a sequence of an effector, for example, at least one regeneration booster as disclosed herein, for example, according to any one of SEQ ID NOs: 23 to 33; (iii) an expression construct, i.e., a construct including an expression cassette and at least one further vector element, for example, as represented in any one of SEQ ID NOs: 35 to 43, or an empty vector, for example, according to SEQ ID NO: 34; (iv) a vector or expression construct comprising or encoding at least one site-directed nuclease, for example, as represented in any one of SEQ ID NOs: 46 and 50; (v) a suitable vector encoding a guide molecule, in case a nucleic acid-guided site directed nuclease is used, specific for a genomic target sequence of interest, for example, a sequence according to any one of SEQ ID NOs: 47, 49, and 50, wherein the respective guide molecule is compatible with the cognate nucleic acid-guided site directed nuclease, or variant thereof, wherein the respective guide molecule comprised or encoded by according to any one of SEQ ID NOs: 47, 49, and 50 can be easily replaced by another guide molecule targeting a different genomic target site of interest; (vi) a vector encoding at least one repair template sequence of interest; and/or (vii) a vector or expression construct comprising or encoding at least one expressible marker gene, preferably a marker gene, which can be easily detected macroscopically, or microscopically, like a fluorescent marker gene as encoded by, for example, SEQ ID NO: 48. A variety of suitable fluorescent marker proteins and fluorophores applicable over the whole spectrum, i.e., for all fluorescent channels of interest, for use in plant biotechnology for visualization of metabolites in different compartments are available to the skilled person, which may be used according to the present invention. Examples are GFP from *Aequoria victoria*, fluorescent proteins from *Anguilla japonica*, or a mutant or derivative thereof), a red fluorescent protein, a yellow fluorescent protein, a yellow-green fluorescent protein (e.g., mNeonGreen derived from a tetrameric fluorescent protein from the cephalochordate *Branchiostoma lanceolatum*), an orange, a red or far-red fluorescent protein (e.g., tdTomato (tdT), or DsRed), and any of a variety of fluorescent and coloured proteins may be used depending on the target tissue or cell, or a compartment thereof, to be excited and/or visualized at a desired wavelength.

All elements of the expression vector assembly can be individually combined. Further, the elements can be expressed in a stable or transient manner, wherein a transient introduction may be preferably. In certain embodiments, individual elements may not be provided as part of a yet to be expressed (transcribed and/or translated) expression vector, but they may be directly transfected in the active state, simultaneously or subsequently, and can form the expression vector assembly within one and the same IIM cell of interest to be modified. For example, it may be reasonable to first transform part of the expression vector assembly encoding a site-directed nuclease, which takes some time until the construct is expressed, wherein the cognate guide molecule is then transfected in its active RNA stage and/or at least one repair template is then transfected in its active DNA stage in a separate and subsequent introduction step to be rapidly available. The at least one regeneration booster sequence and/or the at least one genome modification or editing system and/or the at least one marker may also be transformed as part of one vector, as part of different vectors, simultaneously, or subsequently. The use of too many individual introduction steps should be avoided, and several components can be combined in one vector of the expression vector assembly, to reduce cellular stress during transformation/transfection. In certain embodiments, the individual provision of elements of the at least one regeneration booster sequence and/or the at least one genome modification or editing system and/or the at least one marker and/or the at least one guide molecule and/or the at least one repair template on several vectors and in several introduction steps may be preferable in case of complex modifications relying on all elements so that all elements are functionally expressed and/or present in a cell to be active in a concerted manner.

The present invention is further illustrated by the following non-limiting Examples.

EXAMPLES

Example 1: Plant Immature Inflorescence Preparation for Different Target Plants A: Maize Plant Cultivation Depending on seed germination rate, 1-2 seeds per well are planted into a deep 50-well plug tray (FIG. 1A) placed further within a tray without holes (FIG. 1B). After germination only one seedling per well is kept. The soil used is MetroMix360/Turface 3:1 blend. The seeds are germinated and growing in a growth chamber at 28° C. for day and 22° C. for night, light intensity of 400-600 μmol $m^{-2}$ $s^{-1}$ and 14-16 hours day length, 50% humidity. Maize plants are fertilized at every watering using Jack's 15-5-15 Ca—Mg diluted to 150 ppm nitrogen. Plants are watered as needed.

It is a huge advantage that this cultivation method is not associated with pollen contamination issues, therefore, allowing that multiple genotypes can be grown in in the same tray, as shown in FIG. 2. The outer dimensions of the deep 50-well tray as shown in FIG. 2 were chosen as follows: 21¼"×11¼"×2¼, with cell dimensions: 1¾"×1¾".

Obviously, these dimensions may vary depending on the target plant (and thus the morphological characteristics thereof) of interest.

B: Maize Immature Tassel Isolation

Maize immature tassels from the plants at late V6 to late V7 stages (FIG. 2) are used. It most likely takes 25-32 days to reach these stages for different genotypes after seed planting when cultured at the growth conditions described above. The developmental stages of immature tassels are determined using, for example, a Zeiss stereo microscope. Maize immature tassel isolation usually comprises the steps of 1. Harvesting stalk segment with immature tassel from maize plants by retrieving the stalk segment between the base (near to soil) and the youngest leaf collar and removing all the leaf blades;
2. (Optional) Rinsing the stalk segments with tap water, and dry with paper towel;
3. Surface spraying the stalk segments with 70% ethanol, and manually removing the first leaf sheath from stalk in a laminar hood;
4. Repeating step 3, and carefully remove each leaf sheaths from stalk, one by one from the bottom to top, until the last 3$^{rd}$ leaf sheath;
5. Trimming the stalk segments and spraying them with 70% ethanol (the last ethanol spray);
6. Transferring the segments onto a clear petri dish in the hood;
7. Under a dissection microscope: carefully removing all remaining leaves so that the immature tassels are ready for transformation (FIG. 3A).

The isolated maize immature tassel comprising of primary and branch inflorescence meristems, and which further comprising of spikelet meristem. The floral bract primordia are underdeveloped and the inflorescence meristem is open (FIG. 3A).

C: Maize Immature Ear Isolation

Maize immature ears used for the methods in the present invention are derived from the plants at the development stages of V8 to late V10. It most likely takes 5-6 weeks from seed planting to the immature ear harvesting. Ears are located at each of stalk nodes, enclosed by the leaf sheath, and normally surrounded by husk leaves. The developmental stages of immature ears are determined using, for example, a Zeiss stereo microscope. Maize immature ear isolation comprises the steps of 1. Harvesting the stalk with immature ears from corn plants by retrieving the stalk segment between the base (near to soil) and the youngest leaf collar and removing all the leaf blades;
2. (Optional) Rinsing the stem segments with tap water, and drying with paper towel;
3. Surface spraying the stalk segments with 70% ethanol, and manually removing the first leaf sheath from stalk, and isolating the first immature ear shoot carefully at the first stalk node in a laminar hood;
4. Repeating step 3, isolating all immature ear shoots at each of the stalk nodes, one by one from the bottom to top, in the hood;
5. Spraying the ear shoots with 70% ethanol (the last ethanol spray), and transferring the shoots into a clear petri dish;
6. Under a dissection microscope: carefully removing all the husks from each of ear shoots, and the immature ear meristems are ready for transformation.

Isolating maize immature ears comprising of ear spikelet in pairs of rows. The floral bract primordia are underdeveloped and the inflorescence meristem is open (FIG. 3B).

D: Rye Plant Cultivation

KWS bono rye were grown in a growth chamber. Two KWS bono rye seeds are planted into a 1801 deep inserts plug pot (placed into a 18-count holding tray without holes). After germination, only one seedling per pot is kept.

The soil used was Berger 35% Bark. The seeds are germinated and growing in a growth chamber at constant 20° to 21° C., with light intensity of 400-600 μmol $m^{-2}$ $s^{-1}$ and 14 hours day length, 50% humidity. The rye plants were fertilized three time a week with Jack's 15-16-17 peat lite at an E.C. of 1.0+ the E.C. of the water. The plants were checked twice a day for watering needs and are watered from top as needed.

After the plants have germinated and produced one to two tillers, the plants were moved to a vernalization chamber at a temperature of 0° to 5° C. for 40 days. Once they are moved back to the normally growth condition they will begin their reproductive development.

E: Rye Immature Inflorescence Isolation

The developmental stages of rye immature inflorescences were determined using a Zeiss stereo microscope. When the first node of stem was visible the inflorescences of a rye plant are in DR (double ridge/spikelet meristem stage) stage. About 1 week later, the second node is emerging, floret meristem development begins, and the plant is in FM (floret meristem) stage. After 5-7 more days, the third stem internode begins to elongate, and anther primordia are visible, and the plant is in AM (anther primordium/meristem) stage and is ready to enter the booting stage.

Rye immature inflorescences at the development stages of late double ridge (DR) to late anther meristem (AM) are used for the methods in the present invention. At these stages the rye shoots are elongated with 1-3 visible nodes.

The rye immature inflorescence isolation comprises the steps of:

1. Harvesting the rye shoots at the right development stages from the base of the stalks (near to soil) and removing all the leaf blades;
2. (Optional) Rinsing the stem segments with tap water, and drying with paper towel;
3. Surface spraying the shoots with 70% ethanol, and manually removing the first leaf sheath from stalk in a laminar hood;
4. Repeating step 3, and carefully removing each leaf sheaths from stalk, one by one from the bottom to top, until the flag leaf sheath;
5. Trimming the stalk segments and spray with 70% ethanol (the last ethanol spray);
6. Transferring the segments onto a clear petri dish in the hood;
7. Under a dissection microscope: carefully removing the flag leaf sheath, and all of immature bracts, and the immature inflorescence is ready for transformation (FIG. 3C).

Example 2: Transient Biolistic Transformation of Immature Tassels from Maize Elites Maize immature tassel preparation was performed as detailed above (Example 1).

Microparticle Bombardment

Figure 5:
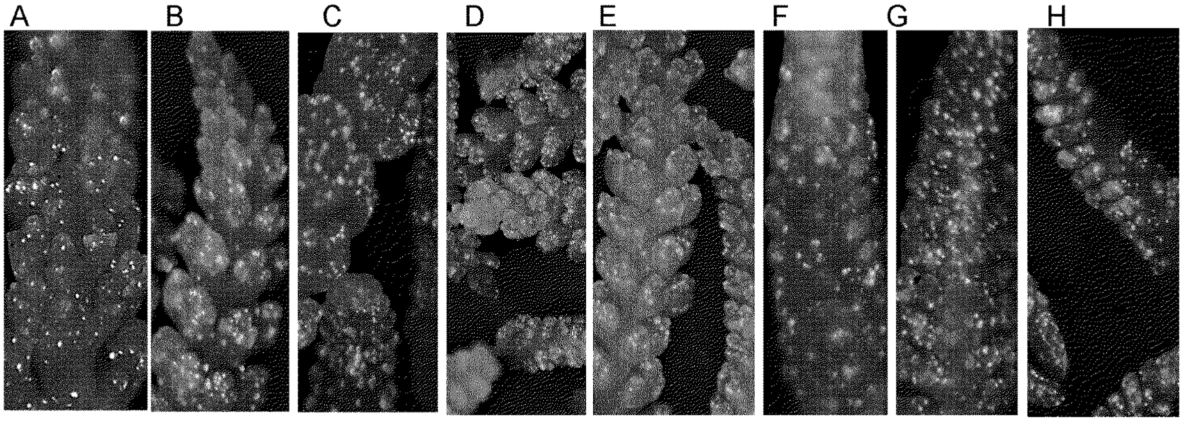
FIG. 5 shows fluorescence images (a green fluorescent marker gene was used and its expression in the target tissue was visualized accordingly) of maize immature inflorescence 20 hours after bombardment with plasmid pGEP837 (see FIG. 4). (A)-(H): 29-day-old immature tassels from maize inbred lines. (A): Maize elite 4V-40171; (B): maize elite 5V-50269; (C): maize elite 5V-50266; (D): maize elite 3V-30261; (E): maize elite 16V-0089; (F): maize elite 4V-40131; (G): maize elite 2V-20121; (H): maize elite 3V-30315.

The freshly isolated immature tassels from different inbred elites were placed onto an osmatic medium plate (e.g. IM_OS medium) for 4 hours. Particle bombardment was conducted using a Bio-Rad PDS-1000/He particle gun. The bombardment conditions were: 30 mm/Hg vacuum, 1,350 psi helium pressure. Per bombardment, 200 ng of plasmid DNA pGEP837 (FIG. 4) was coated onto 100 μg of 0.6 μm gold particles using calcium-spermidine method. Four bombardments per sample plate were performed. The bombarded immature tassels were kept on the osmotic medium plate for another 20 hours after the bombardment. A green fluorescence reporter encoding gene (FIG. 4) was used for monitoring biolistic transformation and the gene expression. Efficient transient expression of the reporter gene was observed in all tested inbred elites 20 hours after the bombardment (FIG. 5).

Figure 8:
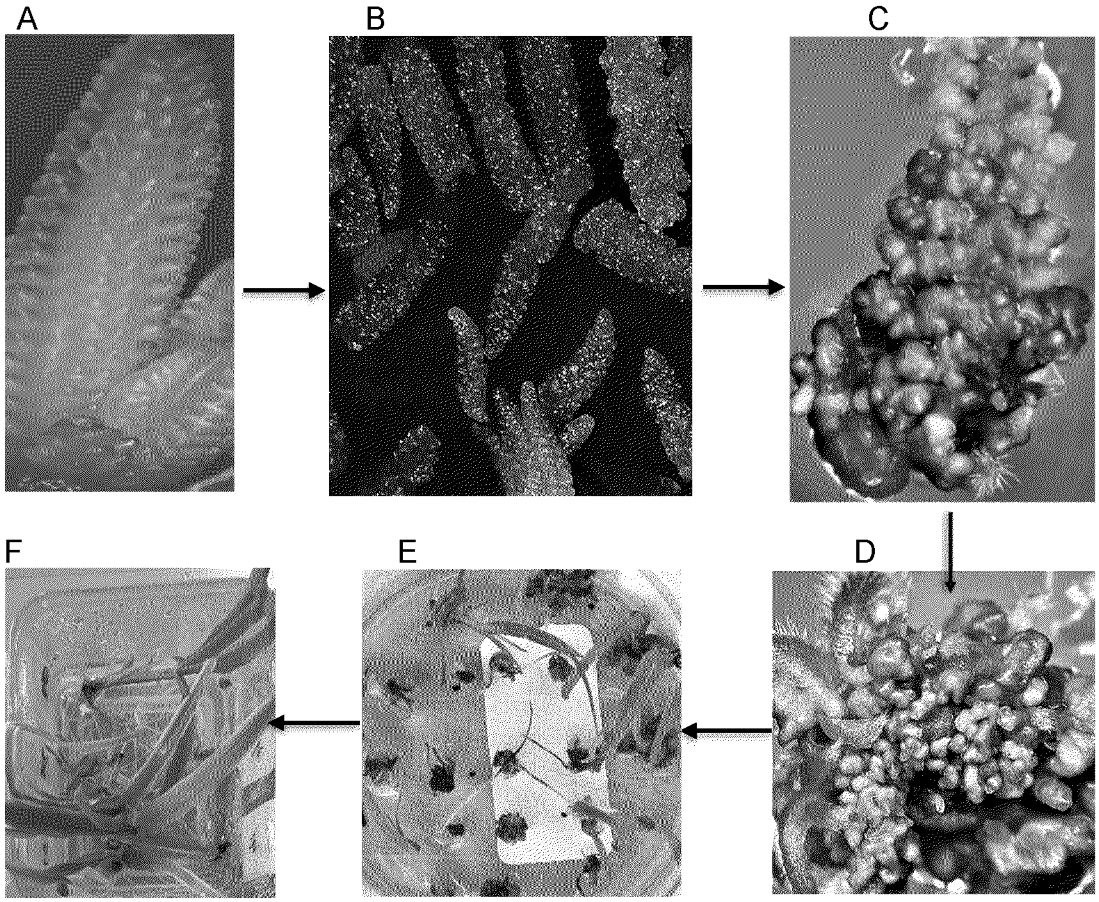
FIG. 8 shows a work-flow for genome editing via biolistic bombardment and direct meristem regeneration from immature tassels of maize A188. (A): A fresh isolate immature tassel ready for bombardment; (B): fluorescence images (a green fluorescent marker gene was used and its expression in the target tissue was visualized accordingly) of the immature tassels 20 hours after bombardment with plasmid pGEP837 (see FIG. 4); (C): meristem proliferation step I for 7 days; (D): meristem proliferation step II for 7 days; (E): plantlet development in shooting medium for 7 days; (F): plantlet development in rooting medium for 7 days.

Example 3: Efficient Genome Editing by Transient Biolistic Transformation and Direct Meristem Regeneration from Maize A188 Immature Tassel A freshly isolated immature tassel from 28-day-old A188 seedling is shown in FIG. 8A, which was prepared as described in Example 1 and bombarded as detailed in Example 2.

Figure 6:
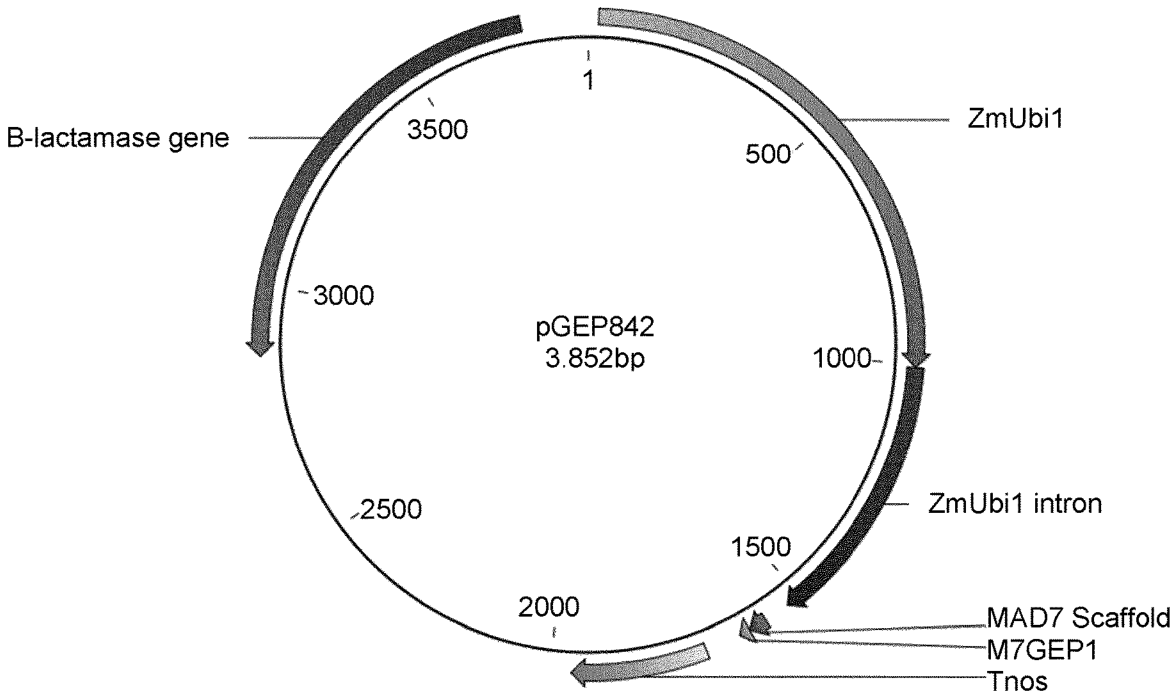
FIG. 6 shows a genome editing crRNA construct pGEP842 map. m7GEP1 defines the crRNA, which target to maize HMG13 gene. ZmUbi1 defines the promoter and intron from maize Ubiquitin 1 gene. Tnos defines the nos terminator.
Figure 7:
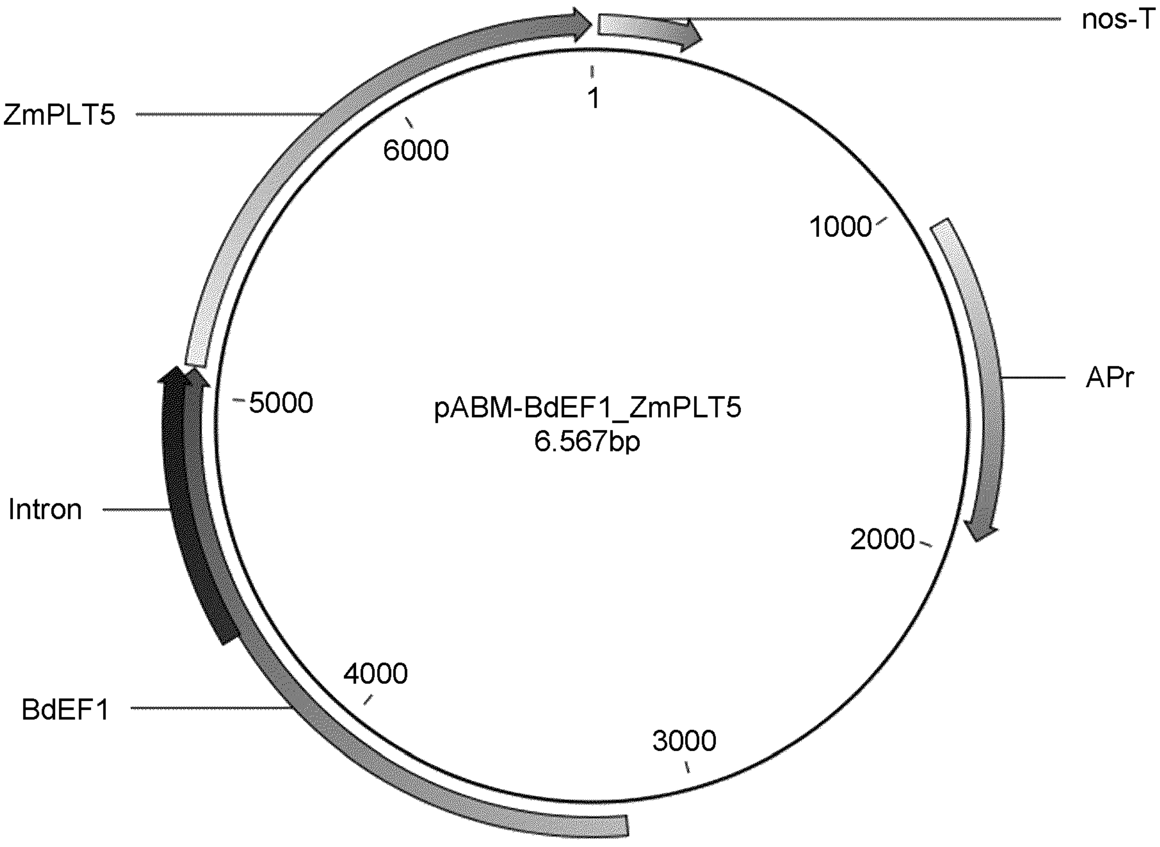
FIG. 7 shows a maize PLT5 expression construct pABM-BdEF1_ZmPLT5 map. ZMPLT5 is driven by the strong constitutive EF1 promoter from *Brachypodium* (pBdEF1).

Construct pGEP837 contains the expression cassette of CRISPR nuclease MAD7 (FIG. 4), while pGEP842 harbors the expression cassette of CRISPR sgRNA m7GEP1, which targets to maize endogenous HMG13 gene (FIG. 6). Construct pABM-BdEF1_ZmPLT5 encloses a maize regeneration boost gene PLT5 expression cassette (FIG. 7).

200 ng of plasmid DNA pGEP837, 300 ng of plasmid DNA pGEP842, and 100 ng of pABM-BdEF1_ZmPLT5, were co-coated onto 100 g of 0.4 μm gold particles using calcium-spermidine method, and the three constructs were co-delivered into the cells of A188 immature tassel (FIG. 8A) by particle bombardment at 1,350 psi rupture pressure, 4 bombardment shots per sample plate. The bombarded A188 immature tassel was kept on the osmotic IM_OS plate for another 20 hours after the bombardment. Efficient transient expression of the reporter gene could be demonstrated as shown in FIG. 8B.

A: Direct Meristem Regeneration of Maize Immature Tassels hours after the bombardment the A188 immature tassel was subject to direct meristem regeneration, which comprising the steps of:

Step I: cutting the bombarded immature tassel branches into a segment of 3-5 mm in length with a sharp blade, and placing them onto an IMSMK5 medium petri dish plate (25×100 mm) at a density of 12 pieces per plate. Sealing the plate with surgical tape, and culturing at 27° C., dark for 2 days, and then transferring the plates and culture at 25° C., weak light (10~50 μmol $m^{-2}$ $s^{-1}$, gradually increase light intensity), 16/8 h light/dark cycle for a total of 14 days (FIG. 8C).

Step II: removing the developing bracts or leaves, and separating the meristem buds from the step I into small pieces in 2-5 mm diameter, and transferring the meristem buds onto a fresh IMSMK5 medium. Sealing the plate with surgical tape, and culturing at 25° C., light (~100 μmol $m^{-2}$ $s^{-1}$), 16/8 h light/dark cycle, for 2 weeks (FIG. 8D).

Step III: separating the developing shoot buds from the step II, and transferring the shoot buds onto a Shooting medium petro dish (25×100 mm). Sealing the plate with surgical tape and culture at 25° C., light (~100 μmol $m^{-2}$ $s^{-1}$) for 2 weeks (FIG. 8E).

Step IV: removing the developing shoots from step III onto a Rooting medium in phytotray, and culturing at 25° C., light (~100 μmol $m^{-2}$ $s^{-1}$) for 1 week (FIG. 8F).

After 1 week at regeneration step IV, the regenerated plantlets (FIG. 8F) are ready for leaf sampling for molecular analysis or transfer to soil for $T_0$ plant growth and $T_1$ seed production.

The work flow of the direct meristem regeneration of immature tassels is summarized in summarized in Table 1:

TABLE 1

Work flow for SDN-1 generation from maize immature tassel via direct meristem regeneration.

| | Media | Culture conditions | Duration |
|---|---|---|---|
| Step I: SM induction | IMSMK5 | 27° C., dark | 2 weeks |
| Step II: SM development | IMSMK5 | 25° C., light | 2 weeks |
| Step III: Shooting | Shooting medium | 25° C., light | 2 weeks |
| Step III: rooting | Rooting medium | 25° C., light | 1 weeks |

In sum, seventy-two (72) $T_0$ plantlets were regenerated from the 28-day-old A188 immature tassel (FIG. 8A) after the biolistic transformation of the CRISPR constructs. The results are summarized in Table 2:

TABLE 2

SDN-1 efficiency in the regenerated T0 plantlets from a 28-day-old A188 immature tassel by direct meristem regeneration.

| No. plantlets regenerated | No. Bi-allelic SDN-1 | No. mono-allelic SDN-1 | Total SDN-1 | % SDN-1 |
|---|---|---|---|---|
| 72 | 12 | 1 | 13 | 18% |

Molecular screening for the SDN-1 editing using Sanger sequencing coupled with sequence trace decomposition analysis identified 12 bi-allelic and 1 mono-allelic SDN-1 events from the 72 $T_0$ plants, which gives an 18% SDN-1 efficiency (Table 2). A representative sequencing result for a bi-allelic SDN-1 (FIG. 9A) or a mono-allelic SDN-1 event in the $T_0$ plants is shown in FIG. 9B. These results demonstrate that the methods in the present invention by transient particle bombardment and direct meristem regeneration of the cells as part of preferably immature tassel are highly effective and efficient; that, most importantly, the methods are able to achieve single-cell origin regeneration and homogenous genome editing without a conventional selection (e.g. using an antibiotic or herbicide resistant gene) in maize A188.

Example 4: The Genome Editing Events from Transient Biolistic Transformation and Direct Meristem Regeneration of Maize A188 Immature Tassel are Fully Inheritable Four edited $T_0$ plantlets from Example 3 were transferred into soil and the $T_1$ seeds were produced by selfing or backcrossing to WT A188. Mature T1 seeds were soaked in water for about 24 hours, and the T1 embryos were isolated from the T1 seeds for DNA extraction individually. The SDN-1 segregations in the T1 progeny were analyzed by Taqman real time PCR. The results were shown in Table 3 below. The SDN-1 segregation ratios in the T1 progeny from all the tested lines perfectly match to the expectation from the Mendel's law of segregation for a genetic unit, and thus the SDN-1 modification events generated by using the methods from the present invention are fully inheritable (Table 3). These results also are in support of that the methods are able to achieve single-cell origin regeneration and homogenous genome editing without a conventional selection in maize A188.

TABLE 3

SDN-1 segregation ratios in the T1 progeny from 4 T0 lines derived from a 28-day-old A188 immature tassel by direct meristem regeneration.

| To edited event | SDN-1 in $T_0$ | Crossing | SDN-1 ratio in $T_1$ (WT:mono-:Bi-) |
|---|---|---|---|
| xxx-T-0012 | Bi-allelic | selfing | 0:0:9 |
| xxx-T-0013 | Bi-allelic | backcrossing to WT | 0:5:0 |
| xxx-T-0014 | Mono-allelic | sefling | 1:3:2 |
| xxx-T-0017 | Bi-allelic | selfing | 0:0:5 |

Example 5: Genome Editing SDN-1 Via Immature Ear Bombardment and Direct Meristem Regeneration from Maize Elites Three maize seedlings of elite 4V-40171 at V8 stage, 39 days after planting, were harvested for immature ear isolation. For the information about plant immature inflorescence, see Example 1.

11 immature ears were isolated from the three seedlings, which are comprising of ear spikelet in pairs of rows. The floral bract primordia are underdeveloped and the inflorescence meristem is open (FIG. 10).

The immature ears were osmotically treated in IM_OSM medium for 4 hours before the bombardment (FIG. 10B). For each bombardment, 200 ng of plasmid DNA pGEP837, 300 ng of plasmid DNA pGEP842, and 100 ng of pABM-BdEF1_ZmPLT5, were co-coated onto 100 μg of 0.4 μm gold particles using calcium-spermidine method, and the three constructs were co-delivered into the cells of maize 4V-40171 immature ears by the particle bombardment at 1,350 psi rupture pressure, 4 bombardment shots per sample plate. After 20 hours of post-bombardment osmotic treatment on the IM_OSM plate, the bombarded immature ears were subjected to the direct meristem regeneration procedure. For the detailed information on the particle bombardment and direct meristem regeneration of the immature ears, see Example 3.

154 plantlets were regenerated from the 11 bombarded immature ears of maize elite 4V-40171, which demonstrate high regeneration capability of the immature ear from the maize elite using the methods from the present invention. After 1 week, development in the Rooting medium in phytotray, a 5-10 mm leaf tip from each of the leaves of the 154 $T_0$ plantlets are collected for DNA extraction. Genome editing SDN-1 in the regenerated $T_0$ plants were screened using TaqMan Digital Droplet PCR. Five $T_0$ plants with significant SDN-1 modifications were identified. The typical Taqman ddPCR results are shown in Table 4 below. These results indicate the possibility of direct regeneration and genome editing in maize inbred elites by transient particle bombardment and direct meristem regeneration of the cells as part of preferably immature ears.

TABLE 4

Positive SDN-1 events identified from the 154 regenerated T0 plantlets derived from the 4V-40171 immature ears via ddPCR analysis.

| Sample ID | WT Conc | Target Conc | Accepte Droplets | WT Droplets | Positive Droplets | SDN-1% |
|---|---|---|---|---|---|---|
| xxx004-T-110 | 606 | 0.276 | 14253 | 5737 | 2 | 0 |
| xxx004-T-111 | 773 | 0.301 | 15064 | 7254 | 2 | 0 |
| xxx004-T-112 | 1043 | 0 | 14800 | 8699 | 0 | 0 |
| xxx004-T-113 | 360 | 184 | 17857 | 4702 | 1901 | 33.8 |
| xxx004-T-114 | 497 | 15.7 | 19765 | 6811 | 172 | 3.07 |
| xxx004-T-121 | 405 | 32.5 | 18342 | 5343 | 354 | 7.42 |
| xxx004-T-122 | 744 | 32.6 | 16207 | 7597 | 235 | 4.19 |
| xxx004-T-138 | 4.87 | 218 | 17431 | 72 | 2940 | 97.8 |

Compared to the results obtained from the maize A188 in Example 3, the highly chimeric SDN-1 modifications in the elite TO plants also suggest that the mitotic activities in the elite cells may be significantly lower than those from A188 cells (A188 is a highly regenerative maize genotype).

Example 6: Efficient Genome Editing by Transient Biolistic Transformation and Indirect Callus Regeneration with Regeneration Boosters from Maize A188 Immature Tassel For the information about the immature tassel preparation and the particle bombardment, see Examples 1, 2, and 3.

Two A188 immature tassels at V7 stage were harvested, and osmotically treated in two N6_OSM plates (one tassel per plate) for 4 hours before the bombardment. Construct pABM-BdEF1_KWS_RBP4 and pABM-BdEF1_KWS_RBP5 harbor the maize regeneration boost gene KWS_RBP4 (FIG. 11) and KWS_RBP5 expression cassette (FIG. 12), respectively. For each bombardment 200 ng of plasmid DNA pGEP837 and 300 ng of plasmid DNA pGEP842, and 100 ng each of pABM-BdEF1_ZmPLT5 plus either pABM-BdEF1_KWS_RBP4 or pABM-BdEF1_KWS_RBP5, were co-coated onto 100 μg of 0.4 μm gold particles using calcium-spermidine method, and the four constructs were co-delivered into the A188 immature tassel cells by the particle bombardment at 1,350 psi rupture pressure, 4 bombardment shots per sample plate. After 20 hours of post-bombardment osmotic treatment on the N6_OSM plate, the bombarded immature ears were subjected to the indirect callus regeneration procedure, which comprises the steps of:

Step I—embryogenic callus induction: cutting the bombarded immature tassel into a segment of 3-6 mm in length, with a sharp blade, and placing it onto a callus induction medium N6_5Ag in petro dish plate (25×100 mm). Sealing the plate with surgical tape and culture at 27° C., dark, for 3 weeks.

Step II—shoot development and outgrowth: separating of developing embryogenic calluses from the step I into small pieces 2-5 mm in diameter, and transferring the calluses onto a Shooting medium petro dish plate (25×100 mm). Seal the plate with surgical tape and culture at 25° C., light (20-100 μmol $m^{-2}$ $s^{-1}$, gradually increase the light intensity) for 18 days.

Step III—root outgrowth: removing the developing shoots from step III onto a Rooting medium phytotray, and culture at 25° C., light (100 μmol $m^{-2}$ $s^{-1}$) for ~7 days.

Figure 13:
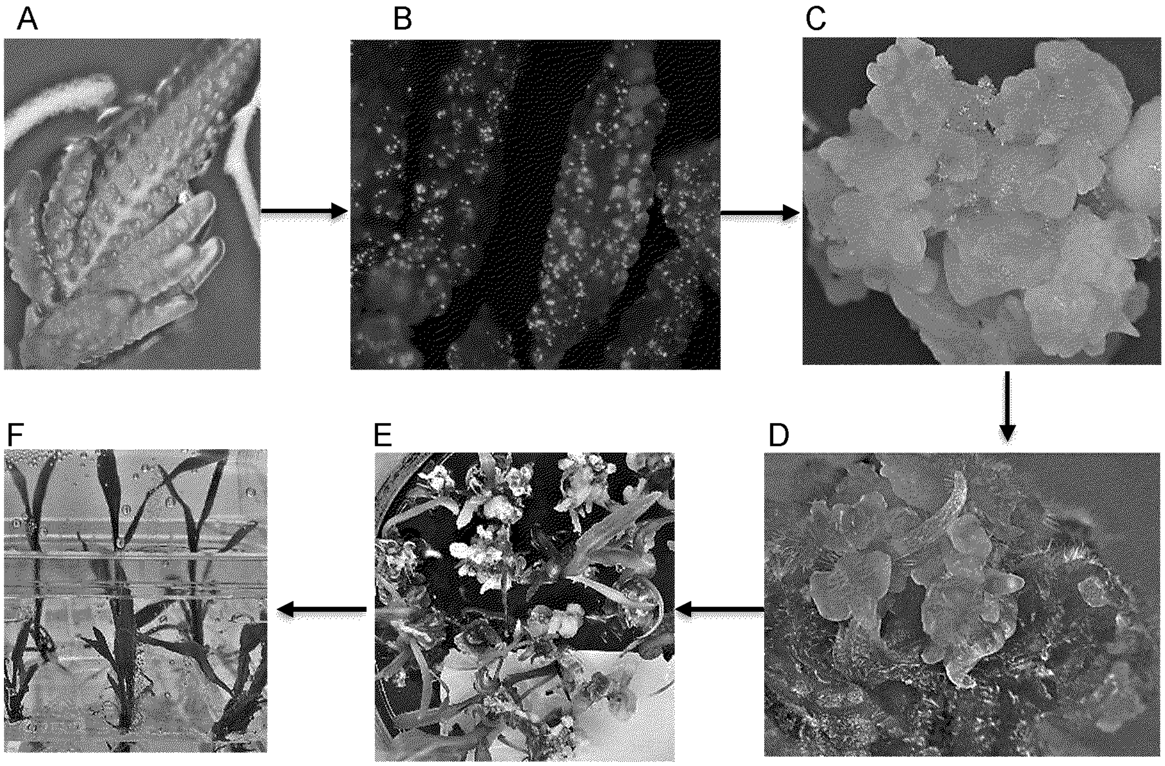
FIG. 13 shows the work-flow for genome editing by biolistic transformation and indirect callus regeneration with regeneration boosters from immature tassels of maize A188. (A): A fresh isolate immature tassel ready for bombardment; (B): a fluorescence image (a green fluorescent marker gene was used and its expression in the target tissue was visualized accordingly) of the immature tassels 20 hours after co-bombardment of plasmid pGEP837/pGEP842 with regeneration boosters ZmPLT5 and KWS_RBP4 or KWS_RBP5; (C): callus induced after 20 days in the callus induction medium; (D): callus greening in shooting medium for 5 days; (E): plantlet development in shooting medium for 12 days; (F): plantlets development in rooting medium for 7 days.

The work flow of the indirect callus regeneration is demonstrated in FIG. 13 and summarized in Table 5.

TABLE 5

Workflow for SDN-1 generation from maize immature tassel via indirect callus regeneration.

| | Media | Culture conditions | Duration |
|---|---|---|---|
| Step I: callus induction | N6_5Ag/IMCIM2* | 27° C., dark | 3 weeks |
| Step II: shooting | Shooting medium | 25° C., light | 2-3 weeks |
| Step III: Rooting | Rooting medium | 25° C., light | 1 weeks |

After one week at regeneration step III, the regenerated plantlets are ready for leaf sampling for molecular analysis or transfer to soil for $T_1$ seed production. For the information on the sampling molecular analysis, see Examples 3, 4, and 5.

Next, fifty-eight (58) plantlets were regenerated from the immature tassel co-bombarded with the boost ZmPLT5 and KWS_RBP4 constructs. 42, out of the 58 regenerated plants were screened for the SDN-1 editing by Sanger sequencing and trace decomposition analysis, and a total of 21 SDN-1 events were identified from the 42 screened $T_0$ plants, which gave a 50% SDN-1 efficiency from this A188 immature tassel.

From the A188 immature tassel that co-bombarded with the boost ZmPLT5 and KWS_RBP5, 80 plantlets were regenerated. 34, out of the 80 $T_0$ plants were screened for the SDN-1 by the Sanger sequencing and trace decomposition analysis. The results showed that 30 plants from the 34 tested To plants had a bi-allelic SDN-1 editing in the target site, which gave an 88% SDN-1 efficiency. The results are summarized in Table 6, and the Sanger sequencing and trace decomposition analysis results from the 34 tested plants were displayed in Table 7, where the four $T_0$ plants with wild type sequence at the target side were highlighted in bold.

TABLE 6

SDN-1 efficiency in the regenerated T0 plantlets from a 28-day-old A188 immature tassel via the indirect callus regeneration with boosters.

| Boosters | No. Regen events | No. events analyzed | No. events with ~100% SDN-1 | No. events with ~50% SDN-1 | Total No. events with ≥50% SDN-1 | % SDN-1 per event |
|---|---|---|---|---|---|---|
| ZmPLT5/RBP4 | 58 | 42 | 7 | 14 | 21 | 50% (21/42) |
| ZmPLT5/RBP5 | 80 | 34 | 30 | 0 | 30 | 88% (30/34) |

TABLE 7

Sanger sequencing trace decomposition analysis of genome editing events in 34 regenerated T0 plantlets from a 28-day-old A188 immature tassel by indirect callus regeneration with booster ZmPLT5 and KWS_RBP5.

| | | | | | | | | | |
|---|---|---|---|---|---|---|---|---|---|
| xxxx-T-001 | 23.969 | 9 bp deletion | 13.81 | 9 bp deletion | 11.44 | 10 bp deletion | 0 | wild type | square: 0.7586479701707 |
| xxxx-T-002 | 43.433 | 13 bp deletion | 24.378 | 9 bp deletion | 20.162 | 9 bp deletion | 0 | wild type | square: 0.9230283683580 |
| xxxx-T-003 | 31.135 | 6 bp deletion | 19.999 | 16 bp deletion | 19.607 | 16 bp deletion | 0 | wild type | square: 0.9161726174929 |
| xxxx-T-004 | 49.582 | 22 bp deletion | 34.499 | 7 bp deletion | 2.488 | 7 bp deletion | 0.012 | wild type | square: 0.9183147245080 |
| xxxx-T-005 | 39.686 | 13 bp deletion | 23.767 | 9 bp deletion | 23.598 | 9 bp deletion | 0 | wild type | square: 0.9194836171038 |
| xxxx-T-006 | 30.813 | 13 bp deletion | 19.897 | 9 bp deletion | 19.475 | 9 bp deletion | 0 | wild type | square: 0.9205654657684 |
| xxxx-T-007 | 43.88 | 13 bp deletion | 21.511 | 9 bp deletion | 20.344 | 9 bp deletion | 0 | wild type | square: 0.9081628415044 |
| xxxx-T-008 | 41.686 | 8 bp deletion | 33.357 | 5 bp deletion | 6.722 | 5 bp deletion | 0 | wild type | square: 0.9080586718376 |
| xxxx-T-009 | 29.83 | 6 bp deletion | 20.519 | 16 bp deletion | 18.98 | 16 bp deletion | 0 | wild type | square: 0.9119625939519 |
| xxxx-T-010 | 99.897 | wild type | 0.031 | 34 bp deletion | 0.026 | 34 bp deletion | ### | | square: 0.9999741786167 |
| xxxx-T-011 | 37.373 | 16 bp deletion | 32.891 | 6 bp deletion | 6.645 | 6 bp deletion | 0 | wild type | square: 0.9138174247368 |
| xxxx-T-012 | 31.977 | 6 bp deletion | 24.087 | 16 bp deletion | 22.677 | 16 bp deletion | 0 | wild type | square: 0.9068330392104 |
| xxxx-T-013 | 35.839 | 16 bp deletion | 30.809 | 6 bp deletion | 11.342 | 6 bp deletion | 0 | wild type | square: 0.9074834444915 |
| xxxx-T-014 | 47.815 | 13 bp deletion | 20.629 | 9 bp deletion | 18.797 | 9 bp deletion | 0 | wild type | square: 0.9178566734222 |
| xxxx-T-015 | 24.952 | 10 bp deletion | 23.092 | 9 bp deletion | 21.792 | 9 bp deletion | 0 | wild type | square: 0.8641021002026 |
| xxxx-T-016 | 32.205 | 9 bp deletion | 26.368 | 10 bp deletion | 14.677 | 9 bp deletion | 0 | wild type | square: 0.8690421762185 |
| xxxx-T-017 | 27.035 | 9 bp deletion | 25.743 | 10 bp deletion | 21.271 | 9 bp deletion | 0 | wild type | square: 0.8754330458572 |
| xxxx-T-018 | 44.017 | 13 bp deletion | 23.208 | 9 bp deletion | 19.782 | 9 bp deletion | 0 | wild type | square: 0.9199708107525 |
| xxxx-T-019 | 42.385 | 13 bp deletion | 25.056 | 9 bp deletion | 18.738 | 9 bp deletion | 0 | wild type | square: 0.9152609509911 |
| xxxx-T-020 | 29.088 | 6 bp deletion | 23.886 | 16 bp deletion | 23.577 | 16 bp deletion | 0 | wild type | square: 0.9015976483997 |

TABLE 7-continued

Sanger sequencing trace decomposition analysis of genome editing events in 34 regenerated T0 plantlets from a 28-day-old A188 immature tassel by indirect callus regeneration with booster ZmPLT5 and KWS_RBP5.

| | | | | | | | | | |
|---|---|---|---|---|---|---|---|---|---|
| xxxx-T-021 | 33.19 | 6 bp deletion | 20.959 | 16 bp deletion | 20.191 | 16 bp deletion | 0 | wild type | square: 0.9104306231335 |
| xxxx-T-022 | 42.793 | 13 bp deletion | 23.076 | 9 bp deletion | 21.328 | 9 bp deletion | 0 | wild type | square: 0.9239473757704 |
| xxxx-T-023 | 99.989 | wild type | 0.007 | 9 bp Insertion | 0 | 1 bp deletion | ### | | square: 0.9999545926710 |
| xxxx-T-024 | 43.415 | 13 bp deletion | 22.074 | 9 bp deletion | 21.891 | 9 bp deletion | 0 | wild type | square: 0.9194355944018 |
| xxxx-T-025 | 39.266 | 16 bp deletion | 29.938 | 6 bp deletion | 8.264 | 6 bp deletion | 0 | wild type | square: 0.8941856619070 |
| xxxx-T-026 | 46.506 | 22 bp deletion | 36.554 | 7 bp deletion | 1.953 | 16 bp deletion | 0.058 | wild type | square: 0.9098764137075 |
| xxxx-T-027 | 43.953 | 13 bp deletion | 22.223 | 9 bp deletion | 21.08 | 9 bp deletion | 0 | wild type | square: 0.9091420348440 |
| xxxx-T-028 | 99.815 | wild type | 0.05 | 1 bp Insertion | 0.03 | 1 bp deletion | ### | | square: 0.9999494100923 |
| xxxx-T-029 | 44.083 | 13 bp deletion | 22.959 | 9 bp deletion | 21.829 | 9 bp deletion | 0 | wild type | square: 0.9318512296710 |
| xxxx-T-030 | 34.515 | 16 bp deletion | 32.163 | 6 bp deletion | 6.941 | 16 bp deletion | 0 | wild type | square: 0.90705931481851 |
| xxxx-T-031 | 40.07 | 13 bp deletion | 25.796 | 9 bp deletion | 21.788 | 9 bp deletion | 0 | wild type | square: 0.91859146478582 |
| xxxx-T-032 | 99.891 | wild type | 0.026 | 10 bp deletion | 0.022 | 8 bp Insertion | ### | | square: 0.99995450726958 |
| xxxx-T-033 | 34.902 | 6 bp deletion | 20.418 | 16 bp deletion | 18.803 | 16 bp deletion | 0 | wild type | square: 0.91218703343041 |
| xxxx-T-034 | 38.469 | 16 bp deletion | 33.118 | 6 bp deletion | 8.426 | 6 bp deletion | 0 | wild type | square: 0.91801267185920 |

These results further demonstrate that the methods of the present invention by transient particle bombardment and indirect callus regeneration of the cells as part of preferably immature tassel are highly effective and efficient, and the methods are able to achieve single-cell origin regeneration and homogenous genome editing without a conventional selection in maize A188.

Example 7: Efficient Genome Editing by Transient Biolistic Transformation and Indirect Callus Regeneration with Regeneration Boosters from Immature Tassel of Maize Elites Five advanced inbred elites, including the most important pollen donor and female inbred lines, were tested for the regeneration and genome editing using the methods in the present invention via transient particle bombardment and indirect callus regeneration of the cells as part of preferably immature tassel. To this end, the elite seedlings at V7 stage, 27-30 days after planting, were harvested for immature tassel isolation.

Figure 14:
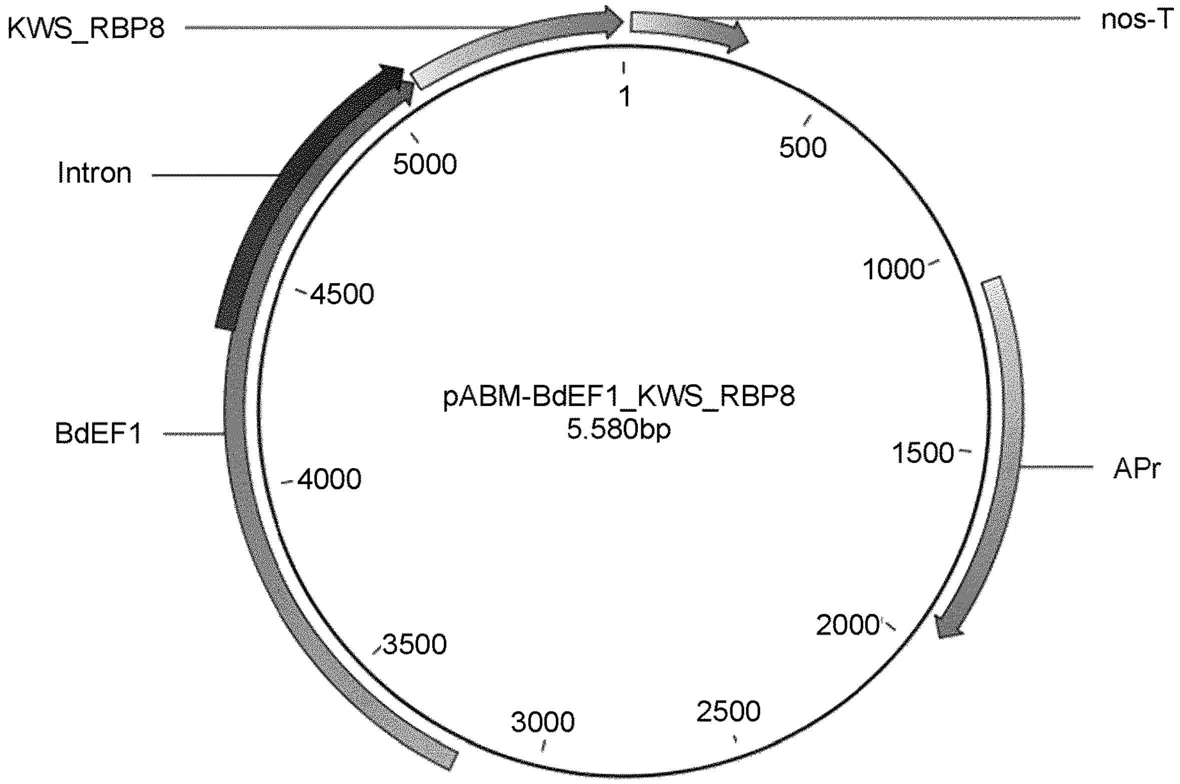
FIG. 14 shows the KWS_RBP8 expression construct pABM-BdEF1_RBP8 map. KWS_RBP8 is driven by the strong constitutive EF1 promoter from *Brachypodium* (pBdEF1).

The immature tassels were osmotically treated in N6_OSM medium for 4 hours before the bombardment. Construct pABM-BdEF1_KWS_RBP8 contains the regeneration KWS_RBP8 expression cassette (FIG. 14). For each bombardment, the two genome editing constructs (200 ng of plasmid DNA pGEP837 and 300 ng of plasmid DNA pGEP842) were co-coated with the two regeneration boost constructs (100 ng each of pABM-BdEF1_ZmPLT5 and pABM-BdEF1_KWS_RBP8) onto 100 μg of 0.6 μm gold particles using calcium-spermidine method. The four co-coated constructs were co-delivered into the maize elite immature tassel by the particle bombardment at 1,100 psi rupture pressure, 4 bombardment shots per sample plate. For more information about the bombardment Example 2. After 20 hours of post-bombardment osmotic treatment on the N6_OSM plate, the bombarded immature tassels were cut into a segment of 3-6 mm in length, with a sharp blade, and place onto a callus induction medium IMCIM2 petro dish plate (25×100 mm). Seal the plate with surgical tape and culture at 27° C., dark, for 3 weeks. For the following steps in the indirect callus regeneration procedure, see Example 6.

After one week development in the Rooting medium in phytotray, a 5-10 mm leaf tip from each of the leaves of the regenerated plantlets were collected for DNA extraction. Genome editing SDN-1 in the regenerated $T_0$ plants were screened using TaqMan Digital Droplet PCR.

The results of the regeneration rates and the genome editing SDN-1 efficiencies from the tested elites were presented in Table 8. Compared to the A188, all the elites were significantly less regenerative, however all the elites tested were indeed regenerative in using the methods of in the present invention. These results indicate the possibility of genotype-independent regeneration and genome editing using by using the methods of in the present invention; that, most importantly, the methods via transient particle bombardment and indirect callus regeneration are able to achieve single-cell origin regeneration and homogenous genome editing without a conventional selection (e.g. using an antibiotic or herbicide resistant gene) directly in maize elites.

TABLE 8

SDN-1 efficiency in the regenerated T0 plantlets from a 29-day-old immature tassel of the most important maize elites by the indirect callus regeneration with boosters ZmPLT5 and KWS_RBP8.

| Elite ID | No. tassels | No. Regenerated (regen.) | % regen. per tassel | No. Mono-SDN-1 | No. Bi-SDN-1 | Total SDN-1 | SDN-1% per regen. | SDN-1% per tassel |
|---|---|---|---|---|---|---|---|---|
| FPA19-71805 | 12 | 14 | 1.2/tassel | 3 | 0 | 3 | 21.4% | 25.0% |
| FUC18-62591 | 6 | 18 | 3.0/tassel | 2 | 3 | 5 | 27.8% | 83.3% |
| WS5-33063 | 12 | 26 | 2.2/tassel | 0 | 2 | 2 | 7.7% | 16.7% |
| PJ0-73631 | 10 | 63 | 6.3/tassel | 6 | 13 | 19 | 30.2% | 190% |
| MMS18-01495 | 7 | 7 | 1.0/tassel | 0 | 4 | 4 | 57.1% | 57.1% |

Example 8: Efficient Genome Editing by Transient Biolistic Transformation and Indirect Callus Regeneration with Regeneration Booster RBP8 from Immature Tassel of Maize Hybrids The F1 hybrids from the reciprocal crosses between A188 and elite 4V-40171 were tested with the methods in the present invention by transient particle bombardment and indirect callus regeneration of the cells as part of preferably immature tassel. The F1 seedlings at V7 stage, 28-29 days after planting, were harvested for immature tassel isolation.

Figure 15:
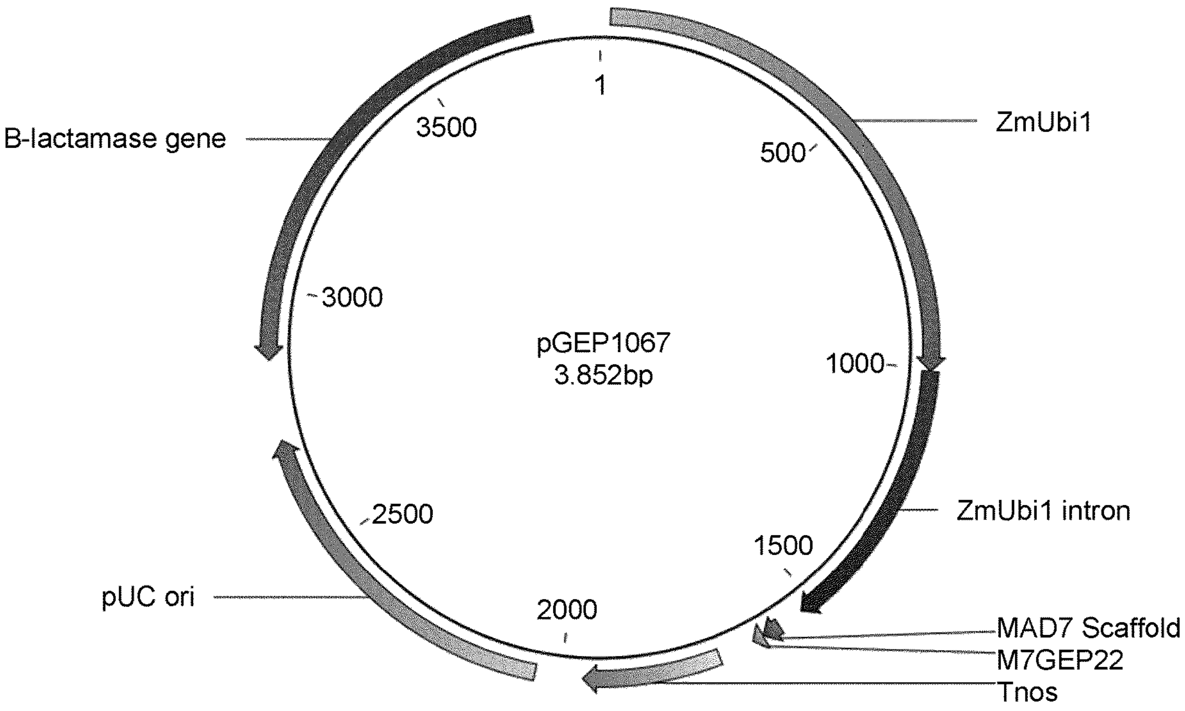
FIG. 15 shows the pGEP22 expression construct pGEP1067 map. m7GEP22 defines the crRNA, which target to the maize endogenous gene HMG13. ZmUbi1 defines the promoter and intron from maize Ubiquitin 1 gene. Tnos defines the nos terminator.

The immature tassels were osmotically treated in N6_OSM medium for 4 hours before the bombardment. Genome editing construct pGEP1067 harbors the sgRNA m7GEP22 expression cassette, which target to the maize endogenous gene HMG13 (FIG. 15). For each bombardment, the two genome editing constructs (200 ng of plasmid DNA pGEP837 and 300 ng of plasmid DNA pGEP1067) were co-coated with 100 ng of the regeneration boost construct pABM-BdEF1_KWS_RBP8 onto 100 μg of 0.6 μm gold particles using calcium-spermidine method. For more information about the bombardment, see Example 2 and Example 7. After 20 hours of post-bombardment osmotic treatment on the N6_OSM plate, the bombarded immature tassels were subjected to the indirect callus regeneration as described in Example 6 and Example 7.

After one week development in the Rooting medium in phytotray, a 5-10 mm leaf tip from each of the leaves of the regenerated plantlets were collected for DNA extraction. Genome editing SDN-1 in the regenerated $T_0$ plants were screened using TaqMan Digital Droplet PCR, and further confirmed by using Sanger sequencing with the genotype-specific primer (e.g. specifically amplifying the A188- or the elite-specific allele) to detect the SDN-1 in genotype-specific allele.

The regeneration rates and genome editing SDN-1 efficiencies from the hybrids are shown in Table 9.

TABLE 9

Genome editing SDN-1 at target pGEP22 (see FIG. 14) from the regenerated T0 plantlets from a 29-day-old immature tassels of maize F1 hybrids by the indirect callus regeneration with boosters KWS_RBP8.

| Genotype | No. tassels | No. Regen plantlets | % regen. | No. Mono-SDN-1 | No. Bi-SDN-1 | Total SDN-1 | SDN-1% per regen | SDN-1% per tassel |
|---|---|---|---|---|---|---|---|---|
| A188 × elite | 8 | 170 | 21.3/tassel | 8 | 14 | 22 | 12.9% | 2.75/tassel |
| elite × A188 | 4 | 41 | 10.3/tassel | 3 | 3 | 6 | 14.6% | 1.5/tassel |

Compared to the regeneration rates from A188 and the elite, the hybrids showed a regeneration capability in between, namely less regenerative than the A188, but more regenerative than the elite. Interestingly the immature tassels from the it seedlings derived from the cross with A188 as the female (A188×4V-40171) were significant more regenerative than those from the cross with the elite as the female. These results suggest maternal effect on plant regeneration.

Sanger sequencing with the genotype-specific primer provides an effective means to distinguish the allelic-specific SDN-1 events. The results shown in Table 10 imply that genome editing may be unbiased regarding allelic preference at the target site, and likely be allele genotype independent. The plant regeneration may be the bottleneck for plant genome modification in recalcitrant elites (Table 10).

TABLE 10

Single-cell origin SDN-1 events in the regenerated T0 plantlets from immature tassels of maize F1 hybrids by the indirect callus regeneration with boosters KWS_RBP8 identified via ddPCR and Sanger sequencing analyses of SDN-1.

| Regenerated Events | Genotype | SDN-1 via Sanger Sequencing A188 | SDN-1 via Sanger Sequencing 5F | SDN-1 % via ddPCR |
|---|---|---|---|---|
| xxx010-T-253 | F1, elite × A188 | 3 bp Deletion | WT | 49.5 |
| xxx010-T-296 | F1, elite × A188 | 8 bp deletion | 3 bp Deletion | 99.9 |
| xxx015-T-051 | F1, A188 × elite | WT | 9 bp Deletion | 49.6 |
| xxx015-T-053 | F1, A188 × elite | 9 bp Deletion | WT | 50.9 |
| xxx015-T-067 | F1, A188 × elite | WT | 7 bp deletion | 48.7 |
| xxx015-T-081 | F1, A188 × elite | 7 bp deletion | WT | 46.2 |
| xxx016-T-037 | F1, elite × A188 | 5 bp deletion | WT | 33.8 |
| xxx016-T-051 | F1, elite × A188 | 7 bp deletion | 6 bp deletion | 93 |
| xxx016-T-081 | F1, elite × A188 | 10 bp deletion | 6 bp deletion | 100 |
| xxx012-T-152 | F1, elite × A188 | 8 bp insertion | 18 bp deletion | 99.9 |
| xxx012-T-158 | F1, elite × A188 | 8 bp deletion | 10 bp deletion | 100 |
| xxx012-T-171 | F1, elite × A188 | 8 bp deletion | 3 bp deletion | 100 |
| xxx012-T-189 | F1, elite × A188 | 8 bp deletion | 10 bp deletion | 100 |

The molecular analysis using TaqMan Digital Droplet PCR and Sanger sequencing with the genotype-specific allelic primer provided solid evidences in support of that the methods in the present invention are able to achieve single-cell origin regeneration and homogenous genome editing without a conventional selection in maize.

Example 9: Stable Transformation Via Particle Bombardment and Indirect Regeneration of Immature Tassels from Maize Elites and Hybrid with a Regeneration Booster The construct pGEP1054 harbors florescence tdTomato gene expression cassette (FIG. 16) was used for monitoring the transformation without a conventional selection. The seedlings at V7 stage, 28-30 days after planting, were harvested for immature tassel isolation. For the information on the immature tassel preparation, again see Example 1.

The immature tassels were osmotically treated in N6_OSM medium for 4 hours before the bombardment. For each bombardment, 200 ng of plasmid DNA pGEP1054 and 100 ng of plasmid DNA pABM-BdEF1_KWS_RBP8 were co-coated onto 100 μg of 0.6 μm gold particles using calcium-spermidine method. For more information about the bombardment, cf. Example 2, Example 6, and Example 7.

Figure 17:
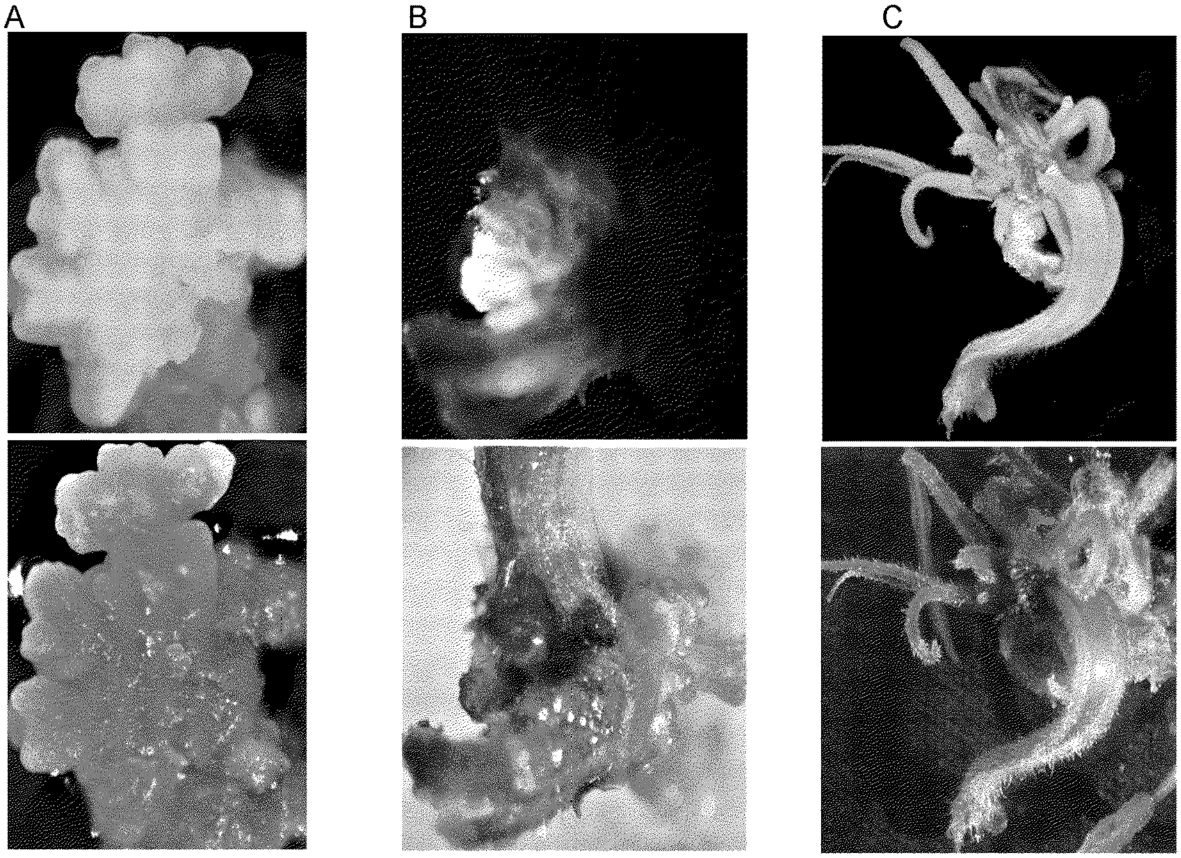
FIG. 17 shows representative images showing stable transformation of the fluorescent report gene tDTomato in corn elites and F1 hybrids with boosters KWS_RBP8. (A): tDTomato expressing calluses indicating the stable transformation event(s) in corn elite MMS18-01495; (B): tDTomato expressing shoot buds indicating the stable transformation event(s) in corn elite PJ0-73631; (C): a tDTomato expressing plantlet indicating the stable transformation event (s) in corn F1 hybrid of elite 4V-40171 (♀)×A188 (♂). The fluorescent images shown at the top panel, while the corresponding bright-field images are shown at the bottom panel.

After 20 hours of post-bombardment osmotic treatment on the N6_OSM plate, the bombarded immature tassels were subjected to the callus induction at 27° C., dark, for 3 weeks (cf. Example 6 and Example 7). After 3 weeks of callus induction, the induced calluses were examined under a florescence microscope for tDTomato florescent signals. The tDTomato florescent calluses indicate foreign DNA integration and stable transformation of the tDTomato gene. The numbers of calluses showing tDTomato florescent signal were recorded and the results are summarized in Table 11. Some representative images showing stable transformation of the fluorescent report gene tDTomato in the regenerated structures are shown in FIG. 17.

These results demonstrate the feasibility of genotype-independent stable transformation via particle bombardment and regeneration of the cells as part of preferably immature tassels without a conventional selection.

TABLE 11

Stable transformation via particle bombardment and indirect regeneration of immature tassels from maize elites and hybrid with a regeneration.

| Genotype | No. tassels | No. Stable tDT events | Stable tDT events/per tassel |
|---|---|---|---|
| PJ0-73631 | 5 | 9 | 1.8/tassel |
| WS5-33063 | 8 | 7 | 0.875/tassel |
| MMS18-01495 | 5 | 4 | 0.8/tassel |
| F1 of 4V-40171 × A188 | 12 | 9 | 0.75/tassel |

Example 10: Biolistic Transformation of Immature Inflorescences from Wheat (*Triticum aestivum* L.) Cultivar Taifun

Wheat Plant Cultivation

Wheat (*Triticum aestivum* L.) cultivar Taifun were grown in a growth chamber. Two wheat Taifun seeds are planted into a deep inserts plug pot (placed into an 18-count holding tray without holes). After germination only one seedling per pot is kept.

The soil used was Berger 35% Bark. The seeds were germinated and grew in a growth chamber at constant 20° to 21° C., with light intensity of 400-600 μmol $m^{-2}$ $s^{-1}$ and 14 hours day length from September to April, and 16 hours day length from May to August. The humidity was 40%-60%. The wheat plants were fertilized three times a week with Jack's 15-16-17 peat lite at an E.C. of 1.0+the E.C. of the water. The plants were checked twice a day for watering needs and were watered from top as needed.

Wheat Immature Inflorescence (Spike) Isolation

The developmental stages of wheat immature inflorescences were determined using a Zeiss stereo microscope. When the first node of stem was visible the inflorescences of a wheat plant were defined to be in the DR (double ridge/spikelet meristem stage) stage. About 1 week later, the second node is usually emerging, floret meristem development begins, and the plant is in then in the FM (floret meristem) stage. After 5-7 more days, the third stem internode begins to elongate, and anther primordia become visible, and the plant is then in AM (anther primordium) stage and is ready to enter the booting stage.

Wheat immature inflorescences at the development stages of late double ridge (DR) to late anther meristem (AM) are used for the methods in the present invention. At these stages the wheat shoots are elongated with 1-3 visible nodes.

The wheat immature inflorescence isolation comprises the steps of:

1. Harvesting the wheat shoots at the right development stages from the base of the stalks (near to soil) and remove all the leaf blades;
2. (Optional) Rinsing the stem segments with tap water, and dry with paper towel;
3. Surface spraying the shoots with 70% ethanol, and manually removing the first leaf sheath from stalk in a laminar hood;
4. Repeating step 3, and carefully removing each leaf sheaths from stalk, one by one from the bottom to top, until the flag leaf sheath;
5. Trimming the stalk segments and spraying with 70% ethanol (the last ethanol spray);
6. Transferring the segments onto a clear petri dish in the hood;
7. Under a dissection microscope: carefully removing the flag leaf sheath, and all of immature bracts, for providing an immature inflorescence/spike is ready for transformation.

Microparticle Bombardment

Freshly isolated wheat immature spikes were osmotically treated in N6OSM medium for 2-4 hours, as also detailed in Example 2. Three plasmids were co-bombarded, which were: construct GEMT121 (SEQ ID NO: 50) that contains the expression cassettes of the fluorescent report gene tDTomato and CRISPR nuclease LbCpf1 (FIG. 18), GEMT099 (SEQ ID NO: 51) that harbors the expression cassette of CRISPR sgRNA crGEP289 targeting to wheat CPL3 (C-terminal domain phosphatase-like 3) gene (FIG. 19), and construct pABM-BdEF1_KWS_RBP8 (SEQ ID NO: 42) that encloses boost gene KWS_RBP8 expression cassette (FIG. 14). Specifically, 200 ng of plasmid DNA GEMT121, 300 ng of plasmid DNA GEMT099, and 100 ng of pABM-BdEF1_KWS_RBP8, were co-coated onto 100 μg of 0.6 μm gold particles using calcium-spermidine method, and the three constructs were co-delivered into the cells of wheat immature inflorescence meristem by particle bombardment at 900 psi rupture pressure. Two-row spikes of wheat Taifun immature inflorescence were arranged vertically with one-row side inserted onto the osmotic N6OSM medium. Totally six bombardment shots per sample plate were conducted (3 shots per each row-side of the spikes). After bombardment, wheat Taifun immature spikes were kept on the osmotic N6OSM plate flatly for another 16-20 hours, and then the bombarded spikes were cut into 2-5 mm segments and transferred onto an indirect callus regeneration medium, e.g. N6_5Ag for callus induction at 27° C., dark, for 3 weeks. For details, see Example 6, Example 7, and Example 9.

Figure 20:
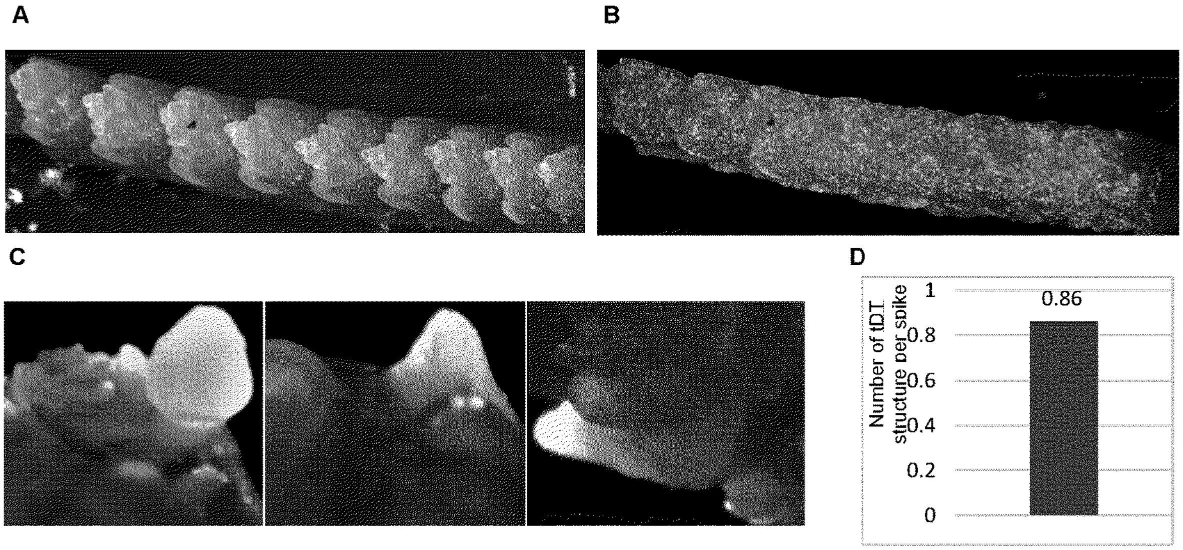
FIG. 20 shows tDTomato fluorescent images of the immature inflorescences from wheat (*Triticum aestivum* L.) cultivar (Taifun) after co-bombardment with plasmid GEMT121 (FIG. 18) and GEMT099 (FIG. 19). Bright field image (A) or tDTomato fluorescent image (B) of wheat immature inflorescence 16 hours after bombardment; (C): tDTomato fluorescent images of wheat immature inflorescences cultured in embryogenic callus induction medium for 3 days; (D): The number of tDTomato positive structures per immature inflorescence initially used.

Biolistic transformation efficiency was monitored by observing the fluorescence tDTomato expression under a microscope 16-20 hours after bombardment. Efficient transformation of the tDTomato in the cells from wheat immature spike was demonstrated, as shown in FIG. 20B.

tDTomato florescent signals in the bombarded immature spike were monitored under a florescence microscope along the callus induction process. Strong and constant tDTomato florescent signals from the growing tips of the bombarded spikelet appeared 3 days after bombardment, indicating stable transformation of the tDTomato gene. The representative results are shown FIG. 20C. The numbers of tDTomato florescent growing structure were presented in FIG. 20D.

These results demonstrate the feasibility of the present methods for rapid and efficient genome modification in wheat.

Example 11: Efficient genome editing by transient biolistic transformation and indirect callus regeneration from wheat immature spike After 16-20 hours of post-bombardment osmotic treatment on the N6_OSM plate, the bombarded wheat immature tassels were subjected to the indirect callus regeneration as detailed in Example 6 and Example 7.

After one week of development in the Rooting medium in phytotray, a 5-10 mm leaf tip from each of the leaves of the regenerated plantlets was collected for DNA extraction. Genome editing SDN-1 in the regenerated $T_0$ wheat plants were screened using TaqMan Digital Droplet PCR, and further confirmed by Sanger sequencing.

Example 12: Biolistic transformation of immature inflorescences from sunflower (*Helianthus annuus*) cultivar velvet Queen Sunflower Plant Cultivation:

Sunflower (*Helianthus annuus*) cultivar velvet Queen were grown in a growth house. Two sunflower velvet Queen seeds were planted into a deep inserts plug pot (placed into an 18-count holding tray without holes). After germination only one seedling per pot was kept.

The soil used was MetroMix360/Turface 3:1 blend. The seeds were germinated and grown in a growth chamber at 25° C. for day and 22° C. for night, light intensity of 400-600 $\mu mol\ m^{-2}\ s^{-1}$ and 14 hours day length, 50% humidity. Sunflower plants are fertilized at every watering using Jack's 15-5-15 Ca—Mg diluted to 150 ppm nitrogen. Plants were watered as needed.

Sunflower Development Stages:

1. Vegetative Emergence (VE): Seedling has emerged and the first leaf beyond the cotyledons is less than 4 cm long.
2. Vegetative stages (V): These are determined by counting the number of true leaves at least 4 cm in length beginning as V-1, V-2, V-3, V-4, etc.
3. Reproductive stage 1 (R1): The terminal bud forms a miniature floral head rather than a cluster of leaves. When viewed from directly above the immature bracts form a many-pointed star-like appearance.
4. Reproductive stage 2 (R2): The immature bud elongates 0.5 to 2.0 cm above the nearest leaf attached to the stem.
5. Reproductive stage 3 (R3): The immature bud elongates more than 2.0 cm above the nearest leaf
6. Reproductive stage 4 (R4): The inflorescence begins to open. When viewed from directly above immature ray flowers are visible.

Sunflower Immature Inflorescence (Head) Isolation:

Sunflower immature inflorescence head from the plants at R1 stages (FIG. 21A) were used. It most likely takes around 30-45 days to reach these stages for different genotypes after seed planting when cultured at the growth conditions described above. Sunflower immature inflorescence head isolation usually comprises the steps of 1. Harvesting the inflorescence head from sunflower plants at R1 stage by cutting the stem above the nearest leaf attached to;
2. (Optional) Rinsing the stalk segments with tap water, and dry with paper towel;

3. Surface spraying the stalk segments with 70% ethanol, and manually removing the leaves;
4. Trimming the stalk heads, carefully removing all remaining young leaves and spraying them with 70% ethanol
5. Transferring the heads onto a clear petri dish in the laminar hood;
6. Under a dissection microscope, carefully removing all bracts to expose the immature inflorescence head, so that the immature tassels are ready for transformation (FIG. 21B).

For bombardment method and fluorescence observation and imaging please see Example 2 and Example 10.

Example 13: Media

The following media were used for the above Examples. As it is known to the skilled person, variations to the media composition can be made depending on the target cells or tissues to be treated and depending on selection criteria. A variety of suitable media is available in the art for a given plant, cell, tissue, or organ to be treated and/or cultivated.

IM_OS: MS salt; LS vitamins; 1×FeEDTA; 100 mg/L casein; 0.5 mg/L kinetin; 30 g/L sucrose, 36.4 g/L of Mannitol, 36.4 g/L of sorbitol; 7 g/L of Gelzan; pH: 5.8.

N6OSM: N6 salts and vitamin, 100 mg/L of Caseine, 0.7 g/L of L-proline, 0.2 M Mannitol (36.4 g/L), 0.2 M sorbitol (36.4 g/L), 20 g/L sucrose, 15 g/L of Bacto-agar, pH 5.8.

IMSMK5: 1×MS salt, 1×KM vitamins, 1×FeEDTA, 1.25 mg/L CuSO4.5H2O, 1.0 g/L of KNO3, 2.0 mg/L Dicamba, 3.0 mg/L BAP, 0.5 mg/L Kinetin, 0.5 g/L of MES, 3% sucrose, 3 g/L Gelzan, pH: 5.8.

IMCIM2: MS salt, LS vitamins, 1.0 g/L of Proline, 5 mg/L Dicamba, 1.0 mg/L 2,4 D, 0.2 mg/L of BAP, 0.5 mg/L kinetin, 1.0 g/L of KNO3, 2.0 mg/L of AgNO3, 3% sucrose, 3 g/L gelrite, pH: 5.8. N6_5Ag: N6 salt and vitamin, 1.0 mg/L of 2, 4-D, 100 mg/L of Caseine, 2.9 g/L of L-proline, 20 g/L sucrose, 5 g/L of glucose, 5 mg/L of AgNO3, 8 g/L of Bacto-agar, pH 5.8.

Shooting medium: 1×MS salt, 1×LS vitamins, 1×FeEDTA, 2.5 mg/L CuSO4.5H2O, 100 mg/L Myo Inosit, 5 mg/L Zeatin, 0.5 g/L of MES, 20 g/L of sucrose, 3 g/L Gelzan, pH: 5.8.

Rooting medium: 1×MS salts, LS vitamins, 1×FeEDTA, 0.5 mg/L MES, 0.5 mg/L IBA, 1.25 mg/L of CuSO4, 20 g/L sucrose, 3 g/L Gelzan.

Example 14: Efficient Plant Regeneration from the Cross-Section Discs of Immature Tassel Center Spike in Corn A188

Tassel inflorescence consists of a symmetrical, many-rowed central axis (center spike) and several asymmetrical, two-ranked branches (branch tassels) (FIG. 3A). Compared to tassel branches, the center spike is relatively large and a major part of tassel inflorescence. However, it is also relatively challenging to obtain even distribution of gold particles in biolistic bombardment of the tassel center spike due to its cylinder shape. To better serve as an explant for biolistic transformation, a tassel center spike can be further cross-sectioned into thin discs for plant transformation and regeneration to increase utilization efficiency.

It is particularly important for some maize elites that the initiation and development of axillary branches are significantly behind that of the center spike, so that the immature tassels therefore consist almost solely of center spike when harvested. The use of cross-section discs of immature center spike is an efficient solution for such maize genotypes.

For information about immature tassel preparation, see examples 1A and 1B. After isolation, under aseptic condition, central tassels are laid onto Whitman filter paper saturated with 1×N6 buffer in a petri dish, quickly cross-sectioned into thin discs about 0.5 mm in depth with a sharp razorblade and transferred onto an osmotic medium plate (N6OSM) immediately for 4 hours of pre-bombardment osmotic treatment.

Figure 22:
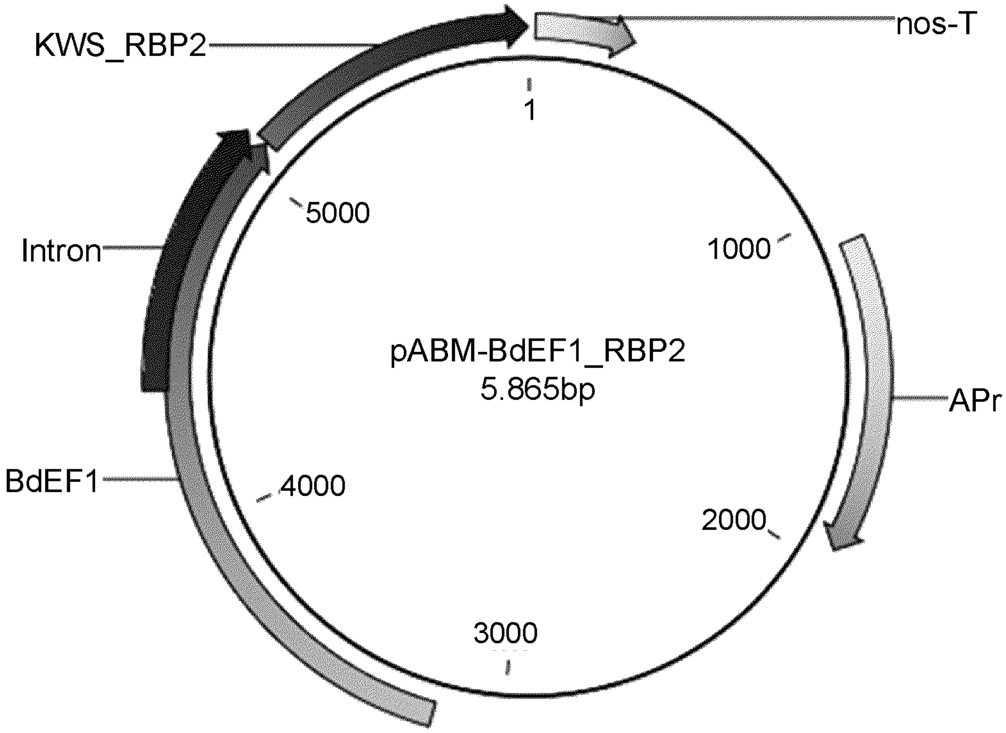
FIG. 22 shows KWS_RBP2 expression construct pABM-BdEF1_RBP2 map. KWS_RBP2 is driven by the strong constitutive EF1 promoter from *Brachypodium* (pBdEF1).

For information about biolistic bombardment and indirect callus regeneration, see examples 2 and 6, respectively. Specifically, 100 ng of plasmid pGEP1054 (containing the fluorescence report gene tDTomato expression cassette, FIG. 16) and 100 ng of pABM-BdEF1_KWS_RBP2 harboring the regeneration boost gene KWS_RBP2 expression cassette (FIG. 22) were co-coated onto 100 μg of 0.6 μm gold particles using the calcium-spermidine method. For more information about the bombardment, see example 2. After 18 hours of post-bombardment osmotic treatment on the N6OSM plate, the bombarded immature tassels were subjected to indirect callus regeneration as described in example 6 and 7.

Figure 23:
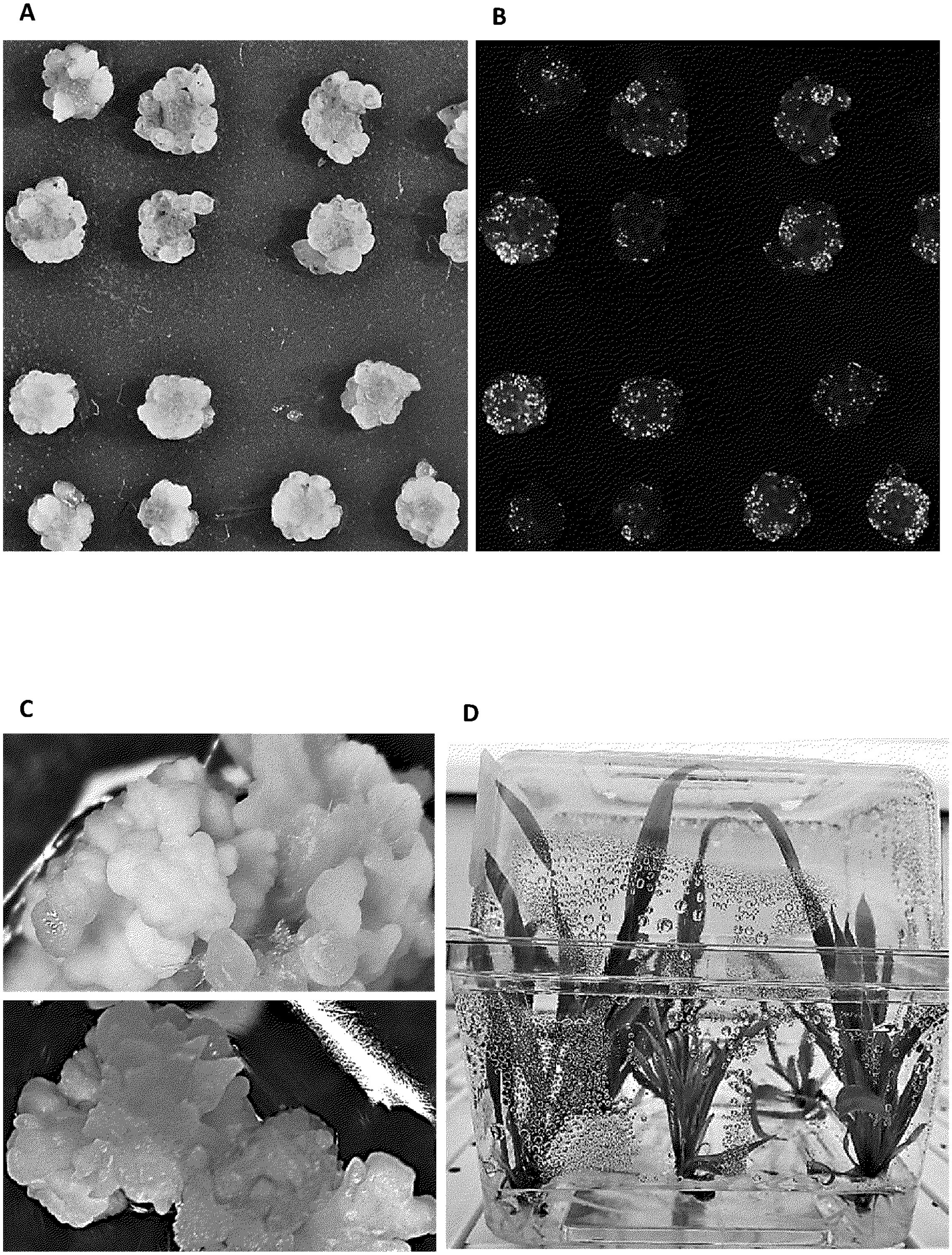
FIG. 23 shows biolistic transformation and plant regeneration from cross-section discs of immature center spike of maize A188. A bright field image (A) and a tDTomato fluorescence image (B) of the bombarded discs 16 hours after bombardment. (C) embryogenic calli were induced from the bombarded inflorescence discs 9 days in the callus induction medium. (D) TO plants 7 days in a maize germination phytotray.

FIG. 23 shows a representative experiment, where two central tassels were cross-sectioned into ~0.5 mm discs (FIG. 23 A), and from which 86 plants were regenerated. It's worth to note that the tDTomato fluorescence signals are mostly derived from the outer ring of discs that is collocated with the spikelet pair meristems (SPM) ring (FIG. 23 B). This result suggests that meristematic cells are suitable for biolistic bombardment.

Figure 16:
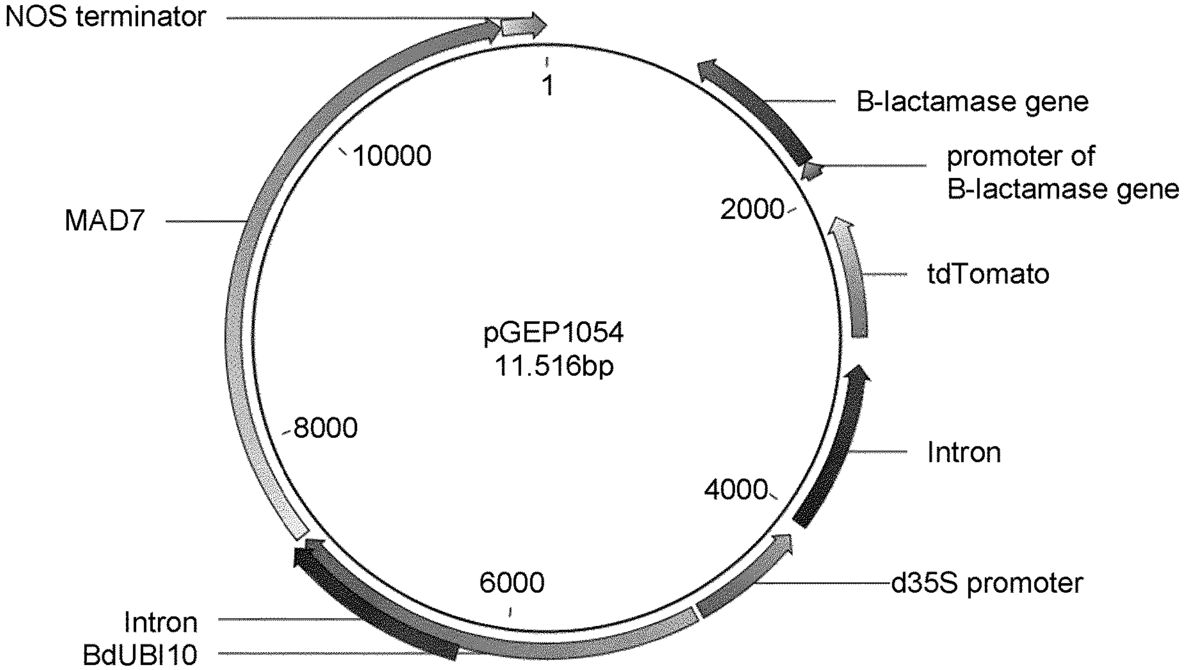
FIG. 16 shows the genome editing nuclease MAD7 expression construct pGEP1054 map. tdTomato defines tdTomato report gene. MAD7 defines the maize codon-optimized CDS of MAD7 nuclease (Inscripta). BdUBI10 defines the *Brachypodium Ubiquitin* 10 promoter. Tnos defines the nos terminator.

Example 15: Efficient Multiplex Genome Editing Via Co-Bombardment and Indirect Callus Regeneration A188 Immature Tassel For information about immature tassel preparation and particle bombardment, see examples 1 and 2. Specifically, co-bombardment consists of 7 plasmids as follows:

100 ng of genome editing construct pGEP1054 harboring CRISPR nuclease MAD7 nuclease expression cassette (FIG. 16)

150 ng each of five guide RNA constructs, which code five CRISPR guide RNA expression cassettes, and target to five locations in the maize target gene annotated as UV-B-insensitive 4-like gene (FIG. 29A).

Figure 24:
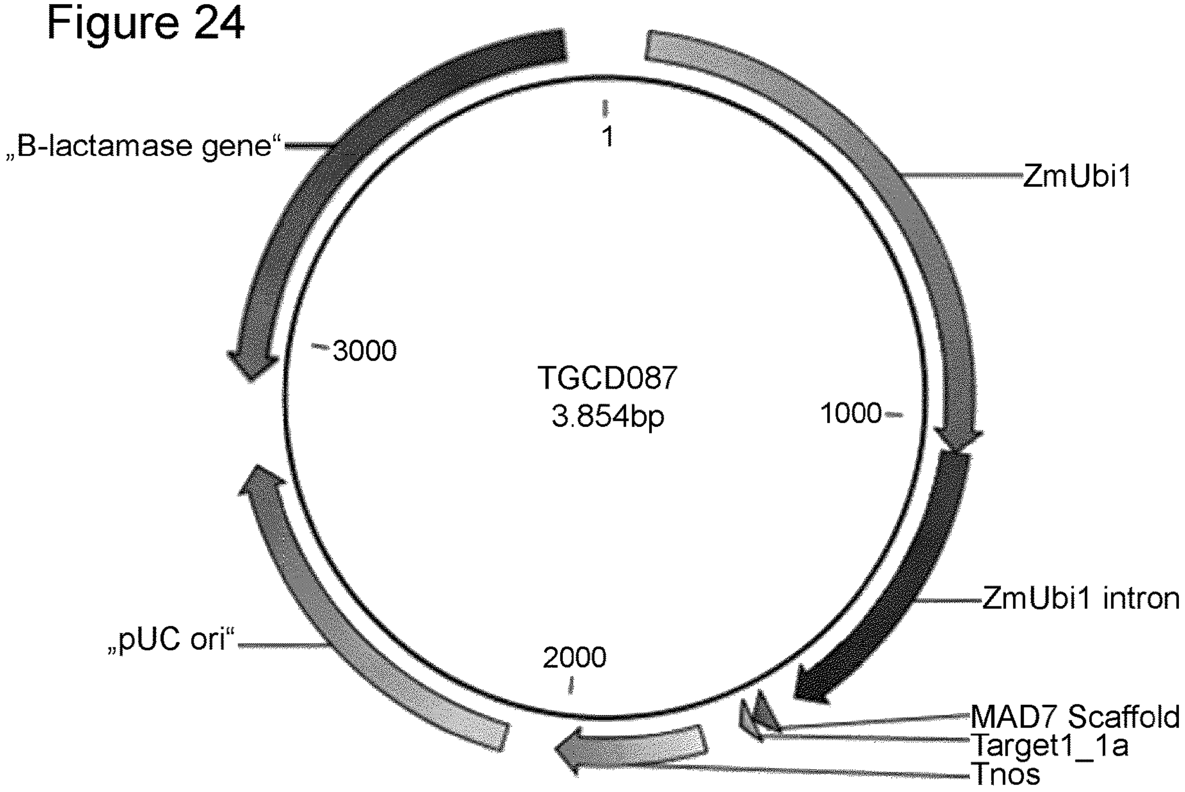
FIG. 24 shows a genome editing crRNA construct TGCD087 map. Target1_1a defines the crRNA, which target to a maize gene annotated as UV-B-insensitive 4-like gene at target 1. ZmUbi1 defines the promoter and intron from maize Ubiquitin 1 gene. Tnos defines the nos terminator.
Figure 25:
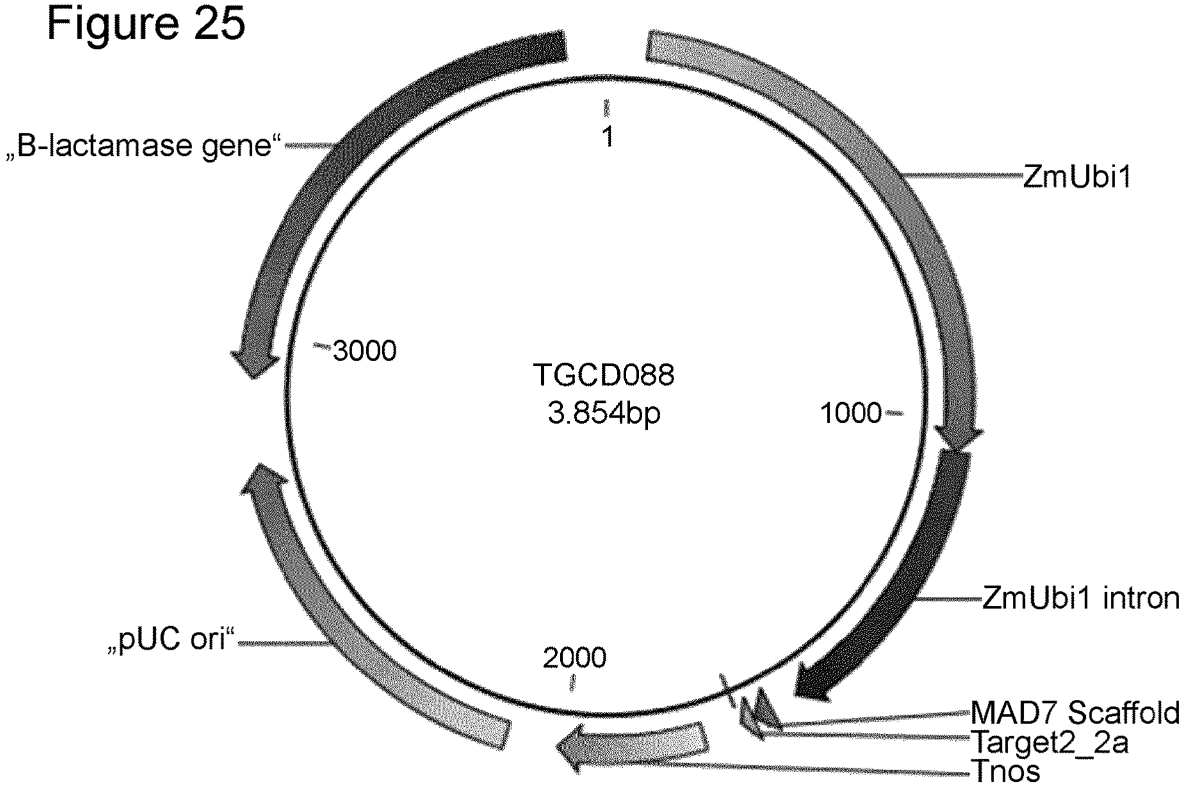
FIG. 25 shows a genome editing crRNA construct TGCD088 map. Target2_2a defines the crRNA, which target to a maize gene annotated as UV-B-insensitive 4-like gene at target 2. ZmUbi1 defines the promoter and intron from maize Ubiquitin 1 gene. Tnos defines the nos terminator.
Figure 26:
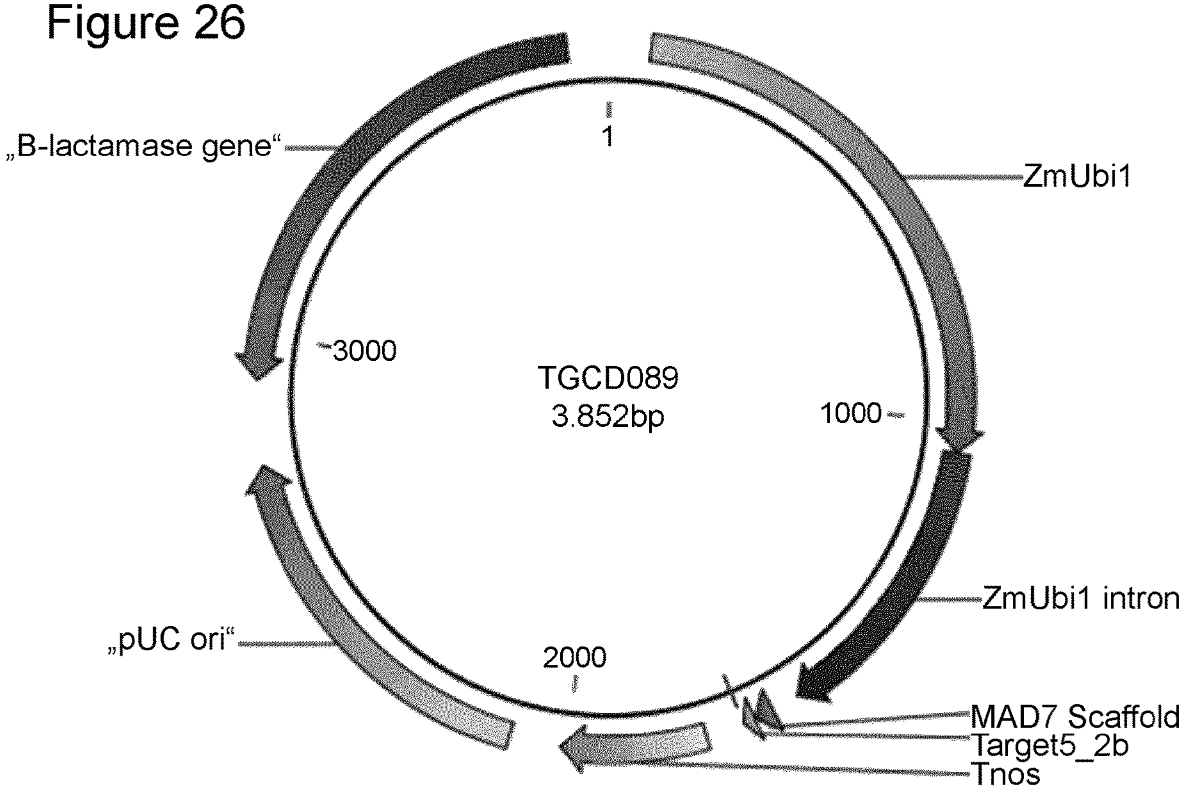
FIG. 26 shows a genome editing crRNA construct TGCD089 map. Target5_2b defines the crRNA, which target to a maize gene annotated as UV-B-insensitive 4-like gene at target 5. ZmUbi1 defines the promoter and intron from maize Ubiquitin 1 gene. Tnos defines the nos terminator.
Figure 27:
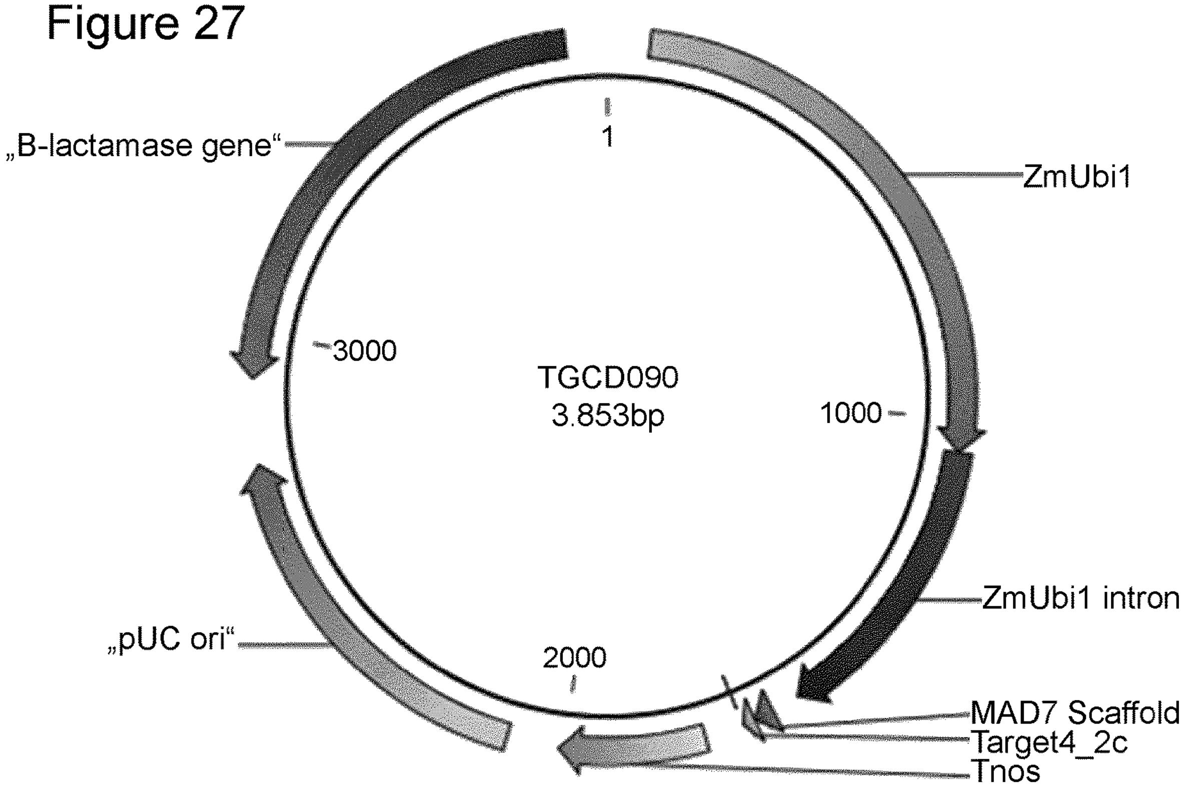
FIG. 27 shows a genome editing crRNA construct TGCD090 map. Target4_2c defines the crRNA, which target to a maize gene annotated as UV-B-insensitive 4-like gene at target 4. ZmUbi1 defines the promoter and intron from maize Ubiquitin 1 gene. Tnos defines the nos terminator.
Figure 28:
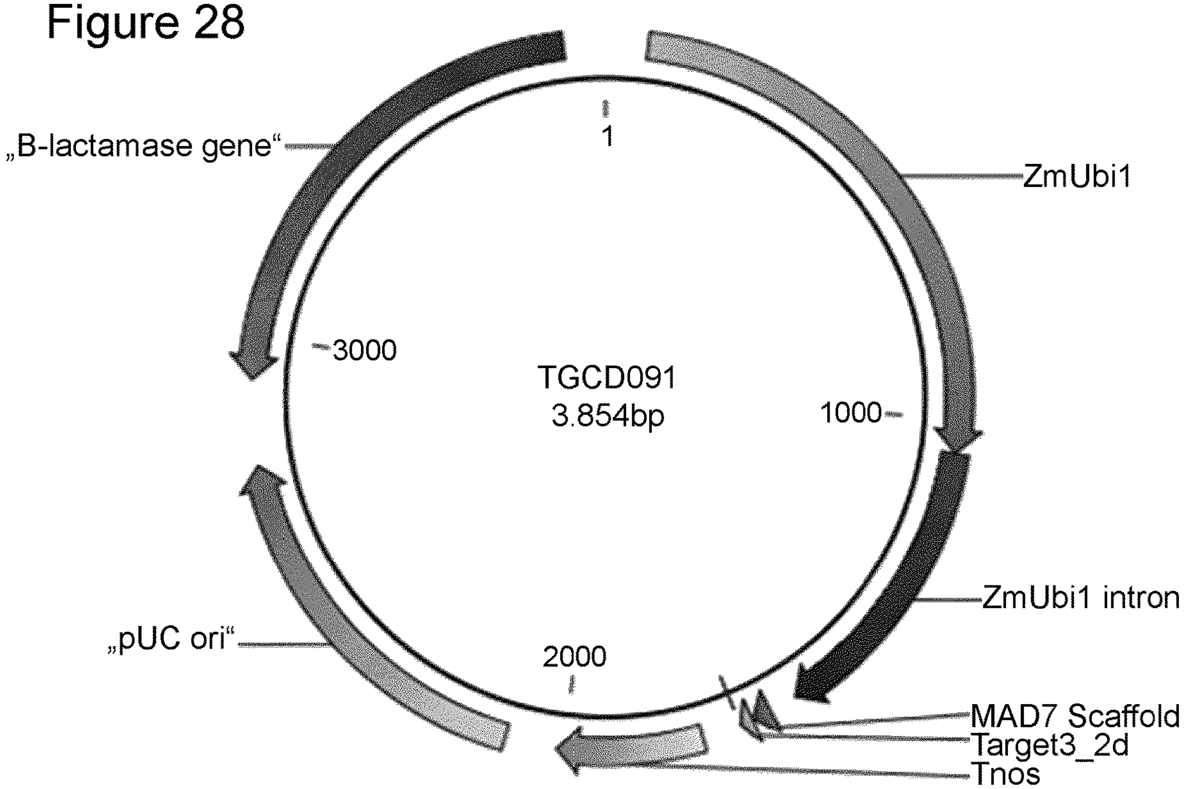
FIG. 28 shows a genome editing crRNA construct TGCD091 map. Target3_2d defines the crRNA, which target to a maize gene annotated as UV-B-insensitive 4-like gene at target 3. ZmUbi1 defines the promoter and intron from maize Ubiquitin 1 gene. Tnos defines the nos terminator.

TGCD087 (FIG. 24), coding the Target 1 guide RNA
TGCD088 (FIG. 25), coding the Target 2 guide RNA
TGCD089 (FIG. 26), coding the Target 5 guide RNA
TGCD090 (FIG. 27) coding the Target 4 guide RNA
TGCG091 (FIG. 28), coding the Target 3 guide RNA 100 ng of pABM-BdEF1_KWS_RBP2 harboring the regeneration boost gene KWS_RBP2 expression cassette.

For each co-bombardment, seven of the above-mentioned plasmids (pGEP1054, TGCG087 to TGCD091, and pABM-BdEF1_KWS_RBP2) were co-coated onto 100 μg of 0.6 μm gold particles using the calcium-spermidine method. For more information about the bombardment, see example 2. After 18 hours of post-bombardment osmotic treatment on the N6OSM plate, bombarded immature tassels were subjected to indirect callus regeneration as described in example 6 and 7.

140 T0 plants were regenerated. After one week of development in the rooting medium in phytotray, a 5-10 mm leaf tip from each of the regenerated plant leaves were collected for DNA extraction. Genome editing SDN-1 in the regenerated TO plants were screened by Sanger sequencing and sequencing trace decomposition analysis. Multiplex genome editing SDN-1 efficiency in the maize target gene from the TO regenerated A188 plants are summarized in FIG. 29 B. 14.3% of the TO plants have a bi-allelic SDN-1 modification at all the five target sequences. These results further demonstrate that the methods of the present invention by transient biolistic co-bombardment and indirect callus regeneration of cells as part of preferably immature tassel is highly effective and efficient, and the methods are able to achieve highly efficient genome editing in multiple locations simultaneously.

The invention claimed is:

1. A method for targeted modification of at least one genomic target sequence in a plant genome, for obtaining a modification of at least one plant immature inflorescence meristem cell, wherein the method comprises the following steps:

(a) providing at least one immature inflorescence meristem cell;

(b) introducing into the at least one immature inflorescence meristem cell:

(i) at least one genome editing system comprising at least one nucleic acid guided nuclease, nickase or an inactivated nuclease, or a sequence encoding the same, and optionally at least one guide molecule, or a sequence encoding the same;

(ii) at least one regeneration booster, or a sequence encoding the same wherein steps (i) and (ii) take place simultaneously, or subsequently, for promoting plant cell proliferation and/or to assist in a targeted modification of at least one genomic target sequence; and (iii) optionally at least one repair template, or a sequence encoding the same; and (c) cultivating the at least one immature inflorescence meristem cell under conditions allowing the expression and/or assembly of the at least one genome editing system and the at least one regeneration booster, the at least one guide molecule, and/or the at least one repair template; and (d) obtaining at least one modified immature inflorescence meristem cell; or (e) obtaining at least one plant tissue, organ, plant, or seed regenerated from the at least one modified immature inflorescence meristem cell; and (f) optionally screening for at least one plant tissue, organ, plant or seed regenerated from the at least one modified immature inflorescence meristem cell in the T0 and/or T1 generation carrying a desired targeted modification, wherein the at least one regeneration booster comprises at least one regeneration booster protein (RBP), or a regeneration booster gene (RBG) sequence encoding the at least one RBP, wherein the at least one RBP has the amino acid sequence of SEQ ID NO: 19, or wherein the at least one RBP is encoded by at least one RBG sequence, the at least one RBG sequence having the nucleotide sequence of SEQ ID NO: 8, or a cognate codon-optimized sequence.

2. The method of claim 1, wherein the method comprises a regeneration step (e), and wherein the regeneration is direct meristem organogenesis, or indirect callus embryogenesis or organogenesis.

3. The method of claim 1, wherein at least one further regeneration booster is introduced, wherein the further regeneration booster, or the sequence encoding the same is selected from babyboom (BBM), WUSCHEL (WUS), WUSCHEL-related homeobox (WOX), RWP-RK domain (RKD), growth-regulating factor (GRF), and leafy cotyledon (LEC).

4. The method of claim 3, wherein the further regeneration booster comprises at least one RBG or PLETHORA (PLT) amino acid sequence, or the nucleotide sequence encoding the same, and wherein the further regeneration booster further comprises:

(i) at least one further RBG and/or PLT sequence, or the sequence encoding the same, and/or (ii) at least one BBM sequence, or the sequence encoding the same, and/or (iii) at least one WOX sequence, or the sequence encoding the same, and/or (iv) at least one RKD sequence, or the sequence encoding the same, and/or (v) at least one GRF sequence, or the sequence encoding the same, and/or (vi) at least one LEC sequence, or the sequence encoding the same, as at least one second regeneration booster, or sequence encoding the same, different to the further regeneration booster.

5. The method of claim 1, wherein the at least one genome editing system and the at least one regeneration booster, or the sequences encoding the same, are introduced into the cell by transformation or transfection mediated by biolistic bombardment, *Agrobacterium*-mediated transformation, micro- or nanoparticle delivery, or by chemical transfection, or a combination thereof, wherein the at least one genome editing system, and the at least one regeneration booster are introduced by biolistic bombardment, wherein the biolistic bombardment comprises a step of osmotic treatment before and/or after bombardment, or wherein the at least one immature inflorescence meristem cell provided in step (a) of claim 1 originates from a cross-section of a spike.

6. The method of claim 1, wherein at least one nucleic acid guided nuclease, nickase or an inactivated nuclease, or a sequence encoding the same, is introduced and is selected from the group consisting of a CRISPR/Cas system, a CRISPR/MAD7 system, a CRISPR/Cfp1 system, a CRISPR/MAD2 system, a CRISPR/Cas9 system, a CRISPR/CasX system, a CRISPR/CasY system, a CRISPR/Cas13 system, or a CRISPR/Csm system, a zinc finger nuclease system, a transcription activator-like nuclease system, and a meganuclease system.

7. The method of claim 1, wherein at least one genome editing system is introduced, wherein the at least one genome editing system further comprises at least one reverse transcriptase and/or at least one cytidine or adenine deaminase, wherein the at least one cytidine or adenine deaminase is independently selected from an apolipoprotein B mRNA-editing complex (APOBEC) family deaminase, an activation-induced cytidine deaminase (AID), an ACF1/ASE deaminase, an ADAT family deaminase, an ADAR2 deaminase, a PmCDA1 deaminase, a TadA derived deaminase, a transposon, and a sequence encoding the aforementioned at least one enzyme.

8. The method of claim 1, wherein the at least one genome editing system further comprises at least one repair template, and wherein the at least one repair template comprises or encodes a double- and/or single-stranded nucleic acid sequence.

9. The method of claim 8, wherein the at least one repair template comprises symmetric or asymmetric homology arms and/or wherein the at least one repair template comprises at least one chemically modified base and/or backbone.

10. The method of claim 1, wherein the at least one genome editing system, optionally the at least one regeneration booster, and optionally the at least one repair template, or the respective sequences encoding the same, are introduced transiently or stably, or as a combination thereof.

11. A plant cell, tissue, organ, plant or seed obtainable by or obtained by the method according to claim 1.

12. The plant cell, tissue, organ, plant or seed according to claim 11, wherein the plant is a monocotyledonous or a dicotyledonous plant.

13. The plant cell, tissue, organ, plant or seed according to claim 11, wherein the plant is a monocotyledonous plant selected from the group consisting of *Agrostis, Aira, Aegilops, Alopecurus, Ammophila, Anthoxanthum, Arrhenatherum, Avena, Beckmannia, Brachypodium, Bromus, Calamagrostis, Coix, Cortaderia, Cymbopogon, Cynodon, Dactylis, Deyeuxia, Deschampsia, Elymus, Elytrigia, Eremopyrum, Eremochloa, Festuca, Glyceria, Helictotrichon, Hordeum, Holcus, Koeleria, Leymus, Lolium, Melica, Muhlenbergia, Poa, Paspalum, Polypogon, Oryza, Panicum, Phragmites, Pryza, Puccinellia, Saccharum, Secale, Sesleria, Setaria, Sorghum, Stipa, Stenotaphrum, Trisetum, Triticum, Zea, Zizania, Zoysia, Brassica, Helianthus*, and *Beta*.

14. An expression construct assembly, comprising (i) at least one vector encoding at least one nucleic acid guided nuclease, nickase or an inactivated nuclease of the genome editing system as defined in claim 8, and (ii) at least one vector encoding at least one regeneration booster, wherein the at least one regeneration booster comprises at least one RBP, or an RBG sequence encoding the at least one RBP, wherein the at least one RBP has the amino acid sequence of SEQ ID NO: 19, or wherein the at least one RBP is encoded by at least one RBG sequence, the at least one RBG sequence having the nucleotide sequence of SEQ ID NO: 8, or a cognate codon-optimized sequence, and (iii) optionally at least one vector encoding at least one guide molecule guiding the at least one nucleic acid guided nuclease, nickase or an inactivated nuclease to the at least one genomic target site of interest; and (iv) optionally at least one vector encoding at least one repair template;

wherein (i), (ii), (iii), and/or (iv) are encoded on the same, or on different vectors.

15. The expression construct assembly of claim 14, wherein the assembly further comprises a vector encoding at least one marker.

16. An isolated nucleic acid sequence encoding a regeneration booster polypeptide, wherein the nucleic acid sequence comprises the nucleic acid sequence of SEQ ID NO: 8, or a nucleic acid sequence encoding a polypeptide comprises the polypeptide sequence of SEQ ID NO: 19, wherein the isolated nucleic acid sequence is operably linked to a heterologous promoter.

17. A recombinant gene comprising the nucleic acid sequence of claim 16.

18. The recombinant gene of claim 17, wherein the gene is operably linked to a promoter driving expression of the gene in a plant cell of interest.

19. A plant cell comprising the expression construct assembly of claim 14, or comprising a recombinant gene comprising the regeneration booster, or comprising an expression cassette or an expression construct comprising the regeneration booster.

20. A plant tissue, organ, whole plant, or a part thereof or a seed comprising the plant cell of claim 19.

* * * * *

SEQUENCE LISTING

```
<160> NUMBER OF SEQ ID NOS: 61

<210> SEQ ID NO 1
<211> LENGTH: 783
<212> TYPE: DNA
<213> ORGANISM: Artificial Sequence
<220> FEATURE:
<223> OTHER INFORMATION: RBG1 CDS seq

<400> SEQUENCE: 1

atggagtcgg gctccgggac ggctgctggc tctggctatg tttacagaca gccaggatca     60

acgcggtgga acccgacagc tgaacaactg tccttgctta gagaaatcta ctaccgcaac    120

ggattgcgga ccccgaccgc ggacgaaatc agacaaatca gctcaaagct ctcaaggtac    180

ggaaaaatag agggcaaaaa cgtttacaac tggttccaga atagacgcgc aagagaaaag    240

cgcaagcaac ggctctctac aatcggctgt gatccagcac tgatcgagat ggggaatgtc    300

gcttcactgg aattcggtac tgagagcgcc ctggaatcgc tgtcgtcagg accatcctca    360

gaactccgcg aagcgccaac gagaaaattt tacgaaaaaa agacggttgg agagaactca    420

actataataa acccagtgga acaaaactgt accctttcct gcggaacgtc ccaagagttc    480

cagtatgcgg tcgattctcg gcgcgtcatg aaagctatgg aggaaaagca ggcgacggac    540

gatgaacccg acggaaataa atggactgag tcaaacagac acgtcaagat tctccagctt    600

ttcccgctcc acaataacga ggatcagaca ttgataaaga gcgacaaaga aatctattgt    660

ttgggctcgt gcgagaagaa aatggatttg tcaccgctgg gtcattcagg ctctcagcgc    720

gcttcggccc ttgacttgtg cctttcattg ggcaacgaat cttgtgggct gcatgataat    780

tga                                                                  783

<210> SEQ ID NO 2
<211> LENGTH: 783
<212> TYPE: DNA
<213> ORGANISM: Artificial Sequence
<220> FEATURE:
<223> OTHER INFORMATION: RBG2 CDS seq

<400> SEQUENCE: 2

atggaatcgg gctccggcac ggcggcaggg tctggttatg tctatcggca gagcggaagc     60

acccggtgga atccaacagc agaacagttg tcgctgctca aggaacttta ttaccggaat    120

ggaattcgga caccgtcggc agatcaaatt aggcaaattt cggcccggct gtccagatac    180

ggcaaaatag aagggaaaaa cgtcttttac tggtttcaaa atcataaagc acgggaacgg    240

cagaagaaaa gactttccac ggtcggctgc gaccctgctc tcatagaaat gggtaacgtc    300

gcgagcttgg aatttgggac cgaaagcgct cttgaatctc tcagctcagg cccgtccagc    360

gagttgcgcg aggctcctac ccgcaagttt tatgagaaga aaaccgttgg tgagaacagc    420

accataatca atcctgttga gcagaactgc acactttctt gcggtacttc gcaggaattt    480

cagtatgctg ttgatagccg ccgggtgatg aaggcaatgg aagagaagca agcaacggat    540

gatgaaccgg acggaaacaa atggacggag tcgaacaggc atgtgaagac cctccctctt    600

ttccccttgc ataataatga agatcagacc ttgatcaagt cggacaagga aatttattgc    660
```

cttgggagct gtgaaaaaaa aatggatctg tccccattgg gacactcggg ctctcagagg 720
gcgtcggcac tggatttgtg cctgtctttg ggtaatgaat cttgtggcct ccacgacaat 780
tga 783

<210> SEQ ID NO 3
<211> LENGTH: 477
<212> TYPE: DNA
<213> ORGANISM: Artificial Sequence
<220> FEATURE:
<223> OTHER INFORMATION: RBG3 CDS seq

<400> SEQUENCE: 3
atggttagca agggggagga ggttattaaa gaattcccag gaagcacccg gtggaatcca 60
acggcggagc aactttcgct ccttcgggaa atttattaca ggaatgggct gagaactccc 120
accgctgacg agatcagaca gatttcatca aaattgtcgc ggtatggtaa gattgaaggg 180
aaaaatgtgt acaactggtt ccagaacaga agagctaggg aaaagagaaa acagcggttg 240
tcaaccatag gctgtggttc ggcggggtcg gccgcaggga gcggagagtt tcgccatgtg 300
aagaccctgc cccttttccc tttgcataat aatgaggatt caggttcgtt ggatctggag 360
ctggaattgg gttttgcctc tgctaccgca gccgcgactt ctggttcaca aagggcgtcg 420
gcattggatc tctgcctgtc ccttggaaat gagtcatgcg gtttgcatga caactga 477

<210> SEQ ID NO 4
<211> LENGTH: 477
<212> TYPE: DNA
<213> ORGANISM: Artificial Sequence
<220> FEATURE:
<223> OTHER INFORMATION: RBG4 CDS seq

<400> SEQUENCE: 4
atggtctcga aaggagaaga ggtcatcaaa gaattttcag gcagcacccg ctggaatccg 60
actgcagaac aactttctct cctcaaagag ctttattaca gaaatgggat cagaacccct 120
tcagcggacc agatacgcca gataagcgcc cgcttgtcga ggtacggcaa aatcgagggg 180
aagaatgttt tttactggtt ccaaaaccat aaagcgaggg agcggcagaa gaaaagactg 240
agcactgtgg gttgtggatc ggcgggatcg gctgccgggt caggtgaatt tcgccatgtt 300
aaaacgcttc cactgtttcc cttgcataat aatgaagaca gcggatcact tgacctggag 360
ctggagttgg gcttcgcttc cgcgacggct gctgcaacat ccggctcgca gcgggcgtcg 420
gcgctggatt tgtgcctttc gctgggaaat gagagctgcg gtcttcatga caactga 477

<210> SEQ ID NO 5
<211> LENGTH: 501
<212> TYPE: DNA
<213> ORGANISM: Artificial Sequence
<220> FEATURE:
<223> OTHER INFORMATION: RBG5 CDS seq

<400> SEQUENCE: 5
atggtgtcta aaggggaaga ggtcataaaa gagttctcag gttctactcg ctggaatcca 60
actgcagaac aactctctct cctgaaggag ctctactatc ggaacggaat acgcacgcct 120
tcggcggacc aaataaggca gatttcagcc cgcctgtcta gatacgggaa aatcgaggga 180
aagaacgtgt tttattggtt ccaaaaccat aaggcaagag agcggcagaa aaaacggctc 240
agcacagtcg gctgtgggtc agccggttcg gcggctggct ctggtgaatt ccgccacgtc 300

```
aaaaccctgc ctctgttccc gctccacaat aatgtcgaga cacttccctt gttcccggag    360

gattccgggt ctctcgactt ggagctcgaa ttgggctttg cctctgccac tgcggcagcg    420

accagcggat cacagagagc ctccgcactg gatctgtgcc tgtcacttgg aaatgaatcg    480

tgcggattgc acgacaattg a                                              501


<210> SEQ ID NO 6
<211> LENGTH: 771
<212> TYPE: DNA
<213> ORGANISM: Artificial Sequence
<220> FEATURE:
<223> OTHER INFORMATION: RBG6 CDS seq

<400> SEQUENCE: 6

atggtgtcta aaggcgaaga ggtcattaag gagttcagcg gctctactag atggaatcca     60

acggccgagc aacttagcct gctcaaagaa ctctattatc gcaatgggat acgcacgccc    120

tctgcagatc agatacgcca aatctcagcg cgcctgtcca ggtatgggaa gattgagggt    180

aaaaacgtct tttactggtt ccaaaatcac aaagcgcgcg agagacagaa gaaaagactc    240

agcaccgttg gttgtgaccc tgctctcatc gagatgggga atgttgcttc cctggagttt    300

ggcacagaga gcgctttgga atcactctct tccggcccct caagcgaact cagagaggct    360

cccactcgga agttttacga gaaaaaaacc gtcggagaaa acagcacgat tatcaacccc    420

gtcgagcaga actgcaccct ctcatgcggc acgtcccagg agtttcagta cgccgtcgac    480

tcgaggagag tgatgaaggc gatggaggaa aagcaagcaa ctgacgacga gcccgacgga    540

aacaagtgga ctgaatccaa tcgccatgtt aaaacgttgc ctttgttccc gctccataac    600

aatgtggaga cgttgccact cttcccggag gactcgggat ctctggactt ggagctggaa    660

ctgggctttg cttcggctac cgcagcagcc acctcgggtt cccagagagc ctcggctctt    720

gatctctgcc tgtcactggg taacgaatct tgcggactgc acgataatta g             771


<210> SEQ ID NO 7
<211> LENGTH: 840
<212> TYPE: DNA
<213> ORGANISM: Artificial Sequence
<220> FEATURE:
<223> OTHER INFORMATION: RBG7 CDS seq

<400> SEQUENCE: 7

atggtttcaa agggggagga ggtcataaaa gaattttctg gcagcactag atggaatccg     60

actgctgagc agttgtctct cctcaaagaa ctttactata ggaacggtat ccgcactccg    120

tccgctgatc aaattcgcca aatttcggcc agactgtcca gatacgggaa aattgaggga    180

aaaaatgttt tctactggtt ccagaatcat aaggcgcgcg aaaggcagaa aaagagactt    240

tcgaccgtcg gatgtgaccc tgcacttatc gaaatgggca atgtcgcgtc gttggagttt    300

ggcaccgaat ccgctctcga atctcttagc tcgggcccct catcggaact cagagaggcc    360

cctaccagaa aattttatga gaaaaagaca gtgggagaga actctacaat cattaacccc    420

gtcgagcaga actgcacatt gagctgtgga acatcgcagg agtttcaata cgcggtggat    480

tcgcgccgcg ttatgaaggc aatggaggag aagcaggcaa cagatgatga gccagacggc    540

aataaatgga ccgaatctaa cagacatgtc aagacactgc cacttttccc tctccacaac    600

aatgtcgaga cactccctct gtttcccgag gattcgggaa gcctggatct tgagctggaa    660

cttggctttg catcaggtgg atctgccggg tcagttgaca cgctgccatt gtttcctaga    720

gaggctgcgg gttctgggga atttgccact gcggctgcga ctagcggatc acagcgcgca    780
```

tcggcgctcg acctctgcct ttctttgggt aacgagtctt gcggcctgca tgacaactga 840

<210> SEQ ID NO 8
<211> LENGTH: 498
<212> TYPE: DNA
<213> ORGANISM: Artificial Sequence
<220> FEATURE:
<223> OTHER INFORMATION: RBG8 CDS seq

<400> SEQUENCE: 8
atggtttcga agggggaaga agtcattaaa gagttttcag ggtctacgcg ctggaaccct 60
accgctgaac aagtcaaggt tttgagggaa atatattacc gcgcgggtct taggacgcca 120
tccgcggatc agatccgcca aatatcctca cagctgaaac ggtatggaaa ggtggaagga 180
aaaaacgtgt tttattggtt ccagaaccat aaagcgcggg aaagacaaaa aaagcggctc 240
agcaccgttg ggagcgctgg ctcagcagcg ggttcaggtg agttcaggca cgttaaaaca 300
ctgcccttgt tccctttgca caataatgaa gactcaggga gcggtttgga cttggatctg 360
aaccttgagt tgcgcctgtc ggcgactgct gctgccactt cgggctcaca gcgggcgtct 420
gccctcgatc tggacttgga gctcagactc ggtttcgcgc ttggtaatga gtcgtgtgga 480
ctgcacgaca actagtga 498

<210> SEQ ID NO 9
<211> LENGTH: 2040
<212> TYPE: DNA
<213> ORGANISM: Zea mays

<400> SEQUENCE: 9
atggcttcag cgaacaactg gctgggcttc tcgctctcgg gccaggataa cccgcagcct 60
aaccaggata gctcgcctgc cgccggtatc gacatctccg gcgccagcga cttctatggc 120
ctgcccacgc agcagggctc cgacgggcat ctcggcgtgc cgggcctgcg ggacgatcac 180
gcttcttatg gtatcatgga ggcctacaac agggttcctc aagaaaccca agattggaac 240
atgaggggct tggactacaa cggcggtggc tcggagctct cgatgcttgt ggggtccagc 300
ggcggcggcg ggggcaacgg caagagggcc gtggaagaca gcgagcccaa gctcgaagat 360
ttcctcggcg gcaactcgtt cgtctccgat caagatcagt ccggcggtta cctgttctct 420
ggagtcccga tagccagcag cgccaatagc aacagcggga gcaacaccat ggagctatcc 480
atgatcaaga cctggctacg gaacaaccag gtggcccagc cccagccgcc agctccacat 540
cagccgcagc ctgaggaaat gagcaccgac gccagcggca gcagctttgg atgctcggat 600
tcgatgggaa ggaacagcat ggtggcggct ggtgggagct cgcagagcct ggcgctctcg 660
atgagcacgg gctcgcacct gcccatggtt gtggccggcg gcagcgccag cggagcggcc 720
tcggagagca cgtcgtcgga gaacaagcga gcgagcggtg ccatggattc gcccggcagc 780
gcggtagaag ccgtaccgag gaagtccatc gacacgttcg ggcaaaggac ctctatatat 840
cgaggtgtaa caaggcatag atggacaggg cggtatgagg ctcatctatg ggataatagt 900
tgtagaagag aagggcagag tcgcaagggt aggcaagttt accttggtgg ctatgacaag 960
gaggacaagg cagcaagggc ttacgatttg gcagctctca agtattgggg cactacgaca 1020
acaacaaatt tccctataag caactacgaa aaggagctag aagaaatgaa acatatgact 1080
agacaggagt acattgcata cctaagaaga aatagcagtg gattttctcg tggggcgtca 1140
aagtatcgtg gagtaactag acatcatcag catgggagat ggcaagcaag gatagggaga 1200
gttgcaggaa acaaggatct ctacttgggc acattcagca ccgaggagga ggcggcggag 1260
gcctacgaca tcgccgcgat caagttccgc ggtctcaacg ccgtcaccaa cttcgacatg 1320
agccgctacg acgtgaagag catcctcgag agcagcacac tgcctgtcgg cggcgcggcc 1380
aggcgcctca aggacgccgt ggaccacgtg gaggccggcg ccactatctg gcgcgccgac 1440
atggacggcg ccgtgatctc ccagctggcc gaagccggga tgggcggcta cgcctcgtac 1500
ggccaccacg gctggccgac catcgcgttc cagcagccgt cgccgctctc cgtccactac 1560
ccgtacggcc agccgtcccg cgggtggtgc aaacccgagc aggacgcggc cgccgccgcg 1620
gcccacagcc tgcaggacct ccagcagctg cacctcggca gcgcggccca caacttcttc 1680
caggcgtcgt cgagctccac agtctacaac ggcggcgccg gcgccagtgg tgggtaccag 1740
ggcctcggtg gtggtagctc cttcctcatg ccgtcgagca ctgtcgtggc ggcggccgac 1800
caggggcaca gcagcacggc aaaccagggg agcacgtgca gctacgggga cgaccaccag 1860
gaggggaagc tcatcggtta cgacgccgcc atggtggcga ccgcagctgg tggagacccg 1920
tacgctgcgg cgaggaacgg gtaccagttc tcgcagggct cgggatccac ggtgagcatc 1980
gcgagggcga acgggtacgc taacaactgg agctctcctt tcaacaacgg catggggtga 2040

<210> SEQ ID NO 10
<211> LENGTH: 1485
<212> TYPE: DNA
<213> ORGANISM: Zea mays

<400> SEQUENCE: 10
atggacacct cgcaccacta tcatccatgg ctcaacttct ccctcgccca ccactgtgac 60
ctcgaggagg aggagagggg cgcggccgcc gagctggccg cgatagccgg cgccgcgccg 120
ccgccgaagc tggaggactt cctcggcgga ggcgtcgcca ccggtggtcc ggaggcggtg 180
gcgcccgcgg agatgtacga ctcggacctc aagttcatag ccgccgccgg gttccttggc 240
ggctcggcgg cggcggcggc gacgtcgccg ctgtcctccc tcgaccaggc cggttccaag 300
ctggccttgc ctgcggcggc ggctgctccg gcgccggagc agaggaaggc cgtcgactcc 360
tttgggcagc gcacgtccat ctaccgcggc gtcacacggc accggtggac tggcaggtac 420
gaggcacatc tgtgggacaa cagctgccga cgcgaagggc agagccgcaa gggccgccaa 480
gtatatttgg gtggctatga taaggaggag aaggctgcca gggcgtatga tcttgcagct 540
ttgaagtact ggggttctag caccaccacc aactttccgg ttgctgagta tgagaaggag 600
gtcgaggaga tgaagaacat gacgcgacaa gagtttgttg cttcccttcg aaggaagagc 660
agtggattct ctcggggtgc ttccatctac agaggtgtaa ccagacatca ccagcatgga 720
cggtggcagg cgaggatcgg aagggtggcc ggtaacaagg acctctacct tgggacgttc 780
agcaccgagg aggaagctgc agaggcctac gacatagcgg ccatcaagtt cagaggcctg 840
aacgccgtca caaacttcga gatcagccgg tacaacgtgg agaccataat gagcagcaac 900
cttccagtcg cgagcatgtc gtcgtcgtcg gcggcggcgg cgggtggccg gagcagcaag 960
gcgctggagt cccctccgtc cggctcgctt gacggcggcg gcggcatgcc agtcgtcgaa 1020
ggcagcacgg caccgccgct gttcattccg gtgaagtacg accagcagca gcaggagtac 1080
ctgtcgatgc tcgcgttgca gcaccaccac cagcagcaac aagcagggaa cctgttgcag 1140
gggccgctag tagggttcgg cggcctctac tcctccgggg tgaacctgga tttcgccaac 1200
tcccacggca cggcggctcc gtcgtcgatg gcccaccact gctacgccaa tggcaccgcg 1260
tccgcctcgc atgagcacca gcaccagcac cagatgcagc agggcggcga gaacgagacg 1320
cagccgcagc cgcagcagag ctccagcagc tgctcctccc tgccattcgc caccccggtc 1380
gctttcaatg ggtcctatga aagctccatc acggcggcag gcccctttgg atactcctac 1440
ccaaatgtgg cagcctttca gacgccgatc tatggaatgg aatga 1485

<210> SEQ ID NO 11
<211> LENGTH: 1470
<212> TYPE: DNA
<213> ORGANISM: Zea mays

<400> SEQUENCE: 11
atggacatgg acatgagctc agcttatccc caccattggc tctccttctc cctctccaac 60
aactaccacc atggcctact cgaggccttc tctaactcct ccggtactcc tcttggagac 120
gagccgggcg cagtggagga gtccccgagg acggtggagg acttcctcgg cggcgtcggt 180
ggcgccggcg ccccgccgca gccggcggct gctgcagatc aggatcacca gcttgtgtgc 240
ggcgagctgg gcagcatcac agccaggttc ttgcgccact acccggcggc gccagctggg 300
acgacggtgg agaaccccgg cgcggtgacc gtggcggcca tgtcgtcgac ggacgtggcg 360
ggggcggagt ccgaccaggc gaggcggccc gccgagacgt tcggccagcg cacatccatc 420
taccgtggcg tcaccaggca ccggtggaca gggagatatg aggcgcactt gtgggacaac 480
agctgccgcc gggagggcca aagccgcaaa ggacgccaag tctacctagg aggctatgac 540
aaggaggaga aggcggctag agcttacgac ctcgccgcgc tcaagtactg gggccctaca 600
accacgacca acttcccggt gtccaactac gagaaggagc tggaggagat gaagtccatg 660
acgcggcagg agttcatcgc gtcgttgcgc aggaagagca gcggcttctc acgaggcgcc 720
tccatctaca gaggagtcac aaggcatcat cagcacggcc ggtggcaggc gaggatcggc 780
agggtggccg gaaacaagga cctgtacttg ggcactttca gtactcagga agaggcggcg 840
gaggcgtacg acatcgctgc gatcaagttc cgcgggctca acgccgtcac caacttcgac 900
atgagccgct acgacgtgga gagcatcctc agcagcgacc tccccgtcgg gggcggagcc 960
accgggcgcg ccgccaagtt cccgttggac tcgctgcagc cggggagcgc tgctgcgatg 1020
atgctcgccg gggctgctgc cgcttcgcag gccaccatgc cgccgtccga gaaggactac 1080
tggtctctgc tcgccctgca ctaccagcag cagcaggagc aggagcggca gttcccggct 1140
tctgcttacg aggcttacgg ctccggcggc gtgaacgtgg acttcacgat gggcaccagt 1200
agcggcaaca acaacaacaa caccggcagc ggcgtcatgt ggggcgccac cactggtgca 1260
gtagtagtgg gacagcaaga cagcagcggc aagcagggca acggctatgc cagcaacatt 1320
ccttatgctg ctgctgctgc tatggtttct ggatctgctg gctacgaggg ctccaccggc 1380
gacaatggaa cctgggttac tacgactatt accagcagca acaccggcac ggctccccac 1440
tactacaact atctcttcgg gatggagtag 1470

<210> SEQ ID NO 12
<211> LENGTH: 260
<212> TYPE: PRT
<213> ORGANISM: Artificial Sequence
<220> FEATURE:
<223> OTHER INFORMATION: protein RBP1 encoded by synthesized SEQ ID NO: 1

<400> SEQUENCE: 12

Met Glu Ser Gly Ser Gly Thr Ala Ala Gly Ser Gly Tyr Val Tyr Arg
1 5 10 15

```
Gln Pro Gly Ser Thr Arg Trp Asn Pro Thr Ala Glu Gln Leu Ser Leu
            20                  25                  30

Leu Arg Glu Ile Tyr Tyr Arg Asn Gly Leu Arg Thr Pro Thr Ala Asp
        35                  40                  45

Glu Ile Arg Gln Ile Ser Ser Lys Leu Ser Arg Tyr Gly Lys Ile Glu
    50                  55                  60

Gly Lys Asn Val Tyr Asn Trp Phe Gln Asn Arg Arg Ala Arg Glu Lys
65                  70                  75                  80

Arg Lys Gln Arg Leu Ser Thr Ile Gly Cys Asp Pro Ala Leu Ile Glu
                85                  90                  95

Met Gly Asn Val Ala Ser Leu Glu Phe Gly Thr Glu Ser Ala Leu Glu
            100                 105                 110

Ser Leu Ser Ser Gly Pro Ser Ser Glu Leu Arg Glu Ala Pro Thr Arg
        115                 120                 125

Lys Phe Tyr Glu Lys Lys Thr Val Gly Glu Asn Ser Thr Ile Ile Asn
    130                 135                 140

Pro Val Glu Gln Asn Cys Thr Leu Ser Cys Gly Thr Ser Gln Glu Phe
145                 150                 155                 160

Gln Tyr Ala Val Asp Ser Arg Arg Val Met Lys Ala Met Glu Glu Lys
                165                 170                 175

Gln Ala Thr Asp Asp Glu Pro Asp Gly Asn Lys Trp Thr Glu Ser Asn
            180                 185                 190

Arg His Val Lys Ile Leu Gln Leu Phe Pro Leu His Asn Asn Glu Asp
        195                 200                 205

Gln Thr Leu Ile Lys Ser Asp Lys Glu Ile Tyr Cys Leu Gly Ser Cys
    210                 215                 220

Glu Lys Lys Met Asp Leu Ser Pro Leu Gly His Ser Gly Ser Gln Arg
225                 230                 235                 240

Ala Ser Ala Leu Asp Leu Cys Leu Ser Leu Gly Asn Glu Ser Cys Gly
                245                 250                 255

Leu His Asp Asn
            260


<210> SEQ ID NO 13
<211> LENGTH: 260
<212> TYPE: PRT
<213> ORGANISM: Artificial Sequence
<220> FEATURE:
<223> OTHER INFORMATION: protein RBP2 encoded by synthesized SEQ ID NO:
      2

<400> SEQUENCE: 13

Met Glu Ser Gly Ser Gly Thr Ala Ala Gly Ser Gly Tyr Val Tyr Arg
1               5                   10                  15

Gln Ser Gly Ser Thr Arg Trp Asn Pro Thr Ala Glu Gln Leu Ser Leu
            20                  25                  30

Leu Lys Glu Leu Tyr Tyr Arg Asn Gly Ile Arg Thr Pro Ser Ala Asp
        35                  40                  45

Gln Ile Arg Gln Ile Ser Ala Arg Leu Ser Arg Tyr Gly Lys Ile Glu
    50                  55                  60

Gly Lys Asn Val Phe Tyr Trp Phe Gln Asn His Lys Ala Arg Glu Arg
65                  70                  75                  80

Gln Lys Lys Arg Leu Ser Thr Val Gly Cys Asp Pro Ala Leu Ile Glu
                85                  90                  95

Met Gly Asn Val Ala Ser Leu Glu Phe Gly Thr Glu Ser Ala Leu Glu
            100                 105                 110
```

Ser Leu Ser Ser Gly Pro Ser Ser Glu Leu Arg Glu Ala Pro Thr Arg
115 120 125

Lys Phe Tyr Glu Lys Lys Thr Val Gly Glu Asn Ser Thr Ile Ile Asn
130 135 140

Pro Val Glu Gln Asn Cys Thr Leu Ser Cys Gly Thr Ser Gln Glu Phe
145 150 155 160

Gln Tyr Ala Val Asp Ser Arg Arg Val Met Lys Ala Met Glu Glu Lys
165 170 175

Gln Ala Thr Asp Asp Glu Pro Asp Gly Asn Lys Trp Thr Glu Ser Asn
180 185 190

Arg His Val Lys Thr Leu Pro Leu Phe Pro Leu His Asn Asn Glu Asp
195 200 205

Gln Thr Leu Ile Lys Ser Asp Lys Glu Ile Tyr Cys Leu Gly Ser Cys
210 215 220

Glu Lys Lys Met Asp Leu Ser Pro Leu Gly His Ser Gly Ser Gln Arg
225 230 235 240

Ala Ser Ala Leu Asp Leu Cys Leu Ser Leu Gly Asn Glu Ser Cys Gly
245 250 255

Leu His Asp Asn
260

<210> SEQ ID NO 14
<211> LENGTH: 158
<212> TYPE: PRT
<213> ORGANISM: Artificial Sequence
<220> FEATURE:
<223> OTHER INFORMATION: protein RBP3 encoded by synthesized SEQ ID NO: 3

<400> SEQUENCE: 14

Met Val Ser Lys Gly Glu Glu Val Ile Lys Glu Phe Pro Gly Ser Thr
1 5 10 15

Arg Trp Asn Pro Thr Ala Glu Gln Leu Ser Leu Leu Arg Glu Ile Tyr
20 25 30

Tyr Arg Asn Gly Leu Arg Thr Pro Thr Ala Asp Glu Ile Arg Gln Ile
35 40 45

Ser Ser Lys Leu Ser Arg Tyr Gly Lys Ile Glu Gly Lys Asn Val Tyr
50 55 60

Asn Trp Phe Gln Asn Arg Arg Ala Arg Glu Lys Arg Lys Gln Arg Leu
65 70 75 80

Ser Thr Ile Gly Cys Gly Ser Ala Gly Ser Ala Ala Gly Ser Gly Glu
85 90 95

Phe Arg His Val Lys Thr Leu Pro Leu Phe Pro Leu His Asn Asn Glu
100 105 110

Asp Ser Gly Ser Leu Asp Leu Glu Leu Glu Leu Gly Phe Ala Ser Ala
115 120 125

Thr Ala Ala Ala Thr Ser Gly Ser Gln Arg Ala Ser Ala Leu Asp Leu
130 135 140

Cys Leu Ser Leu Gly Asn Glu Ser Cys Gly Leu His Asp Asn
145 150 155

<210> SEQ ID NO 15
<211> LENGTH: 158
<212> TYPE: PRT
<213> ORGANISM: Artificial Sequence
<220> FEATURE:
<223> OTHER INFORMATION: protein RBP4 encoded by synthesized SEQ ID NO:

4

<400> SEQUENCE: 15

Met Val Ser Lys Gly Glu Glu Val Ile Lys Glu Phe Ser Gly Ser Thr
1 5 10 15

Arg Trp Asn Pro Thr Ala Glu Gln Leu Ser Leu Leu Lys Glu Leu Tyr
20 25 30

Tyr Arg Asn Gly Ile Arg Thr Pro Ser Ala Asp Gln Ile Arg Gln Ile
35 40 45

Ser Ala Arg Leu Ser Arg Tyr Gly Lys Ile Glu Gly Lys Asn Val Phe
50 55 60

Tyr Trp Phe Gln Asn His Lys Ala Arg Glu Arg Gln Lys Lys Arg Leu
65 70 75 80

Ser Thr Val Gly Cys Gly Ser Ala Gly Ser Ala Ala Gly Ser Gly Glu
85 90 95

Phe Arg His Val Lys Thr Leu Pro Leu Phe Pro Leu His Asn Asn Glu
100 105 110

Asp Ser Gly Ser Leu Asp Leu Glu Leu Glu Leu Gly Phe Ala Ser Ala
115 120 125

Thr Ala Ala Ala Thr Ser Gly Ser Gln Arg Ala Ser Ala Leu Asp Leu
130 135 140

Cys Leu Ser Leu Gly Asn Glu Ser Cys Gly Leu His Asp Asn
145 150 155

<210> SEQ ID NO 16
<211> LENGTH: 166
<212> TYPE: PRT
<213> ORGANISM: Artificial Sequence
<220> FEATURE:
<223> OTHER INFORMATION: protein RBP5 encoded by synthesized SEQ ID NO: 5

<400> SEQUENCE: 16

Met Val Ser Lys Gly Glu Glu Val Ile Lys Glu Phe Ser Gly Ser Thr
1 5 10 15

Arg Trp Asn Pro Thr Ala Glu Gln Leu Ser Leu Leu Lys Glu Leu Tyr
20 25 30

Tyr Arg Asn Gly Ile Arg Thr Pro Ser Ala Asp Gln Ile Arg Gln Ile
35 40 45

Ser Ala Arg Leu Ser Arg Tyr Gly Lys Ile Glu Gly Lys Asn Val Phe
50 55 60

Tyr Trp Phe Gln Asn His Lys Ala Arg Glu Arg Gln Lys Lys Arg Leu
65 70 75 80

Ser Thr Val Gly Cys Gly Ser Ala Gly Ser Ala Ala Gly Ser Gly Glu
85 90 95

Phe Arg His Val Lys Thr Leu Pro Leu Phe Pro Leu His Asn Asn Val
100 105 110

Glu Thr Leu Pro Leu Phe Pro Glu Asp Ser Gly Ser Leu Asp Leu Glu
115 120 125

Leu Glu Leu Gly Phe Ala Ser Ala Thr Ala Ala Ala Thr Ser Gly Ser
130 135 140

Gln Arg Ala Ser Ala Leu Asp Leu Cys Leu Ser Leu Gly Asn Glu Ser
145 150 155 160

Cys Gly Leu His Asp Asn
165

<210> SEQ ID NO 17
<211> LENGTH: 256
<212> TYPE: PRT
<213> ORGANISM: Artificial Sequence
<220> FEATURE:
<223> OTHER INFORMATION: protein RBP6 encoded by synthesized SEQ ID NO: 6

<400> SEQUENCE: 17

```
Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
            20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Cys Asp Pro Ala Leu Ile Glu Met Gly Asn Val Ala
                85                  90                  95

Ser Leu Glu Phe Gly Thr Glu Ser Ala Leu Glu Ser Leu Ser Ser Gly
            100                 105                 110

Pro Ser Ser Glu Leu Arg Glu Ala Pro Thr Arg Lys Phe Tyr Glu Lys
        115                 120                 125

Lys Thr Val Gly Glu Asn Ser Thr Ile Ile Asn Pro Val Glu Gln Asn
    130                 135                 140

Cys Thr Leu Ser Cys Gly Thr Ser Gln Glu Phe Gln Tyr Ala Val Asp
145                 150                 155                 160

Ser Arg Arg Val Met Lys Ala Met Glu Glu Lys Gln Ala Thr Asp Asp
                165                 170                 175

Glu Pro Asp Gly Asn Lys Trp Thr Glu Ser Asn Arg His Val Lys Thr
            180                 185                 190

Leu Pro Leu Phe Pro Leu His Asn Asn Val Glu Thr Leu Pro Leu Phe
        195                 200                 205

Pro Glu Asp Ser Gly Ser Leu Asp Leu Glu Leu Glu Leu Gly Phe Ala
    210                 215                 220

Ser Ala Thr Ala Ala Ala Thr Ser Gly Ser Gln Arg Ala Ser Ala Leu
225                 230                 235                 240

Asp Leu Cys Leu Ser Leu Gly Asn Glu Ser Cys Gly Leu His Asp Asn
                245                 250                 255
```

<210> SEQ ID NO 18
<211> LENGTH: 279
<212> TYPE: PRT
<213> ORGANISM: Artificial Sequence
<220> FEATURE:
<223> OTHER INFORMATION: protein RBP7 encoded by synthesized SEQ ID NO: 7

<400> SEQUENCE: 18

```
Met Val Ser Lys Gly Glu Glu Val Ile Lys Glu Phe Ser Gly Ser Thr
1               5                   10                  15

Arg Trp Asn Pro Thr Ala Glu Gln Leu Ser Leu Leu Lys Glu Leu Tyr
            20                  25                  30

Tyr Arg Asn Gly Ile Arg Thr Pro Ser Ala Asp Gln Ile Arg Gln Ile
        35                  40                  45

Ser Ala Arg Leu Ser Arg Tyr Gly Lys Ile Glu Gly Lys Asn Val Phe
```

```
    50                  55                  60

Tyr Trp Phe Gln Asn His Lys Ala Arg Glu Arg Gln Lys Lys Arg Leu
65                  70                  75                  80

Ser Thr Val Gly Cys Asp Pro Ala Leu Ile Glu Met Gly Asn Val Ala
                85                  90                  95

Ser Leu Glu Phe Gly Thr Glu Ser Ala Leu Glu Ser Leu Ser Ser Gly
            100                 105                 110

Pro Ser Ser Glu Leu Arg Glu Ala Pro Thr Arg Lys Phe Tyr Glu Lys
        115                 120                 125

Lys Thr Val Gly Glu Asn Ser Thr Ile Ile Asn Pro Val Glu Gln Asn
    130                 135                 140

Cys Thr Leu Ser Cys Gly Thr Ser Gln Glu Phe Gln Tyr Ala Val Asp
145                 150                 155                 160

Ser Arg Arg Val Met Lys Ala Met Glu Glu Lys Gln Ala Thr Asp Asp
                165                 170                 175

Glu Pro Asp Gly Asn Lys Trp Thr Glu Ser Asn Arg His Val Lys Thr
            180                 185                 190

Leu Pro Leu Phe Pro Leu His Asn Asn Val Glu Thr Leu Pro Leu Phe
        195                 200                 205

Pro Glu Asp Ser Gly Ser Leu Asp Leu Glu Leu Glu Leu Gly Phe Ala
    210                 215                 220

Ser Gly Gly Ser Ala Gly Ser Val Asp Thr Leu Pro Leu Phe Pro Arg
225                 230                 235                 240

Glu Ala Ala Gly Ser Gly Glu Phe Ala Thr Ala Ala Ala Thr Ser Gly
                245                 250                 255

Ser Gln Arg Ala Ser Ala Leu Asp Leu Cys Leu Ser Leu Gly Asn Glu
            260                 265                 270

Ser Cys Gly Leu His Asp Asn
        275


<210> SEQ ID NO 19
<211> LENGTH: 164
<212> TYPE: PRT
<213> ORGANISM: Artificial Sequence
<220> FEATURE:
<223> OTHER INFORMATION: protein RBP8 encoded by synthesized SEQ ID NO:
      8

<400> SEQUENCE: 19

Met Val Ser Lys Gly Glu Glu Val Ile Lys Glu Phe Ser Gly Ser Thr
1               5                   10                  15

Arg Trp Asn Pro Thr Ala Glu Gln Val Lys Val Leu Arg Glu Ile Tyr
            20                  25                  30

Tyr Arg Ala Gly Leu Arg Thr Pro Ser Ala Asp Gln Ile Arg Gln Ile
        35                  40                  45

Ser Ser Gln Leu Lys Arg Tyr Gly Lys Val Glu Gly Lys Asn Val Phe
    50                  55                  60

Tyr Trp Phe Gln Asn His Lys Ala Arg Glu Arg Gln Lys Lys Arg Leu
65                  70                  75                  80

Ser Thr Val Gly Ser Ala Gly Ser Ala Ala Gly Ser Gly Glu Phe Arg
                85                  90                  95

His Val Lys Thr Leu Pro Leu Phe Pro Leu His Asn Asn Glu Asp Ser
            100                 105                 110

Gly Ser Gly Leu Asp Leu Asp Leu Asn Leu Glu Leu Arg Leu Ser Ala
        115                 120                 125
```

```
Thr Ala Ala Ala Thr Ser Gly Ser Gln Arg Ala Ser Ala Leu Asp Leu
    130                 135                 140

Asp Leu Glu Leu Arg Leu Gly Phe Ala Leu Gly Asn Glu Ser Cys Gly
145                 150                 155                 160

Leu His Asp Asn


<210> SEQ ID NO 20
<211> LENGTH: 679
<212> TYPE: PRT
<213> ORGANISM: Zea mays

<400> SEQUENCE: 20

Met Ala Ser Ala Asn Asn Trp Leu Gly Phe Ser Leu Ser Gly Gln Asp
1               5                   10                  15

Asn Pro Gln Pro Asn Gln Asp Ser Ser Pro Ala Ala Gly Ile Asp Ile
            20                  25                  30

Ser Gly Ala Ser Asp Phe Tyr Gly Leu Pro Thr Gln Gln Gly Ser Asp
        35                  40                  45

Gly His Leu Gly Val Pro Gly Leu Arg Asp Asp His Ala Ser Tyr Gly
    50                  55                  60

Ile Met Glu Ala Tyr Asn Arg Val Pro Gln Glu Thr Gln Asp Trp Asn
65                  70                  75                  80

Met Arg Gly Leu Asp Tyr Asn Gly Gly Gly Ser Glu Leu Ser Met Leu
                85                  90                  95

Val Gly Ser Ser Gly Gly Gly Gly Gly Asn Gly Lys Arg Ala Val Glu
            100                 105                 110

Asp Ser Glu Pro Lys Leu Glu Asp Phe Leu Gly Gly Asn Ser Phe Val
        115                 120                 125

Ser Asp Gln Asp Gln Ser Gly Gly Tyr Leu Phe Ser Gly Val Pro Ile
    130                 135                 140

Ala Ser Ser Ala Asn Ser Asn Ser Gly Ser Asn Thr Met Glu Leu Ser
145                 150                 155                 160

Met Ile Lys Thr Trp Leu Arg Asn Asn Gln Val Ala Gln Pro Gln Pro
                165                 170                 175

Pro Ala Pro His Gln Pro Gln Pro Glu Glu Met Ser Thr Asp Ala Ser
            180                 185                 190

Gly Ser Ser Phe Gly Cys Ser Asp Ser Met Gly Arg Asn Ser Met Val
        195                 200                 205

Ala Ala Gly Gly Ser Ser Gln Ser Leu Ala Leu Ser Met Ser Thr Gly
    210                 215                 220

Ser His Leu Pro Met Val Val Ala Gly Gly Ser Ala Ser Gly Ala Ala
225                 230                 235                 240

Ser Glu Ser Thr Ser Ser Glu Asn Lys Arg Ala Ser Gly Ala Met Asp
                245                 250                 255

Ser Pro Gly Ser Ala Val Glu Ala Val Pro Arg Lys Ser Ile Asp Thr
            260                 265                 270

Phe Gly Gln Arg Thr Ser Ile Tyr Arg Gly Val Thr Arg His Arg Trp
        275                 280                 285

Thr Gly Arg Tyr Glu Ala His Leu Trp Asp Asn Ser Cys Arg Arg Glu
    290                 295                 300

Gly Gln Ser Arg Lys Gly Arg Gln Val Tyr Leu Gly Gly Tyr Asp Lys
305                 310                 315                 320

Glu Asp Lys Ala Ala Arg Ala Tyr Asp Leu Ala Ala Leu Lys Tyr Trp
                325                 330                 335
```

```
Gly Thr Thr Thr Thr Thr Asn Phe Pro Ile Ser Asn Tyr Glu Lys Glu
            340                 345                 350

Leu Glu Glu Met Lys His Met Thr Arg Gln Glu Tyr Ile Ala Tyr Leu
        355                 360                 365

Arg Arg Asn Ser Ser Gly Phe Ser Arg Gly Ala Ser Lys Tyr Arg Gly
    370                 375                 380

Val Thr Arg His His Gln His Gly Arg Trp Gln Ala Arg Ile Gly Arg
385                 390                 395                 400

Val Ala Gly Asn Lys Asp Leu Tyr Leu Gly Thr Phe Ser Thr Glu Glu
                405                 410                 415

Glu Ala Ala Glu Ala Tyr Asp Ile Ala Ala Ile Lys Phe Arg Gly Leu
            420                 425                 430

Asn Ala Val Thr Asn Phe Asp Met Ser Arg Tyr Asp Val Lys Ser Ile
        435                 440                 445

Leu Glu Ser Ser Thr Leu Pro Val Gly Gly Ala Ala Arg Arg Leu Lys
    450                 455                 460

Asp Ala Val Asp His Val Glu Ala Gly Ala Thr Ile Trp Arg Ala Asp
465                 470                 475                 480

Met Asp Gly Ala Val Ile Ser Gln Leu Ala Glu Ala Gly Met Gly Gly
                485                 490                 495

Tyr Ala Ser Tyr Gly His His Gly Trp Pro Thr Ile Ala Phe Gln Gln
            500                 505                 510

Pro Ser Pro Leu Ser Val His Tyr Pro Tyr Gly Gln Pro Ser Arg Gly
        515                 520                 525

Trp Cys Lys Pro Glu Gln Asp Ala Ala Ala Ala Ala Ala His Ser Leu
    530                 535                 540

Gln Asp Leu Gln Gln Leu His Leu Gly Ser Ala Ala His Asn Phe Phe
545                 550                 555                 560

Gln Ala Ser Ser Ser Ser Thr Val Tyr Asn Gly Gly Ala Gly Ala Ser
                565                 570                 575

Gly Gly Tyr Gln Gly Leu Gly Gly Gly Ser Ser Phe Leu Met Pro Ser
            580                 585                 590

Ser Thr Val Val Ala Ala Ala Asp Gln Gly His Ser Ser Thr Ala Asn
        595                 600                 605

Gln Gly Ser Thr Cys Ser Tyr Gly Asp Asp His Gln Glu Gly Lys Leu
    610                 615                 620

Ile Gly Tyr Asp Ala Ala Met Val Ala Thr Ala Ala Gly Gly Asp Pro
625                 630                 635                 640

Tyr Ala Ala Ala Arg Asn Gly Tyr Gln Phe Ser Gln Gly Ser Gly Ser
                645                 650                 655

Thr Val Ser Ile Ala Arg Ala Asn Gly Tyr Ala Asn Asn Trp Ser Ser
            660                 665                 670

Pro Phe Asn Asn Gly Met Gly
        675
```

<210> SEQ ID NO 21
<211> LENGTH: 494
<212> TYPE: PRT
<213> ORGANISM: Zea mays

<400> SEQUENCE: 21

```
Met Asp Thr Ser His His Tyr His Pro Trp Leu Asn Phe Ser Leu Ala
1               5                   10                  15

His His Cys Asp Leu Glu Glu Glu Glu Arg Gly Ala Ala Ala Glu Leu
            20                  25                  30
```

```
Ala Ala Ile Ala Gly Ala Ala Pro Pro Pro Lys Leu Glu Asp Phe Leu
        35                  40                  45

Gly Gly Gly Val Ala Thr Gly Gly Pro Glu Ala Val Ala Pro Ala Glu
    50                  55                  60

Met Tyr Asp Ser Asp Leu Lys Phe Ile Ala Ala Ala Gly Phe Leu Gly
65                  70                  75                  80

Gly Ser Ala Ala Ala Ala Ala Thr Ser Pro Leu Ser Ser Leu Asp Gln
                85                  90                  95

Ala Gly Ser Lys Leu Ala Leu Pro Ala Ala Ala Ala Ala Pro Ala Pro
            100                 105                 110

Glu Gln Arg Lys Ala Val Asp Ser Phe Gly Gln Arg Thr Ser Ile Tyr
        115                 120                 125

Arg Gly Val Thr Arg His Arg Trp Thr Gly Arg Tyr Glu Ala His Leu
    130                 135                 140

Trp Asp Asn Ser Cys Arg Arg Glu Gly Gln Ser Arg Lys Gly Arg Gln
145                 150                 155                 160

Val Tyr Leu Gly Gly Tyr Asp Lys Glu Glu Lys Ala Ala Arg Ala Tyr
                165                 170                 175

Asp Leu Ala Ala Leu Lys Tyr Trp Gly Ser Ser Thr Thr Thr Asn Phe
            180                 185                 190

Pro Val Ala Glu Tyr Glu Lys Glu Val Glu Glu Met Lys Asn Met Thr
        195                 200                 205

Arg Gln Glu Phe Val Ala Ser Leu Arg Arg Lys Ser Ser Gly Phe Ser
    210                 215                 220

Arg Gly Ala Ser Ile Tyr Arg Gly Val Thr Arg His His Gln His Gly
225                 230                 235                 240

Arg Trp Gln Ala Arg Ile Gly Arg Val Ala Gly Asn Lys Asp Leu Tyr
                245                 250                 255

Leu Gly Thr Phe Ser Thr Glu Glu Glu Ala Ala Glu Ala Tyr Asp Ile
            260                 265                 270

Ala Ala Ile Lys Phe Arg Gly Leu Asn Ala Val Thr Asn Phe Glu Ile
        275                 280                 285

Ser Arg Tyr Asn Val Glu Thr Ile Met Ser Ser Asn Leu Pro Val Ala
    290                 295                 300

Ser Met Ser Ser Ser Ser Ala Ala Ala Ala Gly Gly Arg Ser Ser Lys
305                 310                 315                 320

Ala Leu Glu Ser Pro Pro Ser Gly Ser Leu Asp Gly Gly Gly Gly Met
                325                 330                 335

Pro Val Val Glu Gly Ser Thr Ala Pro Pro Leu Phe Ile Pro Val Lys
            340                 345                 350

Tyr Asp Gln Gln Gln Gln Glu Tyr Leu Ser Met Leu Ala Leu Gln His
        355                 360                 365

His His Gln Gln Gln Gln Ala Gly Asn Leu Leu Gln Gly Pro Leu Val
    370                 375                 380

Gly Phe Gly Gly Leu Tyr Ser Ser Gly Val Asn Leu Asp Phe Ala Asn
385                 390                 395                 400

Ser His Gly Thr Ala Ala Pro Ser Ser Met Ala His His Cys Tyr Ala
                405                 410                 415

Asn Gly Thr Ala Ser Ala Ser His Glu His Gln His Gln His Gln Met
            420                 425                 430

Gln Gln Gly Gly Glu Asn Glu Thr Gln Pro Gln Pro Gln Gln Ser Ser
        435                 440                 445
```

Ser Ser Cys Ser Ser Leu Pro Phe Ala Thr Pro Val Ala Phe Asn Gly
    450                 455                 460

Ser Tyr Glu Ser Ser Ile Thr Ala Ala Gly Pro Phe Gly Tyr Ser Tyr
465                 470                 475                 480

Pro Asn Val Ala Ala Phe Gln Thr Pro Ile Tyr Gly Met Glu
                485                 490

<210> SEQ ID NO 22
<211> LENGTH: 489
<212> TYPE: PRT
<213> ORGANISM: Zea mays

<400> SEQUENCE: 22

Met Asp Met Asp Met Ser Ser Ala Tyr Pro His His Trp Leu Ser Phe
1               5                   10                  15

Ser Leu Ser Asn Asn Tyr His His Gly Leu Leu Glu Ala Phe Ser Asn
            20                  25                  30

Ser Ser Gly Thr Pro Leu Gly Asp Glu Pro Gly Ala Val Glu Glu Ser
        35                  40                  45

Pro Arg Thr Val Glu Asp Phe Leu Gly Gly Val Gly Gly Ala Gly Ala
    50                  55                  60

Pro Pro Gln Pro Ala Ala Ala Ala Asp Gln Asp His Gln Leu Val Cys
65                  70                  75                  80

Gly Glu Leu Gly Ser Ile Thr Ala Arg Phe Leu Arg His Tyr Pro Ala
                85                  90                  95

Ala Pro Ala Gly Thr Thr Val Glu Asn Pro Gly Ala Val Thr Val Ala
            100                 105                 110

Ala Met Ser Ser Thr Asp Val Ala Gly Ala Glu Ser Asp Gln Ala Arg
        115                 120                 125

Arg Pro Ala Glu Thr Phe Gly Gln Arg Thr Ser Ile Tyr Arg Gly Val
    130                 135                 140

Thr Arg His Arg Trp Thr Gly Arg Tyr Glu Ala His Leu Trp Asp Asn
145                 150                 155                 160

Ser Cys Arg Arg Glu Gly Gln Ser Arg Lys Gly Arg Gln Val Tyr Leu
                165                 170                 175

Gly Gly Tyr Asp Lys Glu Glu Lys Ala Ala Arg Ala Tyr Asp Leu Ala
            180                 185                 190

Ala Leu Lys Tyr Trp Gly Pro Thr Thr Thr Thr Asn Phe Pro Val Ser
        195                 200                 205

Asn Tyr Glu Lys Glu Leu Glu Glu Met Lys Ser Met Thr Arg Gln Glu
    210                 215                 220

Phe Ile Ala Ser Leu Arg Arg Lys Ser Ser Gly Phe Ser Arg Gly Ala
225                 230                 235                 240

Ser Ile Tyr Arg Gly Val Thr Arg His His Gln His Gly Arg Trp Gln
                245                 250                 255

Ala Arg Ile Gly Arg Val Ala Gly Asn Lys Asp Leu Tyr Leu Gly Thr
            260                 265                 270

Phe Ser Thr Gln Glu Glu Ala Ala Glu Ala Tyr Asp Ile Ala Ala Ile
        275                 280                 285

Lys Phe Arg Gly Leu Asn Ala Val Thr Asn Phe Asp Met Ser Arg Tyr
    290                 295                 300

Asp Val Glu Ser Ile Leu Ser Ser Asp Leu Pro Val Gly Gly Gly Ala
305                 310                 315                 320

Thr Gly Arg Ala Ala Lys Phe Pro Leu Asp Ser Leu Gln Pro Gly Ser
                325                 330                 335

```
Ala Ala Ala Met Met Leu Ala Gly Ala Ala Ala Ala Ser Gln Ala Thr
            340                 345                 350

Met Pro Pro Ser Glu Lys Asp Tyr Trp Ser Leu Leu Ala Leu His Tyr
        355                 360                 365

Gln Gln Gln Gln Glu Gln Glu Arg Gln Phe Pro Ala Ser Ala Tyr Glu
    370                 375                 380

Ala Tyr Gly Ser Gly Gly Val Asn Val Asp Phe Thr Met Gly Thr Ser
385                 390                 395                 400

Ser Gly Asn Asn Asn Asn Asn Thr Gly Ser Gly Val Met Trp Gly Ala
                405                 410                 415

Thr Thr Gly Ala Val Val Val Gly Gln Gln Asp Ser Ser Gly Lys Gln
            420                 425                 430

Gly Asn Gly Tyr Ala Ser Asn Ile Pro Tyr Ala Ala Ala Ala Ala Met
        435                 440                 445

Val Ser Gly Ser Ala Gly Tyr Glu Gly Ser Thr Gly Asp Asn Gly Thr
    450                 455                 460

Trp Val Thr Thr Thr Ile Thr Ser Ser Asn Thr Gly Thr Ala Pro His
465                 470                 475                 480

Tyr Tyr Asn Tyr Leu Phe Gly Met Glu
                485


<210> SEQ ID NO 23
<211> LENGTH: 2961
<212> TYPE: DNA
<213> ORGANISM: Artificial Sequence
<220> FEATURE:
<223> OTHER INFORMATION: recombinant BdEF1_RBG1_expression_cassette

<400> SEQUENCE: 23

cttcaccgcc attgcaaaaa ttgtcaataa atatttagag tgggtggcat cagaaaaaca     60

tctctagtgg actctcttcc tatcatagct actcgggctg tagatagaac gagggcacaa    120

gagttgggtg gcgtaggttt actcgtgacc tcaactcttt tggctgtgtc ttacgtctaa    180

gatgggtttg gcatgtgaga aacataggtc taagcaattc atgttagggc tgttgcattg    240

ttgttgcatc aaccaaatgt ccagatagca gttcatgcta catctagttg aaaaccctca    300

tcattaggcg gaacatgtgt tcttttttag catagtcaaa gtcagattgc ggcactcgct    360

catccacgga aagaatttcc cctgtgcagg catctcgatc aaaagacgca aattaatttt    420

tgaatagcga tataacaata tctaattaac gtttcttgtt ttctgcgaaa tgtctttcat    480

cataaaatga gtcatctcga tgagcccaag tgacatagcc caacacccca ccccaccaat    540

aaaagtgaag aaaacatgtt gggaaaacta taccaagtaa aatacgagtt gttctaaaga    600

aaaagtaaag tacgagttag atcgcaccct gtcctggagt gtggcttgat gatccaactc    660

ctagcattgt atccctgttt ttggatgatg taactattat ttacaatgaa taaagaggtg    720

ttttactagt aaaaaaatct tgaggggagg agaaaataat ggaggtcttt tttcaaaccg    780

atggactatt atttttagtg aaagagaata atattattgg aaaaattatt ctatccactt    840

attttatatt ggcagaatac aaagaatggt ggggtccacg cggaacttgc ggcccccgaa    900

acctatcgag ggcgcggtac ccaagcaagg aacggaggaa acttgcgggg cccgaaacct    960

agtgataaaa ggcatatcat ccacacgatg aagatctgac ggaccatatc tcccaccacg   1020

gaaagccatc agacgaggat cagacggcca ggaaggaacc ctagcgcccg ccggtgccaa   1080

tataaagcgc cactctctct cgtcttaagc cccagcctct ccattcccct ctccctctcg   1140
```

```
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggagtcggg ctccgggacg gctgctggct   1920
ctggctatgt ttacagacag ccaggatcaa cgcggtggaa cccgacagct gaacaactgt   1980
ccttgcttag agaaatctac taccgcaacg gattgcggac cccgaccgcg gacgaaatca   2040
gacaaatcag ctcaaagctc tcaaggtacg gaaaaataga gggcaaaaac gtttacaact   2100
ggttccagaa tagacgcgca agagaaaagc gcaagcaacg gctctctaca atcggctgtg   2160
atccagcact gatcgagatg gggaatgtcg cttcactgga attcggtact gagagcgccc   2220
tggaatcgct gtcgtcagga ccatcctcag aactccgcga agcgccaacg agaaaatttt   2280
acgaaaaaaa gacggttgga gagaactcaa ctataataaa cccagtggaa caaaactgta   2340
ccctttcctg cggaacgtcc caagagttcc agtatgcggt cgattctcgg cgcgtcatga   2400
aagctatgga ggaaaagcag gcgacggacg atgaacccga cggaaataaa tggactgagt   2460
caaacagaca cgtcaagatt ctccagcttt tcccgctcca caataacgag gatcagacat   2520
tgataaagag cgacaaagaa atctattgtt tgggctcgtg cgagaagaaa atggatttgt   2580
caccgctggg tcattcaggc tctcagcgcg cttcggccct tgacttgtgc ctttcattgg   2640
gcaacgaatc ttgtgggctg catgataatt gaaagcttac gcgtgtcgac tcgaatttcc   2700
ccgatcgttc aaacatttgg caataaagtt tcttaagatt gaatcctgtt gccggtcttg   2760
cgatgattat catataattt ctgttgaatt acgttaagca tgtaataatt aacatgtaat   2820
gcatgacgtt atttatgaga tgggttttta tgattagagt cccgcaatta tacatttaat   2880
acgcgataga aaacaaaata tagcgcgcaa actaggataa attatcgcgc gcggtgtcat   2940
ctatgttact agatcgctcg a                                             2961
```

<210> SEQ ID NO 24
<211> LENGTH: 2961
<212> TYPE: DNA
<213> ORGANISM: Artificial Sequence
<220> FEATURE:
<223> OTHER INFORMATION: recombinant BdEF1_RBG2_expression_cassette

<400> SEQUENCE: 24

```
cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
```

```
ttgttgcatc aaccaaatgt ccagatagca gttcatgcta catctagttg aaaaccctca    300
tcattaggcg gaacatgtgt tcttttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggaatcggg ctccggcacg gcggcagggt   1920
ctggttatgt ctatcggcag agcggaagca cccggtggaa tccaacagca gaacagttgt   1980
cgctgctcaa ggaactttat taccggaatg gaattcggac accgtcggca gatcaaatta   2040
ggcaaatttc ggcccggctg tccagatacg gcaaaataga agggaaaaac gtcttttact   2100
ggtttcaaaa tcataaagca cgggaacggc agaagaaaag actttccacg gtcggctgcg   2160
accctgctct catagaaatg ggtaacgtcg cgagcttgga atttgggacc gaaagcgctc   2220
ttgaatctct cagctcaggc ccgtccagcg agttgcgcga ggctcctacc cgcaagtttt   2280
atgagaagaa aaccgttggt gagaacagca ccataatcaa tcctgttgag cagaactgca   2340
cactttcttg cggtacttcg caggaatttc agtatgctgt tgatagccgc cgggtgatga   2400
aggcaatgga agagaagcaa gcaacggatg atgaaccgga cggaaacaaa tggacggagt   2460
cgaacaggca tgtgaagacc ctccctcttt tccccttgca taataatgaa gatcagacct   2520
tgatcaagtc ggacaaggaa atttattgcc ttgggagctg tgaaaaaaaa atggatctgt   2580
```

ccccattggg acactcgggc tctcagaggg cgtcggcact ggatttgtgc ctgtctttgg 2640
gtaatgaatc ttgtggcctc cacgacaatt gaaagcttac gcgtgtcgac tcgaatttcc 2700
ccgatcgttc aaacatttgg caataaagtt tcttaagatt gaatcctgtt gccggtcttg 2760
cgatgattat catataattt ctgttgaatt acgttaagca tgtaataatt aacatgtaat 2820
gcatgacgtt atttatgaga tgggttttta tgattagagt cccgcaatta tacatttaat 2880
acgcgataga aaacaaaata tagcgcgcaa actaggataa attatcgcgc gcggtgtcat 2940
ctatgttact agatcgctcg a 2961

<210> SEQ ID NO 25
<211> LENGTH: 2655
<212> TYPE: DNA
<213> ORGANISM: Artificial Sequence
<220> FEATURE:
<223> OTHER INFORMATION: recombinant BdEF1_RBG3_expression_cassette

<400> SEQUENCE: 25
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatcca tggttagcaa gggggaggag gttattaaag 1920
aattcccagg aagcacccgg tggaatccaa cggcggagca actttcgctc cttcgggaaa 1980
tttattacag gaatgggctg agaactccca ccgctgacga gatcagacag atttcatcaa 2040
aattgtcgcg gtatggtaag attgaaggga aaaatgtgta caactggttc cagaacagaa 2100
gagctaggga aaagagaaaa cagcggttgt caaccatagg ctgtggttcg gcggggtcgg 2160
ccgcagggag cggagagttt cgccatgtga agaccctgcc ccttttccct ttgcataata 2220
atgaggattc aggttcgttg gatctggagc tggaattggg ttttgcctct gctaccgcag 2280
ccgcgacttc tggttcacaa agggcgtcgg cattggatct ctgcctgtcc cttggaaatg 2340
agtcatgcgg tttgcatgac aactgaaagc ttacgcgtgt cgactcgaat ttccccgatc 2400
gttcaaacat ttggcaataa agtttcttaa gattgaatcc tgttgccggt cttgcgatga 2460
ttatcatata atttctgttg aattacgtta agcatgtaat aattaacatg taatgcatga 2520
cgttatttat gagatgggtt tttatgatta gagtcccgca attatacatt taatacgcga 2580
tagaaaacaa aatatagcgc gcaaactagg ataaattatc gcgcgcggtg tcatctatgt 2640
tactagatcg ctcga 2655

<210> SEQ ID NO 26
<211> LENGTH: 2655
<212> TYPE: DNA
<213> ORGANISM: Artificial Sequence
<220> FEATURE:
<223> OTHER INFORMATION: recombinant BdEF1_RBG4_expression_cassette

<400> SEQUENCE: 26
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatcca tggtctcgaa aggagaagag gtcatcaaag 1920
aattttcagg cagcacccgc tggaatccga ctgcagaaca actttctctc ctcaaagagc 1980
tttattacag aaatgggatc agaacccctt cagcggacca gatacgccag ataagcgccc 2040
gcttgtcgag gtacggcaaa atcgagggga agaatgtttt ttactggttc caaaaccata 2100
aagcgaggga gcggcagaag aaaagactga gcactgtggg ttgtggatcg gcgggatcgg 2160
ctgccgggtc aggtgaattt cgccatgtta aaacgcttcc actgtttccc ttgcataata 2220
atgaagacag cggatcactt gacctggagc tggagttggg cttcgcttcc gcgacggctg 2280
ctgcaacatc cggctcgcag cgggcgtcgg cgctggattt gtgcctttcg ctgggaaatg 2340
agagctgcgg tcttcatgac aactgaaagc ttacgcgtgt cgactcgaat ttccccgatc 2400
gttcaaacat ttggcaataa agtttcttaa gattgaatcc tgttgccggt cttgcgatga 2460
ttatcatata atttctgttg aattacgtta agcatgtaat aattaacatg taatgcatga 2520
cgttatttat gagatgggtt tttatgatta gagtcccgca attatacatt taatacgcga 2580
tagaaaacaa aatatagcgc gcaaactagg ataaattatc gcgcgcggtg tcatctatgt 2640
tactagatcg ctcga 2655

<210> SEQ ID NO 27
<211> LENGTH: 2679
<212> TYPE: DNA
<213> ORGANISM: Artificial Sequence
<220> FEATURE:
<223> OTHER INFORMATION: recombinant BdEF1_RBG5_expression_cassette

<400> SEQUENCE: 27
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420

```
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggtgtctaa aggggaagag gtcataaaag   1920
agttctcagg ttctactcgc tggaatccaa ctgcagaaca actctctctc ctgaaggagc   1980
tctactatcg gaacggaata cgcacgcctt cggcggacca aataaggcag atttcagccc   2040
gcctgtctag atacgggaaa atcgagggaa agaacgtgtt ttattggttc caaaaccata   2100
aggcaagaga gcggcagaaa aaacggctca gcacagtcgg ctgtgggtca gccggttcgg   2160
cggctggctc tggtgaattc cgccacgtca aaaccctgcc tctgttcccg ctccacaata   2220
atgtcgagac acttcccttg ttcccggagg attccgggtc tctcgacttg gagctcgaat   2280
tgggctttgc ctctgccact gcggcagcga ccagcggatc acagagagcc tccgcactgg   2340
atctgtgcct gtcacttgga aatgaatcgt gcggattgca cgacaattga aagcttacgc   2400
gtgtcgactc gaatttcccc gatcgttcaa acatttggca ataaagtttc ttaagattga   2460
atcctgttgc cggtcttgcg atgattatca tataatttct gttgaattac gttaagcatg   2520
taataattaa catgtaatgc atgacgttat ttatgagatg ggtttttatg attagagtcc   2580
cgcaattata catttaatac gcgatagaaa acaaaatata gcgcgcaaac taggataaat   2640
tatcgcgcgc ggtgtcatct atgttactag atcgctcga                          2679
```

<210> SEQ ID NO 28

<211> LENGTH: 2949
<212> TYPE: DNA
<213> ORGANISM: Artificial Sequence
<220> FEATURE:
<223> OTHER INFORMATION: recombinant BdEF1_RBG6_expression_cassette

<400> SEQUENCE: 28
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatcca tggtgtctaa aggcgaagag gtcattaagg 1920
agttcagcgg ctctactaga tggaatccaa cggccgagca acttagcctg ctcaaagaac 1980
tctattatcg caatgggata cgcacgccct ctgcagatca gatacgccaa atctcagcgc 2040
gcctgtccag gtatgggaag attgagggta aaaacgtctt ttactggttc caaaatcaca 2100
aagcgcgcga gagacagaag aaaagactca gcaccgttgg ttgtgaccct gctctcatcg 2160
agatggggaa tgttgcttcc ctggagtttg gcacagagag cgctttggaa tcactctctt 2220
ccggcccctc aagcgaactc agagaggctc ccactcggaa gttttacgag aaaaaaaccg 2280
tcggagaaaa cagcacgatt atcaaccccg tcgagcagaa ctgcaccctc tcatgcggca 2340
cgtcccagga gtttcagtac gccgtcgact cgaggagagt gatgaaggcg atggaggaaa 2400
agcaagcaac tgacgacgag cccgacggaa acaagtggac tgaatccaat cgccatgtta 2460
aaacgttgcc tttgttcccg ctccataaca atgtggagac gttgccactc ttcccggagg 2520
actcgggatc tctggacttg gagctggaac tgggctttgc ttcggctacc gcagcagcca 2580
cctcgggttc ccagagagcc tcggctcttg atctctgcct gtcactgggt aacgaatctt 2640
gcggactgca cgataattag aagcttacgc gtgtcgactc gaatttcccc gatcgttcaa 2700
acatttggca ataaagtttc ttaagattga atcctgttgc cggtcttgcg atgattatca 2760
tataatttct gttgaattac gttaagcatg taataattaa catgtaatgc atgacgttat 2820
ttatgagatg ggtttttatg attagagtcc cgcaattata catttaatac gcgatagaaa 2880
acaaaatata gcgcgcaaac taggataaat tatcgcgcgc ggtgtcatct atgttactag 2940
atcgctcga 2949

<210> SEQ ID NO 29
<211> LENGTH: 3018
<212> TYPE: DNA
<213> ORGANISM: Artificial Sequence
<220> FEATURE:
<223> OTHER INFORMATION: recombinant BdEF1_RBG7 expression_cassette

<400> SEQUENCE: 29
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaattttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200

```
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggtttcaaa gggggaggag gtcataaaag   1920
aattttctgg cagcactaga tggaatccga ctgctgagca gttgtctctc ctcaaagaac   1980
tttactatag gaacggtatc cgcactccgt ccgctgatca aattcgccaa atttcggcca   2040
gactgtccag atacgggaaa attgagggaa aaaatgtttt ctactggttc cagaatcata   2100
aggcgcgcga aaggcagaaa aagagacttt cgaccgtcgg atgtgaccct gcacttatcg   2160
aaatgggcaa tgtcgcgtcg ttggagtttg gcaccgaatc cgctctcgaa tctcttagct   2220
cgggcccctc atcggaactc agagaggccc ctaccagaaa attttatgag aaaaagacag   2280
tgggagagaa ctctacaatc attaaccccg tcgagcagaa ctgcacattg agctgtggaa   2340
catcgcagga gtttcaatac gcggtggatt cgcgccgcgt tatgaaggca atggaggaga   2400
agcaggcaac agatgatgag ccagacggca ataaatggac cgaatctaac agacatgtca   2460
agacactgcc acttttccct ctccacaaca atgtcgagac actccctctg tttcccgagg   2520
attcgggaag cctggatctt gagctggaac ttggctttgc atcaggtgga tctgccgggt   2580
cagttgacac gctgccattg tttcctagag aggctgcggg ttctggggaa tttgccactg   2640
cggctgcgac tagcggatca cagcgcgcat cggcgctcga cctctgcctt tctttgggta   2700
acgagtcttg cggcctgcat gacaactgaa agcttacgcg tgtcgactcg aatttccccg   2760
atcgttcaaa catttggcaa taaagtttct taagattgaa tcctgttgcc ggtcttgcga   2820
tgattatcat ataatttctg ttgaattacg ttaagcatgt aataattaac atgtaatgca   2880
tgacgttatt tatgagatgg gtttttatga ttagagtccc gcaattatac atttaatacg   2940
cgatagaaaa caaaatatag cgcgcaaact aggataaatt atcgcgcgcg gtgtcatcta   3000
tgttactaga tcgctcga                                                 3018
```

```
<210> SEQ ID NO 30
<211> LENGTH: 2676
<212> TYPE: DNA
<213> ORGANISM: Artificial Sequence
<220> FEATURE:
<223> OTHER INFORMATION: recombinant BdEF1_RBG8_expression_cassette

<400> SEQUENCE: 30

cttcaccgcc attgcaaaaa ttgtcaataa atatttagag tgggtggcat cagaaaaaca     60
tctctagtgg actctcttcc tatcatagct actcgggctg tagatagaac gagggcacaa    120
gagttgggtg gcgtaggttt actcgtgacc tcaactcttt tggctgtgtc ttacgtctaa    180
gatgggtttg gcatgtgaga aacataggtc taagcaattc atgttagggc tgttgcattg    240
```

```
ttgttgcatc aaccaaatgt ccagatagca gttcatgcta catctagttg aaaaccctca    300
tcattaggcg gaacatgtgt tctttttttag catagtcaaa gtcagattgc ggcactcgct    360
catccacgga aagaattttc cctgtgcagg catctcgatc aaaagacgca aattaatttt    420
tgaatagcga tataacaata tctaattaac gtttcttgtt ttctgcgaaa tgtctttcat    480
cataaaatga gtcatctcga tgagcccaag tgacatagcc caacacccca ccccaccaat    540
aaaagtgaag aaaacatgtt gggaaaacta taccaagtaa aatacgagtt gttctaaaga    600
aaaagtaaag tacgagttag atcgcaccct gtcctggagt gtggcttgat gatccaactc    660
ctagcattgt atccctgttt ttggatgatg taactattat ttacaatgaa taaagaggtg    720
ttttactagt aaaaaaatct tgaggggagg agaaaataat ggaggtcttt tttcaaaccg    780
atggactatt atttttagtg aaagagaata atattattgg aaaaattatt ctatccactt    840
attttatatt ggcagaatac aaagaatggt ggggtccacg cggaacttgc ggcccccgaa    900
acctatcgag ggcgcggtac ccaagcaagg aacggaggaa acttgcgggg cccgaaacct    960
agtgataaaa ggcatatcat ccacacgatg aagatctgac ggaccatatc tcccaccacg   1020
gaaagccatc agacgaggat cagacggcca ggaaggaacc ctagcgcccg ccggtgccaa   1080
tataaagcgc cactctctct cgtcttaagc cccagcctct ccattcccct ctccctctcg   1140
ccgccgccgt ctccttctcc tactcccttc gaggtgtgtt gttcatccgt cccgaatcca   1200
tccatcccct cttcagatgt gttgttcatg gctctaatag ctctagatct gcttgtttgt   1260
gttgtttagc tctagatcta ctcgcgcgcg cttctctctc gatctcctgt agaacaattt   1320
tggttggttt tttgtgcata tccatggtaa ttttgtctgc aatatggagg aggctttcta   1380
agctcctacg tagcatcgat ctttagaatt ccctcggttt ctgtttattt cttcgcgagg   1440
gctctctgtt atctgtagga gtagctgtaa gcgcggttcg ttacggatta atcgtcatgc   1500
ttagttgaac ctatcggtcg aaggatttgt gtgggttgtc gtgtagaatt gacaccatct   1560
acttactgta ctgatatgcc gatctgtagg atactcttca ttacttttgt ttactgctag   1620
ttgtggtgta gatttagcat tctcaaaccc atgctgtagc gtttctaata ttgttacata   1680
gatctaccgg tgcctgttaa ttgtattcga tcgggcgttt ctacatctgt ccgcccacct   1740
agttttatat gtggtaatca aaattgcgtt gacttcgtga tgctgtctgt gtactgtttt   1800
taatcgctct tacttagatg atcaacatgg tgatggttac gatttactgt tttctaatcc   1860
ctgttacttc gatgctgcag tttggatcca tggtttcgaa gggggaagaa gtcattaaag   1920
agttttcagg gtctacgcgc tggaacccta ccgctgaaca agtcaaggtt ttgagggaaa   1980
tatattaccg cgcgggtctt aggacgccat ccgcggatca gatccgccaa atatcctcac   2040
agctgaaacg gtatggaaag gtggaaggaa aaaacgtgtt ttattggttc cagaaccata   2100
aagcgcggga aagacaaaaa aagcggctca gcaccgttgg gagcgctggc tcagcagcgg   2160
gttcaggtga gttcaggcac gttaaaacac tgcccttgtt ccctttgcac aataatgaag   2220
actcagggag cggtttggac ttggatctga accttgagtt gcgcctgtcg gcgactgctg   2280
ctgccacttc gggctcacag cgggcgtctg ccctcgatct ggacttggag ctcagactcg   2340
gtttcgcgct tggtaatgag tcgtgtggac tgcacgacaa ctagtgaaag cttacgcgtg   2400
tcgactcgaa tttccccgat cgttcaaaca tttggcaata aagtttctta agattgaatc   2460
ctgttgccgg tcttgcgatg attatcatat aatttctgtt gaattacgtt aagcatgtaa   2520
taattaacat gtaatgcatg acgttattta tgagatgggt ttttatgatt agagtcccgc   2580
```

aattatacat ttaatacgcg atagaaaaca aaatatagcg cgcaaactag gataaattat 2640
cgcgcgcggt gtcatctatg ttactagatc gctcga 2676

<210> SEQ ID NO 31
<211> LENGTH: 4224
<212> TYPE: DNA
<213> ORGANISM: Artificial Sequence
<220> FEATURE:
<223> OTHER INFORMATION: recombinant BdEF1_ZmPL T3_expression_cassette

<400> SEQUENCE: 31
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggccccgaa 900 acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatccc ccgggatggc ttcagcgaac aactggctgg 1920
gcttctcgct ctcgggccag gataacccgc agcctaacca ggatagctcg cctgccgccg 1980

```
gtatcgacat ctccggcgcc agcgacttct atggcctgcc cacgcagcag ggctccgacg   2040
ggcatctcgg cgtgccgggc ctgcgggacg atcacgcttc ttatggtatc atggaggcct   2100
acaacagggt tcctcaagaa acccaagatt ggaacatgag ggcttggac tacaacggcg   2160
gtggctcgga gctctcgatg cttgtggggt ccagcggcgg cggcgggggc aacggcaaga   2220
gggccgtgga agacagcgag cccaagctcg aagatttcct cggcggcaac tcgttcgtct   2280
ccgatcaaga tcagtccggc ggttacctgt tctctggagt cccgatagcc agcagcgcca   2340
atagcaacag cgggagcaac accatggagc tatccatgat caagacctgg ctacggaaca   2400
accaggtggc ccagccccag ccgccagctc cacatcagcc gcagcctgag gaaatgagca   2460
ccgacgccag cggcagcagc tttggatgct cggattcgat gggaaggaac agcatggtgg   2520
cggctggtgg gagctcgcag agcctggcgc tctcgatgag cacgggctcg cacctgccca   2580
tggttgtggc cggcggcagc gccagcggag cggcctcgga gagcacgtcg tcggagaaca   2640
agcgagcgag cggtgccatg gattcgcccg gcagcgcggt agaagccgta ccgaggaagt   2700
ccatcgacac gttcgggcaa aggacctcta tatatcgagg tgtaacaagg catagatgga   2760
cagggcggta tgaggctcat ctatgggata atagttgtag aagagaaggg cagagtcgca   2820
agggtaggca agtttacctt ggtggctatg acaaggagga caaggcagca agggcttacg   2880
atttggcagc tctcaagtat tggggcacta cgacaacaac aaatttccct ataagcaact   2940
acgaaaagga gctagaagaa atgaaacata tgactagaca ggagtacatt gcatacctaa   3000
gaagaaatag cagtggattt tctcgtgggg cgtcaaagta tcgtggagta actagacatc   3060
atcagcatgg gagatggcaa gcaaggatag ggagagttgc aggaaacaag gatctctact   3120
tgggcacatt cagcaccgag gaggaggcgg cggaggccta cgacatcgcc gcgatcaagt   3180
tccgcggtct caacgccgtc accaacttcg acatgagccg ctacgacgtg aagagcatcc   3240
tcgagagcag cacactgcct gtcggcggcg cggccaggcg cctcaaggac gccgtggacc   3300
acgtggaggc cggcgccact atctggcgcg ccgacatgga cggcgccgtg atctcccagc   3360
tggccgaagc cgggatgggc ggctacgcct cgtacggcca ccacggctgg ccgaccatcg   3420
cgttccagca gccgtcgccg ctctccgtcc actacccgta cggccagccg tcccgcgggt   3480
ggtgcaaacc cgagcaggac gcggccgccg ccgcggccca cagcctgcag gacctccagc   3540
agctgcacct cggcagcgcg gcccacaact tcttccaggc gtcgtcgagc tccacagtct   3600
acaacggcgg cgccggcgcc agtggtgggt accagggcct cggtggtggt agctccttcc   3660
tcatgccgtc gagcactgtc gtggcggcgg ccgaccaggg gcacagcagc acggcaaacc   3720
aggggagcac gtgcagctac ggggacgacc accaggaggg gaagctcatc ggttacgacg   3780
ccgccatggt ggcgaccgca gctggtggag acccgtacgc tgcggcgagg aacgggtacc   3840
agttctcgca gggctcggga tccacggtga gcatcgcgag ggcgaacggg tacgctaaca   3900
actggagctc tcctttcaac aacggcatgg ggtgaaagct tacgcgtgtc gactcgaatt   3960
tccccgatcg ttcaaacatt tggcaataaa gtttcttaag attgaatcct gttgccggtc   4020
ttgcgatgat tatcatataa tttctgttga attacgttaa gcatgtaata attaacatgt   4080
aatgcatgac gttatttatg agatgggttt ttatgattag agtcccgcaa ttatacattt   4140
aatacgcgat agaaaacaaa atatagcgcg caaactagga taaattatcg cgcgcggtgt   4200
catctatgtt actagatcgc tcga                                          4224
```

<210> SEQ ID NO 32

<211> LENGTH: 3663
<212> TYPE: DNA
<213> ORGANISM: Artificial Sequence
<220> FEATURE:
<223> OTHER INFORMATION: recombinant BdEF1_ZmPL T5_expression_cassette

<400> SEQUENCE: 32
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tctttttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatcca tggacacctc gcaccactat catccatggc 1920
tcaacttctc cctcgcccac cactgtgacc tcgaggagga ggagaggggc gcggccgccg 1980
agctggccgc gatagccggc gccgcgccgc cgccgaagct ggaggacttc ctcggcggag 2040
gcgtcgccac cggtggtccg gaggcggtgg cgcccgcgga gatgtacgac tcggacctca 2100
agttcatagc cgccgccggg ttccttggcg gctcggcggc ggcggcggcg acgtcgccgc 2160
tgtcctccct cgaccaggcc ggttccaagc tggccttgcc tgcggcggcg gctgctccgg 2220
cgccggagca gaggaaggcc gtcgactcct ttgggcagcg cacgtccatc taccgcggcg 2280
tcacacggca ccggtggact ggcaggtacg aggcacatct gtgggacaac agctgccgac 2340
gcgaagggca gagccgcaag ggccgccaag tatatttggg tggctatgat aaggaggaga 2400
aggctgccag ggcgtatgat cttgcagctt tgaagtactg ggttctagc accaccacca 2460 actttccggt tgctgagtat gagaaggagg tcgaggagat gaagaacatg acgcgacaag 2520
agtttgttgc ttcccttcga aggaagagca gtggattctc tcggggtgct tccatctaca 2580
gaggtgtaac cagacatcac cagcatggac ggtggcaggc gaggatcgga agggtggccg 2640
gtaacaagga cctctacctt gggacgttca gcaccgagga ggaagctgca gaggcctacg 2700
acatagcggc catcaagttc agaggcctga acgccgtcac aaacttcgag atcagccggt 2760
acaacgtgga gaccataatg agcagcaacc ttccagtcgc gagcatgtcg tcgtcgtcgg 2820
cggcggcggc gggtggccgg agcagcaagg cgctggagtc cctccgtcc ggctcgcttg 2880 acggcggcgg cggcatgcca gtcgtcgaag gcagcacggc accgccgctg ttcattccgg 2940
tgaagtacga ccagcagcag caggagtacc tgtcgatgct cgcgttgcag caccaccacc 3000
agcagcaaca agcagggaac ctgttgcagg ggccgctagt agggttcggc ggcctctact 3060
cctccggggt gaacctggat ttcgccaact cccacggcac ggcggctccg tcgtcgatgg 3120
cccaccactg ctacgccaat ggcaccgcgt ccgcctcgca tgagcaccag caccagcacc 3180
agatgcagca gggcggcgag aacgagacgc agccgcagcc gcagcagagc tccagcagct 3240
gctcctccct gccattcgcc accccggtcg ctttcaatgg gtcctatgaa agctccatca 3300
cggcggcagg cccctttgga tactcctacc caaatgtggc agcctttcag acgccgatct 3360
atggaatgga atgaaagctt acgcgtgtcg actcgaattt ccccgatcgt tcaaacattt 3420
ggcaataaag tttcttaaga ttgaatcctg ttgccggtct tgcgatgatt atcatataat 3480
ttctgttgaa ttacgttaag catgtaataa ttaacatgta atgcatgacg ttatttatga 3540
gatgggtttt tatgattaga gtcccgcaat tatacattta atacgcgata gaaaacaaaa 3600
tatagcgcgc aaactaggat aaattatcgc gcgcggtgtc atctatgtta ctagatcgct 3660
cga 3663

<210> SEQ ID NO 33
<211> LENGTH: 3648
<212> TYPE: DNA
<213> ORGANISM: Artificial Sequence
<220> FEATURE:
<223> OTHER INFORMATION: recombinant BdEF1_ZmPL T7 expression_cassette

<400> SEQUENCE: 33
cttcaccgcc attgcaaaaa ttgtcaataa atatttagag tgggtggcat cagaaaaaca 60
tctctagtgg actctcttcc tatcatagct actcgggctg tagatagaac gagggcacaa 120
gagttgggtg gcgtaggttt actcgtgacc tcaactcttt tggctgtgtc ttacgtctaa 180
gatgggtttg gcatgtgaga aacataggtc taagcaattc atgttagggc tgttgcattg 240
ttgttgcatc aaccaaatgt ccagatagca gttcatgcta catctagttg aaaaccctca 300
tcattaggcg gaacatgtgt tcttttttag catagtcaaa gtcagattgc ggcactcgct 360
catccacgga aagaatttc cctgtgcagg catctcgatc aaaagacgca aattaatttt 420
tgaatagcga tataacaata tctaattaac gtttcttgtt ttctgcgaaa tgtctttcat 480
cataaaatga gtcatctcga tgagcccaag tgacatagcc caacacccca ccccaccaat 540
aaaagtgaag aaaacatgtt gggaaaacta taccaagtaa aatacgagtt gttctaaaga 600
aaaagtaaag tacgagttag atcgcaccct gtcctggagt gtggcttgat gatccaactc 660
ctagcattgt atccctgttt ttggatgatg taactattat ttacaatgaa taaagaggtg 720
ttttactagt aaaaaaatct tgaggggagg agaaaataat ggaggtcttt tttcaaaccg 780
atggactatt atttttagtg aaagagaata atattattgg aaaaattatt ctatccactt 840
attttatatt ggcagaatac aaagaatggt ggggtccacg cggaacttgc ggcccccgaa 900
acctatcgag ggcgcggtac ccaagcaagg aacggaggaa acttgcgggg cccgaaacct 960
agtgataaaa ggcatatcat ccacacgatg aagatctgac ggaccatatc tcccaccacg 1020
gaaagccatc agacgaggat cagacggcca ggaaggaacc ctagcgcccg ccggtgccaa 1080
tataaagcgc cactctctct cgtcttaagc cccagcctct ccattcccct ctccctctcg 1140
ccgccgccgt ctccttctcc tactcccttc gaggtgtgtt gttcatccgt cccgaatcca 1200
tccatcccct cttcagatgt gttgttcatg gctctaatag ctctagatct gcttgtttgt 1260
gttgtttagc tctagatcta ctcgcgcgcg cttctctctc gatctcctgt agaacaattt 1320
tggttggttt tttgtgcata tccatggtaa ttttgtctgc aatatggagg aggctttcta 1380
agctcctacg tagcatcgat ctttagaatt ccctcggttt ctgtttattt cttcgcgagg 1440
gctctctgtt atctgtagga gtagctgtaa gcgcggttcg ttacggatta atcgtcatgc 1500
ttagttgaac ctatcggtcg aaggatttgt gtgggttgtc gtgtagaatt gacaccatct 1560
acttactgta ctgatatgcc gatctgtagg atactcttca ttacttttgt ttactgctag 1620
ttgtggtgta gatttagcat tctcaaaccc atgctgtagc gtttctaata ttgttacata 1680
gatctaccgg tgcctgttaa ttgtattcga tcgggcgttt ctacatctgt ccgcccacct 1740
agttttatat gtggtaatca aaattgcgtt gacttcgtga tgctgtctgt gtactgtttt 1800
taatcgctct tacttagatg atcaacatgg tgatggttac gatttactgt tttctaatcc 1860
ctgttacttc gatgctgcag tttggatcca tggacatgga catgagctca gcttatcccc 1920
accattggct ctccttctcc ctctccaaca actaccacca tggcctactc gaggccttct 1980
ctaactcctc cggtactcct cttggagacg agccgggcgc agtggaggag tccccgagga 2040
cggtggagga cttcctcggc ggcgtcggtg gcgccggcgc cccgccgcag ccggcggctg 2100
ctgcagatca ggatcaccag cttgtgtgcg gcgagctggg cagcatcaca gccaggttct 2160
tgcgccacta cccggcggcg ccagctggga cgacggtgga gaaccccggc gcggtgaccg 2220
tggcggccat gtcgtcgacg gacgtggcgg gggcggagtc cgaccaggcg aggcggcccg 2280
ccgagacgtt cggccagcgc acatccatct accgtggcgt caccaggcac cggtggacag 2340
ggagatatga ggcgcacttg tgggacaaca gctgccgccg ggagggccaa agccgcaaag 2400
gacgccaagt ctacctagga ggctatgaca aggaggagaa ggcggctaga gcttacgacc 2460
tcgccgcgct caagtactgg gggcctacaa ccacgaccaa cttcccggtg tccaactacg 2520
agaaggagct ggaggagatg aagtccatga cgcggcagga gttcatcgcg tcgttgcgca 2580
ggaagagcag cggcttctca cgaggcgcct ccatctacag aggagtcaca aggcatcatc 2640
agcacggccg gtggcaggcg aggatcggca gggtggccgg aaacaaggac ctgtacttgg 2700
gcactttcag tactcaggaa gaggcggcgg aggcgtacga catcgctgcg atcaagttcc 2760
gcgggctcaa cgccgtcacc aacttcgaca tgagccgcta cgacgtggag agcatcctca 2820
gcagcgacct ccccgtcggg ggcggagcca ccgggcgcgc cgccaagttc ccgttggact 2880
cgctgcagcc ggggagcgct gctgcgatga tgctcgccgg ggctgctgcc gcttcgcagg 2940
ccaccatgcc gccgtccgag aaggactact ggtctctgct cgccctgcac taccagcagc 3000
agcaggagca ggagcggcag ttcccggctt ctgcttacga ggcttacggc tccggcggcg 3060
tgaacgtgga cttcacgatg ggcaccagta gcggcaacaa caacaacaac accggcagcg 3120
gcgtcatgtg gggcgccacc actggtgcag tagtagtggg acagcaagac agcagcggca 3180
agcagggcaa cggctatgcc agcaacattc cttatgctgc tgctgctgct atggtttctg 3240
gatctgctgg ctacgagggc tccaccggcg acaatggaac ctgggttact acgactatta 3300
ccagcagcaa caccggcacg gctcccccact actacaacta tctcttcggg atggagtaga 3360
agcttacgcg tgtcgactcg aatttccccg atcgttcaaa catttggcaa taaagtttct 3420
taagattgaa tcctgttgcc ggtcttgcga tgattatcat ataatttctg ttgaattacg 3480
ttaagcatgt aataattaac atgtaatgca tgacgttatt tatgagatgg gtttttatga 3540
ttagagtccc gcaattatac atttaatacg cgatagaaaa caaaatatag cgcgcaaact 3600
aggataaatt atcgcgcgcg gtgtcatcta tgttactaga tcgctcga 3648

<210> SEQ ID NO 34
<211> LENGTH: 5100
<212> TYPE: DNA
<213> ORGANISM: Artificial Sequence
<220> FEATURE:
<223> OTHER INFORMATION: recombinant pABM-BdEF1_expression_cassette

<400> SEQUENCE: 34 gatccccccgg gctgcaggaa ttcaagctta cgcgtgtcga ctcgaatttc cccgatcgtt 60
caaacatttg gcaataaagt ttcttaagat tgaatcctgt tgccggtctt gcgatgatta 120
tcatataatt tctgttgaat tacgttaagc atgtaataat taacatgtaa tgcatgacgt 180
tatttatgag atgggttttt atgattagag tcccgcaatt atacatttaa tacgcgatag 240
aaaacaaaat atagcgcgca aactaggata aattatcgcg cgcggtgtca tctatgttac 300
tagatcgctc gacgcggccg ccatggccag atcgtaccca attcgcccta tagtgagtcg 360
tattacaatt cactggccgt cgttttacaa cgtcgtgact gggaaaaccc tggcgttacc 420
caacttaatc gccttgcagc acatccccct ttcgccagct ggcgtaatag cgaagaggcc 480
cgcaccgatc gcccttccca acagttgcgc agcctgaatg gcgaatggaa attgtaagcg 540
ttaatatttt gttaaaattc gcgttaaatt tttgttaaat cagctcattt tttaaccaat 600
aggccgaaat cggcaaaatc ccttataaat caaaagaata gaccgagata gggttgagtg 660
ttgttccagt ttggaacaag agtccactat taaagaacgt ggactccaac gtcaaagggc 720
gaaaaaccgt ctatcagggc gatggcccac tacgtgaacc atcaccctaa tcaagttttt 780
tggggtcgag gtgccgtaaa gcactaaatc ggaaccctaa agggagcccc cgatttagag 840
cttgacgggg aaagccggcg aacgtggcga gaaaggaagg gaagaaagcg aaaggagcgg 900
gcgctagggc gctggcaagt gtagcggtca cgctgcgcgt aaccaccaca cccgccgcgc 960
ttaatgcgcc gctacagggc gcgtcaggtg gcacttttcg gggaaatgtg cgcggaaccc 1020
ctatttgttt atttttctaa atacattcaa atatgtatcc gctcatgaga caataaccct 1080
gataaatgct tcaataatat tgaaaaagga agagtatgag tattcaacat ttccgtgtcg 1140
cccttattcc cttttttgcg gcattttgcc ttcctgtttt tgctcaccca gaaacgctgg 1200
tgaaagtaaa agatgctgaa gatcagttgg gtgcacgagt gggttacatc gaactggatc 1260

-continued

```
tcaacagcgg taagatcctt gagagttttc gccccgaaga acgttttcca atgatgagca   1320
cttttaaagt tctgctatgt ggcgcggtat tatcccgtat tgacgccggg caagagcaac   1380
tcggtcgccg catacactat tctcagaatg acttggttga gtactcacca gtcacagaaa   1440
agcatcttac ggatggcatg acagtaagag aattatgcag tgctgccata accatgagtg   1500
ataacactgc ggccaactta cttctgacaa cgatcggagg accgaaggag ctaaccgctt   1560
ttttgcacaa catgggggat catgtaactc gccttgatcg ttgggaaccg gagctgaatg   1620
aagccatacc aaacgacgag cgtgacacca cgatgcctgt agcaatggca acaacgttgc   1680
gcaaactatt aactggcgaa ctacttactc tagcttcccg gcaacaatta atagactgga   1740
tggaggcgga taaagttgca ggaccacttc tgcgctcggc ccttccggct ggctggttta   1800
ttgctgataa atctggagcc ggtgagcgtg ggtctcgcgg tatcattgca gcactggggc   1860
cagatggtaa gccctcccgt atcgtagtta tctacacgac ggggagtcag gcaactatgg   1920
atgaacgaaa tagacagatc gctgagatag gtgcctcact gattaagcat tggtaactgt   1980
cagaccaagt ttactcatat atactttaga ttgatttaaa acttcatttt taatttaaaa   2040
ggatctaggt gaagatcctt tttgataatc tcatgaccaa aatcccttaa cgtgagtttt   2100
cgttccactg agcgtcagac cccgtagaaa agatcaaagg atcttcttga gatccttttt   2160
ttctgcgcgt aatctgctgc ttgcaaacaa aaaaaccacc gctaccagcg gtggtttgtt   2220
tgccggatca agagctacca actctttttc cgaaggtaac tggcttcagc agagcgcaga   2280
taccaaatac tgtccttcta gtgtagccgt agttaggcca ccacttcaag aactctgtag   2340
caccgcctac atacctcgct ctgctaatcc tgttaccagt ggctgctgcc agtggcgata   2400
agtcgtgtct taccgggttg gactcaagac gatagttacc ggataaggcg cagcggtcgg   2460
gctgaacggg gggttcgtgc acacagccca gcttggagcg aacgacctac accgaactga   2520
gatacctaca gcgtgagcta tgagaaagcg ccacgcttcc cgaagggaga aaggcggaca   2580
ggtatccggt aagcggcagg gtcggaacag gagagcgcac gagggagctt ccagggggaa   2640
acgcctggta tctttatagt cctgtcgggt ttcgccacct ctgacttgag cgtcgatttt   2700
tgtgatgctc gtcagggggg cggagcctat ggaaaaacgc cagcaacgcg gcctttttac   2760
ggttcctggc cttttgctgg ccttttgctc acatgttctt tcctgcgtta tcccctgatt   2820
ctgtggataa ccgtattacc gcctttgagt gagctgatac cgctcgccgc agccgaacga   2880
ccgagcgcag cgagtcagtg agcgaggaag cggaagagcg cccaatacgc aaaccgcctc   2940
tccccgcgcg ttggccgatt cattaatgca gctggcacga caggtttccc gactggaaag   3000
cgggcagtga gcgcaacgca attaatgtga gttagctcac tcattaggca ccccaggctt   3060
tacactttat gcttccggct cgtatgttgt gtggaattgt gagcggataa caatttcaca   3120
caggaaacag ctatgaccat gattacgcca agctcgaaat taaccctcac taaagggaac   3180
aaaagctgga ctagaggccc ttaaggcctt actagacttc accgccattg caaaaattgt   3240
caataaatat ttagagtggg tggcatcaga aaaacatctc tagtggactc tcttcctatc   3300
atagctactc gggctgtaga tagaacgagg gcacaagagt tgggtggcgt aggtttactc   3360
gtgacctcaa ctcttttggc tgtgtcttac gtctaagatg ggtttggcat gtgagaaaca   3420
taggtctaag caattcatgt tagggctgtt gcattgttgt tgcatcaacc aaatgtccag   3480
atagcagttc atgctacatc tagttgaaaa ccctcatcat taggcggaac atgtgttctt   3540
ttttagcata gtcaaagtca gattgcggca ctcgctcatc cacggaaaga attttccctg   3600
tgcaggcatc tcgatcaaaa gacgcaaatt aatttttgaa tagcgatata acaatatcta   3660
```

attaacgttt cttgttttct gcgaaatgtc tttcatcata aaatgagtca tctcgatgag 3720
cccaagtgac atagcccaac accccacccc accaataaaa gtgaagaaaa catgttggga 3780
aaactatacc aagtaaaata cgagttgttc taaagaaaaa gtaaagtacg agttagatcg 3840
caccctgtcc tggagtgtgg cttgatgatc caactcctag cattgtatcc ctgtttttgg 3900
atgatgtaac tattatttac aatgaataaa gaggtgtttt actagtaaaa aaatcttgag 3960
gggaggagaa aataatggag gtcttttttc aaaccgatgg actattattt ttagtgaaag 4020
agaataatat tattggaaaa attattctat ccacttattt tatattggca gaatacaaag 4080
aatggtgggg tccacgcgga acttgcggcc cccgaaacct atcgagggcg cggtacccaa 4140
gcaaggaacg gaggaaactt gcggggcccg aaacctagtg ataaaaggca tatcatccac 4200
acgatgaaga tctgacggac catatctccc accacggaaa gccatcagac gaggatcaga 4260
cggccaggaa ggaaccctag cgcccgccgg tgccaatata aagcgccact ctctctcgtc 4320
ttaagcccca gcctctccat tcccctctcc ctctcgccgc cgccgtctcc ttctcctact 4380
cccttcgagg tgtgttgttc atccgtcccg aatccatcca tcccctcttc agatgtgttg 4440
ttcatggctc taatagctct agatctgctt gtttgtgttg tttagctcta gatctactcg 4500
cgcgcgcttc tctctcgatc tcctgtagaa caattttggt tggtttttg tgcatatcca 4560 tggtaatttt gtctgcaata tggaggaggc tttctaagct cctacgtagc atcgatcttt 4620
agaattccct cggtttctgt ttatttcttc gcgagggctc tctgttatct gtaggagtag 4680
ctgtaagcgc ggttcgttac ggattaatcg tcatgcttag ttgaacctat cggtcgaagg 4740
atttgtgtgg gttgtcgtgt agaattgaca ccatctactt actgtactga tatgccgatc 4800
tgtaggatac tcttcattac ttttgtttac tgctagttgt ggtgtagatt tagcattctc 4860
aaacccatgc tgtagcgttt ctaatattgt tacatagatc taccggtgcc tgttaattgt 4920
attcgatcgg gcgtttctac atctgtccgc ccacctagtt ttatatgtgg taatcaaaat 4980
tgcgttgact tcgtgatgct gtctgtgtac tgtttttaat cgctcttact tagatgatca 5040
acatggtgat ggttacgatt tactgttttc taatccctgt tacttcgatg ctgcagtttg 5100

<210> SEQ ID NO 35
<211> LENGTH: 5865
<212> TYPE: DNA
<213> ORGANISM: Artificial Sequence
<220> FEATURE:
<223> OTHER INFORMATION: recombinant pABM-BdEF1_RBG1

<400> SEQUENCE: 35
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcattttta accaataggc cgaaatcggc aaaatccctt 600

```
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gtttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac   1020
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgtttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc cttttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
```

atgtgagtta gctcactcat taggcacccc aggctttaca ctttatgctt ccggctcgta 3060
tgttgtgtgg aattgtgagc ggataacaat ttcacacagg aaacagctat gaccatgatt 3120
acgccaagct cgaaattaac cctcactaaa gggaacaaaa gctggactag aggcccttaa 3180
ggccttacta gacttcaccg ccattgcaaa aattgtcaat aaatatttag agtgggtggc 3240
atcagaaaaa catctctagt ggactctctt cctatcatag ctactcgggc tgtagataga 3300
acgagggcac aagagttggg tggcgtaggt ttactcgtga cctcaactct tttggctgtg 3360
tcttacgtct aagatgggtt tggcatgtga gaaacatagg tctaagcaat tcatgttagg 3420
gctgttgcat tgttgttgca tcaaccaaat gtccagatag cagttcatgc tacatctagt 3480
tgaaaaccct catcattagg cggaacatgt gttctttttt agcatagtca aagtcagatt 3540
gcggcactcg ctcatccacg gaaagaattt tccctgtgca ggcatctcga tcaaaagacg 3600
caaattaatt tttgaatagc gatataacaa tatctaatta acgtttcttg ttttctgcga 3660
aatgtctttc atcataaaat gagtcatctc gatgagccca agtgacatag cccaacaccc 3720
caccccacca ataaaagtga agaaaacatg ttgggaaaac tataccaagt aaaatacgag 3780
ttgttctaaa gaaaaagtaa agtacgagtt agatcgcacc ctgtcctgga gtgtggcttg 3840
atgatccaac tcctagcatt gtatccctgt ttttggatga tgtaactatt atttacaatg 3900
aataaagagg tgttttacta gtaaaaaaat cttgagggga ggagaaaata atggaggtct 3960
tttttcaaac cgatggacta ttatttttag tgaaagagaa taatattatt ggaaaaatta 4020
ttctatccac ttattttata ttggcagaat acaaagaatg gtggggtcca cgcggaactt 4080
gcggcccccg aaacctatcg agggcgcggt acccaagcaa ggaacggagg aaacttgcgg 4140
ggcccgaaac ctagtgataa aaggcatatc atccacacga tgaagatctg acggaccata 4200
tctcccacca cggaaagcca tcagacgagg atcagacggc caggaaggaa ccctagcgcc 4260
cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860
tattgttaca tagatctacc ggtgcctgtt aattgtattc gatcgggcgt ttctacatct 4920
gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggagtcg ggctccggga 5100
cggctgctgg ctctggctat gtttacagac agccaggatc aacgcggtgg aacccgacag 5160
ctgaacaact gtccttgctt agagaaatct actaccgcaa cggattgcgg accccgaccg 5220
cggacgaaat cagacaaatc agctcaaagc tctcaaggta cggaaaaata gagggcaaaa 5280
acgtttacaa ctggttccag aatagacgcg caagagaaaa gcgcaagcaa cggctctcta 5340

```
caatcggctg tgatccagca ctgatcgaga tggggaatgt cgcttcactg gaattcggta   5400

ctgagagcgc cctggaatcg ctgtcgtcag gaccatcctc agaactccgc gaagcgccaa   5460

cgagaaaatt ttacgaaaaa aagacggttg gagagaactc aactataata aacccagtgg   5520

aacaaaactg taccctttcc tgcggaacgt cccaagagtt ccagtatgcg gtcgattctc   5580

ggcgcgtcat gaaagctatg gaggaaaagc aggcgacgga cgatgaaccc gacggaaata   5640

aatggactga gtcaaacaga cacgtcaaga ttctccagct tttcccgctc cacaataacg   5700

aggatcagac attgataaag agcgacaaag aaatctattg tttgggctcg tgcgagaaga   5760

aaatggattt gtcaccgctg ggtcattcag gctctcagcg cgcttcggcc cttgacttgt   5820

gcctttcatt gggcaacgaa tcttgtgggc tgcatgataa ttgaa                  5865
```

<210> SEQ ID NO 36
<211> LENGTH: 5865
<212> TYPE: DNA
<213> ORGANISM: Artificial Sequence
<220> FEATURE:
<223> OTHER INFORMATION: recombinant pABM-BdEF1_RBG2

<400> SEQUENCE: 36

```
agcttacgcg tgtcgactcg aatttccccg atcgttcaaa catttggcaa taaagtttct     60

taagattgaa tcctgttgcc ggtcttgcga tgattatcat ataatttctg ttgaattacg    120

ttaagcatgt aataattaac atgtaatgca tgacgttatt tatgagatgg gtttttatga    180

ttagagtccc gcaattatac atttaatacg cgatagaaaa caaaatatag cgcgcaaact    240

aggataaatt atcgcgcgcg gtgtcatcta tgttactaga tcgctcgacg cggccgccat    300

ggccagatcg tacccaattc gccctatagt gagtcgtatt acaattcact ggccgtcgtt    360

ttacaacgtc gtgactggga aaaccctggc gttacccaac ttaatcgcct tgcagcacat    420

ccccctttcg ccagctggcg taatagcgaa gaggcccgca ccgatcgccc ttcccaacag    480

ttgcgcagcc tgaatggcga atggaaattg taagcgttaa tattttgtta aaattcgcgt    540

taaatttttg ttaaatcagc tcatttttta accaataggc cgaaatcggc aaaatccctt    600

ataaatcaaa agaatagacc gagatagggt tgagtgttgt tccagtttgg aacaagagtc    660

cactattaaa gaacgtggac tccaacgtca aagggcgaaa aaccgtctat cagggcgatg    720

gcccactacg tgaaccatca ccctaatcaa gtttttttggg gtcgaggtgc cgtaaagcac    780

taaatcggaa ccctaaaggg agcccccgat ttagagcttg acggggaaag ccggcgaacg    840

tggcgagaaa ggaagggaag aaagcgaaag gagcgggcgc tagggcgctg gcaagtgtag    900

cggtcacgct gcgcgtaacc accacacccg ccgcgcttaa tgcgccgcta cagggcgcgt    960

caggtggcac ttttcgggga aatgtgcgcg gaacccctat ttgtttattt ttctaaatac   1020

attcaaatat gtatccgctc atgagacaat aaccctgata aatgcttcaa taatattgaa   1080

aaaggaagag tatgagtatt caacatttcc gtgtcgccct tattcccttt tttgcggcat   1140

tttgccttcc tgtttttgct cacccagaaa cgctggtgaa agtaaaagat gctgaagatc   1200

agttgggtgc acgagtgggt tacatcgaac tggatctcaa cagcggtaag atccttgaga   1260

gttttcgccc cgaagaacgt tttccaatga tgagcacttt taaagttctg ctatgtggcg   1320

cggtattatc ccgtattgac gccgggcaag agcaactcgg tcgccgcata cactattctc   1380

agaatgactt ggttgagtac tcaccagtca cagaaaagca tcttacggat ggcatgacag   1440

taagagaatt atgcagtgct gccataacca tgagtgataa cactgcggcc aacttacttc   1500

tgacaacgat cggaggaccg aaggagctaa ccgctttttt gcacaacatg ggggatcatg   1560
```

```
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt tttggatga tgtaactatt atttacaatg   3900
```

```
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggaatcg ggctccggca   5100
cggcggcagg gtctggttat gtctatcggc agagcggaag cacccggtgg aatccaacag   5160
cagaacagtt gtcgctgctc aaggaacttt attaccggaa tggaattcgg acaccgtcgg   5220
cagatcaaat taggcaaatt tcggcccggc tgtccagata cggcaaaata gaagggaaaa   5280
acgtctttta ctggtttcaa aatcataaag cacgggaacg gcagaagaaa agactttcca   5340
cggtcggctg cgaccctgct ctcatagaaa tgggtaacgt cgcgagcttg gaatttggga   5400
ccgaaagcgc tcttgaatct ctcagctcag gcccgtccag cgagttgcgc gaggctccta   5460
cccgcaagtt ttatgagaag aaaaccgttg gtgagaacag caccataatc aatcctgttg   5520
agcagaactg cacactttct tgcggtactt cgcaggaatt tcagtatgct gttgatagcc   5580
gccgggtgat gaaggcaatg gaagagaagc aagcaacgga tgatgaaccg gacggaaaca   5640
aatggacgga gtcgaacagg catgtgaaga ccctccctct tttccccttg cataataatg   5700
aagatcagac cttgatcaag tcggacaagg aaatttattg ccttgggagc tgtgaaaaaa   5760
aaatggatct gtccccattg ggacactcgg gctctcagag ggcgtcggca ctggatttgt   5820
gcctgtcttt gggtaatgaa tcttgtggcc tccacgacaa ttgaa                   5865
```

<210> SEQ ID NO 37
<211> LENGTH: 5559
<212> TYPE: DNA
<213> ORGANISM: Artificial Sequence
<220> FEATURE:
<223> OTHER INFORMATION: recombinant pABM-BdEF1_RBG3

<400> SEQUENCE: 37

```
agcttacgcg tgtcgactcg aatttccccg atcgttcaaa catttggcaa taaagtttct     60
taagattgaa tcctgttgcc ggtcttgcga tgattatcat ataatttctg ttgaattacg    120
```

```
ttaagcatgt aataattaac atgtaatgca tgacgttatt tatgagatgg gtttttatga    180
ttagagtccc gcaattatac atttaatacg cgatagaaaa caaaatatag cgcgcaaact    240
aggataaatt atcgcgcgcg gtgtcatcta tgttactaga tcgctcgacg cggccgccat    300
ggccagatcg tacccaattc gccctatagt gagtcgtatt acaattcact ggccgtcgtt    360
ttacaacgtc gtgactggga aaaccctggc gttacccaac ttaatcgcct tgcagcacat    420
ccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540
taaatttttg ttaaatcagc tcatttttta accaataggc cgaaatcggc aaaatccctt    600
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gttttttggg gtcgaggtgc cgtaaagcac    780
taaatcggaa ccctaaaggg agcccccgat ttagagcttg acggggaaag ccggcgaacg    840
tggcgagaaa ggaagggaag aaagcgaaag gagcgggcgc tagggcgctg gcaagtgtag    900
cggtcacgct gcgcgtaacc accacacccg ccgcgcttaa tgcgccgcta cagggcgcgt    960
caggtggcac ttttcgggga aatgtgcgcg gaacccctat ttgtttattt ttctaaatac   1020
attcaaatat gtatccgctc atgagacaat aaccctgata aatgcttcaa taatattgaa   1080
aaaggaagag tatgagtatt caacatttcc gtgtcgccct tattcccttt tttgcggcat   1140
tttgccttcc tgtttttgct cacccagaaa cgctggtgaa agtaaaagat gctgaagatc   1200
agttgggtgc acgagtgggt tacatcgaac tggatctcaa cagcggtaag atccttgaga   1260
gttttcgccc cgaagaacgt tttccaatga tgagcacttt taaagttctg ctatgtggcg   1320
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
```

agcccagctt ggagcgaacg acctacaccg aactgagata cctacagcgt gagctatgag 2520
aaagcgccac gcttcccgaa gggagaaagg cggacaggta tccggtaagc ggcagggtcg 2580
gaacaggaga gcgcacgagg gagcttccag ggggaaacgc ctggtatctt tatagtcctg 2640
tcgggtttcg ccacctctga cttgagcgtc gatttttgtg atgctcgtca ggggggcgga 2700
gcctatggaa aaacgccagc aacgcggcct ttttacggtt cctggccttt tgctggcctt 2760
ttgctcacat gttctttcct gcgttatccc ctgattctgt ggataaccgt attaccgcct 2820
ttgagtgagc tgataccgct cgccgcagcc gaacgaccga gcgcagcgag tcagtgagcg 2880
aggaagcgga agagcgccca atacgcaaac cgcctctccc cgcgcgttgg ccgattcatt 2940
aatgcagctg gcacgacagg tttcccgact ggaaagcggg cagtgagcgc aacgcaatta 3000
atgtgagtta gctcactcat taggcacccc aggctttaca ctttatgctt ccggctcgta 3060
tgttgtgtgg aattgtgagc ggataacaat ttcacacagg aaacagctat gaccatgatt 3120
acgccaagct cgaaattaac cctcactaaa gggaacaaaa gctggactag aggcccttaa 3180
ggccttacta gacttcaccg ccattgcaaa aattgtcaat aaatatttag agtgggtggc 3240
atcagaaaaa catctctagt ggactctctt cctatcatag ctactcgggc tgtagataga 3300
acgagggcac aagagttggg tggcgtaggt ttactcgtga cctcaactct tttggctgtg 3360
tcttacgtct aagatgggtt tggcatgtga gaaacatagg tctaagcaat tcatgttagg 3420
gctgttgcat tgttgttgca tcaaccaaat gtccagatag cagttcatgc tacatctagt 3480
tgaaaaccct catcattagg cggaacatgt gttctttttt agcatagtca aagtcagatt 3540
gcggcactcg ctcatccacg gaaagaattt tccctgtgca ggcatctcga tcaaaagacg 3600
caaattaatt tttgaatagc gatataacaa tatctaatta acgtttcttg ttttctgcga 3660
aatgtctttc atcataaaat gagtcatctc gatgagccca agtgacatag cccaacaccc 3720
caccccacca ataaaagtga agaaaacatg ttgggaaaac tataccaagt aaaatacgag 3780
ttgttctaaa gaaaaagtaa agtacgagtt agatcgcacc ctgtcctgga gtgtggcttg 3840
atgatccaac tcctagcatt gtatccctgt ttttggatga tgtaactatt atttacaatg 3900
aataaagagg tgttttacta gtaaaaaaat cttgagggga ggagaaaata atggaggtct 3960
tttttcaaac cgatggacta ttatttttag tgaaagagaa taatattatt ggaaaaatta 4020
ttctatccac ttattttata ttggcagaat acaaagaatg gtggggtcca cgcggaactt 4080
gcggcccccg aaacctatcg agggcgcggt acccaagcaa ggaacggagg aaacttgcgg 4140
ggcccgaaac ctagtgataa aaggcatatc atccacacga tgaagatctg acggaccata 4200
tctcccacca cggaaagcca tcagacgagg atcagacggc caggaaggaa ccctagcgcc 4260
cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860

```
tattgttaca tagatctacc ggtgcctgtt aattgtattc gatcgggcgt ttctacatct   4920

gtccgcccac ctagttttat atgtggtaat caaaattgcg ttgacttcgt gatgctgtct   4980

gtgtactgtt tttaatcgct cttacttaga tgatcaacat ggtgatggtt acgatttact   5040

gttttctaat ccctgttact tcgatgctgc agtttggatc catggttagc aagggggagg   5100

aggttattaa agaattccca ggaagcaccc ggtggaatcc aacggcggag caactttcgc   5160

tccttcggga aatttattac aggaatgggc tgagaactcc caccgctgac gagatcagac   5220

agatttcatc aaaattgtcg cggtatggta agattgaagg gaaaaatgtg tacaactggt   5280

tccagaacag aagagctagg gaaaagagaa aacagcggtt gtcaacccata ggctgtggtt   5340

cggcggggtc ggccgcaggg agcggagagt ttcgccatgt gaagaccctg cccctttcc   5400

ctttgcataa taatgaggat tcaggttcgt tggatctgga gctggaattg ggttttgcct   5460

ctgctaccgc agccgcgact tctggttcac aaagggcgtc ggcattggat ctctgcctgt   5520

cccttggaaa tgagtcatgc ggtttgcatg acaactgaa                          5559
```

<210> SEQ ID NO 38
<211> LENGTH: 5559
<212> TYPE: DNA
<213> ORGANISM: Artificial Sequence
<220> FEATURE:
<223> OTHER INFORMATION: recombinant pABM-BdEF1_RBG4

<400> SEQUENCE: 38

```
agcttacgcg tgtcgactcg aatttccccg atcgttcaaa catttggcaa taaagtttct     60

taagattgaa tcctgttgcc ggtcttgcga tgattatcat ataatttctg ttgaattacg    120

ttaagcatgt aataattaac atgtaatgca tgacgttatt tatgagatgg gtttttatga    180

ttagagtccc gcaattatac atttaatacg cgatagaaaa caaaatatag cgcgcaaact    240

aggataaatt atcgcgcgcg gtgtcatcta tgttactaga tcgctcgacg cggccgccat    300

ggccagatcg tacccaattc gccctatagt gagtcgtatt acaattcact ggccgtcgtt    360

ttacaacgtc gtgactggga aaaccctggc gttacccaac ttaatcgcct tgcagcacat    420

ccccctttcg ccagctggcg taatagcgaa gaggcccgca ccgatcgccc ttcccaacag    480

ttgcgcagcc tgaatggcga atggaaattg taagcgttaa tattttgtta aaattcgcgt    540

taaatttttg ttaaatcagc tcatttttta accaataggc cgaaatcggc aaaatccctt    600

ataaatcaaa agaatagacc gagatagggt tgagtgttgt tccagtttgg aacaagagtc    660

cactattaaa gaacgtggac tccaacgtca aagggcgaaa aaccgtctat cagggcgatg    720

gcccactacg tgaaccatca ccctaatcaa gtttttggg gtcgaggtgc cgtaaagcac    780

taaatcggaa ccctaaaggg agcccccgat ttagagcttg acggggaaag ccggcgaacg    840

tggcgagaaa ggaagggaag aaagcgaaag gagcgggcgc tagggcgctg gcaagtgtag    900

cggtcacgct gcgcgtaacc accacacccg ccgcgcttaa tgcgccgcta cagggcgcgt    960

caggtggcac ttttcgggga aatgtgcgcg gaacccctat ttgtttattt ttctaaatac   1020

attcaaatat gtatccgctc atgagacaat aaccctgata aatgcttcaa taatattgaa   1080

aaaggaagag tatgagtatt caacatttcc gtgtcgccct tattcccttt tttgcggcat   1140

tttgccttcc tgtttttgct cacccagaaa cgctggtgaa agtaaaagat gctgaagatc   1200

agttgggtgc acgagtgggt tacatcgaac tggatctcaa cagcggtaag atccttgaga   1260

gttttcgccc cgaagaacgt tttccaatga tgagcacttt taaagttctg ctatgtggcg   1320
```

-continued

```
cggtattatc ccgtattgac gccgggcaag agcaactcgg tcgccgcata cactattctc   1380
agaatgactt ggttgagtac tcaccagtca cagaaaagca tcttacggat ggcatgacag   1440
taagagaatt atgcagtgct gccataacca tgagtgataa cactgcggcc aacttacttc   1500
tgacaacgat cggaggaccg aaggagctaa ccgctttttt gcacaacatg ggggatcatg   1560
taactcgcct tgatcgttgg gaaccggagc tgaatgaagc cataccaaac gacgagcgtg   1620
acaccacgat gcctgtagca atggcaacaa cgttgcgcaa actattaact ggcgaactac   1680
ttactctagc ttcccggcaa caattaatag actggatgga ggcggataaa gttgcaggac   1740
cacttctgcg ctcggccctt ccggctggct ggtttattgc tgataaatct ggagccggtg   1800
agcgtgggtc tcgcggtatc attgcagcac tggggccaga tggtaagccc tcccgtatcg   1860
tagttatcta cacgacgggg agtcaggcaa ctatggatga acgaaataga cagatcgctg   1920
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc cttttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
```

caccccacca ataaaagtga agaaaacatg ttgggaaaac tataccaagt aaaatacgag 3780
ttgttctaaa gaaaaagtaa agtacgagtt agatcgcacc ctgtcctgga gtgtggcttg 3840
atgatccaac tcctagcatt gtatccctgt ttttggatga tgtaactatt atttacaatg 3900
aataaagagg tgttttacta gtaaaaaaat cttgagggga ggagaaaata atggaggtct 3960
tttttcaaac cgatggacta ttatttttag tgaaagagaa taatattatt ggaaaaatta 4020
ttctatccac ttattttata ttggcagaat acaaagaatg gtggggtcca cgcggaactt 4080
gcggcccccg aaacctatcg agggcgcggt acccaagcaa ggaacggagg aaacttgcgg 4140
ggcccgaaac ctagtgataa aaggcatatc atccacacga tgaagatctg acggaccata 4200
tctcccacca cggaaagcca tcagacgagg atcagacggc caggaaggaa ccctagcgcc 4260
cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860
tattgttaca tagatctacc ggtgcctgtt aattgtattc gatcgggcgt ttctacatct 4920
gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggtctcg aaaggagaag 5100
aggtcatcaa agaattttca ggcagcaccc gctggaatcc gactgcagaa caactttctc 5160
tcctcaaaga gctttattac agaaatggga tcagaacccc ttcagcggac cagatacgcc 5220
agataagcgc ccgcttgtcg aggtacggca aaatcgaggg gaagaatgtt ttttactggt 5280
tccaaaacca taaagcgagg gagcggcaga agaaaagact gagcactgtg ggttgtggat 5340
cggcgggatc ggctgccggg tcaggtgaat ttcgccatgt taaaacgctt ccactgtttc 5400
ccttgcataa taatgaagac agcggatcac ttgacctgga gctggagttg ggcttcgctt 5460
ccgcgacggc tgctgcaaca tccggctcgc agcgggcgtc ggcgctggat ttgtgccttt 5520
cgctgggaaa tgagagctgc ggtcttcatg acaactgaa 5559

<210> SEQ ID NO 39
<211> LENGTH: 5583
<212> TYPE: DNA
<213> ORGANISM: Artificial Sequence
<220> FEATURE:
<223> OTHER INFORMATION: recombinant pABM-BdEF1_RBG5

<400> SEQUENCE: 39
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcatttttta accaataggc cgaaatcggc aaaatccctt 600
ataaatcaaa agaatagacc gagatagggt tgagtgttgt tccagtttgg aacaagagtc 660
cactattaaa gaacgtggac tccaacgtca aagggcgaaa aaccgtctat cagggcgatg 720
gcccactacg tgaaccatca ccctaatcaa gttttttggg gtcgaggtgc cgtaaagcac 780
taaatcggaa ccctaaaggg agcccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920
agataggtgc ctcactgatt aagcattggt aactgtcaga ccaagtttac tcatatatac 1980
tttagattga tttaaaactt catttttaat ttaaaaggat ctaggtgaag atcctttttg 2040
ataatctcat gaccaaaatc ccttaacgtg agttttcgtt ccactgagcg tcagaccccg 2100
tagaaaagat caaaggatct tcttgagatc ctttttttct gcgcgtaatc tgctgcttgc 2160
aaacaaaaaa accaccgcta ccagcggtgg tttgtttgcc ggatcaagag ctaccaactc 2220
tttttccgaa ggtaactggc ttcagcagag cgcagatacc aaatactgtc cttctagtgt 2280
agccgtagtt aggccaccac ttcaagaact ctgtagcacc gcctacatac ctcgctctgc 2340
taatcctgtt accagtggct gctgccagtg gcgataagtc gtgtcttacc gggttggact 2400
caagacgata gttaccggat aaggcgcagc ggtcgggctg aacggggggt tcgtgcacac 2460
agcccagctt ggagcgaacg acctacaccg aactgagata cctacagcgt gagctatgag 2520
aaagcgccac gcttcccgaa gggagaaagg cggacaggta tccggtaagc ggcagggtcg 2580

```
gaacaggaga gcgcacgagg gagcttccag gggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
```

gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggtgtct aaaggggaag 5100
aggtcataaa agagttctca ggttctactc gctggaatcc aactgcagaa caactctctc 5160
tcctgaagga gctctactat cggaacggaa tacgcacgcc ttcggcggac caaataaggc 5220
agatttcagc ccgcctgtct agatacggga aaatcgaggg aaagaacgtg ttttattggt 5280
tccaaaacca taaggcaaga gagcggcaga aaaaacggct cagcacagtc ggctgtgggt 5340
cagccggttc ggcggctggc tctggtgaat tccgccacgt caaaaccctg cctctgttcc 5400
cgctccacaa taatgtcgag acacttccct tgttcccgga ggattccggg tctctcgact 5460
tggagctcga attgggcttt gcctctgcca ctgcggcagc gaccagcgga tcacagagag 5520
cctccgcact ggatctgtgc ctgtcacttg gaaatgaatc gtgcggattg cacgacaatt 5580
gaa 5583

<210> SEQ ID NO 40
<211> LENGTH: 5853
<212> TYPE: DNA
<213> ORGANISM: Artificial Sequence
<220> FEATURE:
<223> OTHER INFORMATION: recombinant pABM-BdEF1_RBG6

<400> SEQUENCE: 40
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcatttttta accaataggc cgaaatcggc aaaatccctt 600
ataaatcaaa agaatagacc gagatagggt tgagtgttgt tccagtttgg aacaagagtc 660
cactattaaa gaacgtggac tccaacgtca aagggcgaaa aaccgtctat cagggcgatg 720
gcccactacg tgaaccatca ccctaatcaa gtttttgggg gtcgaggtgc cgtaaagcac 780
taaatcggaa ccctaaaggg agcccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920
agataggtgc ctcactgatt aagcattggt aactgtcaga ccaagtttac tcatatatac 1980
tttagattga tttaaaactt catttttaat ttaaaaggat ctaggtgaag atcctttttg 2040
ataatctcat gaccaaaatc ccttaacgtg agttttcgtt ccactgagcg tcagaccccg 2100
tagaaaagat caaaggatct tcttgagatc cttttttttct gcgcgtaatc tgctgcttgc 2160
aaacaaaaaa accaccgcta ccagcggtgg tttgtttgcc ggatcaagag ctaccaactc 2220
tttttccgaa ggtaactggc ttcagcagag cgcagatacc aaatactgtc cttctagtgt 2280
agccgtagtt aggccaccac ttcaagaact ctgtagcacc gcctacatac ctcgctctgc 2340
taatcctgtt accagtggct gctgccagtg gcgataagtc gtgtcttacc gggttggact 2400
caagacgata gttaccggat aaggcgcagc ggtcgggctg aacggggggt tcgtgcacac 2460
agcccagctt ggagcgaacg acctacaccg aactgagata cctacagcgt gagctatgag 2520
aaagcgccac gcttcccgaa gggagaaagg cggacaggta tccggtaagc ggcagggtcg 2580
gaacaggaga gcgcacgagg gagcttccag ggggaaacgc ctggtatctt tatagtcctg 2640
tcgggtttcg ccacctctga cttgagcgtc gatttttgtg atgctcgtca ggggggcgga 2700
gcctatggaa aaacgccagc aacgcggcct ttttacggtt cctggccttt tgctggcctt 2760
ttgctcacat gttctttcct gcgttatccc ctgattctgt ggataaccgt attaccgcct 2820
ttgagtgagc tgataccgct cgccgcagcc gaacgaccga gcgcagcgag tcagtgagcg 2880
aggaagcgga agagcgccca atacgcaaac cgcctctccc cgcgcgttgg ccgattcatt 2940
aatgcagctg gcacgacagg tttcccgact ggaaagcggg cagtgagcgc aacgcaatta 3000
atgtgagtta gctcactcat taggcacccc aggctttaca ctttatgctt ccggctcgta 3060
tgttgtgtgg aattgtgagc ggataacaat ttcacacagg aaacagctat gaccatgatt 3120
acgccaagct cgaaattaac cctcactaaa gggaacaaaa gctggactag aggcccttaa 3180
ggccttacta gacttcaccg ccattgcaaa aattgtcaat aaatatttag agtgggtggc 3240
atcagaaaaa catctctagt ggactctctt cctatcatag ctactcgggc tgtagataga 3300
acgagggcac aagagttggg tggcgtaggt ttactcgtga cctcaactct tttggctgtg 3360
tcttacgtct aagatgggtt tggcatgtga gaaacatagg tctaagcaat tcatgttagg 3420
gctgttgcat tgttgttgca tcaaccaaat gtccagatag cagttcatgc tacatctagt 3480
tgaaaaccct catcattagg cggaacatgt gttctttttt agcatagtca aagtcagatt 3540
gcggcactcg ctcatccacg gaaagaattt tccctgtgca ggcatctcga tcaaaagacg 3600
caaattaatt tttgaatagc gatataacaa tatctaatta acgtttcttg ttttctgcga 3660
aatgtctttc atcataaaat gagtcatctc gatgagccca agtgacatag cccaacaccc 3720

```
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggtgtct aaaggcgaag   5100
aggtcattaa ggagttcagc ggctctacta gatggaatcc aacggccgag caacttagcc   5160
tgctcaaaga actctattat cgcaatggga tacgcacgcc ctctgcagat cagatacgcc   5220
aaatctcagc gcgcctgtcc aggtatggga agattgaggg taaaaacgtc ttttactggt   5280
tccaaaatca caaagcgcgc gagagacaga agaaaagact cagcaccgtt ggttgtgacc   5340
ctgctctcat cgagatgggg aatgttgctt ccctggagtt tggcacagag agcgctttgg   5400
aatcactctc ttccggcccc tcaagcgaac tcagagaggc tcccactcgg aagttttacg   5460
agaaaaaaac cgtcggagaa aacagcacga ttatcaaccc cgtcgagcag aactgcaccc   5520
tctcatgcgg cacgtcccag gagtttcagt acgccgtcga ctcgaggaga gtgatgaagg   5580
cgatggagga aaagcaagca actgacgacg agcccgacgg aaacaagtgg actgaatcca   5640
atcgccatgt taaaacgttg cctttgttcc cgctccataa caatgtggag acgttgccac   5700
tcttcccgga ggactcggga tctctggact tggagctgga actgggcttt gcttcggcta   5760
ccgcagcagc cacctcgggt tcccagagag cctcggctct tgatctctgc ctgtcactgg   5820
gtaacgaatc ttgcggactg cacgataatt aga                                5853
```

<210> SEQ ID NO 41
<211> LENGTH: 5922
<212> TYPE: DNA
<213> ORGANISM: Artificial Sequence
<220> FEATURE:
<223> OTHER INFORMATION: recombinant pABM-BdEF1_RBG7

<400> SEQUENCE: 41
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcatttttta accaataggc cgaaatcggc aaaatccctt 600
ataaatcaaa agaatagacc gagatagggt tgagtgttgt tccagtttgg aacaagagtc 660
cactattaaa gaacgtggac tccaacgtca aagggcgaaa aaccgtctat cagggcgatg 720
gcccactacg tgaaccatca ccctaatcaa gttttttggg gtcgaggtgc cgtaaagcac 780
taaatcggaa ccctaaaggg agcccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920
agataggtgc ctcactgatt aagcattggt aactgtcaga ccaagtttac tcatatatac 1980
tttagattga tttaaaactt catttttaat ttaaaaggat ctaggtgaag atcctttttg 2040
ataatctcat gaccaaaatc ccttaacgtg agttttcgtt ccactgagcg tcagaccccg 2100
tagaaaagat caaaggatct tcttgagatc ctttttttct gcgcgtaatc tgctgcttgc 2160
aaacaaaaaa accaccgcta ccagcggtgg tttgtttgcc ggatcaagag ctaccaactc 2220
tttttccgaa ggtaactggc ttcagcagag cgcagatacc aaatactgtc cttctagtgt 2280

```
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttatttttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
cgccggtgcc aatataaagc gccactctct ctcgtcttaa gccccagcct ctccattccc   4320
ctctccctct cgccgccgcc gtctccttct cctactccct tcgaggtgtg ttgttcatcc   4380
gtcccgaatc catccatccc ctcttcagat gtgttgttca tggctctaat agctctagat   4440
ctgcttgttt gtgttgttta gctctagatc tactcgcgcg cgcttctctc tcgatctcct   4500
gtagaacaat tttggttggt tttttgtgca tatccatggt aattttgtct gcaatatgga   4560
ggaggctttc taagctccta cgtagcatcg atctttagaa ttccctcggt ttctgtttat   4620
ttcttcgcga gggctctctg ttatctgtag gagtagctgt aagcgcggtt cgttacggat   4680
```

```
taatcgtcat gcttagttga acctatcggt cgaaggattt gtgtgggttg tcgtgtagaa   4740
ttgacaccat ctacttactg tactgatatg ccgatctgta ggatactctt cattactttt   4800
gtttactgct agttgtggtg tagatttagc attctcaaac ccatgctgta gcgtttctaa   4860
tattgttaca tagatctacc ggtgcctgtt aattgtattc gatcgggcgt ttctacatct   4920
gtccgcccac ctagttttat atgtggtaat caaaattgcg ttgacttcgt gatgctgtct   4980
gtgtactgtt tttaatcgct cttacttaga tgatcaacat ggtgatggtt acgatttact   5040
gttttctaat ccctgttact tcgatgctgc agtttggatc catggtttca aagggggagg   5100
aggtcataaa agaattttct ggcagcacta gatggaatcc gactgctgag cagttgtctc   5160
tcctcaaaga actttactat aggaacggta tccgcactcc gtccgctgat caaattcgcc   5220
aaatttcggc cagactgtcc agatacggga aaattgaggg aaaaaatgtt ttctactggt   5280
tccagaatca taaggcgcgc gaaaggcaga aaaagagact ttcgaccgtc ggatgtgacc   5340
ctgcacttat cgaaatgggc aatgtcgcgt cgttggagtt tggcaccgaa tccgctctcg   5400
aatctcttag ctcgggcccc tcatcggaac tcagagaggc ccctaccaga aaattttatg   5460
agaaaaagac agtgggagag aactctacaa tcattaaccc cgtcgagcag aactgcacat   5520
tgagctgtgg aacatcgcag gagtttcaat acgcggtgga ttcgcgccgc gttatgaagg   5580
caatggagga gaagcaggca acagatgatg agccagacgg caataaatgg accgaatcta   5640
acagacatgt caagacactg ccacttttcc ctctccacaa caatgtcgag acactccctc   5700
tgtttcccga ggattcggga agcctggatc ttgagctgga acttggcttt gcatcaggtg   5760
gatctgccgg gtcagttgac acgctgccat tgtttcctag agaggctgcg ggttctgggg   5820
aatttgccac tgcggctgcg actagcggat cacagcgcgc atcggcgctc gacctctgcc   5880
tttctttggg taacgagtct tgcggcctgc atgacaactg aa                      5922
```

<210> SEQ ID NO 42
<211> LENGTH: 5580
<212> TYPE: DNA
<213> ORGANISM: Artificial Sequence
<220> FEATURE:
<223> OTHER INFORMATION: recombinant pABM-BdEF1_RBG8

<400> SEQUENCE: 42

```
agcttacgcg tgtcgactcg aatttccccg atcgttcaaa catttggcaa taaagtttct     60
taagattgaa tcctgttgcc ggtcttgcga tgattatcat ataatttctg ttgaattacg    120
ttaagcatgt aataattaac atgtaatgca tgacgttatt tatgagatgg gtttttatga    180
ttagagtccc gcaattatac atttaatacg cgatagaaaa caaaatatag cgcgcaaact    240
aggataaatt atcgcgcgcg gtgtcatcta tgttactaga tcgctcgacg cggccgccat    300
ggccagatcg tacccaattc gccctatagt gagtcgtatt acaattcact ggccgtcgtt    360
ttacaacgtc gtgactggga aaaccctggc gttacccaac ttaatcgcct tgcagcacat    420
ccccctttcg ccagctggcg taatagcgaa gaggcccgca ccgatcgccc ttcccaacag    480
ttgcgcagcc tgaatggcga atggaaattg taagcgttaa tattttgtta aaattcgcgt    540
taaatttttg ttaaatcagc tcatttttta accaataggc cgaaatcggc aaaatccctt    600
ataaatcaaa agaatagacc gagatagggt tgagtgttgt tccagtttgg aacaagagtc    660
cactattaaa gaacgtggac tccaacgtca aagggcgaaa aaccgtctat cagggcgatg    720
gcccactacg tgaaccatca ccctaatcaa gtttttggg gtcgaggtgc cgtaaagcac     780
```

taaatcggaa ccctaaaggg agccccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920
agataggtgc ctcactgatt aagcattggt aactgtcaga ccaagtttac tcatatatac 1980
tttagattga tttaaaactt catttttaat ttaaaaggat ctaggtgaag atcctttttg 2040
ataatctcat gaccaaaatc ccttaacgtg agttttcgtt ccactgagcg tcagaccccg 2100
tagaaaagat caaaggatct tcttgagatc cttttttct gcgcgtaatc tgctgcttgc 2160
aaacaaaaaa accaccgcta ccagcggtgg tttgtttgcc ggatcaagag ctaccaactc 2220
tttttccgaa ggtaactggc ttcagcagag cgcagatacc aaatactgtc cttctagtgt 2280
agccgtagtt aggccaccac ttcaagaact ctgtagcacc gcctacatac ctcgctctgc 2340
taatcctgtt accagtggct gctgccagtg gcgataagtc gtgtcttacc gggttggact 2400
caagacgata gttaccggat aaggcgcagc ggtcgggctg aacggggggt tcgtgcacac 2460
agcccagctt ggagcgaacg acctacaccg aactgagata cctacagcgt gagctatgag 2520
aaagcgccac gcttcccgaa gggagaaagg cggacaggta tccggtaagc ggcagggtcg 2580
gaacaggaga gcgcacgagg gagcttccag ggggaaacgc ctggtatctt tatagtcctg 2640
tcgggtttcg ccacctctga cttgagcgtc gatttttgtg atgctcgtca ggggggcgga 2700
gcctatggaa aaacgccagc aacgcggcct ttttacggtt cctggccttt tgctggcctt 2760
ttgctcacat gttctttcct gcgttatccc ctgattctgt ggataaccgt attaccgcct 2820
ttgagtgagc tgataccgct cgccgcagcc gaacgaccga gcgcagcgag tcagtgagcg 2880
aggaagcgga agagcgccca atacgcaaac cgcctctccc cgcgcgttgg ccgattcatt 2940
aatgcagctg gcacgacagg tttcccgact ggaaagcggg cagtgagcgc aacgcaatta 3000
atgtgagtta gctcactcat taggcacccc aggctttaca ctttatgctt ccggctcgta 3060
tgttgtgtgg aattgtgagc ggataacaat ttcacacagg aaacagctat gaccatgatt 3120
acgccaagct cgaaattaac cctcactaaa gggaacaaaa gctggactag aggcccttaa 3180
ggccttacta gacttcaccg ccattgcaaa aattgtcaat aaatatttag agtgggtggc 3240
atcagaaaaa catctctagt ggactctctt cctatcatag ctactcgggc tgtagataga 3300
acgagggcac aagagttggg tggcgtaggt ttactcgtga cctcaactct tttggctgtg 3360
tcttacgtct aagatgggtt tggcatgtga gaaacatagg tctaagcaat tcatgttagg 3420
gctgttgcat tgttgttgca tcaaccaaat gtccagatag cagttcatgc tacatctagt 3480
tgaaaaccct catcattagg cggaacatgt gttctttttt agcatagtca aagtcagatt 3540
gcggcactcg ctcatccacg gaaagaattt tccctgtgca ggcatctcga tcaaaagacg 3600
caaattaatt tttgaatagc gatataacaa tatctaatta acgtttcttg ttttctgcga 3660
aatgtctttc atcataaaat gagtcatctc gatgagccca agtgacatag cccaacaccc 3720
caccccacca ataaaagtga agaaaacatg ttgggaaaac tataccaagt aaaatacgag 3780
ttgttctaaa gaaaaagtaa agtacgagtt agatcgcacc ctgtcctgga gtgtggcttg 3840
atgatccaac tcctagcatt gtatccctgt ttttggatga tgtaactatt atttacaatg 3900
aataaagagg tgttttacta gtaaaaaaat cttgagggga ggagaaaata atggaggtct 3960
tttttcaaac cgatggacta ttatttttag tgaaagagaa taatattatt ggaaaaatta 4020
ttctatccac ttattttata ttggcagaat acaaagaatg gtggggtcca cgcggaactt 4080
gcggcccccg aaacctatcg agggcgcggt acccaagcaa ggaacggagg aaacttgcgg 4140
ggcccgaaac ctagtgataa aaggcatatc atccacacga tgaagatctg acggaccata 4200
tctcccacca cggaaagcca tcagacgagg atcagacggc caggaaggaa ccctagcgcc 4260
cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860
tattgttaca tagatctacc ggtgcctgtt aattgtattc gatcgggcgt ttctacatct 4920
gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggtttcg aaggggggaag 5100
aagtcattaa agagttttca gggtctacgc gctggaaccc taccgctgaa caagtcaagg 5160
ttttgaggga aatatattac cgcgcgggtc ttaggacgcc atccgcggat cagatccgcc 5220
aaatatcctc acagctgaaa cggtatggaa aggtggaagg aaaaaacgtg ttttattggt 5280
tccagaacca taaagcgcgg gaaagacaaa aaaagcggct cagcaccgtt gggagcgctg 5340
gctcagcagc gggttcaggt gagttcaggc acgttaaaac actgcccttg ttccctttgc 5400
acaataatga agactcaggg agcggtttgg acttggatct gaaccttgag ttgcgcctgt 5460
cggcgactgc tgctgccact tcgggctcac agcgggcgtc tgccctcgat ctggacttgg 5520
agctcagact cggtttcgcg cttggtaatg agtcgtgtgg actgcacgac aactagtgaa 5580

<210> SEQ ID NO 43
<211> LENGTH: 7128
<212> TYPE: DNA
<213> ORGANISM: Artificial Sequence
<220> FEATURE:
<223> OTHER INFORMATION: recombinant pABM-BdEF1_ZmPL T3

<400> SEQUENCE: 43
gatcccccgg gatggcttca gcgaacaact ggctgggctt ctcgctctcg ggccaggata 60
acccgcagcc taaccaggat agctcgcctg ccgccggtat cgacatctcc ggcgccagcg 120
acttctatgg cctgcccacg cagcagggct ccgacgggca tctcggcgtg ccgggcctgc 180
gggacgatca cgcttcttat ggtatcatgg aggcctacaa cagggttcct caagaaaccc 240
aagattggaa catgaggggc ttggactaca acggcggtgg ctcggagctc tcgatgcttg 300
tggggtccag cggcggcggc gggggcaacg gcaagagggc cgtggaagac agcgagccca 360
agctcgaaga tttcctcggc ggcaactcgt tcgtctccga tcaagatcag tccggcggtt 420
acctgttctc tggagtcccg atagccagca gcgccaatag caacagcggg agcaacacca 480
tggagctatc catgatcaag acctggctac ggaacaacca ggtggcccag ccccagccgc 540
cagctccaca tcagccgcag cctgaggaaa tgagcaccga cgccagcggc agcagctttg 600
gatgctcgga ttcgatggga aggaacagca tggtggcggc tggtgggagc tcgcagagcc 660
tggcgctctc gatgagcacg ggctcgcacc tgcccatggt tgtggccggc ggcagcgcca 720
gcggagcggc ctcggagagc acgtcgtcgg agaacaagcg agcgagcggt gccatggatt 780
cgcccggcag cgcggtagaa gccgtaccga ggaagtccat cgacacgttc gggcaaagga 840
cctctatata tcgaggtgta acaaggcata gatggacagg gcggtatgag gctcatctat 900
gggataatag ttgtagaaga gaagggcaga gtcgcaaggg taggcaagtt taccttggtg 960
gctatgacaa ggaggacaag gcagcaaggg cttacgattt ggcagctctc aagtattggg 1020
gcactacgac aacaacaaat ttccctataa gcaactacga aaaggagcta gaagaaatga 1080
aacatatgac tagacaggag tacattgcat acctaagaag aaatagcagt ggattttctc 1140
gtggggcgtc aaagtatcgt ggagtaacta gacatcatca gcatgggaga tggcaagcaa 1200
ggatagggag agttgcagga aacaaggatc tctacttggg cacattcagc accgaggagg 1260
aggcggcgga ggcctacgac atcgccgcga tcaagttccg cggtctcaac gccgtcacca 1320
acttcgacat gagccgctac gacgtgaaga gcatcctcga gagcagcaca ctgcctgtcg 1380
gcggcgcggc caggcgcctc aaggacgccg tggaccacgt ggaggccggc gccactatct 1440
ggcgcgccga catggacggc gccgtgatct cccagctggc cgaagccggg atgggcggct 1500
acgcctcgta cggccaccac ggctggccga ccatcgcgtt ccagcagccg tcgccgctct 1560
ccgtccacta cccgtacggc cagccgtccc gcgggtggtg caaacccgag caggacgcgg 1620
ccgccgccgc ggcccacagc ctgcaggacc tccagcagct gcacctcggc agcgcggccc 1680
acaacttctt ccaggcgtcg tcgagctcca cagtctacaa cggcggcgcc ggcgccagtg 1740
gtgggtacca gggcctcggt ggtggtagct ccttcctcat gccgtcgagc actgtcgtgg 1800
cggcggccga ccaggggcac agcagcacgg caaaccaggg gagcacgtgc agctacgggg 1860
acgaccacca ggaggggaag ctcatcggtt acgacgccgc catggtggcg accgcagctg 1920
gtggagaccc gtacgctgcg gcgaggaacg ggtaccagtt ctcgcagggc tcgggatcca 1980
cggtgagcat cgcgagggcg aacgggtacg ctaacaactg gagctctcct ttcaacaacg 2040
gcatggggtg aaagcttacg cgtgtcgact cgaatttccc cgatcgttca aacatttggc 2100
aataaagttt cttaagattg aatcctgttg ccggtcttgc gatgattatc atataatttc 2160
tgttgaatta cgttaagcat gtaataatta acatgtaatg catgacgtta tttatgagat 2220
gggtttttat gattagagtc ccgcaattat acatttaata cgcgatagaa aacaaaatat 2280
agcgcgcaaa ctaggataaa ttatcgcgcg cggtgtcatc tatgttacta gatcgctcga 2340
cgcggccgcc atggccagat cgtacccaat tcgccctata gtgagtcgta ttacaattca 2400
ctggccgtcg ttttacaacg tcgtgactgg gaaaaccctg gcgttaccca acttaatcgc 2460
cttgcagcac atcccccttt cgccagctgg cgtaatagcg aagaggcccg caccgatcgc 2520
ccttcccaac agttgcgcag cctgaatggc gaatggaaat tgtaagcgtt aatattttgt 2580
taaaattcgc gttaaatttt tgttaaatca gctcattttt taaccaatag gccgaaatcg 2640
gcaaaatccc ttataaatca aaagaataga ccgagatagg gttgagtgtt gttccagttt 2700
ggaacaagag tccactatta aagaacgtgg actccaacgt caaagggcga aaaaccgtct 2760
atcagggcga tggcccacta cgtgaaccat caccctaatc aagttttttg gggtcgaggt 2820
gccgtaaagc actaaatcgg aaccctaaag ggagcccccg atttagagct tgacggggaa 2880
agccggcgaa cgtggcgaga aaggaaggga agaaagcgaa aggagcgggc gctagggcgc 2940
tggcaagtgt agcggtcacg ctgcgcgtaa ccaccacacc cgccgcgctt aatgcgccgc 3000
tacagggcgc gtcaggtggc acttttcggg gaaatgtgcg cggaacccct atttgtttat 3060
ttttctaaat acattcaaat atgtatccgc tcatgagaca ataaccctga taaatgcttc 3120
aataatattg aaaaaggaag agtatgagta ttcaacattt ccgtgtcgcc cttattccct 3180
tttttgcggc attttgcctt cctgtttttg ctcacccaga aacgctggtg aaagtaaaag 3240
atgctgaaga tcagttgggt gcacgagtgg gttacatcga actggatctc aacagcggta 3300
agatccttga gagttttcgc cccgaagaac gttttccaat gatgagcact tttaaagttc 3360
tgctatgtgg cgcggtatta tcccgtattg acgccgggca agagcaactc ggtcgccgca 3420
tacactattc tcagaatgac ttggttgagt actcaccagt cacagaaaag catcttacgg 3480
atggcatgac agtaagagaa ttatgcagtg ctgccataac catgagtgat aacactgcgg 3540
ccaacttact tctgacaacg atcggaggac cgaaggagct aaccgctttt ttgcacaaca 3600
tgggggatca tgtaactcgc cttgatcgtt gggaaccgga gctgaatgaa gccataccaa 3660
acgacgagcg tgacaccacg atgcctgtag caatggcaac aacgttgcgc aaactattaa 3720
ctggcgaact acttactcta gcttcccggc aacaattaat agactggatg gaggcggata 3780
aagttgcagg accacttctg cgctcggccc ttccggctgg ctggtttatt gctgataaat 3840
ctggagccgg tgagcgtggg tctcgcggta tcattgcagc actggggcca gatggtaagc 3900
cctcccgtat cgtagttatc tacacgacgg ggagtcaggc aactatggat gaacgaaata 3960
gacagatcgc tgagataggt gcctcactga ttaagcattg gtaactgtca gaccaagttt 4020
actcatatat actttagatt gatttaaaac ttcattttta atttaaaagg atctaggtga 4080
agatcctttt tgataatctc atgaccaaaa tcccttaacg tgagttttcg ttccactgag 4140
cgtcagaccc cgtagaaaag atcaaaggat cttcttgaga tccttttttt ctgcgcgtaa 4200
tctgctgctt gcaaacaaaa aaaccaccgc taccagcggt ggtttgtttg ccggatcaag 4260
agctaccaac tctttttccg aaggtaactg gcttcagcag agcgcagata ccaaatactg 4320
tccttctagt gtagccgtag ttaggccacc acttcaagaa ctctgtagca ccgcctacat 4380
acctcgctct gctaatcctg ttaccagtgg ctgctgccag tggcgataag tcgtgtctta 4440
ccgggttgga ctcaagacga tagttaccgg ataaggcgca gcggtcgggc tgaacggggg 4500
gttcgtgcac acagcccagc ttggagcgaa cgacctacac cgaactgaga tacctacagc 4560
gtgagctatg agaaagcgcc acgcttcccg aagggagaaa ggcggacagg tatccggtaa 4620
gcggcagggt cggaacagga gagcgcacga gggagcttcc agggggaaac gcctggtatc 4680
tttatagtcc tgtcgggttt cgccacctct gacttgagcg tcgatttttg tgatgctcgt 4740
caggggggcg gagcctatgg aaaaacgcca gcaacgcggc ctttttacgg ttcctggcct 4800
tttgctggcc ttttgctcac atgttctttc ctgcgttatc ccctgattct gtggataacc 4860
gtattaccgc ctttgagtga gctgataccg ctcgccgcag ccgaacgacc gagcgcagcg 4920
agtcagtgag cgaggaagcg gaagagcgcc caatacgcaa accgcctctc cccgcgcgtt 4980
ggccgattca ttaatgcagc tggcacgaca ggtttcccga ctggaaagcg ggcagtgagc 5040
gcaacgcaat taatgtgagt tagctcactc attaggcacc ccaggcttta cactttatgc 5100
ttccggctcg tatgttgtgt ggaattgtga gcggataaca atttcacaca ggaaacagct 5160
atgaccatga ttacgccaag ctcgaaatta accctcacta aagggaacaa aagctggact 5220
agaggccctt aaggccttac tagacttcac cgccattgca aaaattgtca ataaatattt 5280
agagtgggtg gcatcagaaa aacatctcta gtggactctc ttcctatcat agctactcgg 5340
gctgtagata gaacgagggc acaagagttg ggtggcgtag gtttactcgt gacctcaact 5400
cttttggctg tgtcttacgt ctaagatggg tttggcatgt gagaaacata ggtctaagca 5460
attcatgtta gggctgttgc attgttgttg catcaaccaa atgtccagat agcagttcat 5520
gctacatcta gttgaaaacc ctcatcatta ggcggaacat gtgttctttt ttagcatagt 5580
caaagtcaga ttgcggcact cgctcatcca cggaaagaat tttccctgtg caggcatctc 5640
gatcaaaaga cgcaaattaa tttttgaata gcgatataac aatatctaat taacgtttct 5700
tgttttctgc gaaatgtctt tcatcataaa atgagtcatc tcgatgagcc caagtgacat 5760
agcccaacac cccaccccac caataaaagt gaagaaaaca tgttgggaaa actataccaa 5820
gtaaaatacg agttgttcta aagaaaaagt aaagtacgag ttagatcgca ccctgtcctg 5880
gagtgtggct tgatgatcca actcctagca ttgtatccct gtttttggat gatgtaacta 5940
ttatttacaa tgaataaaga ggtgttttac tagtaaaaaa atcttgaggg gaggagaaaa 6000
taatggaggt ctttttttcaa accgatggac tattattttt agtgaaagag aataatatta 6060
ttggaaaaat tattctatcc acttatttta tattggcaga atacaaagaa tggtggggtc 6120
cacgcggaac ttgcggcccc cgaaacctat cgagggcgcg gtacccaagc aaggaacgga 6180
ggaaacttgc ggggcccgaa acctagtgat aaaaggcata tcatccacac gatgaagatc 6240
tgacggacca tatctcccac cacggaaagc catcagacga ggatcagacg gccaggaagg 6300
aaccctagcg cccgccggtg ccaatataaa gcgccactct ctctcgtctt aagccccagc 6360
ctctccattc ccctctccct ctcgccgccg ccgtctcctt ctcctactcc cttcgaggtg 6420
tgttgttcat ccgtcccgaa tccatccatc ccctcttcag atgtgttgtt catggctcta 6480
atagctctag atctgcttgt ttgtgttgtt tagctctaga tctactcgcg cgcgcttctc 6540
tctcgatctc ctgtagaaca attttggttg gttttttgtg catatccatg gtaattttgt 6600
ctgcaatatg gaggaggctt tctaagctcc tacgtagcat cgatctttag aattccctcg 6660
gtttctgttt atttcttcgc gagggctctc tgttatctgt aggagtagct gtaagcgcgg 6720
ttcgttacgg attaatcgtc atgcttagtt gaacctatcg gtcgaaggat ttgtgtgggt 6780
tgtcgtgtag aattgacacc atctacttac tgtactgata tgccgatctg taggatactc 6840
ttcattactt ttgtttactg ctagttgtgg tgtagattta gcattctcaa acccatgctg 6900
tagcgtttct aatattgtta catagatcta ccggtgcctg ttaattgtat tcgatcgggc 6960
gtttctacat ctgtccgccc acctagtttt atatgtggta atcaaaattg cgttgacttc 7020
gtgatgctgt ctgtgtactg tttttaatcg ctcttactta gatgatcaac atggtgatgg 7080
ttacgattta ctgttttcta atccctgtta cttcgatgct gcagtttg 7128

<210> SEQ ID NO 44
<211> LENGTH: 6567
<212> TYPE: DNA
<213> ORGANISM: Artificial Sequence
<220> FEATURE:
<223> OTHER INFORMATION: recombinant pABM-BdEF1_ZmPL T5

<400> SEQUENCE: 44
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcatttttta accaataggc cgaaatcggc aaaatccctt 600
ataaatcaaa agaatagacc gagatagggt tgagtgttgt tccagtttgg aacaagagtc 660
cactattaaa gaacgtggac tccaacgtca aagggcgaaa aaccgtctat cagggcgatg 720
gcccactacg tgaaccatca ccctaatcaa gttttttggg gtcgaggtgc cgtaaagcac 780
taaatcggaa ccctaaaggg agcccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920
agataggtgc ctcactgatt aagcattggt aactgtcaga ccaagtttac tcatatatac 1980
tttagattga tttaaaactt catttttaat ttaaaaggat ctaggtgaag atcctttttg 2040
ataatctcat gaccaaaatc ccttaacgtg agttttcgtt ccactgagcg tcagaccccg 2100
tagaaaagat caaaggatct tcttgagatc cttttttct gcgcgtaatc tgctgcttgc 2160
aaacaaaaaa accaccgcta ccagcggtgg tttgtttgcc ggatcaagag ctaccaactc 2220
tttttccgaa ggtaactggc ttcagcagag cgcagatacc aaatactgtc cttctagtgt 2280
agccgtagtt aggccaccac ttcaagaact ctgtagcacc gcctacatac ctcgctctgc 2340
taatcctgtt accagtggct gctgccagtg gcgataagtc gtgtcttacc gggttggact 2400
caagacgata gttaccggat aaggcgcagc ggtcgggctg aacggggggt tcgtgcacac 2460
agcccagctt ggagcgaacg acctacaccg aactgagata cctacagcgt gagctatgag 2520
aaagcgccac gcttcccgaa gggagaaagg cggacaggta tccggtaagc ggcagggtcg 2580
gaacaggaga gcgcacgagg gagcttccag ggggaaacgc ctggtatctt tatagtcctg 2640
tcgggtttcg ccacctctga cttgagcgtc gatttttgtg atgctcgtca ggggggcgga 2700
gcctatggaa aaacgccagc aacgcggcct ttttacggtt cctggccttt tgctggcctt 2760
ttgctcacat gttctttcct gcgttatccc ctgattctgt ggataaccgt attaccgcct 2820
ttgagtgagc tgataccgct cgccgcagcc gaacgaccga gcgcagcgag tcagtgagcg 2880
aggaagcgga agagcgccca atacgcaaac cgcctctccc cgcgcgttgg ccgattcatt 2940
aatgcagctg gcacgacagg tttcccgact ggaaagcggg cagtgagcgc aacgcaatta 3000
atgtgagtta gctcactcat taggcacccc aggctttaca ctttatgctt ccggctcgta 3060
tgttgtgtgg aattgtgagc ggataacaat ttcacacagg aaacagctat gaccatgatt 3120
acgccaagct cgaaattaac cctcactaaa gggaacaaaa gctggactag aggcccttaa 3180
ggccttacta gacttcaccg ccattgcaaa aattgtcaat aaatatttag agtgggtggc 3240
atcagaaaaa catctctagt ggactctctt cctatcatag ctactcgggc tgtagataga 3300
acgagggcac aagagttggg tggcgtaggt ttactcgtga cctcaactct tttggctgtg 3360
tcttacgtct aagatgggtt tggcatgtga gaaacatagg tctaagcaat tcatgttagg 3420
gctgttgcat tgttgttgca tcaaccaaat gtccagatag cagttcatgc tacatctagt 3480
tgaaaaccct catcattagg cggaacatgt gttctttttt agcatagtca aagtcagatt 3540
gcggcactcg ctcatccacg gaaagaattt tccctgtgca ggcatctcga tcaaaagacg 3600
caaattaatt tttgaatagc gatataacaa tatctaatta acgtttcttg ttttctgcga 3660
aatgtctttc atcataaaat gagtcatctc gatgagccca agtgacatag cccaacaccc 3720
caccccacca ataaaagtga agaaaacatg ttgggaaaac tataccaagt aaaatacgag 3780
ttgttctaaa gaaaaagtaa agtacgagtt agatcgcacc ctgtcctgga gtgtggcttg 3840
atgatccaac tcctagcatt gtatccctgt ttttggatga tgtaactatt atttacaatg 3900
aataaagagg tgttttacta gtaaaaaaat cttgagggga ggagaaaata atggaggtct 3960
tttttcaaac cgatggacta ttatttttag tgaaagagaa taatattatt ggaaaaatta 4020
ttctatccac ttattttata ttggcagaat acaaagaatg gtggggtcca cgcggaactt 4080
gcggcccccg aaacctatcg agggcgcggt acccaagcaa ggaacggagg aaacttgcgg 4140
ggcccgaaac ctagtgataa aaggcatatc atccacacga tgaagatctg acggaccata 4200
tctcccacca cggaaagcca tcagacgagg atcagacggc caggaaggaa ccctagcgcc 4260
cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860
tattgttaca tagatctacc ggtgcctgtt aattgtattc gatcgggcgt ttctacatct 4920
gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggacacc tcgcaccact 5100
atcatccatg gctcaacttc tccctcgccc accactgtga cctcgaggag gaggagaggg 5160
gcgcggccgc cgagctggcc gcgatagccg gcgccgcgcc gccgccgaag ctggaggact 5220
tcctcggcgg aggcgtcgcc accggtggtc cggaggcggt ggcgcccgcg gagatgtacg 5280
actcggacct caagttcata gccgccgccg ggttccttgg cggctcggcg gcggcggcgg 5340
cgacgtcgcc gctgtcctcc ctcgaccagg ccggttccaa gctggccttg cctgcggcgg 5400
cggctgctcc ggcgccggag cagaggaagg ccgtcgactc ctttgggcag cgcacgtcca 5460
tctaccgcgg cgtcacacgg caccggtgga ctggcaggta cgaggcacat ctgtgggaca 5520
acagctgccg acgcgaaggg cagagccgca agggccgcca agtatatttg ggtggctatg 5580
ataaggagga gaaggctgcc agggcgtatg atcttgcagc tttgaagtac tggggttcta 5640
gcaccaccac caactttccg gttgctgagt atgagaagga ggtcgaggag atgaagaaca 5700
tgacgcgaca agagtttgtt gcttcccttc gaaggaagag cagtggattc tctcggggtg 5760
cttccatcta cagaggtgta accagacatc accagcatgg acggtggcag gcgaggatcg 5820
gaagggtggc cggtaacaag gacctctacc ttgggacgtt cagcaccgag gaggaagctg 5880
cagaggccta cgacatagcg gccatcaagt tcagaggcct gaacgccgtc acaaacttcg 5940
agatcagccg gtacaacgtg gagaccataa tgagcagcaa ccttccagtc gcgagcatgt 6000
cgtcgtcgtc ggcggcggcg gcgggtggcc ggagcagcaa ggcgctggag tcccctccgt 6060
ccggctcgct tgacggcggc ggcggcatgc cagtcgtcga aggcagcacg gcaccgccgc 6120
tgttcattcc ggtgaagtac gaccagcagc agcaggagta cctgtcgatg ctcgcgttgc 6180
agcaccacca ccagcagcaa caagcaggga acctgttgca ggggccgcta gtagggttcg 6240
gcggcctcta ctcctccggg gtgaacctgg atttcgccaa ctcccacggc acggcggctc 6300
cgtcgtcgat ggcccaccac tgctacgcca atggcaccgc gtccgcctcg catgagcacc 6360
agcaccagca ccagatgcag cagggcggcg agaacgagac gcagccgcag ccgcagcaga 6420
gctccagcag ctgctcctcc ctgccattcg ccacccccggt cgctttcaat gggtcctatg 6480
aaagctccat cacggcggca ggcccctttg gatactccta cccaaatgtg gcagcctttc 6540
agacgccgat ctatggaatg gaatgaa 6567

<210> SEQ ID NO 45
<211> LENGTH: 6552
<212> TYPE: DNA
<213> ORGANISM: Artificial Sequence
<220> FEATURE:
<223> OTHER INFORMATION: recombinant pABM-BdEF1_ZmPLT7

<400> SEQUENCE: 45
agcttacgcg tgtcgactcg aatttccccg atcgttcaaa catttggcaa taaagtttct 60
taagattgaa tcctgttgcc ggtcttgcga tgattatcat ataatttctg ttgaattacg 120
ttaagcatgt aataattaac atgtaatgca tgacgttatt tatgagatgg gtttttatga 180
ttagagtccc gcaattatac atttaatacg cgatagaaaa caaaatatag cgcgcaaact 240
aggataaatt atcgcgcgcg gtgtcatcta tgttactaga tcgctcgacg cggccgccat 300
ggccagatcg tacccaattc gccctatagt gagtcgtatt acaattcact ggccgtcgtt 360
ttacaacgtc gtgactggga aaaccctggc gttacccaac ttaatcgcct tgcagcacat 420
ccccctttcg ccagctggcg taatagcgaa gaggcccgca ccgatcgccc ttcccaacag 480
ttgcgcagcc tgaatggcga atggaaattg taagcgttaa tattttgtta aaattcgcgt 540
taaatttttg ttaaatcagc tcatttttta accaataggc cgaaatcggc aaaatccctt 600
ataaatcaaa agaatagacc gagatagggt tgagtgttgt tccagtttgg aacaagagtc 660
cactattaaa gaacgtggac tccaacgtca aagggcgaaa aaccgtctat cagggcgatg 720
gcccactacg tgaaccatca ccctaatcaa gtttttttggg gtcgaggtgc cgtaaagcac 780
taaatcggaa ccctaaaggg agcccccgat ttagagcttg acggggaaag ccggcgaacg 840
tggcgagaaa ggaagggaag aaagcgaaag gagcgggcgc tagggcgctg gcaagtgtag 900
cggtcacgct gcgcgtaacc accacacccg ccgcgcttaa tgcgccgcta cagggcgcgt 960
caggtggcac ttttcgggga aatgtgcgcg gaacccctat ttgtttattt ttctaaatac 1020
attcaaatat gtatccgctc atgagacaat aaccctgata aatgcttcaa taatattgaa 1080
aaaggaagag tatgagtatt caacatttcc gtgtcgccct tattcccttt tttgcggcat 1140
tttgccttcc tgtttttgct cacccagaaa cgctggtgaa agtaaaagat gctgaagatc 1200
agttgggtgc acgagtgggt tacatcgaac tggatctcaa cagcggtaag atccttgaga 1260
gttttcgccc cgaagaacgt tttccaatga tgagcacttt taaagttctg ctatgtggcg 1320
cggtattatc ccgtattgac gccgggcaag agcaactcgg tcgccgcata cactattctc 1380
agaatgactt ggttgagtac tcaccagtca cagaaaagca tcttacggat ggcatgacag 1440
taagagaatt atgcagtgct gccataacca tgagtgataa cactgcggcc aacttacttc 1500
tgacaacgat cggaggaccg aaggagctaa ccgctttttt gcacaacatg ggggatcatg 1560
taactcgcct tgatcgttgg gaaccggagc tgaatgaagc cataccaaac gacgagcgtg 1620
acaccacgat gcctgtagca atggcaacaa cgttgcgcaa actattaact ggcgaactac 1680
ttactctagc ttcccggcaa caattaatag actggatgga ggcggataaa gttgcaggac 1740
cacttctgcg ctcggccctt ccggctggct ggtttattgc tgataaatct ggagccggtg 1800
agcgtgggtc tcgcggtatc attgcagcac tggggccaga tggtaagccc tcccgtatcg 1860
tagttatcta cacgacgggg agtcaggcaa ctatggatga acgaaataga cagatcgctg 1920

```
agataggtgc ctcactgatt aagcattggt aactgtcaga ccaagtttac tcatatatac   1980
tttagattga tttaaaactt catttttaat ttaaaaggat ctaggtgaag atcctttttg   2040
ataatctcat gaccaaaatc ccttaacgtg agttttcgtt ccactgagcg tcagaccccg   2100
tagaaaagat caaaggatct tcttgagatc ctttttttct gcgcgtaatc tgctgcttgc   2160
aaacaaaaaa accaccgcta ccagcggtgg tttgtttgcc ggatcaagag ctaccaactc   2220
tttttccgaa ggtaactggc ttcagcagag cgcagatacc aaatactgtc cttctagtgt   2280
agccgtagtt aggccaccac ttcaagaact ctgtagcacc gcctacatac ctcgctctgc   2340
taatcctgtt accagtggct gctgccagtg gcgataagtc gtgtcttacc gggttggact   2400
caagacgata gttaccggat aaggcgcagc ggtcgggctg aacggggggt tcgtgcacac   2460
agcccagctt ggagcgaacg acctacaccg aactgagata cctacagcgt gagctatgag   2520
aaagcgccac gcttcccgaa gggagaaagg cggacaggta tccggtaagc ggcagggtcg   2580
gaacaggaga gcgcacgagg gagcttccag ggggaaacgc ctggtatctt tatagtcctg   2640
tcgggtttcg ccacctctga cttgagcgtc gatttttgtg atgctcgtca ggggggcgga   2700
gcctatggaa aaacgccagc aacgcggcct ttttacggtt cctggccttt tgctggcctt   2760
ttgctcacat gttctttcct gcgttatccc ctgattctgt ggataaccgt attaccgcct   2820
ttgagtgagc tgataccgct cgccgcagcc gaacgaccga gcgcagcgag tcagtgagcg   2880
aggaagcgga agagcgccca atacgcaaac cgcctctccc cgcgcgttgg ccgattcatt   2940
aatgcagctg gcacgacagg tttcccgact ggaaagcggg cagtgagcgc aacgcaatta   3000
atgtgagtta gctcactcat taggcacccc aggctttaca ctttatgctt ccggctcgta   3060
tgttgtgtgg aattgtgagc ggataacaat ttcacacagg aaacagctat gaccatgatt   3120
acgccaagct cgaaattaac cctcactaaa gggaacaaaa gctggactag aggcccttaa   3180
ggccttacta gacttcaccg ccattgcaaa aattgtcaat aaatatttag agtgggtggc   3240
atcagaaaaa catctctagt ggactctctt cctatcatag ctactcgggc tgtagataga   3300
acgagggcac aagagttggg tggcgtaggt ttactcgtga cctcaactct tttggctgtg   3360
tcttacgtct aagatgggtt tggcatgtga gaaacatagg tctaagcaat tcatgttagg   3420
gctgttgcat tgttgttgca tcaaccaaat gtccagatag cagttcatgc tacatctagt   3480
tgaaaaccct catcattagg cggaacatgt gttctttttt agcatagtca aagtcagatt   3540
gcggcactcg ctcatccacg gaaagaattt tccctgtgca ggcatctcga tcaaaagacg   3600
caaattaatt tttgaatagc gatataacaa tatctaatta acgtttcttg ttttctgcga   3660
aatgtctttc atcataaaat gagtcatctc gatgagccca agtgacatag cccaacaccc   3720
caccccacca ataaaagtga agaaaacatg ttgggaaaac tataccaagt aaaatacgag   3780
ttgttctaaa gaaaaagtaa agtacgagtt agatcgcacc ctgtcctgga gtgtggcttg   3840
atgatccaac tcctagcatt gtatccctgt ttttggatga tgtaactatt atttacaatg   3900
aataaagagg tgttttacta gtaaaaaaat cttgagggga ggagaaaata atggaggtct   3960
tttttcaaac cgatggacta ttattttag tgaaagagaa taatattatt ggaaaaatta   4020
ttctatccac ttattttata ttggcagaat acaaagaatg gtggggtcca cgcggaactt   4080
gcggcccccg aaacctatcg agggcgcggt acccaagcaa ggaacggagg aaacttgcgg   4140
ggcccgaaac ctagtgataa aaggcatatc atccacacga tgaagatctg acggaccata   4200
tctcccacca cggaaagcca tcagacgagg atcagacggc caggaaggaa ccctagcgcc   4260
```

cgccggtgcc aatataaagc gccactctct ctcgtcttaa gccccagcct ctccattccc 4320
ctctccctct cgccgccgcc gtctccttct cctactccct tcgaggtgtg ttgttcatcc 4380
gtcccgaatc catccatccc ctcttcagat gtgttgttca tggctctaat agctctagat 4440
ctgcttgttt gtgttgttta gctctagatc tactcgcgcg cgcttctctc tcgatctcct 4500
gtagaacaat tttggttggt tttttgtgca tatccatggt aattttgtct gcaatatgga 4560
ggaggctttc taagctccta cgtagcatcg atctttagaa ttccctcggt ttctgtttat 4620
ttcttcgcga gggctctctg ttatctgtag gagtagctgt aagcgcggtt cgttacggat 4680
taatcgtcat gcttagttga acctatcggt cgaaggattt gtgtgggttg tcgtgtagaa 4740
ttgacaccat ctacttactg tactgatatg ccgatctgta ggatactctt cattactttt 4800
gtttactgct agttgtggtg tagatttagc attctcaaac ccatgctgta gcgtttctaa 4860
tattgttaca tagatctacc ggtgcctgtt aattgtattc gatcgggcgt ttctacatct 4920
gtccgcccac ctagttttat atgtggtaat caaaattgcg ttgacttcgt gatgctgtct 4980
gtgtactgtt tttaatcgct cttacttaga tgatcaacat ggtgatggtt acgatttact 5040
gttttctaat ccctgttact tcgatgctgc agtttggatc catggacatg gacatgagct 5100
cagcttatcc ccaccattgg ctctccttct ccctctccaa caactaccac catggcctac 5160
tcgaggcctt ctctaactcc tccggtactc ctcttggaga cgagccgggc gcagtggagg 5220
agtccccgag gacggtggag gacttcctcg gcggcgtcgg tggcgccggc gccccgccgc 5280
agccggcggc tgctgcagat caggatcacc agcttgtgtg cggcgagctg ggcagcatca 5340
cagccaggtt cttgcgccac tacccggcgg cgccagctgg gacgacggtg gagaaccccg 5400
gcgcggtgac cgtggcggcc atgtcgtcga cggacgtggc gggggcggag tccgaccagg 5460
cgaggcggcc cgccgagacg ttcggccagc gcacatccat ctaccgtggc gtcaccaggc 5520
accggtggac agggagatat gaggcgcact tgtgggacaa cagctgccgc cgggagggcc 5580
aaagccgcaa aggacgccaa gtctacctag gaggctatga caaggaggag aaggcggcta 5640
gagcttacga cctcgccgcg ctcaagtact gggggcctac aaccacgacc aacttcccgg 5700
tgtccaacta cgagaaggag ctggaggaga tgaagtccat gacgcggcag gagttcatcg 5760
cgtcgttgcg caggaagagc agcggcttct cacgaggcgc ctccatctac agaggagtca 5820
caaggcatca tcagcacggc cggtggcagg cgaggatcgg cagggtggcc ggaaacaagg 5880
acctgtactt gggcactttc agtactcagg aagaggcggc ggaggcgtac gacatcgctg 5940
cgatcaagtt ccgcgggctc aacgccgtca ccaacttcga catgagccgc tacgacgtgg 6000
agagcatcct cagcagcgac ctccccgtcg ggggcggagc caccgggcgc gccgccaagt 6060
tcccgttgga ctcgctgcag ccggggagcg ctgctgcgat gatgctcgcc ggggctgctg 6120
ccgcttcgca ggccaccatg ccgccgtccg agaaggacta ctggtctctg ctcgccctgc 6180
actaccagca gcagcaggag caggagcggc agttcccggc ttctgcttac gaggcttacg 6240
gctccggcgg cgtgaacgtg gacttcacga tgggcaccag tagcggcaac aacaacaaca 6300
acaccggcag cggcgtcatg tggggcgcca ccactggtgc agtagtagtg ggacagcaag 6360
acagcagcgg caagcagggc aacggctatg ccagcaacat tccttatgct gctgctgctg 6420
ctatggtttc tggatctgct ggctacgagg gctccaccgg cgacaatgga acctgggtta 6480
ctacgactat taccagcagc aacaccggca cggctcccca ctactacaac tatctcttcg 6540
ggatggagta ga 6552

<210> SEQ ID NO 46
<211> LENGTH: 11544
<212> TYPE: DNA
<213> ORGANISM: Artificial Sequence
<220> FEATURE:
<223> OTHER INFORMATION: Plasmid pGEP837 MAD7

<400> SEQUENCE: 46
tttgtaggtg ccaccttcct tttctactgt ccttttgatc aagtgacaga tagctgggca 60
atggaatccg aggaggtttc ccgatattac cctttgttga aaagtctcaa tagccctttg 120
gtcttctgag acttgcaggc aagcaagcat gaatgcctgg gggtctcggc gcgccggaga 180
agaactcgag agggaattgc agatcatgag gcagatggct atttttgtgt cacatatgcg 240
caaaaagaga ggctatattt gtgtccctag gttcttcgtt gtattgcagt ttccatatca 300
atctgacttg gtcgcatgag aaattgatgg ttaaataatt tgaatctctc atgtagtatc 360
aactattaga tattattttc accaaatata tttccatcgg agaagaagag gctacagagg 420
aagcagaaga gaggggtggg agaattttta cacttttgta cacccactta aacagcaaaa 480
tccgtatgaa aacaggccca ccaaaacaat gccacgataa caatccgtag aaacaaaagc 540
ttcatttaac agcggcgcaa caaagcacgc ttatccatgg tagttgtagt ccgtatgcga 600
tccaaagatc acgattcacg cgtgacggac ggacgacgcg tgccacacca caactaacgg 660
catccatggt agttgtagtc cgtatgcgat ccaaagatca cgattcacgc gtgacggacg 720
gacgacgcgc gccacaccac aactaacagc gtgagccagc gtccaaactc cggatggcaa 780
cggggacgaa acccgtcggg tagtcactgc ccaaacccgt ccccgcaacc ttcatcccaa 840
acccgtcccc gtttccggtc gcgggtttca gttttctacc agacccgtcc ccatcgggtt 900
tttcatcccc gtcgggaaat ccgaacccgc cagcatttca gcaccaagcc aaagttgcag 960
cagcaacatg aataaaaaac aacccgtttc aacaccaaga taaaacaaaa cattataatt 1020
tagacaacat ttcacacgta taacaataac atatagttct cacatataac aacaccattt 1080
cacacataaa acaacaccat ttgggataaa aatatgggct atatcaggcc atttttatgg 1140
gccatattga gttttcgtgg gtttcacagg taccggattt gtagaatgct gaaccgggtt 1200
tgaaccgtaa aatccgcggg tattgaattt gacccaatcc cgtcgtcccc tggtggggta 1260
aaaacaccat cttgagtcca aacggccacc aaccaaactc cgacggcaac aaacaaacgg 1320
cgttgctttg ctcctcggta tctccgtgac cgctcaatct cccggctgtt tccccggaat 1380
tgcgtggact ctctcatcca cacgcaaacc gcctctccct cctctctcgt cctatccgcc 1440
ccggtgccgt agcctcacgg gactcttctt cctcccttgc tataaaatcc ccgccccctc 1500
ccgtctcctc tccacacatc caaactctca atcgcaccga gaaaaatctc ctagcgatcg 1560
aagcgaagcc tctcccgatc ctctcaaggt acgcccgttt cccgtcgatc ctcctccttc 1620
cgttcgtgtt ctgtagccga tcgattcgat tcccttacac ccgttcgtgt tctctcgtgg 1680
atcgatcgat tgtttgttgc tagaaggaac tcgtagatct ggcgtttatg aactgtgatt 1740
cgggttagtc cagatcgatt caggtcggtc gtcgttgagc ctctcggcta tgtctggatt 1800
atcgtgtaga tctgctggtt cagttgatta tgttcttcta ggagtaattt cgttgggtca 1860
gcgcgatttc tgcttaatct atgctgctta ttgcgcctgt acctatctac taagctatgt 1920
gcacctgtaa ttttgctaga ttattcgttc atcctcgtag ttggtttgtc acagtaatcc 1980
gtatgggttc tgacgatgtt attgttggtc atacctaggc ttctccagat tttattttgt 2040
taaaattgga tagatctgct actgatagtt gatgatggaa tttggtgctg aatctatgct 2100

```
atttattgcg cctatacctg atctatcggg ctatgtacgg ctgtagttta ctggattatt   2160
cgttcatcct cggtagttgg ttcatcgttt gggttctgac gataatattg ttgattatgc   2220
gtaggcttct gcagattgtt gttaaaattg gatacatcgg ttactgatgg ttgatgatag   2280
atttgtgctg aacctatctg tttattgctc ctatacctga tctatagggc tatgtatgcc   2340
tgtaatttac cagattattc gttcatcctc gtagttggtt catctctata attcgtatgg   2400
gttcttatga tgttatcgtt gattatgcct agtcttatac agattattgt gtcaagattg   2460
aatatacctg ctactgatcg gtgataattt ggttagtagt ttgcaatctg ctaggaacac   2520
gttaccactg taatctgtaa acatggtttg ccagagtagt ttgttctact actcttgata   2580
tggttgctga ttttagtcgc ctccttttgg atcatgtatt gatgtccttg cagatttccg   2640
tgtacttacc ccggcttttg tgtacttcgt gttaacaggt ttaaacgaag caaacatggc   2700
atctagcatg gctccaaaga agaagaggaa ggtcaacaac ggcacgaaca acttccagaa   2760
tttcattggc atttccagcc tccagaagac gctccgcaac gccctgatcc ccaccgagac   2820
cacgcagcag ttcatcgtga agaacggcat catcaaggag gacgagctgc gcggcgagaa   2880
caggcagatc ctcaaggaca tcatggacga ctactaccgc ggcttcatct ccgagacgct   2940
ctccagcatc gacgacatcg actggacgag cctgttcgag aagatggaga tccagctcaa   3000
gaacggcgac aacaaggaca ccctgatcaa ggagcagacg gagtaccgca aggccatcca   3060
caagaagttc gcgaacgacg acaggttcaa gaacatgttc tccgccaagc tgatcagcga   3120
catcctcccg gagttcgtga tccacaacaa caactactcc gccagcgaga aggaggagaa   3180
gacccaggtc atcaagctct tctcccgctt cgcgacgagc ttcaaggact acttcaagaa   3240
cagggccaac tgcttctccg cggacgacat ctccagctcc agctgccaca ggatcgtgaa   3300
cgacaacgcc gagatcttct tcagcaacgc gctggtgtac cgcaggatcg tcaagtccct   3360
cagcaacgac gacatcaaca agatctccgg cgacatgaag gactccctga aggagatgag   3420
cctcgaggag atctacagct acgagaagta cggcgagttc atcacccagg agggcatctc   3480
cttctacaac gacatctgcg gcaaggtcaa cagcttcatg aacctctact gccagaagaa   3540
caaggagaac aagaacctct acaagctgca gaagctccac aagcagatcc tgtgcatcgc   3600
cgacacgtcc tacgaggtgc cgtacaagtt cgagtccgac gaggaggtgt accagagcgt   3660
caacggcttc ctggacaaca tctccagcaa gcacatcgtc gagcgcctca ggaagatcgg   3720
cgacaactac aacggctaca acctggacaa gatctacatc gtgagcaagt tctacgagtc   3780
cgtcagccag aagacctacc gcgactggga gacgatcaac acggcgctgg agatccacta   3840
caacaacatc ctccccggca acggcaagtc caaggccgac aaggtgaaga aggcggtcaa   3900
gaacgacctc cagaagagca tcaccgagat caacgagctg gtgtccaact acaagctctg   3960
cagcgacgac aacatcaagg ccgagacgta catccacgag atctcccaca tcctgaacaa   4020
cttcgaggcg caggagctca agtacaaccc ggagatccac ctggtcgagt ccgagctcaa   4080
ggccagcgag ctgaagaacg tgctcgacgt catcatgaac gcgttccact ggtgcagcgt   4140
gttcatgacc gaggagctgg tcgacaagga caacaacttc tacgccgagc tcgaggagat   4200
ctacgacgag atctaccccg tgatctccct gtacaacctc gtgcgcaact acgtcaccca   4260
gaagccgtac agcacgaaga agatcaagct caacttcggc atcccgaccc tggcggacgg   4320
ctggtccaag agcaaggagt actccaacaa cgcgatcatc ctgatgaggg acaacctgta   4380
ctacctcggc atcttcaacg cgaagaacaa gccggacaag aagatcatcg agggcaacac   4440
gagcgagaac aagggcgact acaagaagat gatctacaac ctcctgccgg gccccaacaa   4500
```

```
gatgatcccg aaggtgttcc tctccagcaa gaccggcgtc gagacgtaca agccctccgc   4560
ctacatcctg gagggctaca agcagaacaa gcacatcaag tccagcaagg acttcgacat   4620
caccttctgc cacgacctca tcgactactt caagaactgc atcgcgatcc accccgagtg   4680
gaagaacttc ggcttcgact tctccgacac cagcacgtac gaggacatct ccggcttcta   4740
ccgcgaggtg gagctgcagg gctacaagat cgactggacg tacatcagcg agaaggacat   4800
cgacctcctg caggagaagg gccagctcta cctgttccag atctacaaca aggacttctc   4860
caagaagagc accggcaacg acaacctcca cacgatgtac ctgaagaacc tcttctccga   4920
ggagaacctg aaggacatcg tcctcaagct gaacggcgag gccgagatct tcttcaggaa   4980
gtccagcatc aagaacccga tcatccacaa gaagggcagc atcctcgtga accgcaccta   5040
cgaggcggag gagaaggacc agttcggcaa catccagatc gtcaggaaga acatccccga   5100
gaacatctac caggagctgt acaagtactt caacgacaag tccgacaagg agctgagcga   5160
cgaggccgcg aagctcaaga acgtggtggg ccaccacgag gcggccacca acatcgtgaa   5220
ggactaccgc tacacgtacg acaagtactt cctgcacatg ccgatcacca tcaacttcaa   5280
ggccaacaag acgggcttca tcaacgacag gatcctgcag tacatcgcga aggagaagga   5340
cctccacgtc atcggcatcg accgcggcga gaggaacctc atctacgtgt ccgtcatcga   5400
cacctgcggc aacatcgtgg agcagaagag cttcaacatc gtcaacggct acgactacca   5460
gatcaagctg aagcagcagg agggcgctag gcagatcgcc aggaaggagt ggaaggagat   5520
cggcaagatc aaggagatca aggagggcta cctctccctc gtgatccacg agatcagcaa   5580
gatggtcatc aagtacaacg ccatcatcgc gatggaggac ctctcctacg gcttcaagaa   5640
ggggcgcttc aaggtggaga ggcaggtcta ccagaagttc gagacgatgc tgatcaacaa   5700
gctgaactac ctcgtgttca aggacatcag catcaccgag aacggcggcc tcctgaaggg   5760
ctaccagctg acgtacatcc ccgacaagct caagaacgtg ggccaccagt gcggctgcat   5820
cttctacgtc ccggccgcgt acacctccaa gatcgacccc accacgggct tcgtgaacat   5880
cttcaagttc aaggacctca cggtcgacgc caagcgcgag ttcatcaaga agttcgactc   5940
catccgctac gacagcgaga agaacctgtt ctgcttcacc ttcgactaca acaacttcat   6000
cacccagaac accgtgatgt ccaagtccag ctggagcgtg tacacgtacg gcgtccgcat   6060
caagcgcagg ttcgtcaacg gcaggttctc caacgagagc gacaccatcg acatcacgaa   6120
ggacatggag aagaccctcg agatgacgga catcaactgg agggacggcc acgacctgag   6180
gcaggacatc atcgactacg agatcgtgca gcacatcttc gagatcttcc gcctcaccgt   6240
ccagatgagg aactccctga gcgagctcga ggaccgcgac tacgacaggc tgatctcccc   6300
ggtgctcaac gagaacaaca tcttctacga ctcggctaag gccggcgacg ctctgcccaa   6360
ggacgcggac gccaacggcg cttactgcat cgcgctgaag ggcctctacg agatcaagca   6420
gatcacggag aactggaagg aggacggcaa gttcagccgc gacaagctca agattagcaa   6480
caaggattgg ttcgatttca ttcagaacaa gcggtacctg aagcggccag cggcgactaa   6540
gaaggcgggc caggcaaaga agaagaagtg agtcgaccga tcgttcaaac atttggcaat   6600
aaagtttctt aagattgaat cctgttgccg gtcttgcgat gattatcata taatttctgt   6660
tgaattacgt taagcatgta ataattaaca tgtaatgcat gacgttattt atgagatggg   6720
tttttatgat tagagtcccg caattataca tttaatacgc gatagaaaac aaaatatagc   6780
gcgcaaacta ggataaatta tcgcgcgcgg tgtcatctat gttactagat cgatcccggg   6840
```

agagaccggg atatcgcggc cgcgtcgttc ggctgcggcg agcggtatca gctcactcaa 6900
aggcggtaat acggttatcc acagaatcag gggataacgc aggaaagaac atgtgagcaa 6960
aaggccagca aaaggccagg aaccgtaaaa aggccgcgtt gctggcgttt ttccataggc 7020
tccgcccccc tgacgagcat cacaaaaatc gacgctcaag tcagaggtgg cgaaacccga 7080
caggactata aagataccag gcgtttcccc ctggaagctc cctcgtgcgc tctcctgttc 7140
cgaccctgcc gcttaccgga tacctgtccg cctttctccc ttcgggaagc gtggcgcttt 7200
ctcatagctc acgctgtagg tatctcagtt cggtgtaggt cgttcgctcc aagctgggct 7260
gtgtgcacga accccccgtt cagcccgacc gctgcgcctt atccggtaac tatcgtcttg 7320
agtccaaccc ggtaagacac gacttatcgc cactggcagc agccactggt aacaggatta 7380
gcagagcgag gtatgtaggc ggtgctacag agttcttgaa gtggtggcct aactacggct 7440
acactagaag gacagtattt ggtatctgcg ctctgctgaa gccagttacc ttcggaaaaa 7500
gagttggtag ctcttgatcc ggcaaacaaa ccaccgctgg tagcggtggt ttttttgttt 7560
gcaagcagca gattacgcgc agaaaaaaag gatctcaaga agatcctttg atcttttcta 7620
cggggtctga cgctcagtgg aacgaaaact cacgttaagg gattttggtc atgagattat 7680
caaaaaggat cttcacctag atccttttaa attaaaaatg aagttttaaa tcaatctaaa 7740
gtatatatga gtaaacttgg tctgacagtt accaatgctt aatcagtgag gcacctatct 7800
cagcgatctg tctatttcgt tcatccatag ttgcctgact ccccgtcgtg tagataacta 7860
cgatacggga gggcttacca tctggcccca gtgctgcaat gataccgcga gaaccacgct 7920
caccggctcc agatttatca gcaataaacc agccagccgg aagggccgag cgcagaagtg 7980
gtcctgcaac tttatccgcc tccatccagt ctattaattg ttgccgggaa gctagagtaa 8040
gtagttcgcc agttaatagt ttgcgcaacg ttgttgccat tgctacaggc atcgtggtgt 8100
cacgctcgtc gtttggtatg gcttcattca gctccggttc ccaacgatca aggcgagtta 8160
catgatcccc catgttgtgc aaaaaagcgg ttagctcctt cggtcctccg atcgttgtca 8220
gaagtaagtt ggccgcagtg ttatcactca tggttatggc agcactgcat aattctctta 8280
ctgtcatgcc atccgtaaga tgcttttctg tgactggtga gtactcaacc aagtcattct 8340
gagaatagtg tatgcggcga ccgagttgct cttgcccggc gtcaatacgg gataataccg 8400
cgccacatag cagaacttta aaagtgctca tcattggaaa acgttcttcg gggcgaaaac 8460
tctcaaggat cttaccgctg ttgagatcca gttcgatgta acccactcgt gcacccaact 8520
gatcttcagc atcttttact ttcaccagcg tttctgggtg agcaaaaaca ggaaggcaaa 8580
atgccgcaaa aaagggaata agggcgacac ggaaatgttg aatactcata ctcttccttt 8640
ttcaatatta ttgaagcatt tatcagggtt attgtctcat gagcggatac atatttgaat 8700
gtatttagaa aaataaacaa ataggggttc cgcgcacatt tccccgaaaa gtgccacctg 8760
acgcgccctg tagcggcacg tctaattcgg gggatctgga ttttagtact ggattttggt 8820
tttaggaatt agaaatttta ttgatagaag tattttacaa atacaaatac atactaaggg 8880
tttcttatat gctcaacaca tgagcgaaac cctataggaa ccctaattcc cttatctggg 8940
aactactcac acattattat ggagaaactc gagcttgtcg atcgacatga tcagggagct 9000
ctagattatt tgtatagttc atccatgcca tgtgtaatcc cagcagctgt tacaaactca 9060
agaaggacca tgtggtctct cttttcgttg ggatctttcg aaagggcaga ttgtgtggac 9120
aggtaatggt tgtctggtaa aaggacaggg ccatcgccaa ttggagtatt ttgttgataa 9180
tggtctgcta gttgaacgct tccatcttca atgttgtgtc taattttgaa gttaactttg 9240

```
gttccattct tttgtttgtc tgccatgatg tatacgttgt gggagttgta gttgtattcc   9300
aacttgtggc cgaggatgtt tccgtcctcc ttgaaatcga ttcccttaag ctcgatcctg   9360
ttgacgaggg tgtctccctc aaacttgact tcagcacgtg tcttgtagtt cccgtcgtcc   9420
ttgaagaaga tggtcctctc ctgcacgtat ccctcaggca tggcgctctt gaagaagtcg   9480
tgccgcttca tatgatctgg gtatcttgaa aagcattgta caccataaca gaaagtagtg   9540
acaagtgttg gccaaggaac aggtagtttt ccagtagtgc aaataaattt aagggtaagt   9600
tttccgtatg ttgcatcacc ttcaccctct ccactgacag aaaatttgtg cccattaaca   9660
tcaccatcta attcaacaag aattgggaca actccagtga aaagttcttc tcctttaccc   9720
ataaaaaagg tggcgggatc gcgccctatc gttcgtaaat ggtgaaaatt ttcagaaaat   9780
tgcttttgct ttaaaagaaa tgatttaaat tgctgcaata gaagtagaat gcttgattgc   9840
ttgagattcg tttgttttgt atatgttgtg ttgagaggat cctcaagctt cgacctgcag   9900
aagtaacacc aaacaacagg gtgagcatcg acaaaagaaa cagtaccaag caaataaata   9960
gcgtatgaag gcagggctaa aaaaatccac atatagctgc tgcatatgcc atcatccaag  10020
tatatcaaga tcaaaataat tataaaacat acttgtttat tataatagat aggtactcaa  10080
ggttagagca tatgaataga tgctgcatat gccatcatgt atatgcatca gtaaaaccca  10140
catcaacatg tatacctatc ctagatcgat atttccatcc atcttaaact cgtaactatg  10200
aagatgtatg acacacacat acagttccaa aattaataaa tacaccaggt agtttgaaac  10260
agtattctac tccgatctag aacgaatgaa cgaccgccca accacaccac atcatcacaa  10320
ccaagcgaac aaaagcatct ctgtatatgc atcagtaaaa cccgcatcaa catgtatacc  10380
tatcctagat cgatatttcc atccatcatc ttcaattcgt aactatgaat atgtatggca  10440
cacacataca gatccaaaat taataaatcc accaggtagt ttgaaacaga attctactcc  10500
gatctagaac gaccgcccaa ccagaccaca tcatcacaac caagacaaaa aaaagcatga  10560
aaagatgacc cgacaaacaa gtgcacggca tatattgaaa taaaggaaaa gggcaaacca  10620
aaccctatgc aacgaaacaa aaaaaatcat gaaatcgatc ccgtctgcgg aacggctaga  10680
gccatcccag gattccccaa agagaaacac tggcaagtta gcaatcagaa cgtgtctgac  10740
gtacaggtcg catccgtgta cgaacgctag cagcacggat ctaacacaaa cacggatcta  10800
acacaaacat gaacagaagt agaactaccg ggccctaacc atggaccgga acgccgatct  10860
agagaaggta gagagggggg gggaggacga gcggcgtacc ttgaagcgga ggtgccgacg  10920
ggtggatttg ggggagatcc actagttcta gagcggccgc caccgcggtg gaattctcga  10980
ggtcctctcc aaatgaaatg aacttcctta tatagaggaa gggtcttgcg aaggatagtg  11040
ggattgtgcg tcatccctta cgtcagtgga gatatcacat caatccactt gctttgaaga  11100
cgtggttgga acgtcttctt tttccacgat gctcctcgtg ggtgggggtc catctttggg  11160
accactgtcg gcagaggcat cttgaacgat agcctttcct ttatcgcaat gatggcattt  11220
gtaggtgcca ccttcctttt ctactgtcct tttgatcaag tgaccgatag ctgggcaatg  11280
gaatccgagg aggtttcccg atattaccct ttgttgaaaa gtctcaatag ccctttggtc  11340
ttctgagact gtatctttga tattcttgga gtagacgaga gtgtcgtgct ccaccatgtt  11400
atcacatcaa ttcacttgct ttgaagacgt ggttggaacg tcttcttttt ccacgatgct  11460
cctcgtgggt gggggtccat ctttgggacc actgtcggca gaggcatctt gaacgatagc  11520
ctttccttta tcgcaatgat ggca                                        11544
```

<210> SEQ ID NO 47
<211> LENGTH: 3852
<212> TYPE: DNA
<213> ORGANISM: Artificial Sequence
<220> FEATURE:
<223> OTHER INFORMATION: Plasmid pGEP842 sgRNA m7GEP1

<400> SEQUENCE: 47
ctgacgcgcc ctgtagcggc ctgcagtgca gcgtgacccg gtcgtgcccc tctctagaga 60
taatgagcat tgcatgtcta agttataaaa aattaccaca tattttttt gtcacacttg 120 tttgaagtgc agtttatcta tctttataca tatatttaaa ctttactcta cgaataatat 180
aatctatagt actacaataa tatcagtgtt ttagagaatc atataaatga acagttagac 240
atggtctaaa ggacaattga gtattttgac aacaggactc tacagtttta tctttttagt 300
gtgcatgtgt tctccttttt ttttgcaaat agcttcacct atataatact tcatccattt 360
tattagtaca tccatttagg gtttagggtt aatggttttt atagactaat ttttttagta 420
catctatttt attctatttt agcctctaaa ttaagaaaac taaaactcta ttttagtttt 480
tttatttaat aatttagata taaaatagaa taaaataaag tgactaaaaa ttaaacaaat 540
accctttaag aaattaaaaa aactaaggaa acatttttct tgtttcgagt agataatgcc 600
agcctgttaa acgccgtcga tcgacgagtc taacggacac caaccagcga accagcagcg 660
tcgcgtcggg ccaagcgaag cagacggcac ggcatctctg tcgctgcctc tggacccctc 720
tcgagagttc cgctccaccg ttggacttgc tccgctgtcg gcatccagaa attgcgtggc 780
ggagcggcag acgtgagccg gcacggcagg cggcctcctc ctcctctcac ggcaccggca 840
gctacggggg attcctttcc caccgctcct tcgctttccc ttcctcgccc gccgtaataa 900
atagacaccc cctccacacc ctctttcccc aacctcgtgt tgttcggagc gcacacacac 960
acaaccagat ctcccccaaa tccacccgtc ggcacctccg cttcaaggta cgccgctcgt 1020
cctccccccc cccccctctc taccttctct agatcggcgt tccggtccat ggttagggcc 1080
cggtagttct acttctgttc atgtttgtgt tagatccgtg tttgtgttag atccgtgctg 1140
ctagcgttcg tacacggatg cgacctgtac gtcagacacg ttctgattgc taacttgcca 1200
gtgtttctct ttggggaatc ctgggatggc tctagccgtt ccgcagacgg gatcgatcta 1260
ggataggtat acatgttgat gtgggtttta ctgatgcata tacatgatgg catatgcagc 1320
atctattcat atgctctaac cttgagtacc tatctattat aataaacaag tatgttttat 1380
aattattttg atcttgatat acttggatga tggcatatgc agcagctata tgtggatttt 1440
tttagccctg ccttcatacg ctatttattt gcttggtact gtttcttttg tcgatgctca 1500
ccctgttgtt tggtgttact tctgcaggga tccaaattac tgatgagtcc gtgaggacga 1560
aacgagtaag ctcgtcgtca aaagaccttt ttaatttcta ctcttgtaga tctcgtcacg 1620
attcccctct ccggccggca tggtcccagc ctcctcgctg gcgccggctg ggcaacatgc 1680
ttcggcatgg cgaatgggac cgatcgttca aacatttggc aataaagttt cttaagattg 1740
aatcctgttg ccggtcttgc gatgattatc atataatttc tgttgaatta cgttaagcat 1800
gtaataatta acatgtaatg catgacgtta tttatgagat gggtttttat gattagagtc 1860
ccgcaattat acatttaata cgcgatagaa aacaaaatat agcgcgcaaa ctaggataaa 1920
ttatcgcgcg cggtgtcatc tatgttacta gatcgatcgt cgttcggctg cggcgagcgg 1980
tatcagctca ctcaaaggcg gtaatacggt tatccacaga atcaggggat aacgcaggaa 2040
agaacatgtg agcaaaaggc cagcaaaagg ccaggaaccg taaaaaggcc gcgttgctgg 2100

```
cgtttttcca taggctccgc cccccctgacg agcatcacaa aaatcgacgc tcaagtcaga   2160
ggtggcgaaa cccgacagga ctataaagat accaggcgtt tccccctgga agctccctcg   2220
tgcgctctcc tgttccgacc ctgccgctta ccggatacct gtccgccttt ctcccttcgg   2280
gaagcgtggc gctttctcat agctcacgct gtaggtatct cagttcggtg taggtcgttc   2340
gctccaagct gggctgtgtg cacgaacccc ccgttcagcc cgaccgctgc gccttatccg   2400
gtaactatcg tcttgagtcc aacccggtaa gacacgactt atcgccactg gcagcagcca   2460
ctggtaacag gattagcaga gcgaggtatg taggcggtgc tacagagttc ttgaagtggt   2520
ggcctaacta cggctacact agaagaacag tatttggtat ctgcgctctg ctgaagccag   2580
ttaccttcgg aaaaagagtt ggtagctctt gatccggcaa acaaaccacc gctggtagcg   2640
gtggtttttt tgtttgcaag cagcagatta cgcgcagaaa aaaaggatct caagaagatc   2700
ctttgatctt ttctacgggg tctgacgctc agtggaacga aaactcacgt taagggattt   2760
tggtcatgag attatcaaaa aggatcttca cctagatcct tttaaattaa aaatgaagtt   2820
ttaaatcaat ctaaagtata tatgagtaaa cttggtctga cagttaccaa tgcttaatca   2880
gtgaggcacc tatctcagcg atctgtctat ttcgttcatc catagttgcc tgactccccg   2940
tcgtgtagat aactacgata cgggagggct taccatctgg ccccagtgct gcaatgatac   3000
cgcgagaccc acgctcaccg gctccagatt tatcagcaat aaaccagcca gccggaaggg   3060
ccgagcgcag aagtggtcct gcaactttat ccgcctccat ccagtctatt aattgttgcc   3120
gggaagctag agtaagtagt tcgccagtta atagtttgcg caacgttgtt gccattgcta   3180
caggcatcgt ggtgtcacgc tcgtcgtttg gtatggcttc attcagctcc ggttcccaac   3240
gatcaaggcg agttacatga tcccccatgt tgtgcaaaaa agcggttagc tccttcggtc   3300
ctccgatcgt tgtcagaagt aagttggccg cagtgttatc actcatggtt atggcagcac   3360
tgcataattc tcttactgtc atgccatccg taagatgctt ttctgtgact ggtgagtact   3420
caaccaagtc attctgagaa tagtgtatgc ggcgaccgag ttgctcttgc ccggcgtcaa   3480
tacgggataa taccgcgcca catagcagaa ctttaaaagt gctcatcatt ggaaaacgtt   3540
cttcggggcg aaaactctca aggatcttac cgctgttgag atccagttcg atgtaaccca   3600
ctcgtgcacc caactgatct tcagcatctt ttactttcac cagcgtttct gggtgagcaa   3660
aaacaggaag gcaaaatgcc gcaaaaaagg gaataagggc gacacggaaa tgttgaatac   3720
tcatactctt cctttttcaa tattattgaa gcatttatca gggttattgt ctcatgagcg   3780
gatacatatt tgaatgtatt tagaaaaata aacaaatagg ggttccgcgc acatttcccc   3840
gaaaagtgcc ac                                                      3852
```

<210> SEQ ID NO 48
<211> LENGTH: 11516
<212> TYPE: DNA
<213> ORGANISM: Artificial Sequence
<220> FEATURE:
<223> OTHER INFORMATION: Plasmid pGEP1054 Map and Plasmid tdTomato

<400> SEQUENCE: 48

```
gggatatcgc ggccgcgtcg ttcggctgcg gcgagcggta tcagctcact caaaggcggt     60
aatacggtta tccacagaat caggggataa cgcaggaaag aacatgtgag caaaaggcca    120
gcaaaaggcc aggaaccgta aaaaggccgc gttgctggcg tttttccata ggctccgccc    180
ccctgacgag catcacaaaa atcgacgctc aagtcagagg tggcgaaacc cgacaggact    240
```

-continued

```
ataaagatac caggcgtttc cccctggaag ctccctcgtg cgctctcctg ttccgaccct    300
gccgcttacc ggatacctgt ccgcctttct cccttcggga agcgtggcgc tttctcatag    360
ctcacgctgt aggtatctca gttcggtgta ggtcgttcgc tccaagctgg gctgtgtgca    420
cgaacccccc gttcagcccg accgctgcgc cttatccggt aactatcgtc ttgagtccaa    480
cccggtaaga cacgacttat cgccactggc agcagccact ggtaacagga ttagcagagc    540
gaggtatgta ggcggtgcta cagagttctt gaagtggtgg cctaactacg gctacactag    600
aaggacagta tttggtatct gcgctctgct gaagccagtt accttcggaa aaagagttgg    660
tagctcttga tccggcaaac aaaccaccgc tggtagcggt ggtttttttg tttgcaagca    720
gcagattacg cgcagaaaaa aaggatctca agaagatcct ttgatctttt ctacggggtc    780
tgacgctcag tggaacgaaa actcacgtta agggattttg gtcatgagat tatcaaaaag    840
gatcttcacc tagatccttt taaattaaaa atgaagtttt aaatcaatct aaagtatata    900
tgagtaaact tggtctgaca gttaccaatg cttaatcagt gaggcaccta tctcagcgat    960
ctgtctattt cgttcatcca tagttgcctg actccccgtc gtgtagataa ctacgatacg   1020
ggagggctta ccatctggcc ccagtgctgc aatgataccg cgagacccac gctcaccggc   1080
tccagattta tcagcaataa accagccagc cggaagggcc gagcgcagaa gtggtcctgc   1140
aactttatcc gcctccatcc agtctattaa ttgttgccgg gaagctagag taagtagttc   1200
gccagttaat agtttgcgca acgttgttgc cattgctaca ggcatcgtgg tgtcacgctc   1260
gtcgtttggt atggcttcat tcagctccgg ttcccaacga tcaaggcgag ttacatgatc   1320
ccccatgttg tgcaaaaaag cggttagctc cttcggtcct ccgatcgttg tcagaagtaa   1380
gttggccgca gtgttatcac tcatggttat ggcagcactg cataattctc ttactgtcat   1440
gccatccgta agatgctttt ctgtgactgg tgagtactca accaagtcat tctgagaata   1500
gtgtatgcgg cgaccgagtt gctcttgccc ggcgtcaata cgggataata ccgcgccaca   1560
tagcagaact ttaaaagtgc tcatcattgg aaaacgttct tcggggcgaa aactctcaag   1620
gatcttaccg ctgttgagat ccagttcgat gtaacccact cgtgcaccca actgatcttc   1680
agcatctttt actttcacca gcgtttctgg gtgagcaaaa acaggaaggc aaaatgccgc   1740
aaaaaaggga ataagggcga cacggaaatg ttgaatactc atactcttcc tttttcaata   1800
ttattgaagc atttatcagg gttattgtct catgagcgga tacatatttg aatgtattta   1860
gaaaaataaa caaatagggg ttccgcgcac atttccccga aaagtgccac ctgacgcgcc   1920
ctgtagcggc acgtctaatt cggggggatct ggattttagt actggatttt ggttttagga   1980
attagaaatt ttattgatag aagtatttta caaatacaaa tacatactaa gggtttctta   2040
tatgctcaac acatgagcga aaccctatag gaaccctaat tcccttatct gggaactact   2100
cacacattat tatggagaaa ctcgagcttg tcgatcgaca tgatcaggga gctctcaggt   2160
acctctagac ttgtacagct cgtccatgcc gtacaggaac aggtggtggc ggccctcgga   2220
gcgctcgtac tgttccacga tggtgtagtc ctcgttgtgg gaggtgatgt ccagcttggt   2280
gtccacgtag tagtagccgg gcagttgcac gggcttcttg gccatgtaga tggtcttgaa   2340
ctccaccagg tagtggccgc cgtccttcag cttcagggcc tggtggatct cgcccttcag   2400
cacgccgtcg cgggggtaca ggcgctcggt ggaggcctcc cagcccatgg tcttcttctg   2460
cattacgggg ccgtcggggg ggaagttggt gccgcgcatc ttcaccttgt agatcagcgt   2520
gccgtcctgc agggaggagt cctgggtcac ggtcaccaga ccgccgtcct cgaagttcat   2580
cacgcgctcc cacttgaagc cctcggggaa ggacagcttc ttgtaatcgg ggatgtcggc   2640
```

ggggtgcttc acgtacgcct tggagccgta catgaactgg ggggacagga tgtcccaggc 2700
gaagggcagg gggccgccct tggtcacctt cagcttggcg gtctgggtgc cctcgtaggg 2760
gcggccctcg ccctcgccct cgatctcgaa ctcgtggccg ttcatggagc cctccatgcg 2820
caccttgaag cgcatgaact ctttgatgac ctcctcgccc ttgctcacca tggtggcggg 2880
atcgcgccct atcgttcgta aatggtgaaa attttcagaa aattgctttt gctttaaaag 2940
aaatgattta aattgctgca atagaagtag aatgcttgat tgcttgagat tcgtttgttt 3000
tgtatatgtt gtgttgagag gatcctctag agtcgacctg cagaagtaac accaaacaac 3060
agggtgagca tcgacaaaag aaacagtacc aagcaaataa atagcgtatg aaggcagggc 3120
taaaaaaatc cacatatagc tgctgcatat gccatcatcc aagtatatca agatcaaaat 3180
aattataaaa catacttgtt tattataata gataggtact caaggttaga gcatatgaat 3240
agatgctgca tatgccatca tgtatatgca tcagtaaaac ccacatcaac atgtatacct 3300
atcctagatc gatatttcca tccatcttaa actcgtaact atgaagatgt atgacacaca 3360
catacagttc caaaattaat aaatacacca ggtagtttga aacagtattc tactccgatc 3420
tagaacgaat gaacgaccgc ccaaccacac cacatcatca caaccaagcg aacaaaagca 3480
tctctgtata tgcatcagta aaacccgcat caacatgtat acctatccta gatcgatatt 3540
tccatccatc atcttcaatt cgtaactatg aatatgtatg gcacacacat acagatccaa 3600
aattaataaa tccaccaggt agtttgaaac agaattctac tccgatctag aacgaccgcc 3660
caaccagacc acatcatcac aaccaagaca aaaaaaagca tgaaaagatg acccgacaaa 3720
caagtgcacg gcatatattg aaataaagga aaagggcaaa ccaaacccta tgcaacgaaa 3780
caaaaaaaat catgaaatcg atcccgtctg cggaacggct agagccatcc caggattccc 3840
caaagagaaa cactggcaag ttagcaatca gaacgtgtct gacgtacagg tcgcatccgt 3900
gtacgaacgc tagcagcacg gatctaacac aaacacggat ctaacacaaa catgaacaga 3960
agtagaacta ccgggcccta accatggacc ggaacgccga tctagagaag gtagagaggg 4020
ggggggagga cgagcggcgt accttgaagc ggaggtgccg acgggtggat ttgggggaga 4080
tccactagtt ctagagcggc cgccaccgcg gtggaattct cgaggtcctc tccaaatgaa 4140
atgaacttcc ttatatagag gaagggtctt gcgaaggata gtgggattgt gcgtcatccc 4200
ttacgtcagt ggagatatca catcaatcca cttgctttga agacgtggtt ggaacgtctt 4260
ctttttccac gatgctcctc gtgggtgggg gtccatcttt gggaccactg tcggcagagg 4320
catcttgaac gatagccttt cctttatcgc aatgatggca tttgtaggtg ccaccttcct 4380
tttctactgt ccttttgatc aagtgaccga tagctgggca atggaatccg aggaggtttc 4440
ccgatattac cctttgttga aaagtctcaa tagccctttg gtcttctgag actgtatctt 4500
tgatattctt ggagtagacg agagtgtcgt gctccaccat gttatcacat caattcactt 4560
gctttgaaga cgtggttgga acgtcttctt tttccacgat gctcctcgtg ggtgggggtc 4620
catctttggg accactgtcg gcagaggcat cttgaacgat agcctttcct ttatcgcaat 4680
gatggcattt gtaggtgcca ccttcctttt ctactgtcct tttgatcaag tgacagatag 4740
ctgggcaatg gaatccgagg aggtttcccg atattaccct ttgttgaaaa gtctcaatag 4800
ccctttggtc ttctgagacc tgcaggcaag caagcatgaa tgcctgggcg cgccggagaa 4860
gaactcgaga gggaattgca gatcatgagg cagatggcta tttttgtgtc acatatgcgc 4920
aaaaagagag gctatatttg tgtccctagg ttcttcgttg tattgcagtt tccatatcaa 4980
tctgacttgg tcgcatgaga aattgatggt taaataattt gaatctctca tgtagtatca 5040
actattagat attattttca ccaaatatat ttccatcgga gaagaagagg ctacagagga 5100
agcagaagag aggggtggga gaatttttac acttttgtac acccacttaa acagcaaaat 5160
ccgtatgaaa acaggcccac caaaacaatg ccacgataac aatccgtaga aacaaaagct 5220
tcatttaaca gcggcgcaac aaagcacgct tatccatggt agttgtagtc cgtatgcgat 5280
ccaaagatca cgattcacgc gtgacggacg gacgacgcgt gccacaccac aactaacggc 5340
atccatggta gttgtagtcc gtatgcgatc caaagatcac gattcacgcg tgacggacgg 5400
acgacgcgcg ccacaccaca actaacagcg tgagccagcg tccaaactcc ggatggcaac 5460
ggggacgaaa cccgtcgggt agtcactgcc caaacccgtc cccgcaacct tcatcccaaa 5520
cccgtccccg tttccggtcg cgggtttcag ttttctacca gacccgtccc catcgggttt 5580
ttcatccccg tcgggaaatc cgaacccgcc agcatttcag caccaagcca aagttgcagc 5640
agcaacatga ataaaaaaca acccgtttca acaccaagat aaaacaaaac attataattt 5700
agacaacatt tcacacgtat aacaataaca tatagttctc acatataaca acaccatttc 5760
acacataaaa caacaccatt tgggataaaa atatgggcta tatcaggcca tttttatggg 5820
ccatattgag ttttcgtggg tttcacaggt accggatttg tagaatgctg aaccgggttt 5880
gaaccgtaaa atccgcgggt attgaatttg acccaatccc gtcgtcccct ggtggggtaa 5940
aaacaccatc ttgagtccaa acggccacca accaaactcc gacggcaaca aacaaacggc 6000
gttgctttgc tcctcggtat ctccgtgacc gctcaatctc ccggctgttt ccccggaatt 6060
gcgtggactc tctcatccac acgcaaaccg cctctccctc ctctctcgtc ctatccgccc 6120
cggtgccgta gcctcacggg actcttcttc ctcccttgct ataaaatccc cgccccctcc 6180
cgtctcctct ccacacatcc aaactctcaa tcgcaccgag aaaaatctcc tagcgatcga 6240
agcgaagcct ctcccgatcc tctcaaggta cgcccgtttc ccgtcgatcc tcctccttcc 6300
gttcgtgttc tgtagccgat cgattcgatt cccttacacc cgttcgtgtt ctctcgtgga 6360
tcgatcgatt gtttgttgct agaaggaact cgtagatctg gcgtttatga actgtgattc 6420
gggttagtcc agatcgattc aggtcggtcg tcgttgagcc tctcggctat gtctggatta 6480
tcgtgtagat ctgctggttc agttgattat gttcttctag gagtaatttc gttgggtcag 6540
cgcgatttct gcttaatcta tgctgcttat tgcgcctgta cctatctact aagctatgtg 6600
cacctgtaat tttgctagat tattcgttca tcctcgtagt tggtttgtca cagtaatccg 6660
tatgggttct gacgatgtta ttgttggtca tacctaggct tctccagatt ttattttgtt 6720
aaaattggat agatctgcta ctgatagttg atgatggaat ttggtgctga atctatgcta 6780
tttattgcgc ctatacctga tctatcgggc tatgtacggc tgtagtttac tggattattc 6840
gttcatcctc ggtagttggt tcatcgtttg ggttctgacg ataatattgt tgattatgcg 6900
taggcttctg cagattgttg ttaaaattgg atacatcggt tactgatggt tgatgataga 6960
tttgtgctga acctatctgt ttattgctcc tatacctgat ctatagggct atgtatgcct 7020
gtaatttacc agattattcg ttcatcctcg tagttggttc atctctataa ttcgtatggg 7080
ttcttatgat gttatcgttg attatgccta gtcttataca gattattgtg tcaagattga 7140
atatacctgc tactgatcgg tgataatttg gttagtagtt tgcaatctgc taggaacacg 7200
ttaccactgt aatctgtaaa catggtttgc cagagtagtt tgttctacta ctcttgatat 7260
ggttgctgat tttagtcgcc tccttttgga tcatgtattg atgtccttgc agatttccgt 7320
gtacttaccc cggcttttgt gtacttcgtg ttaacaggtt taaacgaagc aaacatggca 7380

```
tctagcatgg ctccaaagaa gaagaggaag gtcaacaacg gcacgaacaa cttccagaat   7440
ttcattggca tttccagcct ccagaagacg ctccgcaacg ccctgatccc caccgagacc   7500
acgcagcagt tcatcgtgaa gaacggcatc atcaaggagg acgagctgcg cggcgagaac   7560
aggcagatcc tcaaggacat catggacgac tactaccgcg gcttcatctc cgagacgctc   7620
tccagcatcg acgacatcga ctggacgagc ctgttcgaga agatggagat ccagctcaag   7680
aacggcgaca acaaggacac cctgatcaag gagcagacgg agtaccgcaa ggccatccac   7740
aagaagttcg cgaacgacga caggttcaag aacatgttct ccgccaagct gatcagcgac   7800
atcctcccgg agttcgtgat ccacaacaac aactactccg ccagcgagaa ggaggagaag   7860
acccaggtca tcaagctctt ctcccgcttc gcgacgagct tcaaggacta cttcaagaac   7920
agggccaact gcttctccgc ggacgacatc tccagctcca gctgccacag gatcgtgaac   7980
gacaacgccg agatcttctt cagcaacgcg ctggtgtacc gcaggatcgt caagtccctc   8040
agcaacgacg acatcaacaa gatctccggc gacatgaagg actccctgaa ggagatgagc   8100
ctcgaggaga tctacagcta cgagaagtac ggcgagttca tcacccagga gggcatctcc   8160
ttctacaacg acatctgcgg caaggtcaac agcttcatga acctctactg ccagaagaac   8220
aaggagaaca agaacctcta caagctgcag aagctccaca agcagatcct gtgcatcgcc   8280
gacacgtcct acgaggtgcc gtacaagttc gagtccgacg aggaggtgta ccagagcgtc   8340
aacggcttcc tggacaacat ctccagcaag cacatcgtcg agcgcctcag gaagatcggc   8400
gacaactaca acggctacaa cctggacaag atctacatcg tgagcaagtt ctacgagtcc   8460
gtcagccaga agacctaccg cgactgggag acgatcaaca cggcgctgga gatccactac   8520
aacaacatcc tccccggcaa cggcaagtcc aaggccgaca aggtgaagaa ggcggtcaag   8580
aacgacctcc agaagagcat caccgagatc aacgagctgg tgtccaacta caagctctgc   8640
agcgacgaca acatcaaggc cgagacgtac atccacgaga tctcccacat cctgaacaac   8700
ttcgaggcgc aggagctcaa gtacaacccg gagatccacc tggtcgagtc cgagctcaag   8760
gccagcgagc tgaagaacgt gctcgacgtc atcatgaacg cgttccactg gtgcagcgtg   8820
ttcatgaccg aggagctggt cgacaaggac aacaacttct acgccgagct cgaggagatc   8880
tacgacgaga tctaccccgt gatctccctg tacaacctcg tgcgcaacta cgtcacccag   8940
aagccgtaca gcacgaagaa gatcaagctc aacttcggca tcccgaccct ggcggacggc   9000
tggtccaaga gcaaggagta ctccaacaac gcgatcatcc tgatgaggga caacctgtac   9060
tacctcggca tcttcaacgc gaagaacaag ccggacaaga agatcatcga gggcaacacg   9120
agcgagaaca agggcgacta caagaagatg atctacaacc tcctgccggg ccccaacaag   9180
atgatcccga aggtgttcct ctccagcaag accggcgtcg agacgtacaa gccctccgcc   9240
tacatcctgg agggctacaa gcagaacaag cacatcaagt ccagcaagga cttcgacatc   9300
accttctgcc acgacctcat cgactacttc aagaactgca tcgcgatcca ccccgagtgg   9360
aagaacttcg gcttcgactt ctccgacacc agcacgtacg aggacatctc cggcttctac   9420
cgcgaggtgg agctgcaggg ctacaagatc gactggacgt acatcagcga gaaggacatc   9480
gacctcctgc aggagaaggg ccagctctac ctgttccaga tctacaacaa ggacttctcc   9540
aagaagagca ccggcaacga caacctccac acgatgtacc tgaagaacct cttctccgag   9600
gagaacctga aggacatcgt cctcaagctg aacggcgagg ccgagatctt cttcaggaag   9660
tccagcatca agaacccgat catccacaag aagggcagca tcctcgtgaa ccgcacctac   9720
```

```
gaggcggagg agaaggacca gttcggcaac atccagatcg tcaggaagaa catccccgag   9780
aacatctacc aggagctgta caagtacttc aacgacaagt ccgacaagga gctgagcgac   9840
gaggccgcga agctcaagaa cgtggtgggc caccacgagg cggccaccaa catcgtgaag   9900
gactaccgct acacgtacga caagtacttc ctgcacatgc cgatcaccat caacttcaag   9960
gccaacaaga cgggcttcat caacgacagg atcctgcagt acatcgcgaa ggagaaggac  10020
ctccacgtca tcggcatcga ccgcggcgag aggaacctca tctacgtgtc cgtcatcgac  10080
acctgcggca acatcgtgga gcagaagagc ttcaacatcg tcaacggcta cgactaccag  10140
atcaagctga agcagcagga gggcgctagg cagatcgcca ggaaggagtg gaaggagatc  10200
ggcaagatca aggagatcaa ggagggctac ctctccctcg tgatccacga gatcagcaag  10260
atggtcatca agtacaacgc catcatcgcg atggaggacc tctcctacgg cttcaagaag  10320
gggcgcttca aggtggagag gcaggtctac cagaagttcg agacgatgct gatcaacaag  10380
ctgaactacc tcgtgttcaa ggacatcagc atcaccgaga acggcggcct cctgaagggc  10440
taccagctga cgtacatccc cgacaagctc aagaacgtgg gccaccagtg cggctgcatc  10500
ttctacgtcc cggccgcgta cacctccaag atcgacccca ccacgggctt cgtgaacatc  10560
ttcaagttca aggacctcac ggtcgacgcc aagcgcgagt tcatcaagaa gttcgactcc  10620
atccgctacg acagcgagaa gaacctgttc tgcttcacct tcgactacaa caacttcatc  10680
acccagaaca ccgtgatgtc caagtccagc tggagcgtgt acacgtacgg cgtccgcatc  10740
aagcgcaggt tcgtcaacgg caggttctcc aacgagagcg acaccatcga catcacgaag  10800
gacatggaga agaccctcga gatgacggac atcaactgga gggacggcca cgacctgagg  10860
caggacatca tcgactacga gatcgtgcag cacatcttcg agatcttccg cctcaccgtc  10920
cagatgagga actccctgag cgagctcgag gaccgcgact acgacaggct gatctccccg  10980
gtgctcaacg agaacaacat cttctacgac tcggctaagg ccggcgacgc tctgcccaag  11040
gacgcggacg ccaacggcgc ttactgcatc gcgctgaagg gcctctacga gatcaagcag  11100
atcacggaga actggaagga ggacggcaag ttcagccgcg acaagctcaa gattagcaac  11160
aaggattggt tcgatttcat tcagaacaag cggtacctga agcggccagc ggcgactaag  11220
aaggcgggcc aggcaaagaa gaagaagtga gtcgaccgat cgttcaaaca tttggcaata  11280
aagtttctta agattgaatc ctgttgccgg tcttgcgatg attatcatat aatttctgtt  11340
gaattacgtt aagcatgtaa taattaacat gtaatgcatg acgttattta tgagatgggt  11400
ttttatgatt agagtcccgc aattatacat ttaatacgcg atagaaaaca aaatatagcg  11460
cgcaaactag gataaattat cgcgcgcggt gtcatctatg ttactagatc gatccc      11516
```

<210> SEQ ID NO 49
<211> LENGTH: 3852
<212> TYPE: DNA
<213> ORGANISM: Artificial Sequence
<220> FEATURE:
<223> OTHER INFORMATION: Plasmid pGEP1067 sgRNA m7GEP22

<400> SEQUENCE: 49

```
ctgacgcgcc ctgtagcggc ctgcagtgca gcgtgacccg gtcgtgcccc tctctagaga     60
taatgagcat tgcatgtcta agttataaaa aattaccaca tattttttt gtcacacttg    120
tttgaagtgc agtttatcta tctttataca tatatttaaa ctttactcta cgaataatat    180
aatctatagt actacaataa tatcagtgtt ttagagaatc atataaatga acagttagac    240
atggtctaaa ggacaattga gtattttgac aacaggactc tacagtttta tctttttagt    300
```

-continued

```
gtgcatgtgt tctccttttt ttttgcaaat agcttcacct atataatact tcatccattt    360
tattagtaca tccatttagg gtttagggtt aatggttttt atagactaat ttttttagta    420
catctatttt attctatttt agcctctaaa ttaagaaaac taaaactcta ttttagtttt    480
tttatttaat aatttagata taaaatagaa taaaataaag tgactaaaaa ttaaacaaat    540
accctttaag aaattaaaaa aactaaggaa acatttttct tgtttcgagt agataatgcc    600
agcctgttaa acgccgtcga tcgacgagtc taacggacac caaccagcga accagcagcg    660
tcgcgtcggg ccaagcgaag cagacggcac ggcatctctg tcgctgcctc tggacccctc    720
tcgagagttc cgctccaccg ttggacttgc tccgctgtcg gcatccagaa attgcgtggc    780
ggagcggcag acgtgagccg gcacggcagg cggcctcctc ctcctctcac ggcaccggca    840
gctacggggg attcctttcc caccgctcct tcgctttccc ttcctcgccc gccgtaataa    900
atagacaccc cctccacacc ctctttcccc aacctcgtgt tgttcggagc gcacacacac    960
acaaccagat ctccccccaaa tccacccgtc ggcacctccg cttcaaggta cgccgctcgt   1020
cctccccccc cccccctctc taccttctct agatcggcgt tccggtccat ggttagggcc   1080
cggtagttct acttctgttc atgtttgtgt tagatccgtg tttgtgttag atccgtgctg   1140
ctagcgttcg tacacggatg cgacctgtac gtcagacacg ttctgattgc taacttgcca   1200
gtgtttctct ttggggaatc ctgggatggc tctagccgtt ccgcagacgg gatcgatcta   1260
ggataggtat acatgttgat gtgggtttta ctgatgcata tacatgatgg catatgcagc   1320
atctattcat atgctctaac cttgagtacc tatctattat aataaacaag tatgttttat   1380
aattattttg atcttgatat acttggatga tggcatatgc agcagctata tgtggatttt   1440
tttagccctg ccttcatacg ctatttattt gcttggtact gtttcttttg tcgatgctca   1500
ccctgttgtt tggtgttact tctgcaggga tccaaattac tgatgagtcc gtgaggacga   1560
aacgagtaag ctcgtcgtca aaagaccttt ttaatttcta ctcttgtaga tttcagagca   1620
ctgcagctaa gaggccggca tggtcccagc ctcctcgctg gcgccggctg ggcaacatgc   1680
ttcggcatgg cgaatgggac cgatcgttca aacatttggc aataaagttt cttaagattg   1740
aatcctgttg ccggtcttgc gatgattatc atataatttc tgttgaatta cgttaagcat   1800
gtaataatta acatgtaatg catgacgtta tttatgagat gggtttttat gattagagtc   1860
ccgcaattat acatttaata cgcgatagaa aacaaaatat agcgcgcaaa ctaggataaa   1920
ttatcgcgcg cggtgtcatc tatgttacta gatcgatcgt cgttcggctg cggcgagcgg   1980
tatcagctca ctcaaaggcg gtaatacggt tatccacaga atcaggggat aacgcaggaa   2040
agaacatgtg agcaaaaggc cagcaaaagg ccaggaaccg taaaaaggcc gcgttgctgg   2100
cgtttttcca taggctccgc ccccctgacg agcatcacaa aaatcgacgc tcaagtcaga   2160
ggtggcgaaa cccgacagga ctataaagat accaggcgtt tccccctgga agctccctcg   2220
tgcgctctcc tgttccgacc ctgccgctta ccggatacct gtccgccttt ctcccttcgg   2280
gaagcgtggc gctttctcat agctcacgct gtaggtatct cagttcggtg taggtcgttc   2340
gctccaagct gggctgtgtg cacgaacccc ccgttcagcc cgaccgctgc gccttatccg   2400
gtaactatcg tcttgagtcc aacccggtaa gacacgactt atcgccactg gcagcagcca   2460
ctggtaacag gattagcaga gcgaggtatg taggcggtgc tacagagttc ttgaagtggt   2520
ggcctaacta cggctacact agaagaacag tatttggtat ctgcgctctg ctgaagccag   2580
ttaccttcgg aaaaagagtt ggtagctctt gatccggcaa acaaaccacc gctggtagcg   2640
```

```
gtggtttttt tgtttgcaag cagcagatta cgcgcagaaa aaaaggatct caagaagatc   2700

ctttgatctt ttctacgggg tctgacgctc agtggaacga aaactcacgt taagggattt   2760

tggtcatgag attatcaaaa aggatcttca cctagatcct tttaaattaa aaatgaagtt   2820

ttaaatcaat ctaaagtata tatgagtaaa cttggtctga cagttaccaa tgcttaatca   2880

gtgaggcacc tatctcagcg atctgtctat ttcgttcatc catagttgcc tgactccccg   2940

tcgtgtagat aactacgata cgggagggct taccatctgg ccccagtgct gcaatgatac   3000

cgcgagaccc acgctcaccg gctccagatt tatcagcaat aaaccagcca gccggaaggg   3060

ccgagcgcag aagtggtcct gcaactttat ccgcctccat ccagtctatt aattgttgcc   3120

gggaagctag agtaagtagt tcgccagtta atagtttgcg caacgttgtt gccattgcta   3180

caggcatcgt ggtgtcacgc tcgtcgtttg gtatggcttc attcagctcc ggttcccaac   3240

gatcaaggcg agttacatga tcccccatgt tgtgcaaaaa agcggttagc tccttcggtc   3300

ctccgatcgt tgtcagaagt aagttggccg cagtgttatc actcatggtt atggcagcac   3360

tgcataattc tcttactgtc atgccatccg taagatgctt ttctgtgact ggtgagtact   3420

caaccaagtc attctgagaa tagtgtatgc ggcgaccgag ttgctcttgc ccggcgtcaa   3480

tacgggataa taccgcgcca catagcagaa ctttaaaagt gctcatcatt ggaaaacgtt   3540

cttcggggcg aaaactctca aggatcttac cgctgttgag atccagttcg atgtaaccca   3600

ctcgtgcacc caactgatct tcagcatctt ttactttcac cagcgtttct gggtgagcaa   3660

aaacaggaag gcaaaatgcc gcaaaaaagg gaataagggc gacacggaaa tgttgaatac   3720

tcatactctt cctttttcaa tattattgaa gcatttatca gggttattgt ctcatgagcg   3780

gatacatatt tgaatgtatt tagaaaaata aacaaatagg ggttccgcgc acatttcccc   3840

gaaaagtgcc ac                                                       3852
```

<210> SEQ ID NO 50
<211> LENGTH: 11413
<212> TYPE: DNA
<213> ORGANISM: Artificial Sequence
<220> FEATURE:
<223> OTHER INFORMATION: Construct GEMT121 encoding tdT as marker and LbCpf1

<400> SEQUENCE: 50

```
tttgtaggtg ccaccttcct tttctactgt ccttttgatc aagtgacaga tagctgggca     60

atggaatccg aggaggtttc ccgatattac cctttgttga aaagtctcaa tagccctttg    120

gtcttctgaa cctgcaggca agcaagcatg aatgcctggg cgcgccggag aagaactcga    180

gagggaattg cagatcatga ggcagatggc tatttttgtg tcacatatgc gcaaaaagag    240

aggctatatt tgtgtcccta ggttcttcgt tgtattgcag tttccatatc aatctgactt    300

ggtcgcatga gaaattgatg gttaaataat ttgaatctct catgtagtat caactattag    360

atattatttt caccaaatat atttccatcg gagaagaaga ggctacagag gaagcagaag    420

agaggggtgg gagaattttt acacttttgt acacccactt aaacagcaaa atccgtatga    480

aaacaggccc accaaaacaa tgccacgata acaatccgta gaaacaaaag cttcatttaa    540

cagcggcgca acaaagcacg cttatccatg gtagttgtag tccgtatgcg atccaaagat    600

cacgattcac gcgtgacgga cggacgacgc gtgccacacc acaactaacg gcatccatgg    660

tagttgtagt ccgtatgcga tccaaagatc acgattcacg cgtgacggac ggacgacgcg    720

cgccacacca caactaacag cgtgagccag cgtccaaact ccggatggca acggggacga    780
```

```
aacccgtcgg gtagtcactg cccaaacccg tccccgcaac cttcatccca aacccgtccc    840
cgtttccggt cgcgggtttc agttttctac cagacccgtc cccatcgggt ttttcatccc    900
cgtcgggaaa tccgaacccg ccagcatttc agcaccaagc caaagttgca gcagcaacat    960
gaataaaaaa caacccgttt caacaccaag ataaaacaaa acattataat ttagacaaca   1020
tttcacacgt ataacaataa catatagttc tcacatataa caacaccatt tcacacataa   1080
aacaacacca tttgggataa aaatatgggc tatatcaggc catttttatg ggccatattg   1140
agttttcgtg ggtttcacag gtaccggatt tgtagaatgc tgaaccgggt ttgaaccgta   1200
aaatccgcgg gtattgaatt tgacccaatc ccgtcgtccc ctggtggggt aaaaacacca   1260
tcttgagtcc aaacggccac caaccaaact ccgacggcaa caaacaaacg gcgttgcttt   1320
gctcctcggt atctccgtga ccgctcaatc tcccggctgt ttccccggaa ttgcgtggac   1380
tctctcatcc acacgcaaac cgcctctccc tcctctctcg tcctatccgc cccggtgccg   1440
tagcctcacg ggactcttct tcctcccttg ctataaaatc cccgcccccct cccgtctcct  1500
ctccacacat ccaaactctc aatcgcaccg agaaaaatct cctagcgatc gaagcgaagc   1560
ctctcccgat cctctcaagg tacgcccgtt tcccgtcgat cctcctcctt ccgttcgtgt   1620
tctgtagccg atcgattcga ttcccttaca cccgttcgtg ttctctcgtg gatcgatcga   1680
ttgtttgttg ctagaaggaa ctcgtagatc tggcgtttat gaactgtgat tcgggttagt   1740
ccagatcgat tcaggtcggt cgtcgttgag cctctcggct atgtctggat tatcgtgtag   1800
atctgctggt tcagttgatt atgttcttct aggagtaatt tcgttgggtc agcgcgattt   1860
ctgcttaatc tatgctgctt attgcgcctg tacctatcta ctaagctatg tgcacctgta   1920
attttgctag attattcgtt catcctcgta gttggtttgt cacagtaatc cgtatgggtt   1980
ctgacgatgt tattgttggt catacctagg cttctccaga ttttattttg ttaaaattgg   2040
atagatctgc tactgatagt tgatgatgga atttggtgct gaatctatgc tatttattgc   2100
gcctatacct gatctatcgg gctatgtacg gctgtagttt actggattat tcgttcatcc   2160
tcggtagttg gttcatcgtt tgggttctga cgataatatt gttgattatg cgtaggcttc   2220
tgcagattgt tgttaaaatt ggatacatcg gttactgatg gttgatgata gatttgtgct   2280
gaacctatct gtttattgct cctatacctg atctataggg ctatgtatgc ctgtaattta   2340
ccagattatt cgttcatcct cgtagttggt tcatctctat aattcgtatg ggttcttatg   2400
atgttatcgt tgattatgcc tagtcttata cagattattg tgtcaagatt gaatatacct   2460
gctactgatc ggtgataatt tggttagtag tttgcaatct gctaggaaca cgttaccact   2520
gtaatctgta aacatggttt gccagagtag tttgttctac tactcttgat atggttgctg   2580
attttagtcg cctcctttg gatcatgtat tgatgtcctt gcagatttcc gtgtacttac   2640
cccggctttt gtgtacttcg tgttaacagg tcgccttagg gaagcaaaca tggcatctag   2700
catggcgccg aagaagaagc gcaaggtgtc caagctcgag aagttcacga actgctactc   2760
cctctccaag accctccgct tcaaggccat ccccgtgggc aagacccagg agaacatcga   2820
caacaagcgc ctcctggtcg aggacgagaa gagggcggag gactacaagg gcgtgaagaa   2880
gctcctggac cgctactacc tctccttcat caacgacgtc ctgcacagca tcaagctcaa   2940
gaacctgaac aactacatct ccctgttccg caagaagacg aggaccgaga aggagaacaa   3000
ggagctcgag aacctggaga tcaacctccg caaggagatc gccaaggcgt tcaagggcaa   3060
cgagggctac aagagcctgt tcaagaagga catcatcgag acgatcctcc cggagttcct   3120
ggacgacaag gacgagatcg ccctcgtgaa ctccttcaac ggcttcacca cggcgttcac   3180
```

```
cggcttcttc gacaaccgcg agaacatgtt cagcgaggag gccaagtcca cgagcatcgc   3240
gttccgctgc atcaacgaga acctgaccag gtacatctcc aacatggaca tcttcgagaa   3300
ggtcgacgcc atcttcgaca agcacgaggt gcaggagatc aaggagaaga tcctcaacag   3360
cgactacgac gtcgaggact tcttcgaggg cgagttcttc aacttcgtcc tgacgcagga   3420
gggcatcgac gtgtacaacg ccatcatcgg tggcttcgtg accgagtccg gcgagaagat   3480
caagggcctc aacgagtaca tcaacctgta caaccagaag accaagcaga agctcccgaa   3540
gttcaagccc ctctacaagc aggtcctgtc cgaccgcgag tccctgagct tctacggcga   3600
gggctacacg agcgacgagg aggtcctcga ggtgttcagg aacaccctga acaagaacag   3660
cgagatcttc tccagcatca agaagctcga gaagctgttc aagaacttcg acgagtactc   3720
cagcgccggc atcttcgtca agaacggccc ggcgatctcc acgatcagca aggatatctt   3780
cggcgagtgg aacgtgatca gggacaagtg gaacgccgag tacgacgaca tccacctcaa   3840
gaagaaggcg gtggtcaccg agaagtacga ggacgaccgc aggaagtcct tcaagaagat   3900
cggctccttc agcctcgagc agctgcagga gtacgccgac gcggacctct ccgtggtcga   3960
gaagctgaag gagatcatca tccagaaggt cgacgagatc tacaaggtgt acggctccag   4020
cgagaagctg ttcgacgccg acttcgtcct cgagaagtcc ctgaagaaga acgacgccgt   4080
ggtcgcgatc atgaaggacc tcctggactc cgtgaagagc ttcgagaact acatcaaggc   4140
gttcttcggc gagggcaagg agacgaaccg cgacgagtcc ttctacggcg acttcgtcct   4200
cgcctacgac atcctcctga aggtggacca catctacgac gcgatcagga actacgtgac   4260
ccagaagccg tacagcaagg acaagttcaa gctgtacttc cagaaccccc agttcatgcg   4320
cggctgggac aaggacaagg agacggacta ccgcgccacc atcctccgct acggcagcaa   4380
gtactacctg gccatcatgg acaagaagta cgcgaagtgc ctccagaaga tcgacaagga   4440
cgacgtcaac ggcaactacg agaagatcaa ctacaagctc ctgccgggcc ccaacaagat   4500
gctgccgagg gtgttcttct ccaagaagtg gatggcctac tacaacccca gcgaggacat   4560
ccagaagatc tacaagaacg gcacgttcaa gaagggcgac atgttcaacc tcaacgactg   4620
ccacaagctg atcgacttct tcaaggactc catcagccgc tacccgaagt ggtccaacgc   4680
ctacgacttc aacttcagcg agacagagaa gtacaaggac atcgcgggct tctacaggga   4740
ggtcgaggag cagggctaca aggtgtcctt cgagtccgcc agcaagaagg aggtcgacaa   4800
gctcgtggag gagggcaagc tgtacatgtt ccagatctac aacaaggact tctccgacaa   4860
gagccacggc acgcccaacc tccacaccat gtacttcaag ctcctgttcg acgagaacaa   4920
ccacggccag atccgcctct ccggcggcgc cgagctgttc atgaggaggg cgagcctcaa   4980
gaaggaggag ctggtggtcc accccgctaa cagcccaatc gcgaacaaga acccggacaa   5040
ccccaagaag accacgaccc tctcctacga cgtgtacaag gacaagcgct tcagcgagga   5100
ccagtacgag ctgcacatcc cgatcgccat caacaagtgc cccaagaaca tcttcaagat   5160
caacaccgag gtcagggtgc tcctgaagca cgacgacaac ccctacgtga tcggcatcga   5220
ccgcggcgag aggaacctcc tgtacatcgt ggtcgtggac ggcaagggca acatcgtgga   5280
gcagtactcc ctgaacgaga tcatcaacaa cttcaacggc atccgcatca agacggacta   5340
ccacagcctc ctggacaaga aggagaagga gcgcttcgag gccaggcaga actggacctc   5400
catcgagaac atcaaggagc tcaaggcggg ctacatcagc caggtcgtgc acaagatctg   5460
cgagctggtc gagaagtacg acgccgtgat cgcgctcgag gacctgaact ccggcttcaa   5520
```

gaacagcagg gtcaaggtgg agaagcaggt ctaccagaag ttcgagaaga tgctcatcga 5580
caagctgaac tacatggtgg acaagaagtc caacccgtgc gctacgggcg gcgcgctcaa 5640
gggctaccag atcaccaaca agttcgagag cttcaagtcc atgagcaccc agaacggctt 5700
catcttctac atcccggcct ggctgacgtc caagatcgac cccagcaccg gcttcgtcaa 5760
cctcctgaag acgaagtaca cctccatcgc ggacagcaag aagttcatct ccagcttcga 5820
ccgcatcatg tatgtgccgg aggaggacct cttcgagttc gccctggact acaagaactt 5880
ctccaggacg gacgcggatt acatcaagaa gtggaagctc tacagctacg gcaaccgcat 5940
caggatcttc cgcaacccca agaagaacaa cgtcttcgac tgggaggagg tgtgcctcac 6000
ctccgcctac aaggagctgt tcaacaagta cggcatcaac taccagcagg gcgacatcag 6060
ggcgctcctg tgcgagcaga gcgacaaggc cttctactcc agcttcatgg cgctcatgtc 6120
cctcatgctg cagatgcgca acagcatcac gggcaggacc gacgtcgact tcctgatctc 6180
cccggtgaag aacagcgacg gcatcttcta cgacagccgc aactacgagg cccaggagaa 6240
cgcgatcctg ccaaagaacg cggacgccaa cggcgcctac aacatcgcga ggaaggtgct 6300
gtgggccatc ggccagttca agaaggcgga ggacgagaag ctcgacaagg tcaagatcgc 6360
catctccaac aaggagtggc tggagtacgc gcagacctcg gtgaagcaca agaggcccgc 6420
tgccaccaag aaggcgggcc aggccaagaa gaagaagtga cctcagccga tcgttcaaac 6480
atttggcaat aaagtttctt aagattgaat cctgttgccg gtcttgcgat gattatcata 6540
taatttctgt tgaattacgt taagcatgta ataattaaca tgtaatgcat gacgttattt 6600
atgagatggg tttttatgat tagagtcccg caattataca tttaatacgc gatagaaaac 6660
aaaatatagc gcgcaaacta ggataaatta tcgcgcgcgg tgtcatctat gttactagat 6720
cgatcccggg atatcgcggc cggtcgttcg gctgcggcga gcggtatcag ctcactcaaa 6780
ggcggtaata cggttatcca cagaatcagg ggataacgca ggaaagaaca tgtgagcaaa 6840
aggccagcaa aaggccagga accgtaaaaa ggccgcgttg ctggcgtttt tccataggct 6900
ccgcccccct gacgagcatc acaaaaatcg acgctcaagt cagaggtggc gaaacccgac 6960
aggactataa agataccagg cgtttccccc tggaagctcc ctcgtgcgct ctcctgttcc 7020
gaccctgccg cttaccggat acctgtccgc ctttctccct tcgggaagcg tggcgctttc 7080
tcatagctca cgctgtaggt atctcagttc ggtgtaggtc gttcgctcca agctgggctg 7140
tgtgcacgaa ccccccgttc agcccgaccg ctgcgcctta tccggtaact atcgtcttga 7200
gtccaacccg gtaagacacg acttatcgcc actggcagca gccactggta acaggattag 7260
cagagcgagg tatgtaggcg gtgctacaga gttcttgaag tggtggccta actacggcta 7320
cactagaagg acagtatttg gtatctgcgc tctgctgaag ccagttacct tcggaaaaag 7380
agttggtagc tcttgatccg gcaaacaaac caccgctggt agcggtggtt tttttgtttg 7440
caagcagcag attacgcgca gaaaaaaagg atctcaagaa gatcctttga tcttttctac 7500
ggggtctgac gctcagtgga acgaaaactc acgttaaggg attttggtca tgagattatc 7560
aaaaaggatc ttcacctaga tccttttaaa ttaaaaatga agttttaaat caatctaaag 7620
tatatatgag taaacttggt ctgacagtta ccaatgctta atcagtgagg cacctatctc 7680
agcgatctgt ctatttcgtt catccatagt tgcctgactc cccgtcgtgt agataactac 7740
gatacgggag ggcttaccat ctggccccag tgctgcaatg ataccgcgag acccacgctc 7800
accggctcca gatttatcag caataaacca gccagccgga agggccgagc gcagaagtgg 7860
tcctgcaact ttatccgcct ccatccagtc tattaattgt tgccgggaag ctagagtaag 7920
tagttcgcca gttaatagtt tgcgcaacgt tgttgccatt gctacaggca tcgtggtgtc 7980
acgctcgtcg tttggtatgg cttcattcag ctccggttcc caacgatcaa ggcgagttac 8040
atgatccccc atgttgtgca aaaaagcggt tagctccttc ggtcctccga tcgttgtcag 8100
aagtaagttg gccgcagtgt tatcactcat ggttatggca gcactgcata attctcttac 8160
tgtcatgcca tccgtaagat gcttttctgt gactggtgag tactcaacca agtcattctg 8220
agaatagtgt atgcggcgac cgagttgctc ttgcccggcg tcaatacggg ataataccgc 8280
gccacatagc agaactttaa aagtgctcat cattggaaaa cgttcttcgg ggcgaaaact 8340
ctcaaggatc ttaccgctgt tgagatccag ttcgatgtaa cccactcgtg cacccaactg 8400
atcttcagca tcttttactt tcaccagcgt ttctgggtga gcaaaaacag gaaggcaaaa 8460
tgccgcaaaa aagggaataa gggcgacacg gaaatgttga atactcatac tcttcctttt 8520
tcaatattat tgaagcattt atcagggtta ttgtctcatg agcggataca tatttgaatg 8580
tatttagaaa aataaacaaa taggggttcc gcgcacattt ccccgaaaag tgccacctga 8640
cgcgccctgt agcggcacgt ctaattcggg ggatctggat tttagtactg gattttggtt 8700
ttaggaatta gaaattttat tgatagaagt attttacaaa tacaaataca tactaagggt 8760
ttcttatatg ctcaacacat gagcgaaacc ctataggaac cctaattccc ttatctggga 8820
actactcaca cattattatg gagaaactcg agcttgtcga tcgacatgat cagggagctc 8880
tcaggtacct ctagacttgt acagctcgtc catgccgtac aggaacaggt ggtggcggcc 8940
ctcggagcgc tcgtactgtt ccacgatggt gtagtcctcg ttgtgggagg tgatgtccag 9000
cttggtgtcc acgtagtagt agccgggcag ttgcacgggc ttcttggcca tgtagatggt 9060
cttgaactcc accaggtagt ggccgccgtc cttcagcttc agggcctggt ggatctcgcc 9120
cttcagcacg ccgtcgcggg ggtacaggcg ctcggtggag gcctcccagc ccatggtctt 9180
cttctgcatt acggggccgt cggggggaa gttggtgccg cgcatcttca ccttgtagat 9240
cagcgtgccg tcctgcaggg aggagtcctg ggtcacggtc accagaccgc cgtcctcgaa 9300
gttcatcacg cgctcccact tgaagccctc ggggaaggac agcttcttgt aatcggggat 9360
gtcggcgggg tgcttcacgt acgccttgga gccgtacatg aactgggggg acaggatgtc 9420
ccaggcgaag ggcagggggc cgcccttggt caccttcagc ttggcggtct gggtgccctc 9480
gtaggggcgg ccctcgccct cgccctcgat ctcgaactcg tggccgttca tggagccctc 9540
catgcgcacc ttgaagcgca tgaactcttt gatgacctcc tcgcccttgc tcaccatggt 9600
ggcgggatcg cgccctatcg ttcgtaaatg gtgaaaattt tcagaaaatt gcttttgctt 9660
taaaagaaat gatttaaatt gctgcaatag aagtagaatg cttgattgct tgagattcgt 9720
ttgttttgta tatgttgtgt tgagaggatc ctctagagtc gacctgcaga agtaacacca 9780
aacaacaggg tgagcatcga caaaagaaac agtaccaagc aaataaatag cgtatgaagg 9840
cagggctaaa aaaatccaca tatagctgct gcatatgcca tcatccaagt atatcaagat 9900
caaaataatt ataaaacata cttgtttatt ataatagata ggtactcaag gttagagcat 9960
atgaatagat gctgcatatg ccatcatgta tatgcatcag taaaacccac atcaacatgt 10020
atacctatcc tagatcgata tttccatcca tcttaaactc gtaactatga agatgtatga 10080
cacacacata cagttccaaa attaataaat acaccaggta gtttgaaaca gtattctact 10140
ccgatctaga acgaatgaac gaccgcccaa ccacaccaca tcatcacaac caagcgaaca 10200
aaagcatctc tgtatatgca tcagtaaaac ccgcatcaac atgtatacct atcctagatc 10260
gatatttcca tccatcatct tcaattcgta actatgaata tgtatggcac acacatacag 10320
atccaaaatt aataaatcca ccaggtagtt tgaaacagaa ttctactccg atctagaacg 10380
accgcccaac cagaccacat catcacaacc aagacaaaaa aaagcatgaa aagatgaccc 10440
gacaaacaag tgcacggcat atattgaaat aaaggaaaag ggcaaaccaa accctatgca 10500
acgaaacaaa aaaaatcatg aaatcgatcc cgtctgcgga acggctagag ccatcccagg 10560
attccccaaa gagaaacact ggcaagttag caatcagaac gtgtctgacg tacaggtcgc 10620
atccgtgtac gaacgctagc agcacggatc taacacaaac acggatctaa cacaaacatg 10680
aacagaagta gaactaccgg gccctaacca tggaccggaa cgccgatcta gagaaggtag 10740
agaggggggg ggaggacgag cggcgtacct tgaagcggag gtgccgacgg gtggatttgg 10800
gggagatcca ctagttctag agcggccgcc accgcggtgg aattctcgag gtcctctcca 10860
aatgaaatga acttccttat atagaggaag ggtcttgcga aggatagtgg gattgtgcgt 10920
catcccttac gtcagtggag atatcacatc aatccacttg ctttgaagac gtggttggaa 10980
cgtcttcttt ttccacgatg ctcctcgtgg gtgggggtcc atctttggga ccactgtcgg 11040
cagaggcatc ttgaacgata gcctttcctt tatcgcaatg atggcatttg taggtgccac 11100
cttccttttc tactgtcctt ttgatcaagt gaccgatagc tgggcaatgg aatccgagga 11160
ggtttcccga tattaccctt tgttgaaaag tctcaatagc cctttggtct tctgagactg 11220
tatctttgat attcttggag tagacgagag tgtcgtgctc caccatgtta tcacatcaat 11280
tcacttgctt tgaagacgtg gttggaacgt cttctttttc cacgatgctc ctcgtgggtg 11340
ggggtccatc tttgggacca ctgtcggcag aggcatcttg aacgatagcc tttcctttat 11400
cgcaatgatg gca 11413

<210> SEQ ID NO 51
<211> LENGTH: 3841
<212> TYPE: DNA
<213> ORGANISM: Artificial Sequence
<220> FEATURE:
<223> OTHER INFORMATION: Construct GEMT099

<400> SEQUENCE: 51
ctgacgcgcc ctgtagcggc ctgcagtgca gcgtgacccg gtcgtgcccc tctctagaga 60
taatgagcat tgcatgtcta agttataaaa aattaccaca tatttttttt gtcacacttg 120
tttgaagtgc agtttatcta tctttataca tatatttaaa ctttactcta cgaataatat 180
aatctatagt actacaataa tatcagtgtt ttagagaatc atataaatga acagttagac 240
atggtctaaa ggacaattga gtattttgac aacaggactc tacagtttta tctttttagt 300
gtgcatgtgt tctccttttt ttttgcaaat agcttcacct atataatact tcatccattt 360
tattagtaca tccatttagg gtttagggtt aatggttttt atagactaat ttttttagta 420
catctatttt attctatttt agcctctaaa ttaagaaaac taaaactcta ttttagtttt 480
tttatttaat aatttagata taaaatagaa taaaataaag tgactaaaaa ttaaacaaat 540
accctttaag aaattaaaaa aactaaggaa acatttttct tgtttcgagt agataatgcc 600
agcctgttaa acgccgtcga tcgacgagtc taacggacac caaccagcga accagcagcg 660
tcgcgtcggg ccaagcgaag cagacggcac ggcatctctg tcgctgcctc tggacccctc 720
tcgagagttc cgctccaccg ttggacttgc tccgctgtcg gcatccagaa attgcgtggc 780
ggagcggcag acgtgagccg gcacggcagg cggcctcctc ctcctctcac ggcaccggca 840
gctacggggg attcctttcc caccgctcct tcgctttccc ttcctcgccc gccgtaataa 900

```
atagacaccc cctccacacc ctctttcccc aacctcgtgt tgttcggagc gcacacacac    960
acaaccagat ctcccccaaa tccacccgtc ggcacctccg cttcaaggta cgccgctcgt   1020
cctccccccc cccccctctc taccttctct agatcggcgt tccggtccat ggttagggcc   1080
cggtagttct acttctgttc atgtttgtgt tagatccgtg tttgtgttag atccgtgctg   1140
ctagcgttcg tacacggatg cgacctgtac gtcagacacg ttctgattgc taacttgcca   1200
gtgtttctct ttggggaatc ctgggatggc tctagccgtt ccgcagacgg gatcgatcta   1260
ggataggtat acatgttgat gtgggtttta ctgatgcata tacatgatgg catatgcagc   1320
atctattcat atgctctaac cttgagtacc tatctattat aataaacaag tatgttttat   1380
aattattttg atcttgatat acttggatga tggcatatgc agcagctata tgtggatttt   1440
tttagccctg ccttcatacg ctatttattt gcttggtact gtttcttttg tcgatgctca   1500
ccctgttgtt tggtgttact tctgcaggga tccaaattac tgatgagtcc gtgaggacga   1560
aacgagtaag ctcgtctaat ttctactaag tgtagatctg ttggagaggc taacccccac   1620
tggccggcat ggtcccagcc tcctcgctgg cgccggctgg gcaacatgct tcggcatggc   1680
gaatgggacc gatcgttcaa acatttggca ataaagtttc ttaagattga atcctgttgc   1740
cggtcttgcg atgattatca tataatttct gttgaattac gttaagcatg taataattaa   1800
catgtaatgc atgacgttat ttatgagatg ggtttttatg attagagtcc cgcaattata   1860
catttaatac gcgatagaaa acaaaatata gcgcgcaaac taggataaat tatcgcgcgc   1920
ggtgtcatct atgttactag atcgatcgtc gttcggctgc ggcgagcggt atcagctcac   1980
tcaaaggcgg taatacggtt atccacagaa tcaggggata acgcaggaaa gaacatgtga   2040
gcaaaaggcc agcaaaaggc caggaaccgt aaaaaggccg cgttgctggc gtttttccat   2100
aggctccgcc cccctgacga gcatcacaaa aatcgacgct caagtcagag gtggcgaaac   2160
ccgacaggac tataaagata ccaggcgttt ccccctggaa gctccctcgt gcgctctcct   2220
gttccgaccc tgccgcttac cggatacctg tccgcctttc tcccttcggg aagcgtggcg   2280
ctttctcata gctcacgctg taggtatctc agttcggtgt aggtcgttcg ctccaagctg   2340
ggctgtgtgc acgaaccccc cgttcagccc gaccgctgcg ccttatccgg taactatcgt   2400
cttgagtcca acccggtaag acacgactta tcgccactgg cagcagccac tggtaacagg   2460
attagcagag cgaggtatgt aggcggtgct acagagttct tgaagtggtg gcctaactac   2520
ggctacacta gaagaacagt atttggtatc tgcgctctgc tgaagccagt taccttcgga   2580
aaaagagttg gtagctcttg atccggcaaa caaaccaccg ctggtagcgg tggttttttt   2640
gtttgcaagc agcagattac gcgcagaaaa aaaggatctc aagaagatcc tttgatcttt   2700
tctacggggt ctgacgctca gtggaacgaa aactcacgtt aagggatttt ggtcatgaga   2760
ttatcaaaaa ggatcttcac ctagatcctt ttaaattaaa aatgaagttt taaatcaatc   2820
taaagtatat atgagtaaac ttggtctgac agttaccaat gcttaatcag tgaggcacct   2880
atctcagcga tctgtctatt tcgttcatcc atagttgcct gactccccgt cgtgtagata   2940
actacgatac gggagggctt accatctggc cccagtgctg caatgatacc gcgagaccca   3000
cgctcaccgg ctccagattt atcagcaata aaccagccag ccggaagggc cgagcgcaga   3060
agtggtcctg caactttatc cgcctccatc cagtctatta attgttgccg ggaagctaga   3120
gtaagtagtt cgccagttaa tagtttgcgc aacgttgttg ccattgctac aggcatcgtg   3180
gtgtcacgct cgtcgtttgg tatggcttca ttcagctccg gttcccaacg atcaaggcga   3240
```

```
gttacatgat cccccatgtt gtgcaaaaaa gcggttagct ccttcggtcc tccgatcgtt   3300

gtcagaagta agttggccgc agtgttatca ctcatggtta tggcagcact gcataattct   3360

cttactgtca tgccatccgt aagatgcttt tctgtgactg gtgagtactc aaccaagtca   3420

ttctgagaat agtgtatgcg gcgaccgagt tgctcttgcc cggcgtcaat acgggataat   3480

accgcgccac atagcagaac tttaaaagtg ctcatcattg gaaaacgttc ttcggggcga   3540

aaactctcaa ggatcttacc gctgttgaga tccagttcga tgtaacccac tcgtgcaccc   3600

aactgatctt cagcatcttt tactttcacc agcgtttctg ggtgagcaaa aacaggaagg   3660

caaaatgccg caaaaaaggg aataagggcg acacggaaat gttgaatact catactcttc   3720

ctttttcaat attattgaag catttatcag ggttattgtc tcatgagcgg atacatattt   3780

gaatgtattt agaaaaataa acaaataggg gttccgcgca catttccccg aaaagtgcca   3840

c                                                                   3841
```

<210> SEQ ID NO 52
<211> LENGTH: 1104
<212> TYPE: DNA
<213> ORGANISM: Triticum aestivum

<400> SEQUENCE: 52

```
atggagatgc aacaacaata cttcgggggg gacggcgatg cggactggtt ccatcaactc     60

gcattgcttc ccccacttcc aatctcatcg tctctccccc cactcccgat gtcagagggc    120

tcatgtctcc ctatggcagc agcagctgca gctgcactcc cccttggcga ttgctcgagc    180

gccctcatga tacgccctga ggaacagatg tcttgccttc caatgaaccc ctctccagcg    240

gtcgtcgacg atgtctactc ttcctacgca ccgaacaatg tcgacgtgtt gccgccattc    300

ccggcaggac ttgacgacgc tctgttgatg gagtcttttt ctgacatcga cctcgaggag    360

tttgctgacg catttggcca caagatcaag acagaacccc tcgacgatgc catggtcccc    420

gcggaccacg acttcgcggc tcaagcccaa caggcctgcc ctgtggtcat catgaatcag    480

caacaactca acgcacccag agacgtgcgc ctgctcattg acccggatga tgatgacagc    540

accgtggtgg ccgggggcta tgaagctgca gcggtggggt gcgccgagca gaaacaggtc    600

aggccagcac cacgtagggt gagaaagagc tcaggcggcg caagaccagc cgcgggagga    660

aagtccctcg atcacatcgg attcgaggaa ctcaggacct atttctatat gccaatcacc    720

aaggcagcga gggaaatgaa cgtggggctg acagtcctga agaagagatg ccgggaactg    780

ggggtggcgc gctggccaca cagaaagatg aagtctctga gaagcctgat cctcaacatt    840

caggagatgg ggaagggcgc aacatctccc gcagccgtgc agggggaact tgaagcgctt    900

gagaggtatt gcgccattat ggaggagaac ccggctatag agctcaccga gcaaacgaag    960

aagctcaggc aggcttgttt caaagagaat tataagcggc gtagagccgc cgcttctgtt   1020

aatcttctcg atcactgcta taacgatctg gcatctcatg agcagcaaat gcctctccca   1080

caaatgggat tctttggatt ttag                                          1104
```

<210> SEQ ID NO 53
<211> LENGTH: 367
<212> TYPE: PRT
<213> ORGANISM: Triticum aestivum

<400> SEQUENCE: 53

```
Met Glu Met Gln Gln Gln Tyr Phe Gly Gly Asp Gly Asp Ala Asp Trp
1               5                   10                  15
```

```
Phe His Gln Leu Ala Leu Leu Pro Pro Leu Pro Ile Ser Ser Ser Leu
            20                  25                  30

Pro Pro Leu Pro Met Ser Glu Gly Ser Cys Leu Pro Met Ala Ala Ala
        35                  40                  45

Ala Ala Ala Ala Leu Pro Leu Gly Asp Cys Ser Ser Ala Leu Met Ile
    50                  55                  60

Arg Pro Glu Glu Gln Met Ser Cys Leu Pro Met Asn Pro Ser Pro Ala
65                  70                  75                  80

Val Val Asp Asp Val Tyr Ser Ser Tyr Ala Pro Asn Asn Val Asp Val
                85                  90                  95

Leu Pro Pro Phe Pro Ala Gly Leu Asp Asp Ala Leu Leu Met Glu Ser
            100                 105                 110

Phe Ser Asp Ile Asp Leu Glu Glu Phe Ala Asp Ala Phe Gly His Lys
        115                 120                 125

Ile Lys Thr Glu Pro Leu Asp Asp Ala Met Val Pro Ala Asp His Asp
    130                 135                 140

Phe Ala Ala Gln Ala Gln Gln Ala Cys Pro Val Val Ile Met Asn Gln
145                 150                 155                 160

Gln Gln Leu Asn Ala Pro Arg Asp Val Arg Leu Leu Ile Asp Pro Asp
                165                 170                 175

Asp Asp Asp Ser Thr Val Val Ala Gly Gly Tyr Glu Ala Ala Ala Val
            180                 185                 190

Gly Cys Ala Glu Gln Lys Gln Val Arg Pro Ala Pro Arg Arg Val Arg
        195                 200                 205

Lys Ser Ser Gly Gly Ala Arg Pro Ala Ala Gly Gly Lys Ser Leu Asp
    210                 215                 220

His Ile Gly Phe Glu Glu Leu Arg Thr Tyr Phe Tyr Met Pro Ile Thr
225                 230                 235                 240

Lys Ala Ala Arg Glu Met Asn Val Gly Leu Thr Val Leu Lys Lys Arg
                245                 250                 255

Cys Arg Glu Leu Gly Val Ala Arg Trp Pro His Arg Lys Met Lys Ser
            260                 265                 270

Leu Arg Ser Leu Ile Leu Asn Ile Gln Glu Met Gly Lys Gly Ala Thr
        275                 280                 285

Ser Pro Ala Ala Val Gln Gly Glu Leu Glu Ala Leu Glu Arg Tyr Cys
    290                 295                 300

Ala Ile Met Glu Glu Asn Pro Ala Ile Glu Leu Thr Glu Gln Thr Lys
305                 310                 315                 320

Lys Leu Arg Gln Ala Cys Phe Lys Glu Asn Tyr Lys Arg Arg Arg Ala
                325                 330                 335

Ala Ala Ser Val Asn Leu Leu Asp His Cys Tyr Asn Asp Leu Ala Ser
            340                 345                 350

His Glu Gln Gln Met Pro Leu Pro Gln Met Gly Phe Phe Gly Phe
        355                 360                 365
```

<210> SEQ ID NO 54
<211> LENGTH: 25
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)..(10)
<223> OTHER INFORMATION: Any amino acid
<220> FEATURE:

```
<221> NAME/KEY: MOD_RES
<222> LOCATION: (12)..(21)
<223> OTHER INFORMATION: Any amino acid
<220> FEATURE:
<221> NAME/KEY: MOD_RES
<222> LOCATION: (23)..(24)
<223> OTHER INFORMATION: Any amino acid

<400> SEQUENCE: 54

Cys Xaa Xaa Xaa Xaa Xaa Xaa Xaa Xaa Xaa Cys Xaa Xaa Xaa Xaa Xaa
1               5                   10                  15

Xaa Xaa Xaa Xaa Xaa Cys Xaa Xaa His
            20                  25


<210> SEQ ID NO 55
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

tttgatttac tcgtcacgat tcccctctcc tggtcgaact tttcaggtgg ggaaagctgc     60

tggcga                                                                66


<210> SEQ ID NO 56
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56

tttgatttac tcgtcaggaa agctgctggc gacaggtgga aatc                      44


<210> SEQ ID NO 57
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

tttgatttac tcgtcacgat tcctggtcga acttttcagg tggggaaagc tgctggcg       58


<210> SEQ ID NO 58
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58

tttgatttac aggtggggaa agctgctggc gacaggtgga aatc                      44


<210> SEQ ID NO 59
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 59

tttgatttac tcgtcacgat tcccctctcc tggtcgaact tttcaggtgg ggaaagctgc     60

tgg                                                                   63


<210> SEQ ID NO 60
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 60

tttgatttac tcgtcacgat tccccgaact tttcaggtgg ggaaagctgc tggcga         56


<210> SEQ ID NO 61
<211> LENGTH: 56
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61

tttgatttac tcgtcacgat tcccctaact tttcaggtgg ggaaagctgc tggcga         56
```